(12) United States Patent
Tang et al.

(10) Patent No.: US 10,759,812 B2
(45) Date of Patent: Sep. 1, 2020

(54) THIENOPYRIMIDINE DERIVATIVE AND USE THEREOF IN MEDICINE

(71) Applicants: SUNSHINE LAKE PHARMA CO., LTD., Dongguan, Guangdong (CN); NORTH & SOUTH BROTHER PHARMACY INVESTMENT COMPANY LIMITED, Wanchai (HK)

(72) Inventors: Wanjun Tang, Dongguan (CN); Xinye Yang, Dongguan (CN); Zheng Gu, Dongguan (CN); Chenlu Li, Dongguan (CN); Zongyuan Zhang, Dongguan (CN); Zhifu Wan, Dongguan (CN); Xiaojun Wang, Dongguan (CN); Yingjun Zhang, Dongguan (CN)

(73) Assignee: Sunshine Lake Pharma Co., Ltd., Dongguan, Guangdong (CN)

( * ) Notice: Subject to any disclaimer, the term of this patent is extended or adjusted under 35 U.S.C. 154(b) by 0 days.

(21) Appl. No.: 16/476,290

(22) PCT Filed: Jan. 22, 2018

(86) PCT No.: PCT/CN2018/073581
§ 371 (c)(1),
(2) Date: Jul. 7, 2019

(87) PCT Pub. No.: WO2018/133858
PCT Pub. Date: Jul. 26, 2018

(65) Prior Publication Data
US 2019/0352311 A1 Nov. 21, 2019

(30) Foreign Application Priority Data

Jan. 22, 2017 (CN) .......................... 2017 1 00522753

(51) Int. Cl.
| | | |
|---|---|---|
| *C07D 495/04* | (2006.01) |
| *C07D 519/00* | (2006.01) |
| *A61K 31/519* | (2006.01) |
| *A61P 1/16* | (2006.01) |
| *A61P 3/04* | (2006.01) |
| *A61P 3/10* | (2006.01) |
| *A61P 35/00* | (2006.01) |

(52) U.S. Cl.
CPC .......... *C07D 495/04* (2013.01); *A61K 31/519* (2013.01); *A61P 1/16* (2018.01); *A61P 3/04* (2018.01); *A61P 3/10* (2018.01); *A61P 35/00* (2018.01); *C07D 519/00* (2013.01)

(58) Field of Classification Search
CPC .. C07D 495/04; C07D 519/00; A61K 31/519; A61P 35/00; A61P 3/04; A61P 3/10; A61P 1/16

USPC ........................................ 544/280; 514/265.1
See application file for complete search history.

(56) References Cited

U.S. PATENT DOCUMENTS

| | | |
|---|---|---|
| 6,130,223 A | 10/2000 | Jonas et al. |
| 8,969,557 B2 | 3/2015 | Harriman et al. |
| 9,765,089 B2 | 9/2017 | Greenwood et al. |
| 9,988,399 B2 | 6/2018 | Greenwood et al. |
| 10,179,793 B2 | 1/2019 | Ghosh et al. |
| 10,208,044 B2 | 2/2019 | Greenwood et al. |
| 2007/0208040 A1 | 9/2007 | Elzein et al. |
| 2017/0166582 A1 | 6/2017 | Ghosh et al. |
| 2017/0166583 A1 | 6/2017 | Ghosh et al. |
| 2017/0166584 A1 | 6/2017 | Ghosh et al. |
| 2017/0166585 A1 | 6/2017 | Bennett et al. |
| 2018/0021341 A1 | 1/2018 | Harriman et al. |

FOREIGN PATENT DOCUMENTS

| | | |
|---|---|---|
| WO | WO2015003881 A1 | 1/2015 |
| WO | WO2015007451 A1 | 1/2015 |
| WO | WO2017147161 A1 | 8/2017 |
| WO | WO2018028721 A1 | 2/2018 |
| WO | WO2018171698 A1 | 9/2018 |
| WO | WO2018171699 A1 | 9/2018 |
| WO | WO2018228369 A1 | 12/2018 |

OTHER PUBLICATIONS

Atzrodt et al. Angew. Chem. Int. Ed. 2007, 46, 7744-7765.*
Cecil Textbook of Medicine, edited by Bennet, J.C., and Plum F., 20th edition,vol. 1, 1004-1010, 1996.*
Freshney et al Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
ISR of PCT/CN2018/073581.
Written Opinion of the ISA of PCT/CN2018/073581.

* cited by examiner

*Primary Examiner* — Venkataraman Balasubramanian
(74) *Attorney, Agent, or Firm* — Kam Wah Law

(57) ABSTRACT

The present invention relates to a thienopyrimidine derivative and use thereof in medicine, and also to a pharmaceutical composition containing the compound. The compound or pharmaceutical composition is used for inhibiting acetyl-CoA carboxylase (ACC). The present invention also relates to a method of preparing such compound and pharmaceutical composition, as well as their use in the treatment or prevention of diseases regulated by acetyl-CoA carboxylase in mammals, especially in humans.

14 Claims, No Drawings

THIENOPYRIMIDINE DERIVATIVE AND USE THEREOF IN MEDICINE

CROSS-REFERENCE TO RELATED APPLICATIONS

This is a U.S. national stage application of the International Patent Application No. PCT/CN2018/073581, filed Jan. 22, 2018, which claims priority to Chinese Patent Application No. 201710052275.3, filed Jan. 22, 2017, both of which are incorporated herein by reference in their entirety.

FIELD OF THE INVENTION

The present invention relates to thienopyrimidine derivatives having enzyme inhibition activity and pharmaceutical compositions thereof, the compounds and compositions can be used in the manufacture of a medicament for treating a disorder or disease regulated by acetyl-CoA carboxylase.

BACKGROUND OF THE INVENTION

Acetyl-CoA carboxylase (ACC) is the limited enzyme in the first step of the synthesis process of fatty acid, carboxylation of acetyl-CoA with $HCO_3^-$ carboxy donor in the present of ATP and $Mg^{2+}$ is carried out to form malonyl coenzyme A, which is a biotin dependent enzyme.

This enzyme pertains to specific tissue enzyme in human and other mammal, which has two subtype, ACC1 and ACC2, there are some differences in tissue distribution and function between the two subtype; ACC1 ordinarily express in all tissues, the expression is most in lipogenic tissue (e.g. liver and adipose tissue), ACC2 has the highest expression in skeletal muscle and heart, and less expression in liver. Biosynthesis of long chain fatty acid is catalyzed by ACC1, acetyl-CoA is metabolized via Krebs cycle if it is not carboxylated to form malonyl coenzyme A; production of malonyl coenzyme A on cytoplasmic surface of the mitochondria is catalyzed by ACC2, the amount of fatty acid used for β-oxidation is regulated by inhibiting carnitine palmityl transferase (CPT-1).

The research shows that ACC inhibitor can inhibit ACC1 to reduce synthesis of fatty acid, and can inhibit ACC2 to promote oxidation of fatty acid in liver, and then reduce accumulation of lipid in vivo, which can effectively treat diseases or disorders associated with obesity, hypertension, diabetes, tumor, dyslipidemia and hyperlipidemia, and type II diabetes induced by liver insulin resistance caused by accumulation of lipid in liver, non-alcoholic fatty liver disease (NAFLD) and non-alcoholic steatohepatitis (NASH).

Non-alcoholic steatohepatitis (NASH) is a chronic progressive disease induced by accumulation of lipid in liver, which can cause liver cirrhosis, liver failure and hepatocellular carcinoma. There are a lot of induction factors of NASH, e.g. age, obesity, body mass index (BMI), insulin sensitivity, dyslipidemia, hypertension and abnormally active related enzymes of liver function (e.g. alanine aminotransferase (ALT) and aspartate aminotransferase (AST)), and so on. It is reported that having metabolism syndrome symptoms (mainly centripetal obesity, hypertension, insulin resistance, high triglyceride, and low density lipoprotein) of patients is positively related to the risk of NASH. Results of liver biopsy shows that NASH accompanied by severe fibrosis in 66% diabetic or obese patients over age 50. About 12% people were deeply affected by this disease in US, the proportion increased to 22% in diabetes, more significantly, about 15~25% NASH patients will suffer from cirrhosis, this is another reason for liver cancer second only to viral hepatitis and alcoholic hepatitis. Cirrhosis is primary reason for death caused by hepatic diseases, which directly cause hepatic decompensation and about 4% death rate every year.

Other alternative therapies for obesity, hypertension, diabetes, dyslipidemia are still needed, but for NASH, the present therapies are limited.

SUMMARY OF THE INVENTION

The present invention relates to a compound as an acetyl-CoA carboxylas (ACC) inhibitor and a pharmaceutical composition containing this compound. The present invention further relates to use of the compound or the composition thereof in the manufacture of a medicament for inhibiting ACC activity to treat a disorder or disease. The present invention further describes the synthetic method of the compound. The compounds of the invention show good bioactivity and pharmacokinetic properties.

As used herein, inhibition of ACC refers to only inhibition of ACC1, only inhibition of ACC2 or simultaneous inhibition of ACC1 and ACC2. Any one inhibition of ACC sub-type should advantageously affect disorders associated with the metabolic syndrome. Optimized ACC inhibitors should inhibit both isoenzyme of this enzyme.

Specifically,

In one aspect, provided herein is a compound having Formula (I) or a stereoisomer, a geometric isomer, a tautomer, an N-oxide, a hydrate, a solvate, a metabolite, a pharmaceutically acceptable salt or a prodrug thereof,

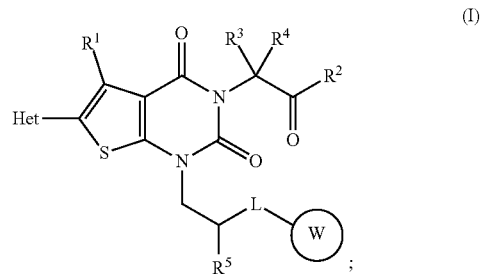

wherein

Het is —C(=O)NR$^a$R$^b$, —C(=NR)NR$^a$R$^b$, —NH—C(=NR)NR$^a$R$^b$, 3-10 membered heterocyclyl or 5-10 membered heteroaryl; wherein each of 3-10 membered heterocyclyl and 5-10 membered heteroaryl is independently and optionally substituted with H, D, oxo (=O), F, Cl, Br, I, hydroxy, amino, nitro, cyano, $C_{1-6}$ alkyl, $C_{1-6}$ alkoxy, $C_{1-6}$ haloalkyl, carboxy and —C(=O)NH$_2$;

R$^1$ is H, D, F, Cl, Br, I, hydroxy, amino, nitro, cyano, $C_{1-6}$ alkyl, $C_{1-6}$ alkoxy or $C_{1-6}$ haloalkyl;

R$^2$ is —OR or —NR$^a$R$^b$;

wherein each R, R$^a$ and R$^b$ is independently H, D, $C_{1-6}$ alkyl, $C_{1-6}$ haloalkyl or $C_{3-8}$ cycloalkyl; or R$^a$ and R$^b$, together with the N atom to which they are attached, form 3-10 membered heterocyclyl; wherein 3-10 membered heterocyclyl is optionally substituted with oxo (=O), F, Cl, Br, I, hydroxy, amino, nitro, cyano, $C_{1-6}$ alkyl, $C_{1-6}$ alkoxy and $C_{1-6}$ haloalkyl;

each of R$^3$ and R$^4$ is independently H, D, $C_{1-6}$ alkyl, $C_{1-6}$ hydroxyalkyl or $C_{1-6}$ haloalkyl;

L is —O—, —O-methylene-, —O-ethylene-, —S— or —NH—;

R⁵ is $C_{6-10}$ aryl or 5-10 membered heteroaryl, each of $C_{6-10}$ aryl and 5-10 membered heteroaryl is independently and optionally substituted with 1, 2 or 3 R⁶; wherein R⁶ is H, D, F, Cl, Br, I, hydroxy, amino, nitro, cyano, $C_{1-6}$ alkyl, $C_{1-6}$ alkoxy, $C_{1-6}$ haloalkyl, $C_{1-6}$ haloalkoxy, $C_{1-6}$ cyanoalkyl or $C_{1-6}$ hydroxyalkyl;

W is fused cyclyl, bridged cyclyl or spiro cyclyl, wherein fused cyclyl, bridged cyclyl or spiro cyclyl is saturated or partially unsaturated 6-12 membered cyclyl containing 0, 1, 2, 3 or 4 heteroatoms independently selected from N, O or S; and wherein W is optionally substituted with 1, 2, 3, 4 or 5 substituents independently selected from D, oxo (=O), F, Cl, Br, I, hydroxy, amino, nitro, cyano, —C(=O)OR, —C(=O)NR$^a$R$^b$, —C(=NR)NR$^a$R$^b$, —NH—C(=NR) NR$^a$R$^b$, —SO₂R, —SO₂NR$^a$R$^b$, $C_{1-6}$ alkyl, $C_{3-6}$ cycloalkyl, $C_{1-6}$ alkoxy, $C_{1-6}$ haloalkoxy, $C_{1-6}$ alkylamino, $C_{1-6}$ haloalkyl, $C_{1-6}$ cyanoalkyl and $C_{1-6}$ hydroxyalkyl.

In some embodiments, Het is 5-6 membered heterocyclyl or 5-6 membered heteroaryl; wherein each of 5-6 membered heterocyclyl and 5-6 membered heteroaryl is independently and optionally substituted with H, D, oxo (=O), F, Cl, Br, I, hydroxy, amino, nitro, cyano, $C_{1-3}$ alkyl, $C_{1-3}$ alkoxy, $C_{1-3}$ haloalkyl, carboxy and —C(=O)NH₂.

In some embodiments, Het is pyrrolidyl, tetrahydrofuryl, imidazolidinyl, pyrazolidyl, tetrahydropyranyl, piperidyl, piperazinyl, morpholinyl, thiomorpholinyl, pyrrolyl, furyl, thienyl, pyrazolyl, imidazolyl, oxazolyl, thiazolyl, triazolyl, tetrazolyl, pyridyl, pyrimidinyl, pyridazinyl or pyrazinyl, wherein each of pyrrolidyl, tetrahydrofuryl, imidazolidinyl, pyrazolidyl, tetrahydropyranyl, piperidyl, piperazinyl, morpholinyl, thiomorpholinyl, pyrrolyl, furyl, thienyl, pyrazolyl, imidazolyl, oxazolyl, thiazolyl, triazolyl, tetrazolyl, pyridyl, pyrimidinyl, pyridazinyl and pyrazinyl is independently and optionally substituted with H, D, oxo (=O), F, Cl, Br, I, hydroxy, amino, nitro, cyano, methyl, ethyl, isopropyl, methoxy, ethoxy, isopropoxy, trifluoromethyl, difluoromethyl, carboxy and —C(=O)NH₂.

In some embodiments, R¹ is H, D, F, Cl, Br, I, hydroxy, amino, nitro, cyano, $C_{1-3}$ alkyl, $C_{1-3}$ alkoxy or $C_{1-3}$ haloalkyl;

R² is —OR or —NR$^a$R$^b$;

wherein each R, R$^a$ and R$^b$ is independently H, D, $C_{1-3}$ alkyl, $C_{1-3}$ haloalkyl or $C_{3-6}$ cycloalkyl; or R$^a$ and R$^b$, together with the N atom to which they are attached, form 4-6 membered heterocyclyl; and wherein 4-6 membered heterocyclyl is optionally substituted with oxo (=O), F, Cl, Br, I, hydroxy, amino, nitro, cyano, $C_{1-3}$ alkyl, $C_{1-3}$ alkoxy and $C_{1-3}$ haloalkyl;

each of R³ and R⁴ is independently H, D, $C_{1-3}$ alkyl, $C_{1-3}$ hydroxyalkyl or $C_{1-3}$ haloalkyl.

In some embodiments, R¹ is H, D, F, Cl, Br, I, hydroxy, amino, nitro, cyano, methyl, ethyl, methoxy, ethoxy, isopropoxy, trifluoromethyl, difluoromethyl or trifluoroethyl;

R² is —OR or —NR$^a$R$^b$;

wherein each R, R$^a$ and R$^b$ is independently H, D, methyl, ethyl, n-propyl, isopropyl, trifluoromethyl, difluoromethyl, trifluoroethyl, cyclopropyl, cyclohexyl, cyclopentyl or cyclohexyl; or R$^a$ and R$^b$, together with the N atom to which they are attached, form heterocyclyl selected from heterocyclyl groups represented by formulae (I-a) to (I-k):

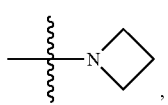
(I-a)

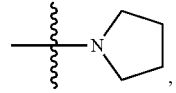
(I-b)

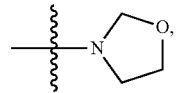
(I-c)

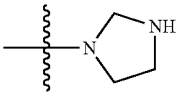
(I-d)

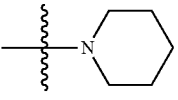
(I-e)

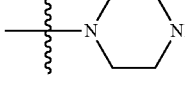
(I-f)

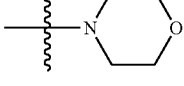
(I-g)

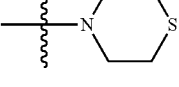
(I-h)

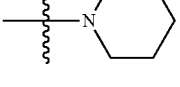
(I-i)

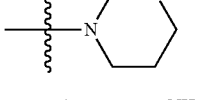
and
(I-j)

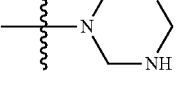
(I-k)

wherein heterocyclyl groups represented by formulae (I-a) to (I-k) are optionally substituted with oxo (=O), D, F, Cl, Br, I, hydroxy, amino, nitro, cyano, methyl, ethyl, isopropyl, methoxy, ethoxy, trifluoromethyl, difluoromethyl or trifluoroethyl;

each of R³ and R⁴ is independently H, D, methyl, ethyl, n-propyl, hydroxymethyl, hydroxyethyl, trifluoromethyl or 2-fluoroethyl.

In some embodiments, R⁵ is phenyl, naphthyl, 1,2,3,4-tetrahydronaphthyl or 5-6 membered heteroaryl, wherein each of phenyl, naphthyl, 1,2,3,4-tetrahydronaphthyl and 5-6 membered heteroaryl is independently and optionally substituted with 1, 2 or 3 R⁶; wherein R⁶ is H, D, F, Cl, Br, I, hydroxy, amino, nitro, cyano, $C_{1-3}$ alkyl, $C_{1-3}$ alkoxy, $C_{1-3}$ haloalkyl, $C_{1-3}$ haloalkoxy, $C_{1-3}$ cyanoalkyl or $C_{1-3}$ hydroxyalkyl.

In other embodiments, R⁵ is phenyl, naphthyl, 1,2,3,4-tetrahydronaphthyl, imidazolyl, pyrazolyl, furyl, thienyl, oxazolyl, oxadiazolyl, thiazolyl, thiadiazolyl, triazolyl, tetrazolyl, pyridyl, pyrimidinyl, pyranyl or pyridazinyl, wherein each of phenyl, naphthyl, 1,2,3,4-tetrahydronaphthyl, imidazolyl, pyrazolyl, furyl, thienyl, oxazolyl, oxadiazolyl, thiazolyl, thiadiazolyl, triazolyl, tetrazolyl, pyridyl, pyrimidinyl, pyranyl and pyridazinyl is independently and optionally substituted with 1, 2 or 3 $R^6$; and wherein $R^6$ is H, D, F, Cl, Br, I, hydroxy, amino, nitro, cyano, methyl, ethyl, n-propyl, isopropyl, methoxy, ethoxy, isopropoxy, trifluoromethyl, difluoromethyl, trifluoromethoxy, difluoromethoxy, hydroxymethyl, hydroxyethyl, cyanomethyl or cyanoethyl.

In some embodiments, W has one of the following structures:

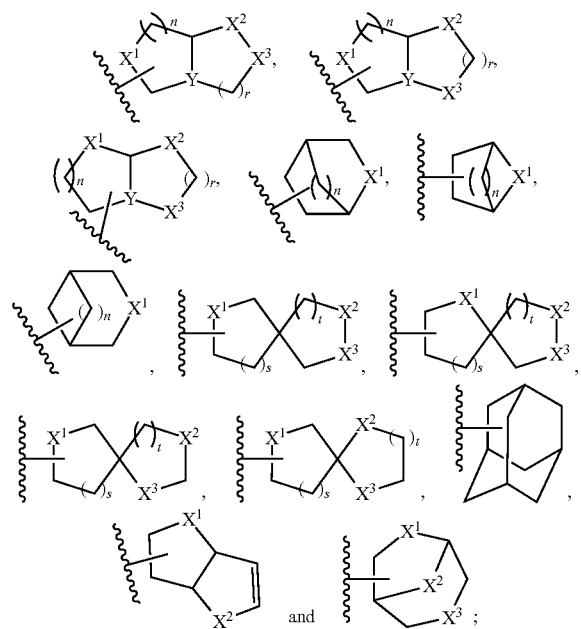

each of $X^1$, $X^2$, $X^3$ is independently bond, —CH$_2$—, —O—, —S— or —NH—;
Y is CH or N;
each r, s, t and n is independently 0, 1, 2, or 3;
each W is optionally substituted with 1, 2, 3, 4 or 5 substituents independently selected from D, oxo (=O), F, Cl, Br, I, hydroxy, amino, nitro, cyano, —C(=O)OH, —C(=O)NH$_2$, —C(=NH)NH$_2$, —NH—C(=NH)NH$_2$, —SO$_2$CH$_3$, —SO$_2$C$_2$H$_5$, $C_{1-3}$ alkyl, $C_{3-6}$ cycloalkyl, $C_{1-3}$ alkoxy, $C_{1-3}$ haloalkoxy, $C_{1-3}$ alkylamino, $C_{1-3}$ haloalkyl, $C_{1-3}$ cyanoalkyl and $C_{1-3}$ hydroxyalkyl.

In other embodiments, W has one of the following structures:

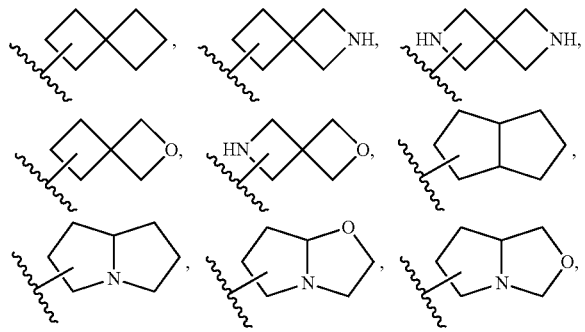

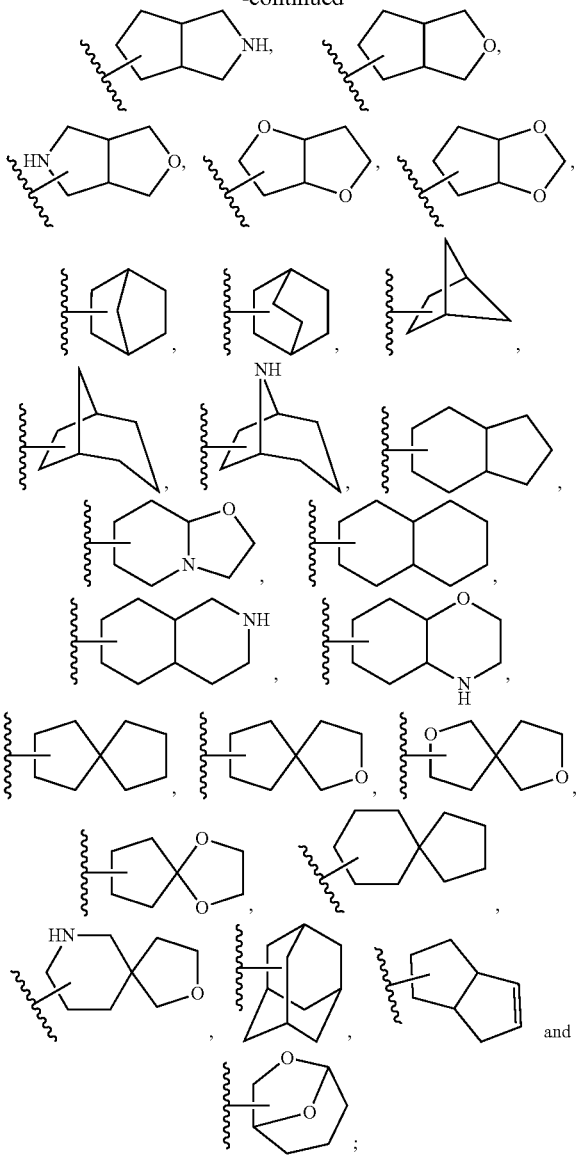

each W is optionally substituted with 1, 2, 3, 4 or 5 substituents independently selected from D, oxo (=O), F, Cl, Br, I, hydroxy, amino, nitro, cyano, —C(=O)OH, —C(=O)NH$_2$, —C(=NH)NH$_2$, —NH—C(=NH)NH$_2$, —SO$_2$CH$_3$, —SO$_2$C$_2$H$_5$, methyl, ethyl, isopropyl, n-butyl, cyclopropyl, cyclobutyl, cyclopentyl, cyclohexyl, trifluoromethyl, difluoromethyl, methoxy, ethoxy, isopropoxy, trifluoromethoxy, difluoromethoxy, methylamino, cyanomethyl and hydroxymethyl.

In one aspect, provided herein is a pharmaceutical composition comprising a compound of formula (I) or a stereoisomer, a geometric isomer, a tautomer, an N-oxide, a hydrate, a solvate, a metabolite, a pharmaceutically acceptable salt or a prodrug thereof, or a pharmaceutically acceptable carrier, excipient, diluent, adjuvant, vehicle or a combination thereof.

In one aspect, provided herein is use of the compound of formula (I) or the pharmaceutical composition thereof in the manufacture of a medicament for preventing, managing, treating or lessening a disorder or disease regulated by acetyl-CoA carboxylase.

In some embodiments, the disorder or disease regulated by acetyl-CoA carboxylase disclosed herein is a metabolism disorder or neoplastic disorder.

In other embodiments, the disorder or disease regulated by acetyl-CoA carboxylase disclosed herein comprises insulin resistance insulin resistance, obesity, dyslipidemia, metabolic syndrome, type II diabetes, non-alcoholic fatty liver disease and non-alcoholic steatohepatitis.

In other embodiments, the neoplastic disorder disclosed herein comprises breast cancer, pancreatic cancer, renal cell cancer, hepatocellular carcinoma, malignant melanoma and other skin tumor, non-small cell bronchial carcinoma, endometrial carcinoma, colorectal cancer and prostate cancer.

In one aspect, provided herein is a compound of formula (I) or a pharmaceutical composition thereof for use in preventing, managing, treating or lessening a disorder or disease regulated by acetyl-CoA carboxylase.

In one aspect, provided herein is a method of preventing, managing, treating or lessening a disorder or disease regulated by acetyl-CoA carboxylase in a patient comprising administering to the patient a therapeutically effective amount of a compound of formula (I) or a pharmaceutical composition thereof.

In other aspect, provided herein is a method of preparing, separating or purifying the compound of Formula (I).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and the Handbook of Chemistry and Physics, 75th Ed. 1994. Additionally, general principles of organic chemistry are described in Sorrell et al., "Organic Chemistry", University Science Books, Sausalito: 1999, and "March's Advanced Organic Chemistry", by Michael B. Smith and Jerry March, John Wiley & Sons, New York: 2007, all of which are incorporated herein by reference in their entireties.

The term "comprise" is an open expression, it means comprising the contents disclosed herein, but don't exclude other contents.

As described herein, compounds disclosed herein may optionally be substituted with one or more substituents, e.g. are illustrated generally below, or as exemplified by particular classes, subclasses, and species of the invention. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substituents may be, but not limited to, H, F, Cl, Br, I, nitro, cyano, oxo (=O), hydroxy, alkyl, hydroxyalkyl, alkylamino, aminoalkyl, haloalkoxy, cycloalkyl, amino, aryl, heterocyclyl, heteroaryl, alkenyl, alkynyl, cycloalkyl-oxy, alkoxy, alkoxyalkyl, haloalkyl, —COOH, -alkylene-C(=O)O-alkyl, -alkylene-S(=O)$_2$-alkyl, -alkylene-S(=O)$_2$-amino, —S(=O)$_2$-alkyl, —S(=O)$_2$-amino, —S(=O)$_2$OH, —O-alkylene-C(=O)O-alkyl, —O-alkylene-S(=O)$_2$-alkyl, —O-alkylene-S(=O)$_2$-amino, —O-alkylene-S(=O)$_2$OH, —C(=O)NH$_2$, —C(=O)NH-alkyl, —C(=O)N(alkyl)-alkyl, —C(=O)NHS(=O)$_2$-alkyl, —C(=O)NHS(=O)$_2$-amino, —C(=O)NHS(=O)$_2$OH, —N(haloalkyl)-alkyl, —N(alkyl)-S(=O)$_2$-alkyl, —NHS(=O)$_2$-alkyl, —NHS(=O)$_2$-haloalkyl, —N(alkyl)S(=O)$_2$-haloalkyl, —N(alkyl)S(=O)$_2$-alkylamino, —NHC(=O)-alkyl, —NHC(=O)-haloalkyl, —N(alkyl)C(=O)-haloalkyl, —N(alkyl)C(=O)-alkylamino, —N(alkyl)C(=O)O-alkyl, —NHC(=O)O-alkyl, —NHC(=O)O-haloalkyl, —N(alkyl)C(=O)O-haloalkyl, —N(alkyl)C(=O)O-aminoalkyl, —NHC(=O)—NH$_2$, —NHC(=O)NH-(alkyl), —NHC(=O)NH(haloalkyl), —NHC(=O)N(alkyl)-alkyl, —OC(=O)-alkyl, —OC(=O)-amino, —OC(=O)-alkylamino, —OC(=O)-aminoalkyl, —OC(=O)-alkoxy, —C(=O)N(alkyl)S(=O)$_2$-alkyl, —C(=O)N(alkyl)S(=O)$_2$-amino, —C(=O)NH—S(=O)$_2$OH, —C(=NH)NH$_2$, —C(=NH)NH-alkyl, —C(=NH)N(alkyl)-alkyl, —C(=N-alkyl)-NH$_2$, —C(=O)NH-alkylene-S(=O)$_2$OH, —C(=O)NHC(=O)OH, —C(=O)NHC(=O)O-alkyl, —C(=O)N(alkyl)C(=O)O-alkyl, —C(=O)NH-alkylene-C(=O)OH and —C(=O)NH-alkylene-C(=O)O-alkyl, and so on.

The term "alkyl" or "alkyl group" refers to a saturated linear or branched-chain monovalent hydrocarbon radical of 1 to 20 carbon atoms, or 1-10 carbon atoms, or 1-6 carbon atoms, or 1-4 carbon atoms, or 1-3 carbon atoms, or 1-2 carbon atoms, wherein the alkyl radical may be optionally and independently substituted with one or more substituents described herein. Some non-limiting examples of the alkyl group further include, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C (CH$_3$)$_3$, n-heptyl and n-octyl, etc. The term "alkyl" or the prefix "alk-" is inclusive of both straight chain and branched saturated carbon chain. The term "alkylidene" or "alkylene" used herein refers to a saturated divalent hydrocarbon group derived from a straight or branched chain saturated hydrocarbon by the removal of two hydrogen atoms. Examples of alkylene groups include, but are not limited to, methylene, ethylene, isopropylene, and the like.

The term "alkenyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp$^2$ double bond, wherein the alkenyl radical may be independently unsubstituted or substituted with one or more substituents described herein, and includes radicals having "cis" and "trans" orientations, or alternatively, "E" and "Z" orientations. Examples of the alkenyl group include, but are not limited to, vinyl (—CH═CH$_2$), allyl (—CH$_2$CH═CH$_2$), butenyl (—CH$_2$CH$_2$CH═CH$_2$) and the like.

The term "alkynyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one carbon-carbon, sp triple bond, wherein the alkynyl radical may be optionally and independently substituted with one or more substituents described herein. Specific examples of the alkynyl group include, but are not limited to, ethynyl (—C≡CH), propargyl (—CH$_2$C≡CH).

The term "heteroatom" refers to one or more of oxygen (O), sulfur(S), nitrogen (N), phosphorus (P) and silicon (Si), including any oxidized form of nitrogen (N), sulfur (S), or phosphorus (P); primary, secondary, tertiary or quaternary ammonium salts; or a substitutable nitrogen of a heterocyclic ring, for example, N (as in 3,4-dihydro-2H-pyrrolyl), NH (as in pyrrolidinyl) or NR (as in N-substituted pyrrolidinyl); or —C(═O)— of heterocycle oxidated from —CH$_2$—.

The term "halogen" refers to F (fluorine), Cl (chlorine), Br (bromine), or I (iodine).

The term "unsaturated" refers to a moiety having one or more units of unsaturation.

The term "alkoxy" or "alkyl-oxy" refers to an alkyl group, as defined herein, attached to the other moiety of the compound molecular through an oxygen atom. In some embodiments, the alkoxy group is C$_{1-4}$ alkoxy. Some non-limiting examples of the alkoxy group include methoxy, ethoxy, propoxy and butoxy, and the like. The alkoxy group may be optionally and independently substituted with one or more substituents disclosed herein.

The term "alkoxyalkyl" refers to an alkyl group substituted with one or more alkoxy groups, wherein the alkoxy and alkyl are as defined herein. In some embodiments, the alkoxyalkyl is C$_{1-6}$ alkoxy-C$_{1-6}$-alkyl. In other embodiments, the alkoxyalkyl is C$_{1-3}$ alkoxy-C$_{1-3}$-alkyl. The "alkoxyalkyl" group may be optionally substituted with one or more substituents disclosed herein.

The terms "haloalkyl", "haloalkenyl" or "haloalkoxy" refer to alkyl, alkenyl or alkoxy, as the case may be, substituted with one or more halogen atoms. In some embodiments, haloalkyl is haloC$_{1-6}$ alkyl. In other embodiments, haloalkyl is haloC$_{1-3}$ alkyl. In some embodiments, haloalkyl-oxy or haloalkoxy is haloC$_{1-6}$ alkyl-oxy or haloC$_{1-6}$ alkoxy. In other embodiments, haloalkyl-oxy or haloalkoxy is haloC$_{1-3}$alkyl-oxy or haloC$_{1-3}$ alkoxy. Some non-limiting examples of such groups include trifluoromethyl, difluoromethyl, 2-chloro-vinyl, 2,2-difluoroethyl, difluoromethoxy, trifluoromethoxy, and the like. And wherein optionally each of the haloalkyl, haloalkenyl or haloalkoxy may be optionally and independently substituted with one or more substituents described herein.

The term "hydroxyalkyl" refers to an alkyl group substituted with one or more hydroxy groups. In some embodiments, hydroxyalkyl is hydroxyC$_{1-6}$alkyl. In other embodiments, hydroxyalkyl is hydroxyC$_{1-3}$ alkyl. Some non-limiting examples include hydroxymethyl, 2-hydroxyethyl, 3-hydroxypropyl, and the like. The "hydroxyalkyl" group may be optionally substituted with one or more substituents disclosed herein.

The term "cyanoalkyl" refers to an alkyl group substituted with one or more cyano groups. In some embodiments, cyanoalkyl is cyanoC$_{1-6}$alkyl. In other embodiments, cyanoalkyl is cyanoC$_{1-3}$ alkyl. Some non-limiting examples include cyanomethyl, 2-cyanoethyl, 3-cyanopropyl, and the like. The "cyanoalkyl" group may be optionally substituted with one or more substituents disclosed herein.

The term "alkylamino" refers to "N-alkylamino" and "N,N-dialkylamino" wherein amino groups are independently substituted with one alkyl radical or two alkyl radicals, respectively. In some embodiments, the alkylamino is a C$_{1-6}$ alkylamino group. In other embodiments, the alkylamino is a C$_{1-3}$ alkylamino group. Some non-limiting examples of such group include N-methylamino, N-ethylamino, N,N-dimethylamino, N,N-diethylamino, and the like. And wherein the alkylamino radical is optionally substituted with one or more substituents described herein.

The term "cycloalkyl" or "cycloalkane" refers to a monovalent or multivalent saturated ring having 3 to 12 carbon atoms as a monocyclic, bicyclic, or tricyclic ring system, but not containing an aromatic ring. In some embodiments, the cycloalkyl group contains 3 to 10 carbon atoms. In other embodiments, the cycloalkyl group contains 3 to 8 carbon atoms. In still other embodiments, the cycloalkyl group contains 3 to 6 carbon atoms. Some non-limiting examples of such group include cyclopropyl, cyclobutyl, cyclopentyl and cyclohexyl, etc. The cycloalkyl group may be optionally substituted with one or more substituents disclosed herein.

The term "cycloalkyloxy" refers to a cycloalkyl group, attached to the rest part of the molecule through an oxygen atom. Wherein the cycloalkyl group is as defined herein.

The term "cycloalkylalkyl" refers to a cycloalkyl group attached to the rest of the molecule through an alkyl group, wherein the cycloalkyl and alkyl are as defined herein.

The term "carbocyclyl", "carbocycle" or "carbocyclic ring" refers to a monovalent or multivalent, nonaromatic, saturated or partially unsaturated ring having 3 to 12 carbon atoms as a monocyclic, bicyclic or tricyclic hydrocarbon. A carbobicyclyl group includes a spiro carbobicyclyl group or a fused carbobicyclyl group. Suitable carbocyclyl groups include, but are not limited to, cycloalkyl, cycloalkenyl and cycloalkynyl. In one embodiment, the cycloalkyl group contains 4 to 8 carbon atoms. In other embodiment, the cycloalkyl group contains 4 to 6 carbon atoms. Further examples of carbocyclyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. The cycloalkyl group may be optionally substituted with one or more substituents disclosed herein.

The term "heterocycle", "heterocyclyl", or "heterocyclic ring" as used interchangeably herein refers to a saturated or partially unsaturated monocyclic, bicyclic or tricyclic ring containing 3-12 ring atoms of which at least one ring atom is heteroatom, but not containing an aromatic ring. In some embodiments, "heterocyclyl" or "heterocycle" contains 3-10 ring atoms; in some embodiments, "heterocyclyl" or "heterocycle" contains 3-8 ring atoms; in other embodiments, "heterocyclyl" or "heterocycle" contains 5-8 ring atoms; in yet other embodiments, "heterocyclyl" or "heterocycle" contains 3-6 ring atoms; in still yet other embodiments, "heterocyclyl" or "heterocycle" contains 5-6 ring atoms; in still yet other embodiments, "heterocyclyl" or "heterocycle" contains 4-6 ring atoms; unless otherwise indicated, heterocyclyl may be a carbon radical or heteroatom radical, heteroatom is as defined herein. Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, 2-oxa-5-azabicyclo[2.2.1]hept-5-yl. Some non-limiting examples of heterocyclyl wherein —CH$_2$— group is replaced by —C(=O)— moiety include 2-oxopyrrolidinyl, oxo-1,3-thiazolidinyl, 2-piperidinonyl, 3,5-dioxopiperidinyl, pyrimidinedione-yl, and the like. Some non-limiting examples of heterocyclyl wherein the ring sulfur atom is oxidized is sulfolanyl and 1,1-dioxo-thiomorpholinyl. The heterocyclyl group may be optionally substituted with one or more substituents disclosed herein.

The term "heterocyclylalkyl" refers to a heterocyclyl group attached to the rest of the molecule through an alkyl group, wherein the heterocyclyl and alkyl are as defined herein.

The term "aryl" refers to monocyclic, bicyclic and tricyclic carbocyclic ring systems having a total of six to fourteen ring members, or six to twelve ring members, or six to ten ring members, wherein at least one ring in the system is aromatic, wherein each ring in the system contains 3 to 7 ring members and that has a single point or multipoint of attachment to the rest of the molecule. The term "aryl" may be used interchangeably with the term "aryl ring" or "aromatic". Examples of aryl ring may include phenyl, naphthyl and anthracene. The aryl group may be optionally and independently substituted with one or more substituents disclosed herein.

The term "heteroaryl" refers to monocyclic, bicyclic and tricyclic carbocyclic ring systems having a total of five to twelve ring members, or five to ten ring members, or five to six ring members, wherein at least one ring in the system is aromatic, and in which at least one ring member is selected from heteroatom, and wherein each ring in the system contains 5 to 7 ring members and that has a single point or multipoint of attachment to the rest of the molecule. The term "heteroaryl" and "heteroaromatic ring" or "heteroaromatic compound" can be used interchangeably herein. The heteroaryl group is optionally substituted with one or more substituents disclosed herein. In one embodiment, 5-10 membered heteroaryl comprises 1, 2, 3 or 4 heteroatoms independently selected from O, S and N, wherein N may be oxidated.

Some non-limiting examples of heteroaryl rings include furanyl, imidazolyl (e.g. N-imidazolyl, 2-imidazolyl, 4-imidazolyl, 5-imidazolyl), isoxazolyl, oxazolyl (e.g. 2-oxazolyl, 4-oxazolyl, 5-oxazolyl), pyrrolyl (e.g. N-pyrrolyl, 2-pyrrolyl, 3-pyrrolyl), pyridyl, pyrimidinyl (e.g. 2-pyrimidinyl, 4-pyrimidinyl, 5-pyrimidinyl), pyridazinyl, thiazolyl (e.g. 2-thiazolyl, 4-thiazolyl, 5-thiazolyl), tetrazolyl (e.g. 5-tetrazolyl), triazolyl, thienyl (e.g. 2-thienyl, 3-thienyl), pyrazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothienyl, indolyl (e.g. 2-indolyl), purinyl, quinolinyl (e.g. 2-quinolinyl, 3-quinolinyl, 4-quinolinyl), 1,2,3,4-tetrahydroisoquinolinyl, 1,3-benzodioxolyl, indolinyl, isoquinolinyl (e.g. 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, or [1,2,4]triazolo[1,5-a]pyridyl, and the like.

The term "fused cycle" or "fused cycle" as refers to a monovalent or multivalent saturated or partially unsaturated fused ring system, which refers to a nonaromatic bicyclic ring system. The fused ring system may be fused carbocycle, also may be fused heterocycle. Such a system may contain isolated or conjugated unsaturation, but not aromatic rings in its core structure. Some non-limiting examples of the fused cyclyl included octahydrocyclopentadienyl, hexhydro-1H-pyrrolizinyl, hexhydropyrrolo[2,1-b]oxazolyl, hexhydropyrrolo[2,1-c]oxazolyl, octahydrocyclopenteno[c]pyrrolyl, hexhydro-1H-cyclopenteno[c]furyl, hexhydro-1H-furo[3,4-c]pyrrolyl, hexhydrofuro[3,2-b]furyl, tetrahydro-3aH-cyclopenteno[d][1,3]dioxolyl, octahydro-1H-indenyl, hexhydro-2H-oxazolo[3,2-a]pyridyl, decahydronaphthyl, decahydroisoquinolyl, decahydroquinolyl, octahydro-2H-benzo[b][1,4]oxazinyl, and so on. And wherein the fused cyclyl group is optionally substituted with one or more substituents described herein.

The term "spiro cyclyl" or "spiro cycle" refers to a monovalent or multivalent saturated or partially unsaturated ring system, wherein a ring originating from a particular annular carbon of another ring. The spiro ring system may be fused carbocycle, also may be fused heterocycle. Some non-limiting examples of the spiro cyclyl included spiro[3.3]heptyl, 2-azaspiro[3.3]heptyl, 2,6-diazaspiro[3.3]heptyl, 2-oxaspiro[3.3]heptyl, 2-oxa-6-azaspiro[3.3]heptyl, spiro[4.4]nonyl, 2-oxaspiro[4.4]nonyl, 1,4-dioxaspiro[4.4]nonyl, spiro[4.5]decyl, 2-oxa-7-azaspiro[4.5]decyl, 2,7-dioxaspiro[4.4]nonyl, and the like. And wherein the spiro cyclyl group is optionally substituted with one or more substituents described herein.

The term "bridged cyclyl" or "bridged cycle" refers to a saturated or unsaturated bridged ring system, which refers to a bicyclic ring system that is not aromatic. Such a system may contain isolated or conjugated unsaturation, but not aromatic rings in its core structure. The "bridged cyclyl" or "bridged cycle" may be bridged carbocycle or bridged heterocycle, the heteroatom is selected from N, O, P and S, wherein the S or P is optionally substituted with one or more oxo to provide the group SO or SO$_2$, PO or PO$_2$. Some non-limiting examples of the bridged cyclyl include bicyclo[2.2.1]heptyl, bicyclo[2.2.2]octyl, (1r,4r)-bicyclo[2.1.1]hexyl, (1R,5S)-bicyclo[3.2.1]octyl, (1R,5S)-8-azabicyclo[3.2.1]octyl, adamantyl, and the like. The "bridged cyclyl" or "bridged cycle" can be substituted by a substituent disclosed herein.

As described herein, a bond drawn from a substituent to the center of one ring within a ring system represents substitution of the substituent at any substitutable or reasonable position on the ring. For example, Formula (a)

represents mono- or poly-substitutions of a substituent R at any substitutable or reasonable position on pyridine ring.

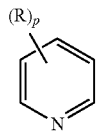

(a)

As described herein, a bond connected to the center of one ring within a ring system (as shown in Formula (b)) represents that a bond in any reasonable and connectable position of the ring can connect to the rest of the molecule. Formula (b) represents that any reasonable and connectable position of octahydrocyclopenteno[c]pyrrole ring can connect to the rest of the molecule.

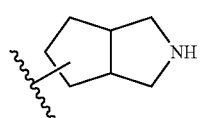

(b)

Furthermore, unless otherwise stated, the phrase "each . . . is independently" is used interchangeably with the phrase "each (of) . . . and . . . is independently". It should be understood broadly that the specific options expressed by the same symbol are independently of each other in different radicals; or the specific options expressed by the same symbol are independently of each other in same radicals.

Unless otherwise stated, structures depicted herein are also meant to include all isomeric (e.g., enantiomeric, diastereomeric, and geometric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric mixtures of the present compounds are within the scope disclosed herein.

Unless otherwise stated, structures and the compound depicted herein are also meant to include all isomeric (e.g., enantiomeric, diastereomeric, and geometric (conformational isomerism)) forms of the structure, N-oxide, a hydrate, a solvate, a metabolite, a pharmaceutically acceptable salt or a prodrug thereof. Therefore, single stereochemical isomers, enantiomeric isomers, diastereomeric isomers, geometric isomers, conformational isomers, N-oxide, a hydrate, a solvate, a metabolite, a pharmaceutically acceptable salt or a prodrug thereof of the present compounds are within the scope disclosed herein. Additionally, unless otherwise stated, structures depicted herein are also meant to include compounds that differ only in the presence of one or more isotopically enriched atoms.

"Metabolite" depicted herein which show the similar active with compound of Form (I) or Form (II) in vivo or in vitro is a product produced through metabolism in the body of a specified compound or pharmaceutically acceptable salt, analogue or ramification thereof. The metabolites of a compound may be identified using routine techniques known in the art and their activities determined using tests e.g. those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

Stereochemical definitions and conventions used herein generally follow S. P Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof e.g. racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, e.g. keto-enol and imine-enamine isomerizations. Valence tautomers include interconversions by reorganization of some of the bonding electrons.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in J. Pharmacol Sci, 1977, 66:1-19, which is incorporated herein by reference. Some non-limiting examples of pharmaceutically acceptable and nontoxic salts include salts of an amino group formed with inorganic acids e.g. hydrochloric acid, hydrobromic acid, phosphoric acid, sulfuric acid and perchloric acid or with organic acids e.g. acetic acid, oxalic acid, maleic acid, tartaric acid, citric acid, succinic acid and malonic acid or by using other methods used in the art e.g. ion exchange. Other pharmaceutically acceptable salts include adipate, malate, 2-hydroxypropionate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts derived from appropriate bases include alkali metal, alkaline earth metal, ammonium and N+(C1-4 alkyl)4 salts. This invention also envisions the quaternization of any basic nitrogen-containing groups of the compounds disclosed herein. Water or oil soluble or dispersable products may be obtained by such quaternization. Representative alkali or alkaline earth metal used for forming salts include sodium, lithium, potassium, calcium, magnesium, and the like. Further pharmaceutically acceptable salts include, when appropriate, nontoxic ammonium, quaternary ammonium, and amine cations formed using counterions e.g. halide, hydroxide, carboxylate, sulfate, phosphate, nitrate, $C_{1-8}$ sulfonate or aryl sulfonate.

The term "hydrate" refers to the complex where the solvent molecule is water.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine.

An "ester" refers to an in vivo hydrolysable ester of a compound of the Formula (I) containing hydroxy group, for example, a pharmaceutically acceptable ester which is hydrolysed in the human or animal body to produce the parent alcohol. Some non-limiting examples of in vivo hydrolysable ester forming groups for hydroxy include phosphate, acetoxymethoxy, 2,2-dimethylpropionyloxymethoxy, alkanoyl, benzoyl, phenylacetyl, alkoxycarbonyl, dialkylcarbamoyl, N-(dialkylaminoethyl)-N-alkylcarbamoyl, and the like.

An "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent e.g. hydrogen peroxide or a per-acid (e.g. a peroxycarboxylic acid) (See, Advanced Organic Chemistiy, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent e.g. dichloromethane.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_1$-$C_{24}$) esters, acyloxymethyl esters, carbonates, carbamates and amino acid esters. For example, a compound disclosed herein that contains a hydroxy group may be acylated at this position in its prodrug form. Other prodrug forms include phosphates, e.g., those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, Nature Review Drug Discovery, 2008, 7, 255-270, and S. J. Hecker et al., Prodrugs of Phosphates and Phosphonates, Journal of Medicinal Chemistry, 2008, 51, 2328-2345, all of which are incorporated herein by reference in their entireties.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include methyl, methoxymethyl, acetyl and silyl, and so on. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl) ethoxy-methy-1,2-(p-toluenesulfonyl) ethyl, 2-(p-nitrophenylsulfenyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P J. Kocienski, Protecting Groups, Thieme, Stuttgart, 2005.

The term "therapeutically effective amount" refers to an amount of the compound of formula (I) which is sufficient to achieve the stated effect. Accordingly, a therapeutical effective amount of a compound of formula (I) used in for the treatment of a condition regulated by ACC will be an amount sufficient for the treatment of the condition regulated by ACC.

The term "nonalcoholic fatty liver (NAFLD)" used herein refers to a metabolic disease associated with insulin resistance, comprises simple fatty liver (SFL), nonalcoholic steatohepatitis (NASH), fatty hepatic fibrosis and cirrhotic.

The term "ACC inhibitors" used herein refers to substances which can bind to ACC and inhibit its activity.

The terms "a," "an," "the" and similar terms used in the context of the present invention (especially in the context of the claims) are to be construed to cover both the singular and plural unless otherwise indicated herein or clearly contradicted by the context.

DESCRIPTION OF COMPOUNDS OF THE INVENTION

The present invention provides a compound or a pharmaceutical composition thereof, which may be an ACC inhibitor. The present invention further relates to use of the compound or the composition thereof in the manufacture of a medicament for inhibiting ACC activity to treat a disorder or disease. The present invention further describes the synthetic method of the compound. The compounds of the invention show good bioactivity and pharmacokinetic properties.

In one aspect, provided herein is a compound having Formula (I) or a stereoisomer, a geometric isomer, a tautomer, an N-oxide, a hydrate, a solvate, a metabolite, a pharmaceutically acceptable salt or a prodrug thereof,

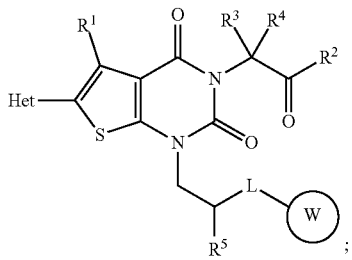

(I)

wherein Het, $R^1$, $R^2$, $R^3$, $R^4$, $R^5$, L and W are as defined herein.

In some embodiments, Het is —C(=O)$NR^aR^b$, —C(=NR)$NR^aR^b$, —NH—C(=NR)$NR^aR^b$, 3-10 membered heterocyclyl or 5-10 membered heteroaryl; wherein each of 3-10 membered heterocyclyl and 5-10 membered heteroaryl is independently and optionally substituted with H, D, oxo (=O), F, Cl, Br, I, hydroxy, amino, nitro, cyano, $C_{1-6}$ alkyl, $C_{1-6}$ alkoxy, $C_{1-6}$ haloalkyl, carboxy and —C(=O)$NH_2$; $R^a$ and $R^b$ are as defined herein.

In some embodiments, $R^1$ is H, D, F, Cl, Br, I, hydroxy, amino, nitro, cyano, $C_{1-6}$ alkyl, $C_{1-6}$ alkoxy or $C_{1-6}$ haloalkyl.

In some embodiments, $R^2$ is —OR or —$NR^aR^b$; R, $R^a$ and $R^b$ are as defined herein.

In some embodiments, R is H, D, $C_{1-6}$ alkyl, $C_{1-6}$ haloalkyl or $C_{3-8}$ cycloalkyl.

In some embodiments, $R^a$ is H, D, $C_{1-6}$ alkyl, $C_{1-6}$ haloalkyl or $C_{3-8}$ cycloalkyl.

In some embodiments, $R^b$ is H, D, $C_{1-6}$ alkyl, $C_{1-6}$ haloalkyl or $C_{3-8}$ cycloalkyl.

In some embodiments, $R^a$ and $R^b$, together with the N atom to which they are attached, form 3-10 membered heterocyclyl; wherein 3-10 membered heterocyclyl is optionally substituted with oxo (=O), D, F, Cl, Br, I, hydroxy, amino, nitro, cyano, $C_{1-6}$ alkyl, $C_{1-6}$ alkoxy and $C_{1-6}$ haloalkyl.

In some embodiments, $R^3$ is H, D, $C_{1-6}$ alkyl, $C_{1-6}$ hydroxyalkyl or $C_{1-6}$ haloalkyl.

In some embodiments, $R^4$ is H, D, $C_{1-6}$ alkyl, $C_{1-6}$ hydroxyalkyl or $C_{1-6}$ haloalkyl.

In some embodiments, L is —O—, —O-methylene-, —O-ethylene-, —S— or —NH—.

In some embodiments, $R^5$ is $C_{6-10}$ aryl or 5-10 membered heteroaryl, each of $C_{6-10}$ aryl and 5-10 membered heteroaryl is independently and optionally substituted with 1, 2 or 3 $R^6$; wherein $R^6$ is H, D, F, Cl, Br, I, hydroxy, amino, nitro, cyano, $C_{1-6}$ alkyl, $C_{1-6}$ alkoxy, $C_{1-6}$ haloalkyl, $C_{1-6}$ haloalkoxy, $C_{1-6}$ cyanoalkyl or $C_{1-6}$ hydroxyalkyl.

In some embodiments, W is fused cyclyl, bridged cyclyl or spiro cyclyl, wherein fused cyclyl, bridged cyclyl or spiro cyclyl is saturated or partially unsaturated 6-12 membered cyclyl containing 0, 1, 2, 3 or 4 heteroatoms independently selected from N, O or S, wherein W is optionally substituted with 1, 2, 3, 4 or 5 substituents independently selected from D, oxo (=O), F, Cl, Br, I, hydroxy, amino, nitro, cyano, —C(=O)OR, —C(=O)$NR^aR^b$, —C(=NR)$NR^aR^b$, —NH—C(=NR)$NR^aR^b$, —$SO_2R$, —$SO_2NR^aR^b$, $C_{1-6}$ alkyl, $C_{3-6}$ cycloalkyl, $C_{1-6}$ alkoxy, $C_{1-6}$ haloalkoxy, $C_{1-6}$ alkylamino, $C_{1-6}$ haloalkyl, $C_{1-6}$ cyanoalkyl and $C_{1-6}$ hydroxyalkyl; R, $R^a$ and $R^b$ are as defined herein.

In other embodiments, Het is 5-6 membered heterocyclyl or 5-6 membered heteroaryl; wherein each of 5-6 membered heterocyclyl and 5-6 membered heteroaryl is independently and optionally substituted with H, D, oxo (=O), F, Cl, Br, I, hydroxy, amino, nitro, cyano, $C_{1-3}$ alkyl, $C_{1-3}$ alkoxy, $C_{1-3}$ haloalkyl, carboxy and —C(=O)$NH_2$.

In other embodiments, Het is pyrrolidyl, tetrahydrofuryl, imidazolidinyl, pyrazolidyl, tetrahydropyranyl, piperidyl, piperazinyl, morpholinyl, thiomorpholinyl, pyrrolyl, furyl, thienyl, pyrazolyl, imidazolyl, oxazolyl, thiazolyl, triazolyl, tetrazolyl, pyridyl, pyrimidinyl, pyridazinyl or pyrazinyl, wherein each of pyrrolidyl, tetrahydrofuryl, imidazolidinyl, pyrazolidyl, tetrahydropyranyl, piperidyl, piperazinyl, morpholinyl, thiomorpholinyl, pyrrolyl, furyl, thienyl, pyrazolyl, imidazolyl, oxazolyl, thiazolyl, triazolyl, tetrazolyl, pyridyl, pyrimidinyl, pyridazinyl and pyrazinyl is independently and optionally substituted with H, D, oxo (=O), F, Cl, Br, I, hydroxy, amino, nitro, cyano, methyl, ethyl, isopropyl, methoxy, ethoxy, isopropoxy, trifluoromethyl, difluoromethyl, carboxy and —C(=O)$NH_2$.

In other embodiments, $R^1$ is H, D, F, Cl, Br, I, hydroxy, amino, nitro, cyano, $C_{1-3}$ alkyl, $C_{1-3}$ alkoxy or $C_{1-3}$ haloalkyl;

In other embodiments, $R^1$ is H, D, F, Cl, Br, I, hydroxy, amino, nitro, cyano, methyl, ethyl, methoxy, ethoxy, isopropoxy, trifluoromethyl, difluoromethyl or trifluoroethyl;

In other embodiments, R is H, D, $C_{1-3}$ alkyl, $C_{1-3}$ haloalkyl or $C_{3-6}$ cycloalkyl.

In other embodiments, R is H, D, methyl, ethyl, n-propyl, isopropyl, trifluoromethyl, difluoromethyl, trifluoroethyl, cyclopropyl, cyclohexyl, cyclopentyl or cyclohexyl.

In other embodiments, $R^a$ is H, D, $C_{1-3}$ alkyl, $C_{1-3}$ haloalkyl or $C_{3-6}$ cycloalkyl.

In other embodiments, $R^a$ is H, D, methyl, ethyl, n-propyl, isopropyl, trifluoromethyl, difluoromethyl, trifluoroethyl, cyclopropyl, cyclohexyl, cyclopentyl or cyclohexyl.

In other embodiments, $R^b$ is H, D, $C_{1-3}$ alkyl, $C_{1-3}$ haloalkyl or $C_{3-6}$ cycloalkyl.

In other embodiments, $R^b$ is H, D, methyl, ethyl, n-propyl, isopropyl, trifluoromethyl, difluoromethyl, trifluoroethyl, cyclopropyl, cyclohexyl, cyclopentyl or cyclohexyl.

In other embodiments, $R^a$ and $R^b$, together with the N atom to which they are attached, form 3-6 membered heterocyclyl; wherein 3-6 membered heterocyclyl is optionally substituted with oxo (=O), D, F, Cl, Br, I, hydroxy, amino, nitro, cyano, $C_{1-3}$ alkyl, $C_{1-3}$ alkoxy and $C_{1-3}$ haloalkyl.

In other embodiments, $R^a$ and $R^b$, together with the N atom to which they are attached, form heterocyclyl selected from heterocyclyl groups represented by formulae (I-a) to (I-k):

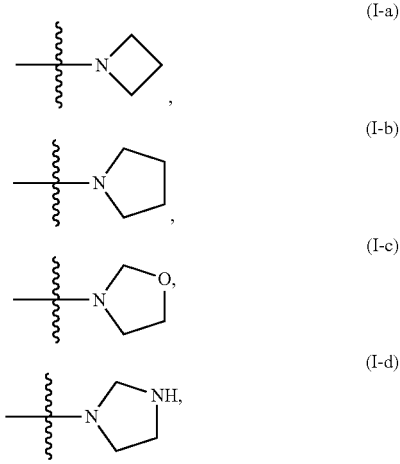

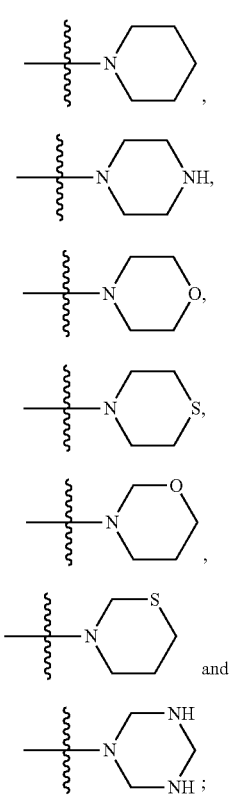

(I-e)

(I-f)

(I-g)

(I-h)

(I-i)

(I-j)

(I-k)

wherein heterocyclyl groups represented by formulae (I-a) to (I-k) are optionally substituted with oxo (=O), D, F, Cl, Br, I, hydroxy, amino, nitro, cyano, methyl, ethyl, isopropyl, methoxy, ethoxy, trifluoromethyl, difluoromethyl or trifluoroethyl.

In other embodiments, $R^3$ is H, D, $C_{1-3}$ alkyl, $C_{1-3}$ hydroxyalkyl or $C_{1-3}$ haloalkyl.

In other embodiments, $R^3$ is H, D, methyl, ethyl, n-propyl, hydroxymethyl, hydroxyethyl, trifluoromethyl or 2-fluoroethyl.

In some embodiments, $R^4$ is H, D, $C_{1-3}$ alkyl, $C_{1-3}$ hydroxyalkyl or $C_{1-3}$ haloalkyl.

In other embodiments, $R^4$ is H, D, methyl, ethyl, n-propyl, hydroxymethyl, hydroxyethyl, trifluoromethyl or 2-fluoroethyl.

In other embodiments, $R^5$ is phenyl, naphthyl, 1,2,3,4-tetrahydronaphthyl or 5-6 membered heteroaryl, wherein each of phenyl, naphthyl, 1,2,3,4-tetrahydronaphthyl and 5-6 membered heteroaryl is independently and optionally substituted with 1, 2 or 3 $R^6$; wherein $R^6$ is H, D, F, Cl, Br, I, hydroxy, amino, nitro, cyano, $C_{1-3}$ alkyl, $C_{1-3}$ alkoxy, $C_{1-3}$ haloalkyl, $C_{1-3}$ haloalkoxy, $C_{1-3}$cyanoalkyl or $C_{1-3}$ hydroxyalkyl.

In other embodiments, $R^5$ is phenyl, naphthyl, 1,2,3,4-tetrahydronaphthyl, imidazolyl, pyrazolyl, furyl, thienyl, oxazolyl, oxadiazolyl, thiazolyl, thiadiazolyl, triazolyl, tetrazolyl, pyridyl, pyrimidinyl, pyranyl or pyridazinyl, wherein each of phenyl, naphthyl, 1,2,3,4-tetrahydronaphthyl, imidazolyl, pyrazolyl, furyl, thienyl, oxadiazolyl, thiazolyl, thiadiazolyl, triazolyl, tetrazolyl, pyridyl, pyrimidinyl, pyranyl or pyridazinyl is independently and optionally substitued with 1, 2 or 3 $R^6$; wherein $R^6$ is H, D, F, Cl, Br, I, hydroxy, amino, nitro, cyano, methyl, ethyl, n-propyl, isopropyl, methoxy, ethoxy, isopropoxy, trifluoromethyl, difluoromethyl, trifluoromethoxy, difluoromethoxy, hydroxymethyl, hydroxyethyl, cyanomethyl or cyanoethyl.

In another embodiments, W has one of the following structures:

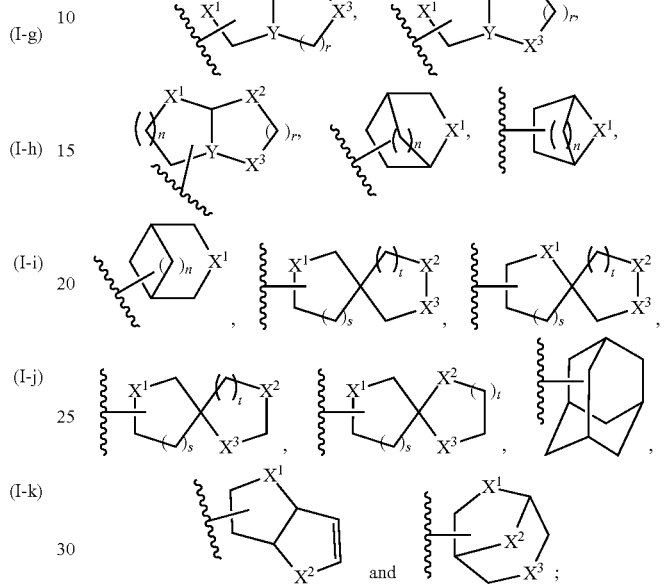

each of $X^1$, $X^2$, $X^3$ is independently bond, —$CH_2$—, —O—, —S— or —NH—;

Y is CH or N;

each r, s, t and n is independently 0, 1, 2, or 3;

each W is optionally substituted with 1, 2, 3, 4 or 5 substituents independently selected from D, oxo (=O), F, Cl, Br, I, hydroxy, amino, nitro, cyano, —C(=O)OH, —C(=O)$NH_2$, —C(=NH)$NH_2$, —NH—C(=NH)$NH_2$, —$SO_2CH_3$, —$SO_2C_2H_5$, $C_{1-3}$ alkyl, $C_{3-6}$ cycloalkyl, $C_{1-3}$ alkoxy, $C_{1-3}$ haloalkoxy, $C_{1-3}$ alkylamino, $C_{1-3}$ haloalkyl, $C_{1-3}$ cyanoalkyl and $C_{1-3}$ hydroxyalkyl.

In some embodiments, W has one of the following structures:

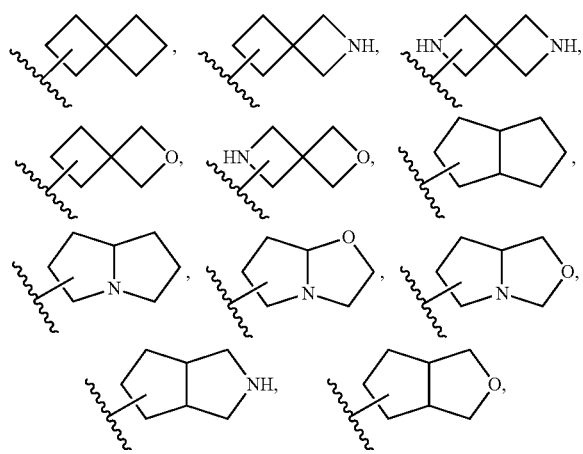

-continued

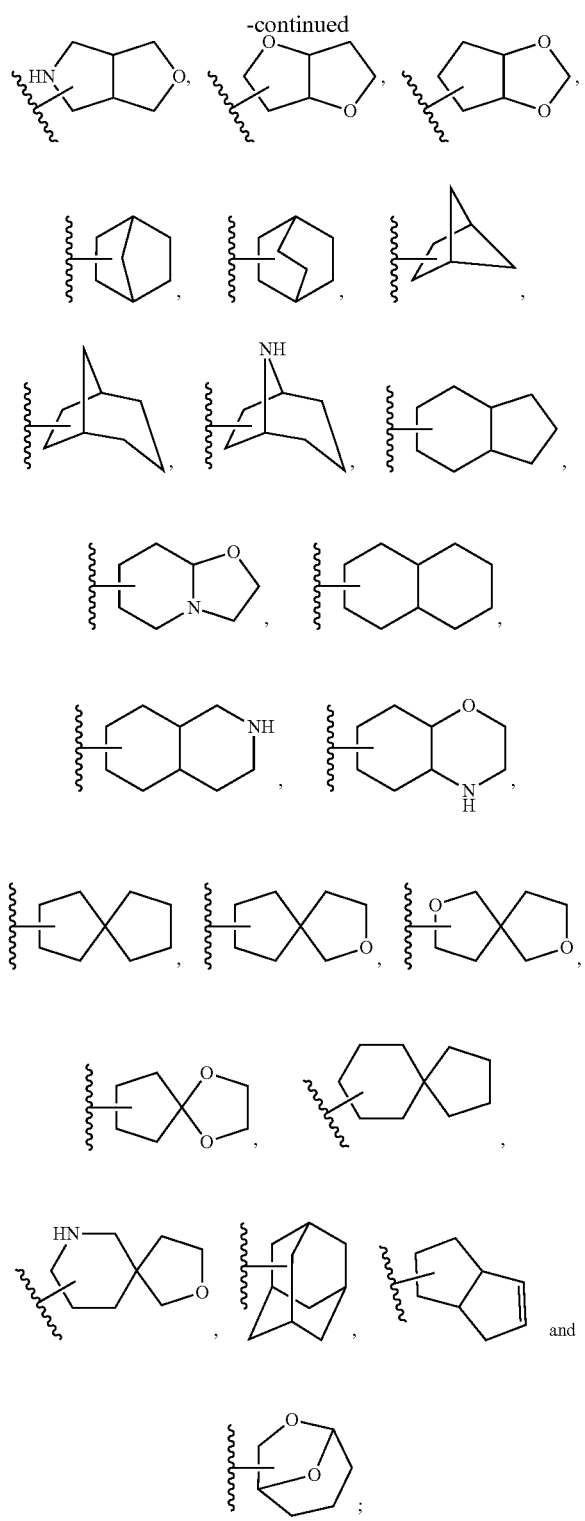

each W is optionally substituted with 1, 2, 3, 4 or 5 substituents independently selected from D, oxo (=O), F, Cl, Br, I, hydroxy, amino, nitro, cyano, —C(=O)OH, —C(=O)NH₂, —C(=NH)NH₂, —NH—C(=NH)NH₂, —SO₂CH₃, —SO₂C₂H₅, methyl, ethyl, isopropyl, n-butyl, cyclopropyl, cyclobutyl, cyclopentyl, cyclohexyl, trifluoromethyl, difluoromethyl, methoxy, ethoxy, isopropoxy, trifluoromethoxy, difluoromethoxy, methylamino, cyanomethyl and hydroxymethyl. In still some embodiments, provided herein is a compound having one of the following structures, or a stereoisomer, a geometric isomer, a tautomer, an N-oxide, a solvate, a hydrate, a metabolite, an ester, a pharmaceutically acceptable salt or a prodrug thereof, but not limited to these compounds:

(23)

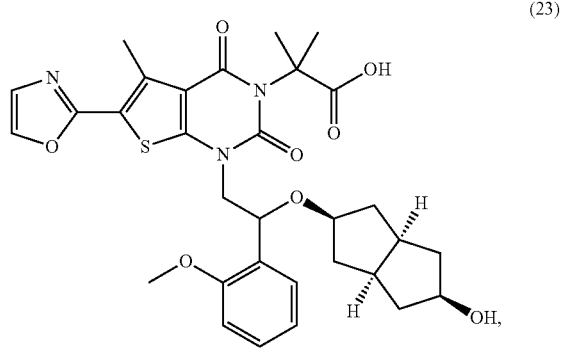

(24)

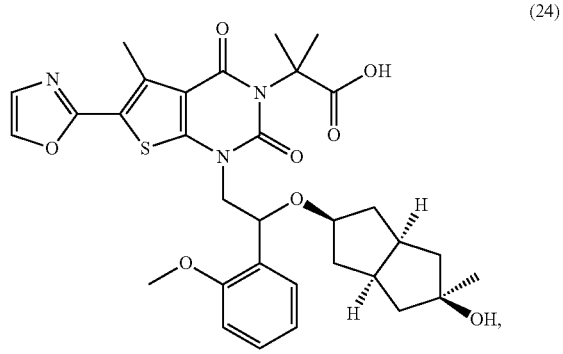

(25)

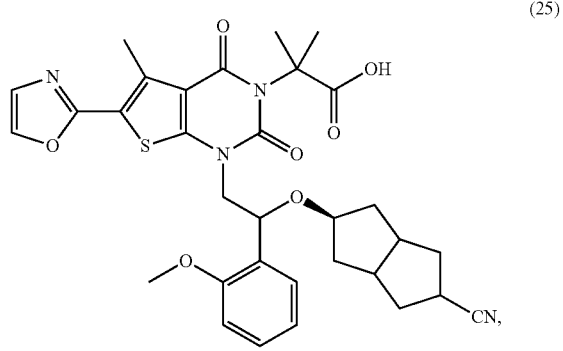

(26)

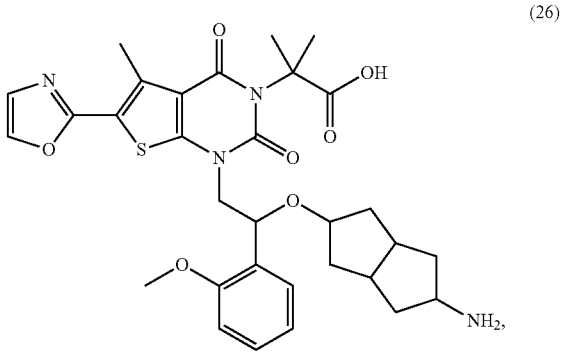

-continued
(27)
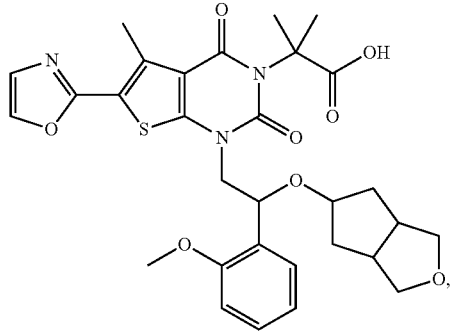
(28)
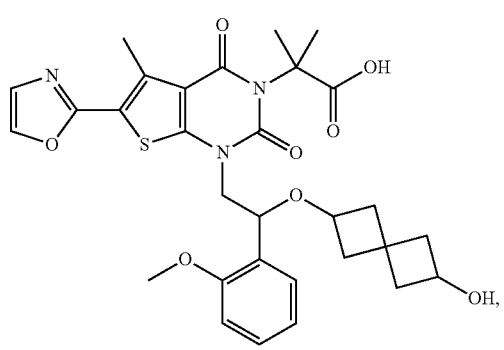
(29)
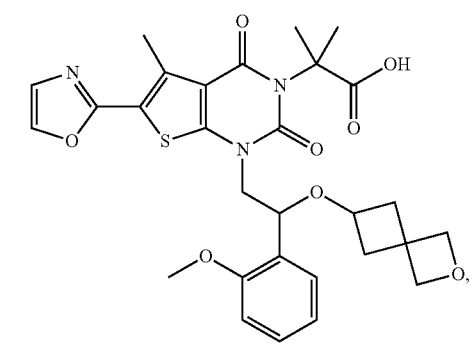
(30)
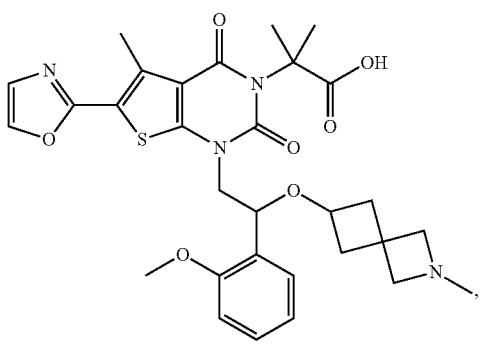
-continued
(31)
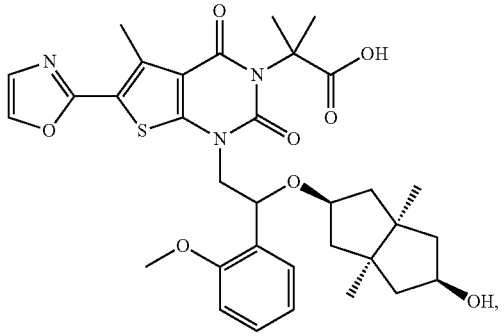
(32)
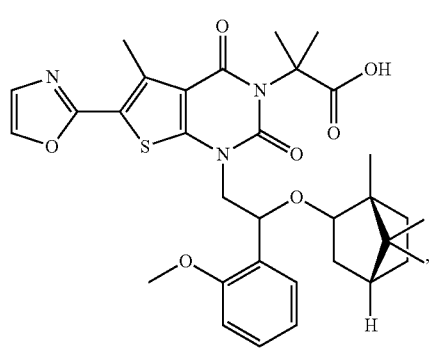
(33)
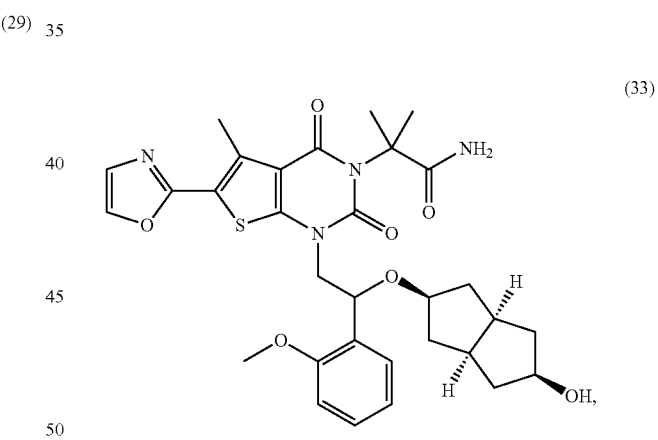
(34)
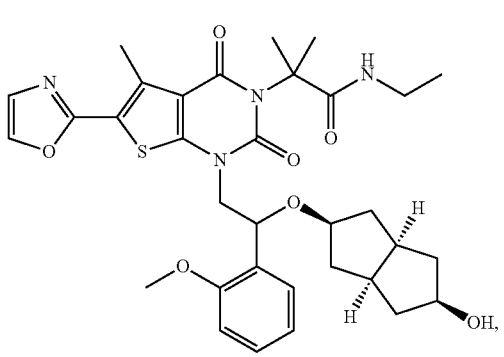

(35)
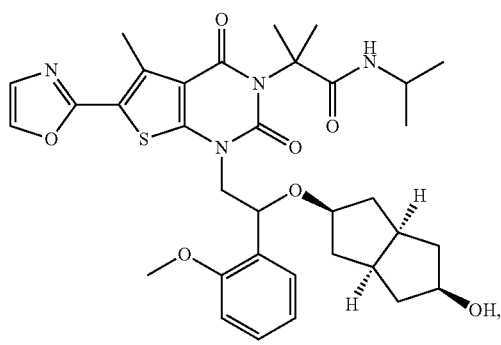
(39)
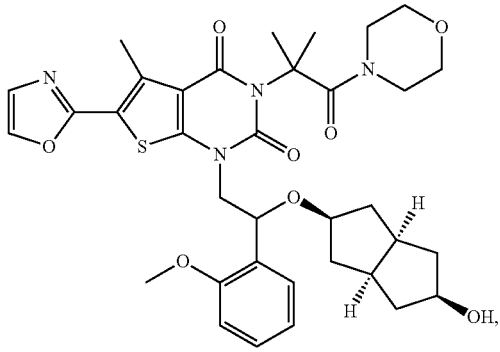
(36)
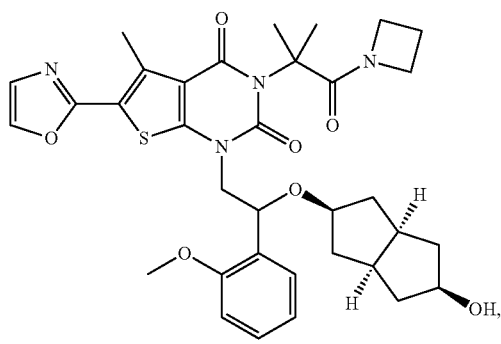
(40)
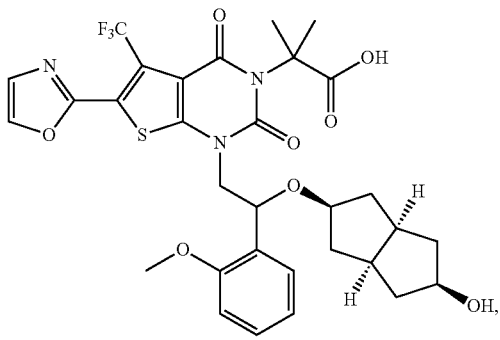
(37)
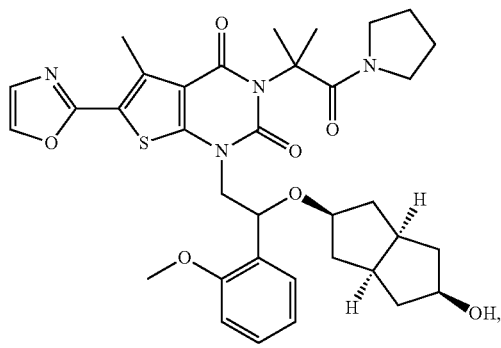
(41)
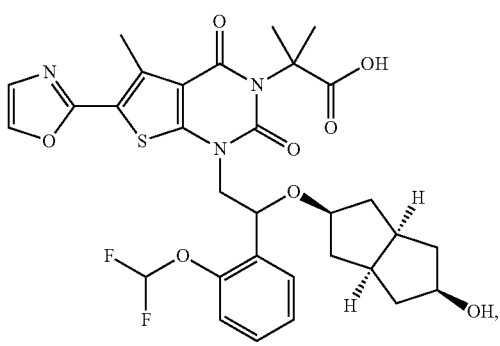
(38)
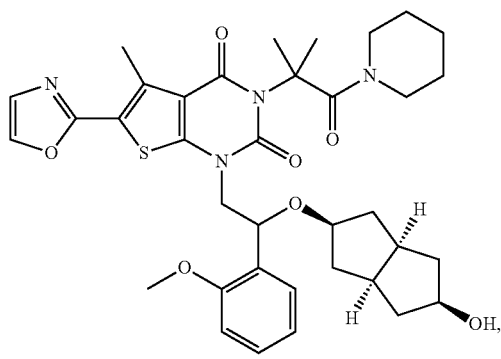
(42)
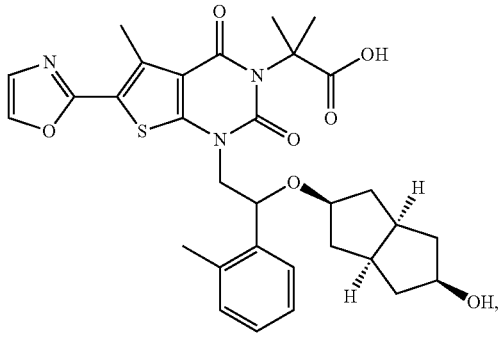

(43)
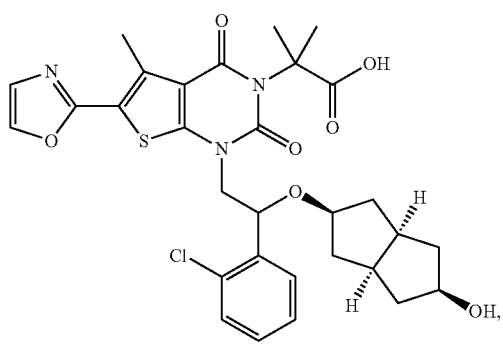
(50)
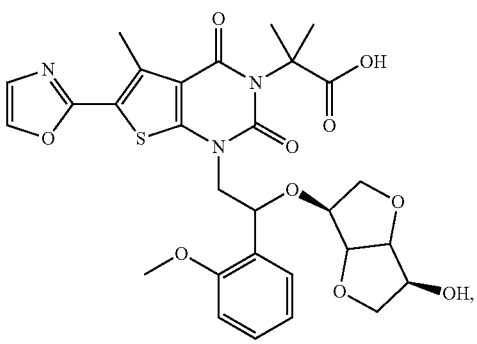
(44)
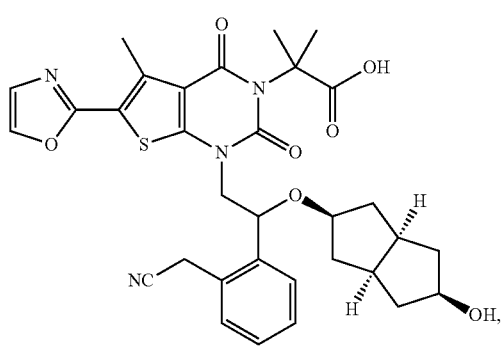
(52)
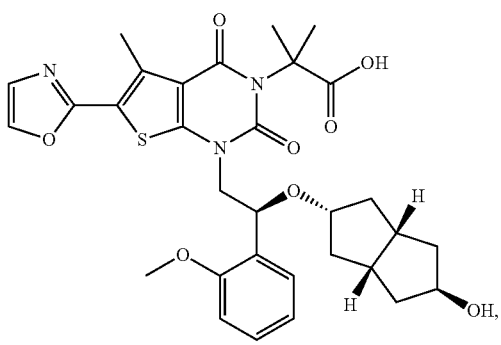
(46)
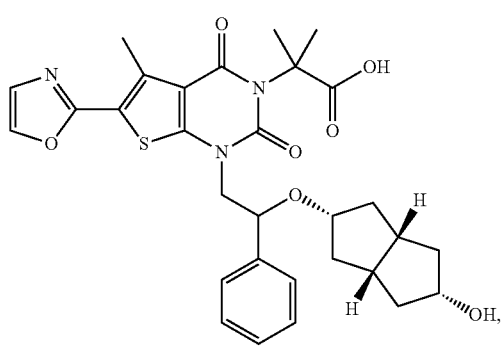
(53)
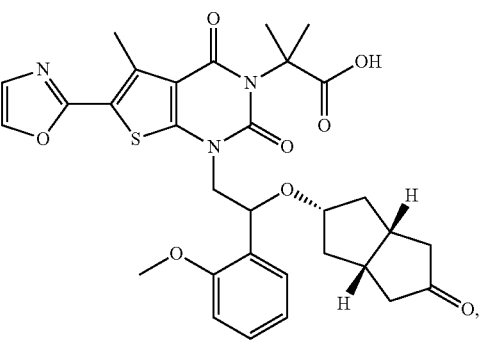
(48)
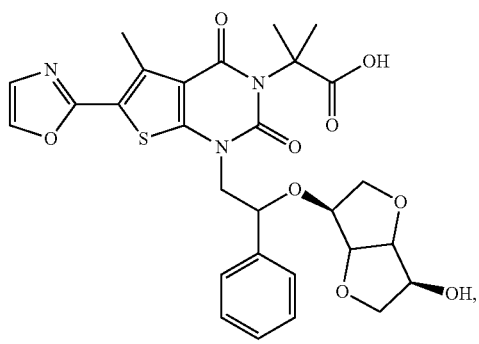
(54)
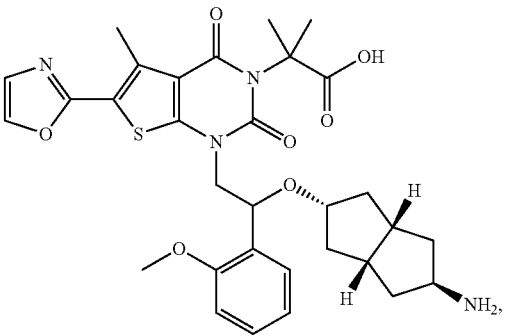

(55)
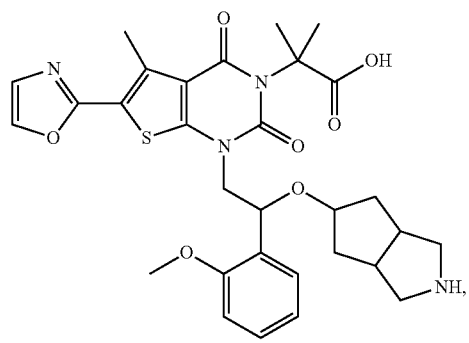
(56)
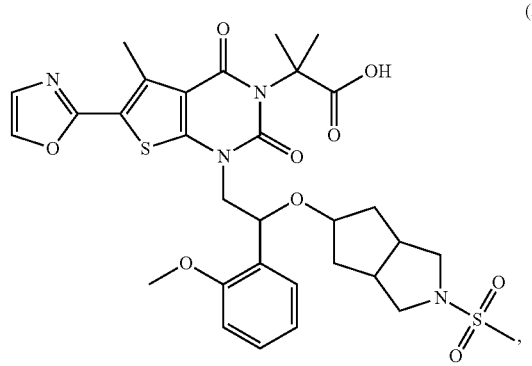
(57)
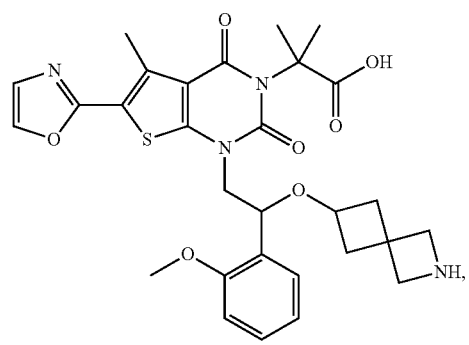
(58)
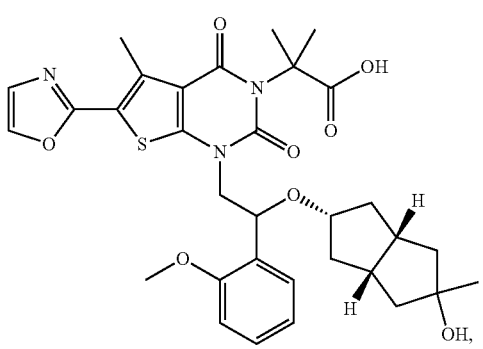
(59)
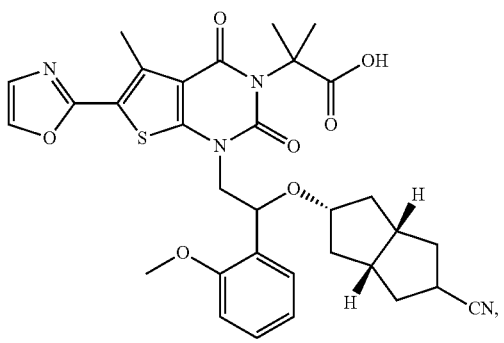
(60)
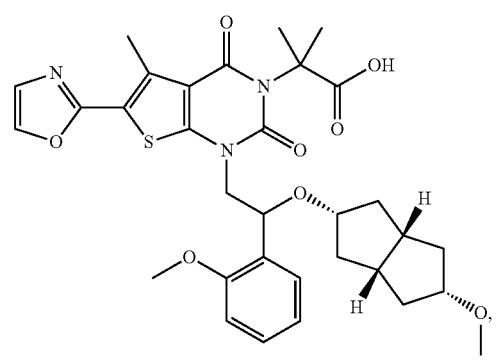
(61)
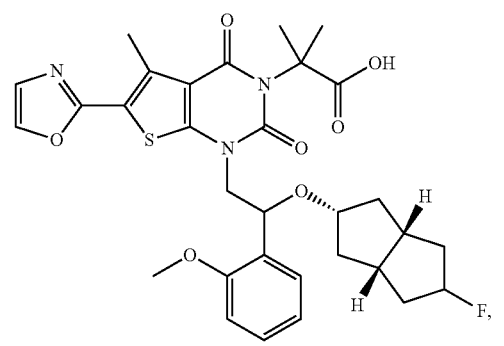
(62)
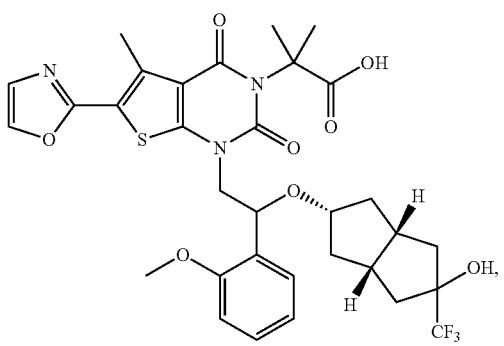

(63)
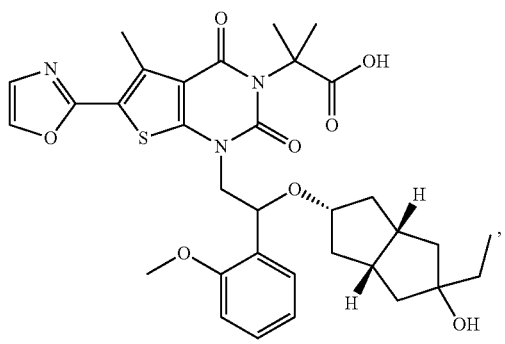
(64)
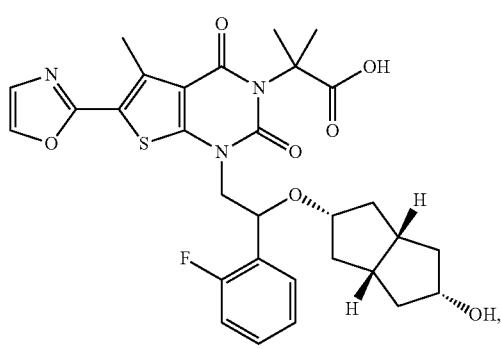
(65)
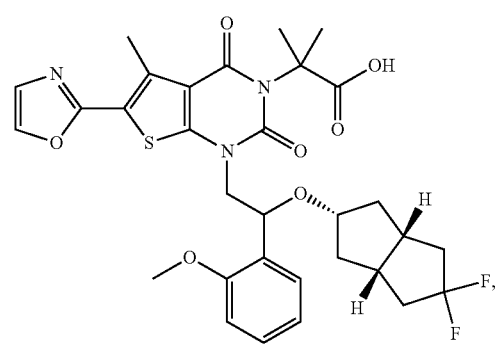
(66)
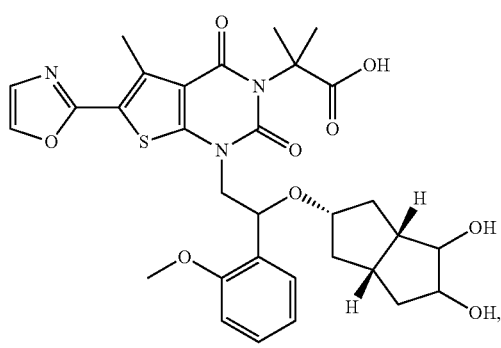
(67)
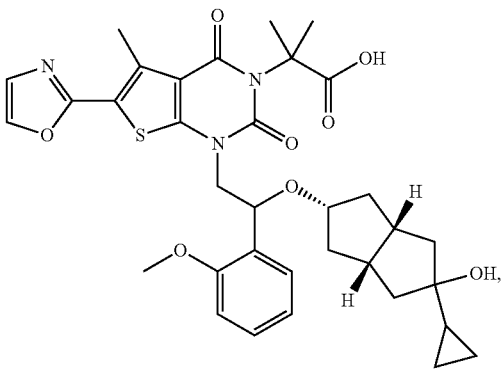
(68)
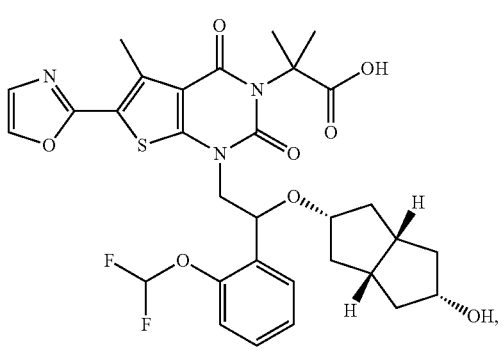
(69)
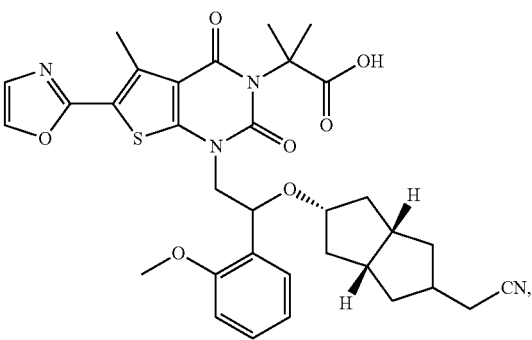
(70)
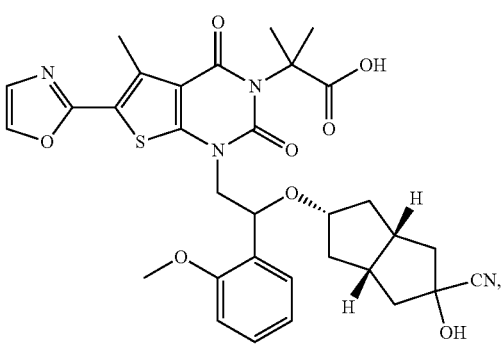

(71) 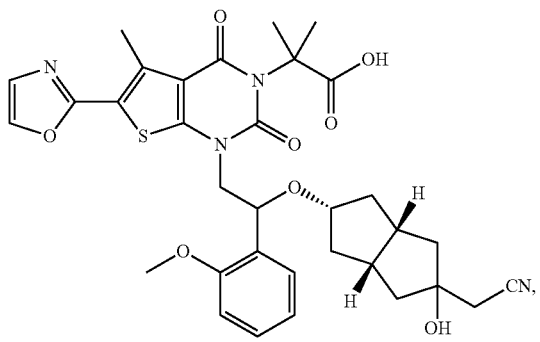

(72) 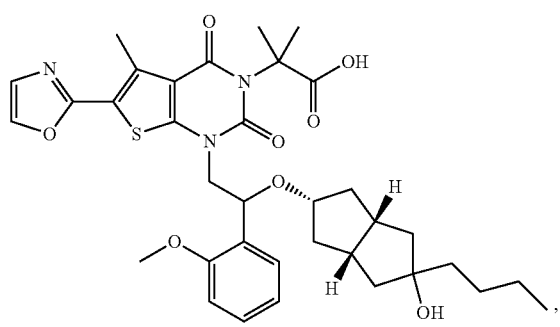

(73) 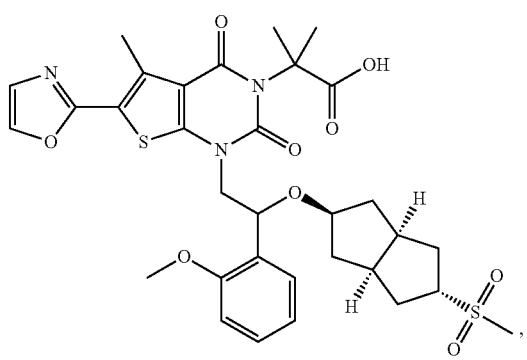

(74) 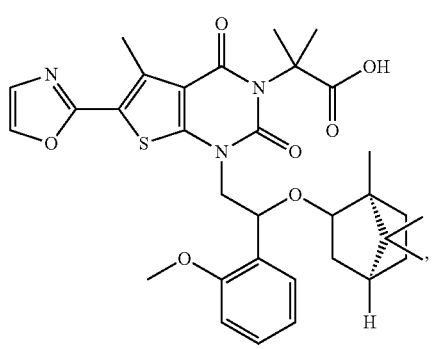

(75) 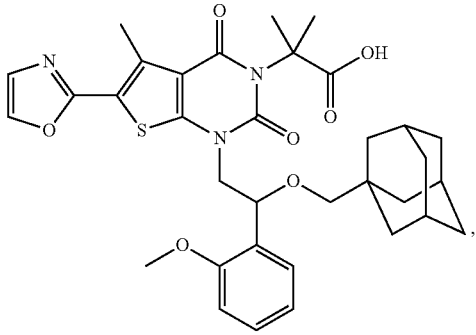

(76) 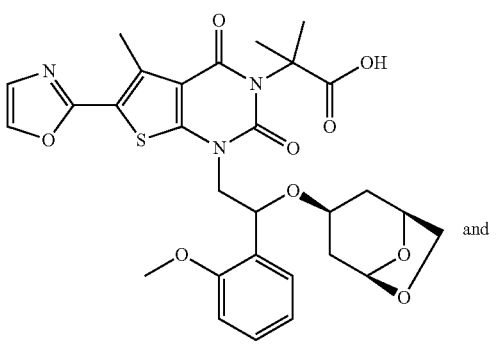 and

(77) 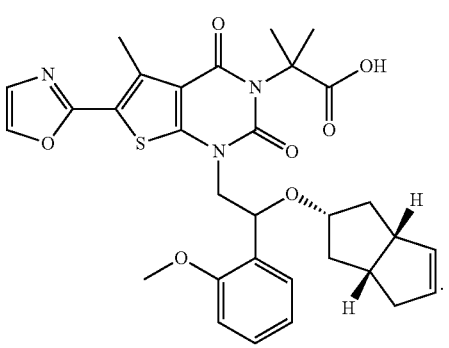

In one aspect, provided herein is a pharmaceutical composition comprising a compound of formula (I) or a stereoisomer, a geometric isomer, a tautomer, an N-oxide, a hydrate, a solvate, a metabolite, a pharmaceutically acceptable salt or a prodrug thereof, or a pharmaceutically acceptable carrier, excipient, diluent, adjuvant, vehicle or a combination thereof.

In one aspect, provided herein is use of the compound of formula (I) or the pharmaceutical composition thereof in the manufacture of a medicament for preventing, treating or lessening a disorder or disease regulated by ACC.

In some embodiments, the disorder or disease regulated by acetyl-CoA carboxylase disclosed herein is a metabolism disorder or neoplastic disorder.

In other embodiments, the disorder or disease regulated by acetyl-CoA carboxylase disclosed herein comprises insulin resistance insulin resistance, obesity, dyslipidemia, metabolic syndrome, type II diabetes, non-alcoholic fatty liver disease and non-alcoholic steatohepatitis.

In other embodiments, the neoplastic disorder disclosed herein comprises breast cancer, pancreatic cancer, renal cell cancer, hepatocellular carcinoma, malignant melanoma and other skin tumor, non-small cell bronchial carcinoma, endometrial carcinoma, colorectal cancer and prostate cancer.

The present invention relates to a method of preventing, managing, treating or lessening a disease regulated by ACC in a patient, comprising administering a therapeutically effective amount of a pharmaceutically acceptable effective amount of the compound to a patient.

In other aspect, provided herein is a method of preparing, separating or purifying the compound of Formula (I).

Pharmaceutical Composition of the Compound of the Invention and Preparations and Administration and Use of the Compound and the Pharmaceutical Composition The characteristics of the pharmaceutical composition of the invention include the compound represented by formula (I) and the compound listed herein and pharmaceutically acceptable carrier, adjuvant, or excipient. The amount of the compound in the composition of the invention can effectively and detectably treat or lessen a disease regulated by ACC.

It will also be appreciated that certain of the compounds disclosed herein can exist in free form for treatment, or where appropriate, as a pharmaceutically acceptable derivative thereof. Provided herein, some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein further comprise a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. As the following described: Troy et al., Remington: The Science and Practice of Pharmacy, 21st ed., 2005, Lippincott Williams & Wilkins, Philadelphia, and Swarbrick et al., Encyclopedia of Pharmaceutical Technology, eds. 19881999, Marcel Dekker, New York, both of which are herein incorporated by reference in their entireties, discloses various carriers used in formulating pharmaceutically acceptable compositions and known techniques for the preparation thereof. Except insofar as any conventional carrier medium incompatible with the compounds disclosed herein, e.g. by producing any undesirable biological effect or otherwise interacting in a deleterious manner with any other components of the pharmaceutically acceptable composition, its use is contemplated to be within the scope of this invention.

The compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, e.g., for example, water, glycols, oils, alcohols, flavoring agents, preservatives, coloring agents and the like in the case of oral liquid preparations, e.g., for example, suspensions, elixirs and solutions; or carriers e.g. starches, sugars, microcrystalline cellulose, diluents, granulating agents, lubricants, binders, disintegrating agents and the like in the case of oral solid preparations e.g., for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder e.g. gum tragacanth, acacia, corn starch or gelatin; excipients e.g. dicalcium phosphate; a disintegrating agent e.g. corn starch, potato starch, alginic acid; a lubricant e.g. magnesium stearate; and a sweetening agent e.g. sucrose, lactose or saccharin. When a dosage unit form is a capsule, it may contain, in addition to materials of the above type, a liquid carrier e.g. a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring e.g. cherry or orange flavor.

Ophthalmic formulations, eye ointments, powders, solutions and the like, are also contemplated as being within the scope of this invention.

The compounds of the present invention may also be administered parenterally. Solutions or suspensions of these active compounds can be prepared in water suitably mixed with a surfactant e.g. hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms e.g. bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

When treating or preventing ACC regulated conditions for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

The compound, composition or pharmaceutically acceptable salt or a hydrate can effectively preventing, managing, treating or lessening a disease regulated by acetyl-CoA carboxylase, in particularly, insulin resistance insulin resistance, obesity, dyslipidemia, metabolic syndrome, type II diabetes, non-alcoholic fatty liver disease and non-alcoholic steatohepatitis.

General Synthetic Procedures

Generally, the compounds disclosed herein may be prepared by methods described herein, wherein the substituents are as defined for Formula (I), Formula (II) or Formula (III) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers e.g. Aldrich Chemical Company, Arco Chemical Company and Alfa Chemical Company, and were used without further purification unless otherwise indicated. Common solvents were purchased from commercial suppliers e.g. Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Glassware was oven dried and/or heat dried.

Column chromatography was conducted using a silica gel column. Silica gel (300-400 mesh) was purchased from Qingdao Ocean Chemical Factory. $^1$H NMR spectra were recorded with a Bruker 400 MHz or 600 MHz spectrometer using $CDCl_3$, $d_6$-DMSO, $CD_3OD$ or $d_6$-acetone as solutions (reported in ppm), and using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), q (quartet), dt (doublet of triplets), tt (triplet of triplets), dddd (doublet of doublet of doublet of doublets), qd (quartet of doublets), ddd (doublet of doublet of doublets), td (triplet of doublets), dq (doublet of quartets), ddt (doublet of doublet of triplets), tdd (triplet of doublet of doublets), dtd (doublet of triplet of doublets). Coupling constants, when given, were reported in Hertz (Hz).

Low-resolution mass spectral (MS) data were determined by an Agilent 6320 Series LC-MS spectrometer equipped with a G1312A binary pump and a G1316A TCC (column was operated at 30° C.). G1329A autosampler and G1315B DAD detector were applied in the analysis, and an ESI source was used in the LC-MS spectrometer.

Low-resolution mass spectral (MS) data were determined by an Agilent 6120 Series LC-MS spectrometer equipped with a G1311A quaternary pump and a G1316A TCC (column was operated at 30° C.). G1329A autosampler and G1315D DAD detector were applied in the analysis, and an ESI source was used on the LC-MS spectrometer.

Both LC-MS spectrometers were equipped with an Agilent Zorbax SB-C18, 2.1×30 mm, 5 µm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were showed in Table 1: The gradient elution conditions were showed in Table 1:

TABLE 1

The gradient condition of the mobile phase in Low-resolution mass spectrum analysis

| Time (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micron, 10 min, 0.6 mL/min flow rate, 5 to 95% 0.1% formic acid in $CH_3CN$) in (0.1% formic acid in $H_2O$). Column was operated at 40° C.

The following abbreviations are used throughout the specification:

CDCl₃ chloroform-d
CD₃OD methyl alcohol-d4
DMF N,N-dimethylformamide
DMSO dimethylsulfoxide
DMSO-d₆ dimethyl sulfoxide-d₆
DCM dichloromethane
EA, EtOAc ethyl acetate
g gram
H₂O water
HCl hydrogen chloride/hydrochloric acid
PE petroleum ether
Pd/C, Pd—C Palladium on activated carbon
mg milligram
M moles per liter
MeOH methanol
mol mole
mmol millimole
MPa mega pascal
mL milliliter
NaOH sodium hydroxide
THF tetrahydrofuran
TBDPS tert-butyldiphenylsilyl
TBS tert-Butyldimethylsilyl
μL microlitre Schenme Typical synthetic procedures for preparing the compounds of the present invention disclosed are shown in the following synthetic scheme. Unless otherwise indicated, Het, $R^1$, $R^2$, $R^3$, $R^4$, $R^5$, L and W are as defined herein.

X is a leaving group, including but not limited to halo atom, methylsulfonyloxy, p-methylphenylsulfonyloxy and so on; compound Q can be obtained by Mitsunobu reaction of compound M and compound P. Compound (I) can be obtained by coupling reaction of compound Q.

Synthesis of Intermediate M

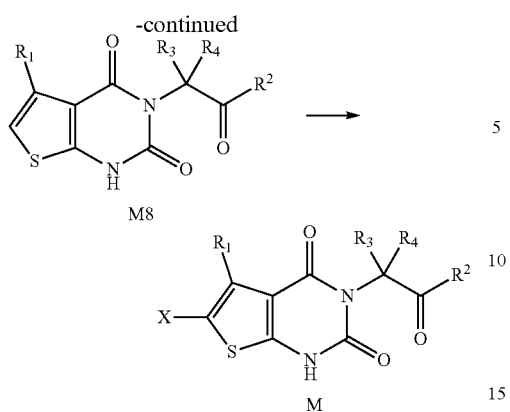

Compound M3 can be obtained by cyclization reaction of compound M1, compound M2 and sublimed sulfur in the present of a base in a suitable solvent. The base includes but not limited to morpholine; the solvent includes but not limited to ethanol.

Compound M5 can be obtained by reaction of compound M3, compound M4 and N,N'-carbonyldiimidazole in the present of a base in a suitable solvent. The base includes but not limited to triethylamine; the solvent includes but not limited to DCM.

Compound M6 can be obtained by condensation reaction of compound M5 in the present of a base in a suitable solvent. The base includes but not limited to sodium ethoxide; the solvent includes but not limited to ethanol.

Compound M7 can be obtained by hydrolyzation of compound M6 in the present of a base in a suitable solvent. The base includes but not limited to sodium hydroxide; the solvent includes but not limited to a mixture solvent of methanol and water.

Compound M8 can be obtained by decarboxylation reaction of compound M7 and silver acetate in the present of a base in a suitable solvent. The base includes but not limited to potassium carbonate; the solvent includes but not limited to N-methylmorpholine.

Compound M can be obtained by halogenation reaction of compound M8 in a suitable solvent. The solvent includes but not limited to methanol, glacial acetic acid and so on.

Synthesis of Intermediate P

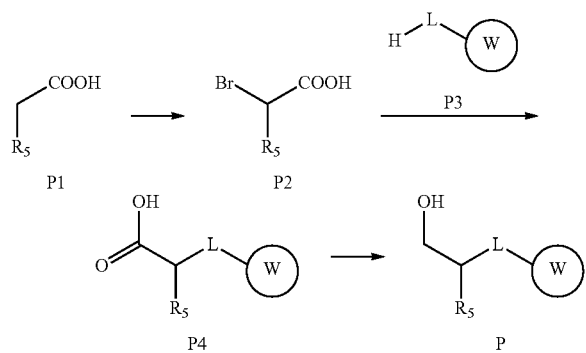

Compound P2 can be obtained by free radical reaction of compound P1 and N-bromosuccinimide under a catalyst in a suitable solvent. The catalyst includes but not limited to azodiisobutyronitrile; the solvent includes but not limited to tetrachloromethane.

Compound P4 can be obtained by substitution reaction of compound P2 and compound P3 in the present of a base in a suitable solvent. The base includes but not limited to sodium hydride, the solvent includes but not limited to tetrahydrofuran.

Compound P can be obtained by reduction reaction of compound P4 in the present of a reductant in a suitable solvent. The reductant includes but not limited to lithium aluminium hydride, the solvent includes but not limited to tetrahydrofuran.

EXAMPLES

Example 1

2-[1-[2-[[(3aS,6aR)-5-hydroxy-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid

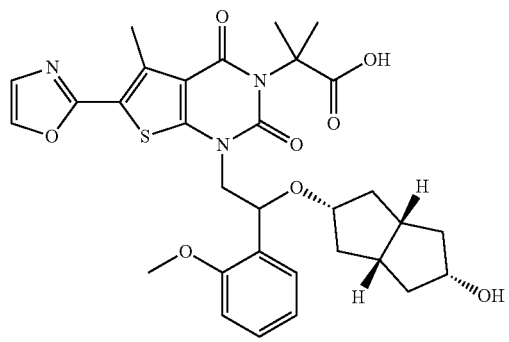

Step 1) diethyl 5-amino-3-methyl-thiophene-2,4-dicarboxylate

Ethyl cyanoacetate (30.00 g, 260.0 mmol), ethyl acetoacetate (33.83 g, 260.0 mmol) and sublimed sulfur (8.36 g, 260.0 mmol) were dissolved in anhydrous ethanol (60 mL) at rt. The solution was heated to 45° C., and then morpholine (34.0 mL, 390 mmol) was added dropwise slowly. After the addition, the resulting mixture was heated to 60° C. and stirred for 4 hours. The reaction was quenched with water (360 mL), and the mixture was cooled to rt with stirring. After a lot of solid precipitated out, the mixture was filtered by suction filtration. The filter cake was washed with 30% ethanol aqueous solution (100 mL) and dried in vacuo to get title compound as yellow solid (54.10 g, 80.9%).

MS (ESI, pos. ion) m/z: 258.2[M+H]+;

Step 2) diethyl 5-[(2-t-butoxy-1,1-dimethyl-2-oxa-ethyl)aminoformamido]-3-methyl-thiophene-2,4-dicarboxylate Diethyl 5-amino-3-methyl-thiophene-2,4-dicarboxylate (20.00 g, 77.73 mmol) was dissolved in DCM (160 mL) at rt, and then triethylamine (43.2 mL, 311 mmol) and N,N'-carbonyldiimidazole (25.72 g, 155.4 mmol) were added. The mixture was stirred for 3 hours, and then t-butyl 2-amino-2-methyl-propionate hydrochloride (16.30 g, 81.63 mmol) was added in portions. The resulting mixture was stirred for another 5 hours. The reaction was quenched with water (300 mL). The resulting mixture was partitioned. The organic layer was washed with water (300 mL×2) and dried over anhydrous sodium sulfate, and filtered by suction filtration. The filtrate was concentrated in vacuo. The residue was triturated with PE and ethyl acetate (V/V=15/1) to give the title compound as light yellow solid (29.10 g, 84.6%).

Step 3) ethyl 3-(2-t-butoxy-1,1-dimethyl-2-oxa-ethyl)-5-methyl-2,4-dioxo-1H-thieno[2,3-d]pyrimidine-6-formate Diethyl 5-[(2-t-butoxy-1,1-dimethyl-2-oxa-ethyl)aminoformamido]-3-methyl-thiophene-2,4-dicarboxylate (58.00 g, 131.1 mmol) was dissolved in anhydrous ethanol (550 mL), and then sodium ethoxide (36.41 g, 524.3 mmol) was added. The mixture was stirred at 80° C. overnight. The mixture was concentrated in vacuo. To the residue was added water (600 mL). The resulting mixture was adjusted to about 5 with dilute hydrochloric acid (2 N). A lot of solid precipitated out. The mixture was stirred for 30 min and filtered by suction filtration. The filter cake was washed with water (100 mL) and dried in vacuo to get the title compound as light yellow solid (51.97 g, 100%). The product was used in the next step without any further purification.

MS (ESI, neg. ion) m/z: 395.1[M−H]$^-$;

Step 4) 3-(2-t-butoxy-1,1-dimethyl-2-oxa-ethyl)-5-methyl-2,4-dioxo-1H-thieno[2,3-d]pyrimidine-6-formic acid Ethyl 3-(2-t-butoxy-1,1-dimethyl-2-oxa-ethyl)-5-methyl-2,4-dioxo-1H-thieno[2,3-d]pyrimidine-6-formate (51.97 g, 131.1 mmol) was dissolved in methanol (250 mL) and tetrahydrofuran (100 mL) at rt, and then a solution of sodium hydroxide (21.40 g, 524.3 mmol) in water (120 mL) and tetrabutylammonium bromide (4.23 g, 13.1 mmol) were added. The mixture was heated to 65° C. and stirred for 2.5 hours. The mixture was concentrated in vacuo. To the residue was added water (600 mL). The resulting mixture was adjusted to about 3 with dilute hydrochloric acid (2 N). A lot of solid precipitated out. The mixture was filtered by suction filtration. The filter cake was washed with water (100 mL) and dried in vacuo to get the title compound as gray solid (46.74 g, 96.8%).

MS (ESI, neg. ion) m/z: 367.1[M−H]$^-$;

Step 5) t-butyl 2-methyl-2-(5-methyl-2,4-dioxo-1H-thieno[2,3-d]pyrimid-3-yl)-6-propionate 3-(2-t-Butoxy-1,1-dimethyl-2-oxa-ethyl)-5-methyl-2,4-dioxo-1H-thieno[2,3-d]pyrimidine-6-formic acid (48.80 g, 132.5 mmol) was dissolved in N-methylpyrrolidone (900 mL) at rt, and then potassium carbonate (22.00 g, 159.2 mmol) and silver acetate (27.07 g, 158.9 mmol) were added. The mixture was heated to 110° C. and stirred for 2 hours. The resulting mixture was cooled to rt and filtered by suction filtration. The filtrate was diluted with water (2 L). The resulting mixture was extracted with ethyl acetate (500 mL×2). The combined organic layers were washed with saturated ammonium chloride solution (500 mL) and saturated aqueous NaCl (200 mL) in turn, and then dried over anhydrous sodium sulfate and concentrated in vacuo. The residue was triturated with PE and ethyl acetate (V/V=10/1) to give the title compound as gray solid (20.54 g, 47.8%).

MS (ESI, neg. ion) m/z: 323.1[M−H]$^-$;

Step 6) t-butyl 2-(6-bromo-5-methyl-2,4-dioxo-1H-thieno[2,3-d]pyrimid-3-yl)-2-methyl-propionate t-Butyl 2-methyl-2-(5-methyl-2,4-dioxo-1H-thieno[2,3-d]pyrimid-3-yl)propionate (20.54 g, 63.32 mmol) and sodium acetate trihydrate (18.96 g, 139.3 mmol) were dissolved in glacial acetic acid (300 mL), and then bromine (3.57 mL, 69.7 mmol) was added dropwise slowly. After the addition, the mixture was stirred at rt for 1 hour. The reaction was quenched with water (100 mL). A lot of solid precipitated out. The mixture was filtered by suction filtration. The filter cake was dissolved in ethyl acetate (500 mL). The solution was washed with saturated sodium thiosulfate solution (100 mL) and saturated aqueous NaCl (200 mL) in turn, and then dried over anhydrous sodium sulfate and filtered by suction filtration. The filtrate was concentrated in vacuo. The residue was triturated with PE and ethyl acetate (V/V=10/1) to get the title compound as white solid (25.00 g, 92.2%).

MS (ESI, pos. ion) m/z: 426.0[M+Na]$^+$;

$^1$H NMR (400 MHz, CDCl$_3$) δ 10.66 (s, 1H), 2.39 (s, 3H), 1.81 (s, 6H), 1.48 (s, 9H)

Step 7) (3'aR,6'aS)-5,5-dimethylspiro[1,3-dioxane-2,5'-2,3,3a,4,6,6a-hexahydro-1H-pentalen]-2'-ol To a solution of (3aR,6aS)-5',5'-dimethylspiro[1,3,3a,4,6,6a-hexahydropentalenyl-5,2'-1,3-dioxane]-2-one (24.50 g, 109.2 mmol) in anhydrous methanol (40 mL) was added sodium borohydride (5.78 g, 150.0 mmol) in portions on an ice bath under N$_2$. The mixture was stirred in the ice bath for 2 hours. The mixture was quenched with water (50 mL) by dropwise addition. The resulting mixture was extracted with ethyl acetate (120 mL×2). The combined organic phases were washed with saturated brine (50 mL), dried over anhydrous sodium sulfate, filtered by suction filtration. The filtrate was concentrated in vacuo. The residue was purified by silica gel chromatograph (PE/EtOAc (V/V)=4/1) to give the title compound as colorless oil (18.00 g, 72.8%).

Step 8) 2-[(3'aR,6'aS)-5,5-dimethylspiro[1,3-dioxane-2,5'-2,3,3a,4,6,6a-hexahydro-1H-pentalenyl]-2'-yl]oxy-2-(2-methoxyphenyl)acetic acid To a solution of (3'aR,6'aS)-5,5-dimethylspiro[1,3-dioxanel-2,5'-2,3,3a,4,6,6a-hexahydro-1H-pentalen]-2'-ol (3.09 g, 13.7 mmol) in anhydrous tetrahydrofuran (20 mL) was added sodium hydride (1.95 g, 48.8 mmol) in portions on an ice bath under N$_2$. After stirring for 15 min on the ice bath, a solution of 2-bromo-2-(methoxyphenyl)acetic acid (3.00 g, 12.2 mmol) in anhydrous tetrahydrofuran (10 mL) was added to the mixture. After the addition, the mixture was moved to rt and stirred for another 4 hours. The mixture was quenched with water (30 mL) by dropwise addition on an ice bath, the resulting mixture was extracted with ethyl acetate (30 mL×2). The combined water layers were adjusted to pH about 3 with dilute hydrochloric acid (2 N), and then extracted with ethyl acetate (30 mL×2). The combined organic layers were washed with saturated brine (30 mL), dried over anhydrous sodium sulfate, filtered by suction filtration. The filtrate was concentrated in vacuo to give the title compound as light yellow oil (2.20 g, 46.0%). The product was used in the next step without any further purification.

Step 9) 2-[(3'aR,6'aS)-5,5-dimethylspiro[1,3-dioxane-2,5'-2,3,3a,4,6,6a-hexahydro-1H-pentalenyl]-2'-yl]oxy-2-(2-methoxyphenyl)ethanol To a solution of 2-[(3'aR,6'aS)-5,5-dimethylspiro[1,3-dioxane-2,5'-2,3,3a,4,6,6a-hexahydro-1H-pentalenyl]-2'-yl]oxy-2-(2-methoxyphenyl)acetic acid (2.20 g, 5.63 mmol) in anhydrous tetrahydrofuran (20 mL) was added lithium aluminum hydride (0.44 g, 11.0 mmol) in portions on an ice bath. After the mixture was stable, the mixture was moved to rt and stirred for 2 hours. The mixture was quenched with water (0.44 mL) by dropwise addition on an ice bath. And then to the mixture were added sodium hydroxide solution (0.44 mL, 15%) and water (1.32 mL) in turn. The resulting mixture was stirred at rt for another 15 min, and anhydrous sodium sulfate was added, the mixture was further stirred for 15 min. The mixture was filtered by suction filtration. The filtrate was concentrated in vacuo. The residue was purified by silica gel chromatograph (PE/EtOAc (V/V)=4/1) to give the title compound as colorless oil (1.30 g, 61.3%).

MS (ESI, pos. ion) m/z: 399.3[M+Na]$^+$;

Step 10) t-butyl 2-[1-[2-[(3'aR,6'aS)-5,5-dimethyl-spiro[1,3-dioxane-2,5'-2,3,3a,4,6,6a-hexahydro-1H-pentalenyl]-2'-yl]oxy-2-(2-methoxyphenyl)ethyl]-6-bromo-5-methyl-2,4-dioxo-thieno[2,3-d]pyrimid-3-yl]-2-methyl-propionate t-Butyl 2-(6-bromo-5-methyl-2,4-dioxo-1H-thieno[2,3-d]pyrimid-3-yl)-2-methyl-propionate (1.45 g, 3.60 mmol), 2-[(3'aR,6'aS)-5,5-dimethylspiro[1,3-dioxane-2,5'-2,3,3a,4,6,6a-hexahydro-1H-pentalenyl]-2'-yl]oxy-2-(2-methoxyphenyl)ethanol (1.30 g, 3.45 mmol), triphenylphosphine (1.80 g, 6.79 mmol) were dissolved in anhydrous tetrahydrofuran (15 mL) at rt. Diisopropylazodicarboxylate (1.40 g, 6.79 mmol) was added to the mixture under $N_2$, the resulting mixture was stirred at rt for 12 hours and concentrated in vacuo. The residue was purified by silica gel chromatograph (PE/EtOAc (V/V)=6/1) to give the title compound as white solid (1.70 g, 64.6%).

Step 11) t-butyl 2-[1-[2-[(3'aR,6'aS)-5,5-dimethyl-spiro[1,3-dioxane-2,5'-2,3,3a,4,6,6a-hexahydro-1H-pentalenyl]-2'-yl]oxy-2-(2-methoxyphenyl)ethyl]-5-methyl-6-oxazol-2-yl-2,4-dioxo-thieno[2,3-d]pyrimid-3-yl]-2-methyl-propionate t-Butyl 2-[1-[2-[(3'aR,6'aS)-5,5-dimethylspiro[1,3-dioxane-2,5'-2,3,3a,4,6,6a-hexahydro-1H-pentalenyl]-2'-yl]oxy-2-(2-methoxyphenyl)ethyl]-6-bromo-5-methyl-2,4-dioxo-thieno[2,3-d]pyrimid-3-yl]-2-methyl-propionate (1.70 g, 2.23 mmol) and 2-tributylstannyloxazole (4.00 g, 11.2 mmol) were dissolved in toluene (20 mL) at rt under $N_2$, and then palladium tetrakis-(triphenylphosphine) (1.30 g, 1.12 mmol) was added. The mixture was stirred at 110° C. for 8 hours. The reaction mixture was concentrated in vacuo to remove the solvent, and the residue was purified by silica gel column chromatography (PE/EA (V/V)=8/1) to give the title compound as white solid (0.75 g, 45.0%).

Step 12) 2-[1-[2-[[(3aR,6aS)-5-oxa-2,3,3a,4,6,6a-hexahydro-1H-pentalenyl-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid t-Butyl 2-[1-[2-[(3'aR,6'aS)-5,5-dimethylspiro[1,3-dioxane-2,5'-2,3,3a,4,6,6a-hexahydro-1H-pentalenyl]-2'-yl]oxy-2-(2-methoxyphenyl)ethyl]-5-methyl-6-oxazol-2-yl-2,4-dioxo-thieno[2,3-d]pyrimid-3-yl]-2-methyl-propionate (0.75 g, 1.0 mmol) was dissolved in DCM (10 mL) at rt, and then 2,2,2-trifluoracetic acid (2 mL) was added. The mixture was stirred for 4 hours. The reaction mixture was concentrated in vacuo to remove the solvent, and the residue was purified by silica gel column chromatography (PE/EA (V/V)=1/1) to give the title compound as light yellow solid (0.500 g, 82.0%).

MS (ESI, pos. ion) m/z: 608.3[M+H]$^+$;

Step 13) 2-[1-[2-[[(3aS,6aR)-5-hydroxy-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid To a solution of 2-[1-[2-[[(3aR,6aS)-5-oxa-2,3,3a,4,6,6a-hexahydro-1H-pentalenyl-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid (0.500 g, 0.82 mmol) in anhydrous methanol (10 mL) was added sodium borohydride (0.10 g, 2.6 mmol) in portions on an ice bath under $N_2$. The mixture was stirred at rt for 6 hours. The mixture was quenched with water (10 mL) by dropwise addition. The resulting mixture was extracted with ethyl acetate (20 mL×2). The combined organic phases were washed with saturated brine (20 mL), dried over anhydrous sodium sulfate, filtered by suction filtration. The filtrate was concentrated in vacuo. The residue was purified by silica gel chromatograph (PE/EtOAc (V/V)=1/1) to give the title compound as white solid (0.43 g, 86.0%).

MS (ESI, pos. ion) m/z: 632.2[M+Na]$^+$;
$^1$H NMR (400 MHz, CDCl$_3$) δ 7.72 (s, 1H), 7.54 (d, J=6.4 Hz, 1H), 7.32 (t, J=6.8 Hz, 1H), 7.25 (s, 1H), 7.04 (t, J=7.4 Hz, 1H), 6.90 (d, J=8.2 Hz, 1H), 5.34-5.29 (m, 1H), 4.34-4.26 (m, 1H), 4.25-4.20 (m, 1H), 4.01-3.95 (m, 1H), 3.93 (s, 3H), 3.84-3.80 (m, 1H), 2.86 (s, 3H), 2.33-2.25 (m, 2H), 2.06-1.92 (m, 4H), 1.89 (s, 3H), 1.84 (s, 3H), 1.75-1.68 (m, 1H), 1.60-1.56 (m, 1H), 1.55-1.50 (m, 2H).

Example 2

2-[1-[2-[[(3aS,6aR)-5-hydroxy-1,2,3,3a,4,5,6,6a-octahydropentalen-2-yl]oxy]-2-phenyl-ethyl]-5-methyl-6-oxazol-2-yl-2,4-dioxo-thieno[2,3-d]pyrimid-3-yl]-2-methyl-propanoic acid

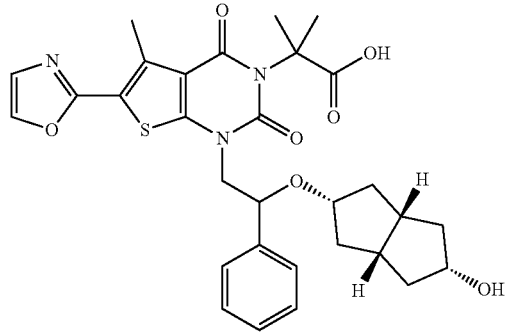 [SMILES: Cc1c(-c2ncco2)sc2c1c(=O)n(C(C)(C)C(=O)O)c(=O)n2CC(O[C@H]1C[C@H]2C[C@@H](O)C[C@H]2C1)c1ccccc1]

2-[1-[2-[[(3aS,6aR)-5-Hydroxy-1,2,3,3a,4,5,6,6a-octahydropentalen-2-yl]oxy]-2-phenyl-ethyl]-5-methyl-6-oxazol-2-yl-2,4-dioxo-thieno[2,3-d]pyrimid-3-yl]-2-methyl-propanoic acid was prepared from 2-bromo-2-phenylacetic acid (0.800 g, 3.72 mmol) according to the method described in Example 1. The obtained title compound is white solid (0.22 g, 95.0%).

MS (ESI, pos. ion) m/z: 580.3[M+H]$^+$;
$^1$H NMR (400 MHz, CDCl$_3$) δ 7.70 (d, J=0.5 Hz, 1H), 7.47-7.44 (m, 2H), 7.43-7.37 (m, 2H), 7.36-7.31 (m, 1H), 7.22 (d, J=0.6 Hz, 1H), 4.98-4.92 (m, 1H), 4.15-4.05 (m, 2H), 3.96-3.89 (m, 1H), 3.84-3.76 (m, 1H), 2.84 (s, 3H), 2.30-2.18 (m, 2H), 2.03-1.91 (m, 2H), 1.89 (s, 3H), 1.85 (s, 3H), 1.83-1.76 (m, 2H), 1.66-1.59 (m, 1H), 1.58-1.51 (m, 1H), 1.39-1.31 (m, 2H).

Example 3

2-[1-[2-(2-methoxyphenyl)-2-(6-oxaspiro[3.3]heptane-2-oxy)ethyl]-5-methyl-6-oxazol-2-yl-2,4-dioxo-thieno[2,3-d]pyrimid-3-yl]-2-methyl-propanoic acid

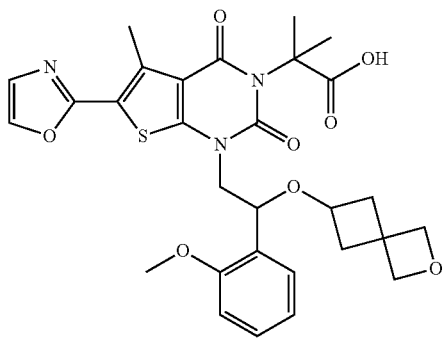 [SMILES: COc1ccccc1C(Cn1c(=O)n(C(C)(C)C(=O)O)c(=O)c2c(C)c(-c3ncco3)sc21)OC1CC2(COC2)C1]

Step 1) 2-(2-methoxyphenyl)-2-(6-oxaspiro[3.3]heptane-2-oxy)acetic acid

To a solution of 6-oxaspiro[3.3]heptane-2-ol (0.86 g, 7.5 mmol) in anhydrous tetrahydrofuran (22 mL) was added sodium hydride (1.10 g, 27.5 mmol) in portions on an ice bath under $N_2$. After stirring for 30 min on the ice bath, a solution of 2-bromo-2-(methoxyphenyl)acetic acid (1.68 g, 6.86 mmol) in anhydrous tetrahydrofuran (5 mL) was added dropwise to the mixture. After the addition, the mixture was moved to rt and stirred for another 4 hours. The mixture was quenched with water (30 mL) by dropwise addition on an ice bath, the resulting mixture was extracted with ethyl acetate (30 mL×2). The combined water layers were adjusted to pH about 3 with dilute hydrochloric acid (1N), and then extracted with isopropyl ether (30 mL×2). The combined organic layers were washed with saturated brine (30 mL), dried over anhydrous sodium sulfate, filtered by suction filtration. The filtrate was concentrated in vacuo to give the title compound as light yellow oil (1.91 g, 100%). The product was used in the next step without any further purification.

Step 2) 2-(2-methoxyphenyl)-2-(6-oxaspiro[3.3]heptane-2-oxy)ethanol

To a solution of 2-(2-methoxyphenyl)-2-(6-oxaspiro[3.3]heptane-2-oxy)acetic acid (1.91 g, 6.86 mmol) in anhydrous tetrahydrofuran (30 mL) was added lithium aluminum hydride (0.39 g, 10 mmol) in portions on an ice bath. After the mixture was stable, the mixture was moved to rt and stirred for 40 min. The mixture was quenched with water (10 mL) by dropwise addition on an ice bath. The resulting mixture was extracted with ethyl acetate (50 mL×2). The combined organic phases were washed with saturated brine (50 mL), dried over anhydrous sodium sulfate, filtered by suction filtration. The filtrate was concentrated in vacuo. The residue was purified by silica gel chromatograph (PE/EtOAc (V/V)=1/1) to give the title compound as colorless oil (0.700 g, 38.6%).

Step 3) t-butyl 2-[6-bromo-1-[2-(2-methoxyphenyl)-2-(6-oxaspiro[3.3]heptane-2-oxy) ethyl]-5-methyl-2,4-dioxo-thieno[2,3-d]pyrimid-3-yl]-2-methyl-propionate t-Butyl 2-[6-bromo-5-methyl-2,4-dioxo-1H-thieno[2,3-d]pyrimid-3-yl]-2-methyl-propionate (1.12 g, 2.78 mmol), 2-(2-methoxyphenyl)-2-(6-oxaspiro[3.3]heptane-2-oxy)ethanol (0.610 g, 2.31 mmol) and triphenylphosphine (1.24 g, 4.63 mmol) were dissolved in anhydrous tetrahydrofuran (15 mL), the air in the system was replaced with $N_2$. Diisopropylazodicarboxylate (0.95 mL, 4.7 mmol) was added dropwise to the mixture. The resulting mixture was stirred at rt for 22.5 hours. The reaction mixture was concentrated in vacuo to remove the solvent, and the residue was purified by silica gel column chromatography (PE/EA (V/V)=8/1) to give the title compound as white solid (1.05 g, 70.0%).

Step 4) t-butyl 2-[1-[2-(2-methoxyphenyl)-2-(6-oxaspiro[3.3]heptane-2-oxy)ethyl]-5-methyl-6-oxazol-2-yl-2,4-dioxo-thieno[2,3-d]pyrimid-3-yl]-2-methyl-propionate t-Butyl 2-[6-bromo-1-[2-(2-methoxyphenyl)-2-(6-oxaspiro[3.3]heptane-2-oxy)ethyl]-5-methyl-2,4-dioxo-thieno[2,3-d]pyrimid-3-yl]-2-methyl-propionate (1.05 g, 1.62 mmol) and 2-tributylstannyloxazole (1.16 g, 3.24 mmol) were dissolved in toluene (10 mL) at rt under $N_2$, and then palladium tetrakis-(triphenylphosphine) (0.56 g, 0.48 mmol) was added. The mixture was stirred at 110° C. for 23.5 hours. The reaction mixture was concentrated in vacuo to remove the solvent, and the residue was purified by silica gel column chromatography (PE/EA (V/V)=5/1) to give the title compound as white solid (0.470 g, 46.0%).

MS (ESI, pos. ion) m/z: 660.2[M+Na]$^+$;

Step 5) 2-[1-[2-(2-methoxyphenyl)-2-(6-oxaspiro[3.3]heptane-2-oxy)ethyl]-5-methyl-6-oxazol-2-yl-2,4-dioxo-thieno[2,3-d]pyrimid-3-yl]-2-methyl-propanoic acid t-Butyl 2-[1-[2-(2-methoxyphenyl)-2-(6-oxaspiro[3.3]heptane-2-oxy)ethyl]-5-methyl-6-oxazol-2-yl-2,4-dioxo-thieno[2,3-d]pyrimid-3-yl]-2-methyl-propionate (0.270 g, 0.423 mmol) was dissolved in DCM (12 mL) at rt, and then 2,2,2-trifluoracetic acid (2 mL) was added. The mixture was stirred for 3 hours. The reaction mixture was concentrated in vacuo to remove the solvent, and the residue was purified by silica gel column chromatography (PE/EA (V/V)=3/1) to give the title compound as white solid (0.050 g, 20.0%).

MS (ESI, pos. ion) m/z: 582.3[M+H]$^+$;

$^1$H NMR (400 MHz, CDCl$_3$) δ 7.72 (s, 1H), 7.50-7.46 (m, 1H), 7.33-7.28 (m, 1H), 7.25 (s, 1H), 7.02 (t, J=7.4 Hz, 1H), 6.86 (d, J=8.2 Hz, 1H), 5.18-5.12 (m, 1H), 4.61-4.51 (m, 4H), 4.21-4.12 (m, 1H), 4.12-4.03 (m, 1H), 3.86 (s, 3H), 3.77-3.68 (m, 1H), 2.87 (s, 3H), 2.48-2.37 (m, 2H), 2.12-2.06 (m, 1H), 1.95-1.89 (m, 1H), 1.87 (s, 3H), 1.84 (s, 3H).

Example 4

2-[1-[2-[[(3S,6S)-3-hydroxy-2,3,3a,5,6,6a-hexahydrofuro[3,2-b]fur-6-yl]oxy]-2-phenyl-ethyl]-5-methyl-6-oxazol-2-yl-2,4-dioxo-thieno[2,3-d]pyrimid-3-yl]-2-methyl-propanoic acid

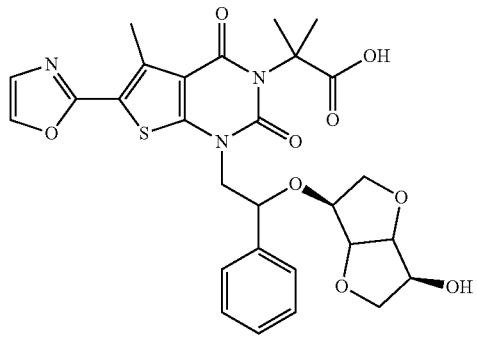 [SMILES: Cc1c(-c2ncco2)sc2c1c(=O)n(C(C)(C)C(=O)O)c(=O)n2CC(O[C@H]1COC2C1OC[C@@H]2O)c1ccccc1]

Step 1) (3S,6S)-6-[t-butyl(dimethyl)silyl]oxy-2,3,3a,5,6,6a-hexahydrofuro[3,2-b]furan-3-ol To a solution of (3S,6S)-2,3,3a,5,6,6a-hexahydrofuro[3,2-b]furan-3,6-diol (4.00 g, 27.4 mmol) in DCM (20 mL) was added t-butyldimethylsilylchloride (4.60 g, 30.5 mmol) slowly under $N_2$, and then imidazole (2.90 g, 42.2 mmol) was added. The mixture was stirred at rt for 22 hours. The mixture was quenched with water (100 mL) by dropwise addition. The resulting mixture was extracted with ethyl acetate (120 mL×2). The combined organic phases were washed with saturated brine (50 mL), dried over anhydrous sodium sulfate, filtered by suction filtration. The filtrate was concentrated in vacuo. The residue was purified by silica gel chromatograph (PE/EtOAc (V/V)=5/1) to give the title compound as colorless oil (3.20 g, 47.8%).

Step 2) 2-[[(3S,6S)-6-[t-butyl(dimethyl)silyl]oxy-2,3,3a,5,6,6a-hexahydrofuro[3,2-b]fur-3-yl]oxy]-2-phenyl-acetic acid To a solution of (3S,6S)-6-[t-butyl(dimethyl)silyl]oxy-2,3,3a,5,6,6a-hexahydrofuro[3,2-b]furan-3-ol (2.00 g, 7.68 mmol) in anhydrous tetrahydrofuran (25 mL) was added sodium hydride (1.30 g, 30.7 mmol) in portions on an ice bath under $N_2$. After stirring for 15 min, a solution of 2-bromo-2-phenylacetic acid (1.85 g, 8.45 mmol) in anhydrous tetrahydrofuran (10 mL) was added dropwise to the mixture. After the addition, the mixture was moved to rt and stirred for another 12 hours. The mixture was quenched with water (20 mL) by dropwise addition on an ice bath, the resulting mixture was washed with ethyl acetate (30 mL×2). The combined water layers were adjusted to pH about 5 with dilute hydrochloric acid (2N), and then extracted with ethyl acetate (50 mL×2). The combined organic layers were washed with saturated brine (30 mL), dried over anhydrous sodium sulfate, filtered by suction filtration. The filtrate was concentrated in vacuo to give the title compound as light yellow oil (1.80 g, 59.4%). The product was used in the next step without any further purification.

MS (ESI, pos. ion) m/z: 417.2[M+Na]$^+$;

Step 3) 2-[[(3S,6S)-6-[t-butyl(dimethyl)silyl]oxy-2,3,3a,5,6,6a-hexahydrofuro[3,2-b]fur-3-yl]oxy]-2-phenyl-ethanol To a solution of 2-[[(3S,6S)-6-[t-butyl(dimethyl)silyl]oxy-2,3,3a,5,6,6a-hexahydrofuro[3,2-b]fur-3-yl]oxy]-2-phenyl-acetic acid (2.48 g, 6.29 mmol) in anhydrous tetrahydrofuran (20 mL) was added lithium aluminum hydride (0.50 g, 13.0 mmol) in portions on an ice bath. After the mixture was stable, the mixture was moved to rt and stirred for 2 hours. The mixture was quenched with water (0.50 mL) by dropwise addition on an ice bath. And then to the mixture were added sodium hydroxide aqueous solution (0.50 mL, 15%) and water (1.50 mL) in turn. The resulting mixture was stirred at rt for another 15 min, and anhydrous sodium sulfate was added, the mixture was further stirred for 15 min. The mixture was filtered by suction filtration. The filtrate was concentrated in vacuo. The residue was purified by silica gel chromatograph (PE/EtOAc (V/V)=10/1) to give the title compound as colorless oil (0.60 g, 25.0%).

MS (ESI, pos. ion) m/z: 403.1[M+Na]$^+$;

Step 4) t-butyl 2-[6-bromo-1-[2-[[(3S,6S)-6-[t-butyl(dimethyl)silyl]oxy-2,3,3a,5,6,6a-hexahydrofuro[3,2-b]fur-3-yl]oxy]-2-phenyl-ethyl]-5-methyl-2,4-dioxo-thieno[2,3-d]pyrimid-3-yl]-2-methyl-propionate t-Butyl 2-(6-bromo-5-methyl-2,4-dioxo-1H-thieno[2,3-d]pyrimid-3-yl)-2-methyl-propionate (0.58 g, 1.4 mmol), 2-[[(3S,6S)-6-[t-butyl(dimethyl)silyl]oxy-2,3,3a,5,6,6a-hexahydrofuro[3,2-b]fur-3-yl]oxy]-2-phenyl-ethanol (0.53 g, 1.4 mmol) and triphenylphosphine (0.75 g, 2.8 mmol) were dissolved in anhydrous tetrahydrofuran (15 mL) at rt. Diisopropylazodicarboxylate (0.56 g, 2.7 mmol) was added to the mixture under $N_2$, the resulting mixture was stirred at rt for 12 hours and concentrated in vacuo. The residue was purified by silica gel chromatograph (PE/EtOAc (V/V)=6/1) to give the title compound as white solid (0.71 g, 67.0%).

Step 5) t-butyl 2-[1-[2-[[(3S,6S)-6-[t-butyl(dimethyl)silyl]oxy-2,3,3a,5,6,6a-hexahydrofuro[3,2-b]fur-3-yl]oxy]-2-phenyl-ethyl]-5-methyl-6-oxazol-2-yl-2,4-dioxo-thieno[2,3-d]pyrimid-3-yl]-2-methyl-propionate t-Butyl 2-[6-bromo-1-[2-[[(3S,6S)-6-[t-butyl(dimethyl)silyl]oxy-2,3,3a,5,6,6a-hexahydrofuro[3,2-b]fur-3-yl]oxy]-2-phenyl-ethyl]-5-methyl-2,4-dioxo-thieno[2,3-d]pyrimid-3-yl]-2-methyl-propionate (0.17 g, 0.22 mmol) and 2-tributylstannyloxazole (0.29 g, 0.67 mmol) were dissolved in toluene (10 mL) at rt under $N_2$, and then palladium tetrakis-(triphenylphosphine) (0.12 g, 0.11 mmol) was added. The mixture was stirred at 110° C. for 12 hours. The reaction mixture was concentrated in vacuo to remove the solvent, and the residue was purified by silica gel column chromatography (PE/EA (V/V)=6/1) to give the title compound as white solid (0.10 g, 60.0%).

MS (ESI, pos. ion) m/z: 777.2[M+Na]$^+$;

Step 6) 2-[1-[2-[[(3S,6S)-3-hydroxy-2,3,3a,5,6,6a-hexahydrofuro[3,2-b]furan6-yl]oxy]-2-phenyl-ethyl]-5-methyl-6-oxazol-2-yl-2,4-dioxo-thieno[2,3-d]pyrimid-3-yl]-2-methyl-propanoic acid t-Butyl 2-[1-[2-[[(3S,6S)-6-[t-butyl(dimethyl)silyl]oxy-2,3,3a,5,6,6a-hexahydrofuro [3,2-b]fur-3-yl]oxy]-2-phenyl-ethyl]-5-methyl-6-oxazol-2-yl-2,4-dioxo-thieno[2,3-d]pyrimid-3-yl]-2-methyl-propionate (0.42 g, 0.56 mmol) was dissolved in DCM (8 mL) at rt, and then 2,2,2-trifluoracetic acid (4 mL) was added. The mixture was stirred for 4 hours. The reaction mixture was concentrated in vacuo to remove the solvent, and the residue was purified by silica gel column chromatography (PE/EA (V/V)=3/1) to give the title compound as light yellow solid (0.22 g, 68.0%).

MS (ESI, pos. ion) m/z: 584.2[M+H]$^+$;

$^1$H NMR (400 MHz, CDCl$_3$) δ 7.73 (s, 1H), 7.50-7.35 (m, 5H), 7.25 (s, 1H), 5.15-5.10 (m, 1H), 4.45 (t, J=4.8 Hz, 1H), 4.35 (t, J=5.1 Hz, 1H), 4.25 (d, J=14.4 Hz, 1H), 4.18-4.11 (m, 1H), 4.04-3.96 (m, 1H), 3.95-3.87 (m, 1H), 3.86-3.82 (m, 1H), 3.82-3.77 (m, 1H), 3.47 (t, J=8.2 Hz, 1H), 3.04 (t, J=8.4 Hz, 1H), 2.87 (s, 3H), 1.90 (s, 3H), 1.87 (s, 3H).

Example 5

2-[1-[2-[[(3S,6S)-3-hydroxy-2,3,3a,5,6,6a-hexahydrofuro[3,2-b]furan6-yl]oxy]-2-(2-methoxy phenyl)ethyl]-5-methyl-6-oxazol-2-yl-2,4-dioxo-thieno[2,3-d]pyrimid-3-yl]-2-methyl-propanoic acid

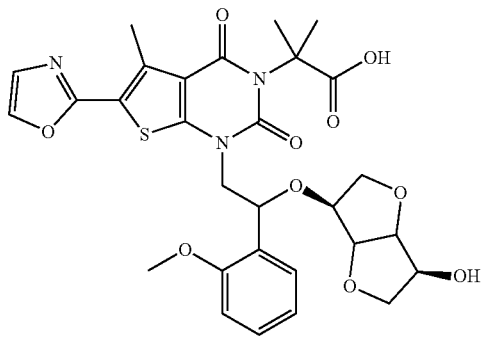 [SMILES: COc1ccccc1C(Cn1c(=O)n(C(C)(C)C(=O)O)c(=O)c2c(C)c(-c3ncco3)sc21)O[C@H]1COC2C1OC[C@@H]2O]

2-[1-[2-[[(3S,6S)-3-Hydroxy-2,3,3a,5,6,6a-hexahydro-furo[3,2-b]furan6-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid was prepared from 2-bromo-2-(methoxyphenyl)acetic acid (1.35 g, 5.51 mmol) according to the method described in Example 4. The obtained title compound is light yellow solid (0.45 g, 74.0%).

MS (ESI, pos. ion) m/z: 636.1[M+Na]$^+$;

$^1$H NMR (400 MHz, CDCl$_3$) δ 7.72 (s, 1H), 7.52-7.45 (m, 1H), 7.37-7.31 (m, 1H), 7.25 (s, 1H), 7.04 (t, J=7.5 Hz, 1H), 6.93 (d, J=8.2 Hz, 1H), 5.55-5.46 (m, 1H), 4.45 (t, J=4.7 Hz, 1H), 4.36 (t, J=5.1 Hz, 1H), 4.22-4.06 (m, 3H), 4.01-3.93 (m, 2H), 3.92 (s, 3H), 3.84-3.78 (m, 1H), 3.55 (t, J=8.0 Hz, 1H), 3.24 (t, J=8.1 Hz, 1H), 2.87 (s, 3H), 1.88 (s, 3H), 1.87 (s, 3H).

Example 6

2-[1-[2-[[(3aR,6aS)-5-oxy-2,3,3a,4,6,6a-hexahydro-1H-pentalenyl-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid

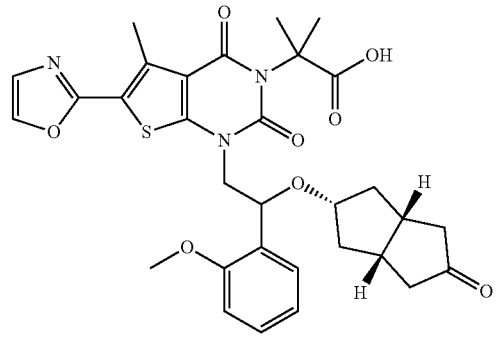 [SMILES: COc1ccccc1C(Cn1c(=O)n(C(C)(C)C(=O)O)c(=O)c2c(C)c(-c3ncco3)sc21)O[C@H]1C[C@H]2CC(=O)C[C@H]2C1]

Step 1) (3aR,6aS)-5',5'-dimethylspiro[1,3,3a,4,6,6a-hexahydropentalenyl-5,2'-1,3-dioxane]-2-one 1,3,3a,4,6,6a-Hexahydropentalenyl-2,5-dione (20.00 g, 144.8 mmol) and 2,2-dimethtylpropane-1,3-diol (16.00 g, 153.6 mmol) were dissolved in toluene (100.00 mL), and then p-toluene sulfonic acid (2.50 g, 14.4 mmol). The mixture was heated to 115° C. and stirred overnight. The reaction was stopped and the mixture was concentrated in vacuo to remove the solvent, and the residue was purified by silica gel column chromatography (PE/EtOAc (V/V)=6/1) to give the title compound as white solid (13.60 g, 41.89%).

Step 2) (3'aR,6'aS)-5,5-dimethylspiro[1,3-dioxane-2,5'-2,3,3a,4,6,6a-hexahydro-1H-pentalenyl]-2'-ol To a solution of (3aR,6aS)-5',5'-dimethylspiro[1,3,3a,4,6,6a-hexahydropentalenyl-5,2'-1,3-dioxane]-2-one (24.50 g, 109.2 mmol) in anhydrous methanol (40 mL) was added sodium borohydride (5.78 g, 150.0 mmol) in portions on an ice bath under N$_2$. The mixture was stirred for 2 hours. The mixture was quenched with water (50 mL) by dropwise addition. The resulting mixture was extracted with ethyl acetate (120 mL×2). The combined organic phases were washed with saturated brine (50 mL), dried over anhydrous sodium sulfate, filtered by suction filtration. The filtrate was concentrated in vacuo. The residue was purified by silica gel chromatograph (PE/EtOAc (V/V)=4/1) to give the title compound as colorless oil (18.00 g, 72.8%).

Step 3) 2-[(3'aR,6'aS)-5,5-dimethylspiro[1,3-dioxane-2,5'-2,3,3a,4,6,6a-hexahydro-1H-pentalenyl]-2'-yl]oxy-2-(2-methoxyphenyl)acetic acid To a solution of (3'aR,6'aS)-5,5-dimethylspiro[1,3-dioxane-2,5'-2,3,3a,4,6,6a-hexahydro-1H-pentalenyl]-2'-ol (3.09 g, 13.7 mmol) in anhydrous tetrahydrofuran (20 mL) was added sodium hydride (1.95 g, 48.8 mmol) in portions on an ice bath under N$_2$. After stirring for 15 min, a solution of 2-bromo-2-(methoxyphenyl)acetic acid (3.00 g, 12.2 mmol) in anhydrous tetrahydrofuran (10 mL) was added to the mixture. After the addition, the mixture was moved to rt and stirred for another 4 hours. The mixture was quenched with water (30 mL) by dropwise addition on an ice bath, the resulting mixture was extracted with ethyl acetate (30 mL×2). The combined water layers were adjusted to pH about 3 with dilute hydrochloric acid (2 N), and then extracted with ethyl acetate (30 mL×2). The combined organic layers were washed with saturated brine (30 mL), dried over anhydrous sodium sulfate, filtered by suction filtration. The filtrate was concentrated in vacuo to give the title compound as light yellow oil (2.20 g, 46.0%).

Step 4) 2-[(3'aR,6'aS)-5,5-dimethylspiro[1,3-dioxane-2,5'-2,3,3a,4,6,6a-hexahydro-1H-pentalenyl]-2'-yl]oxy-2-(2-methoxyphenyl)ethanol To a solution of 2-[(3'aR,6'aS)-5,5-dimethylspiro[1,3-dioxane-2,5'-2,3,3a,4,6,6a-hexahydro-1H-pentalenyl]-2'-yl]oxy-2-(2-methoxyphenyl)acetic acid (2.20 g, 5.63 mmol) in anhydrous tetrahydrofuran (20 mL) was added lithium aluminum hydride (0.44 g, 11.0 mmol) in portions on an ice bath. After the mixture was stable, the mixture was moved to rt and stirred for 2 hours. To the mixture were added slowly water (0.44 mL), sodium hydroxide aqueous solution (0.44 mL, 10%) and water (1.32 mL) in turn by dropwise addition on an ice bath. The resulting mixture was stirred at rt for another 15 min, and anhydrous sodium sulfate was added, the mixture was further stirred for 15 min. The mixture was filtered by suction filtration. The filtrate was concentrated in vacuo. The residue was purified by silica gel chromatograph (PE/EtOAc (V/V)=4/1) to give the title compound as colorless oil (1.30 g, 61.3%).

MS (ESI, pos. ion) m/z: 399.3[M+Na]$^+$;

Step 5) t-butyl 2-[1-[2-[(3'aR,6'aS)-5,5-dimethyl-spiro[1,3-dioxane-2,5'-2,3,3a,4,6,6a-hexahydro-1H-pentalenyl]-2'-yl]oxy-2-(2-methoxyphenyl)ethyl]-6-bromo-5-methyl-2,4-dioxo-thieno[2,3-d]pyrimid-3-yl]-2-methyl-propionate t-Butyl 2-(6-bromo-5-methyl-2,4-dioxo-1H-thieno[2,3-d]pyrimid-3-yl)-2-methyl-propionate (1.45 g, 3.60 mmol) (prepared according to the method described in step 6 of example 1), 2-[(3'aR,6'aS)-5,5-dimethylspiro[1,3-dioxane-2,5'-2,3,3a,4,6,6a-hexahydro-1H-pentalenyl]-2'-yl]oxy-2-(2-methoxyphenyl)ethanol (1.30 g, 3.45 mmol), triphenylphosphine (1.80 g, 6.79 mmol) were dissolved in anhydrous tetrahydrofuran (15 mL) at rt. Diisopropylazodicarboxylate (1.40 g, 6.79 mmol) was added to the mixture under N$_2$, the resulting mixture was stirred at rt for 12 hours and concentrated in vacuo. The residue was purified by silica gel chromatograph (PE/EtOAc (V/V)=6/1) to give the title compound as white solid (1.70 g, 64.6%).

Step 6) t-butyl 2-[1-[2-[(3'aR,6'aS)-5,5-dimethyl-spiro[1,3-dioxane-2,5'-2,3,3a,4,6,6a-hexahydro-1H-pentalenyl]-2'-yl]oxy-2-(2-methoxyphenyl)ethyl]-5-methyl-6-oxazol-2-yl-2,4-dioxo-thieno[2,3-d]pyrimid-3-yl]-2-methyl-propionate t-Butyl 2-[1-[2-[(3'aR,6'aS)-5,5-dimethylspiro[1,3-dioxane-2,5'-2,3,3a,4,6,6a-hexahydro-1H-pentalenyl]-2'-yl]oxy-2-(2-methoxyphenyl)ethyl]-6-bromo-5-methyl-2,4-dioxo-thieno[2,3-d]pyrimid-3-yl]-2-methyl-propionate (1.70 g, 2.23 mmol) and 2-tributylstannyloxazole (4.00 g, 11.2 mmol) were dissolved in toluene (20 mL) at rt under N$_2$, and then palladium tetrakis-(triphenylphosphine) (1.30 g, 1.12 mmol) was added. The mixture was stirred at 110° C. for 8 hours. The reaction mixture was concentrated in vacuo to remove the solvent, and the residue was purified by silica gel column chromatography (PE/EA (V/V)=8/1) to give the title compound as white solid (0.75 g, 45.0%).

Step 7) 2-[1-[2-[[(3aR,6aS)-5-oxy-2,3,3a,4,6,6a-hexahydro-1H-pentalenyl-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid t-Butyl 2-[1-[2-[(3'aR,6'aS)-5,5-dimethylspiro[1,3-dioxane-2,5'-2,3,3a,4,6,6a-hexahydro-1H-pentalenyl]-2'-yl]oxy-2-(2-methoxyphenyl)ethyl]-5-methyl-6-oxazol-2-yl-2,4-dioxo-thieno[2,3-d]pyrimid-3-yl]-2-methyl-propionate (0.75 g, 1.0 mmol) was dissolved in DCM (10 mL) at rt, and then 2,2,2-trifluoracetic acid (2 mL) was added. The mixture was stirred for 4 hours. The reaction mixture was concentrated in vacuo to remove the solvent, and the residue was purified by silica gel column chromatography (PE/EA (V/V)=1/1) to give the title compound as a light yellow solid (0.500 g, 82.0%).

MS (ESI, pos. ion) m/z: 608.3[M+H]$^+$;

$^1$H NMR (400 MHz, CDCl$_3$) δ 7.71 (s, 1H), 7.49 (d, J=6.9 Hz, 1H), 7.34-7.28 (m, 1H), 7.23 (s, 1H), 7.05 (d, J=7.1 Hz, 1H), 6.85 (d, J=7.7 Hz, 1H), 5.31 (t, J=5.5 Hz, 1H), 4.18-4.03 (m, 2H), 3.96-3.90 (m, 1H), 3.82 (s, 3H), 2.86 (s, 3H), 2.70-2.58 (m, 2H), 2.50-2.33 (m, 2H), 2.27-2.09 (m, 2H), 2.06-1.98 (m, 2H), 1.89 (s, 3H), 1.84 (s, 3H), 1.64-1.52 (m, 2H).

Example 7

2-[1-[2-[[(3aR,6aS)-5-hydroxy-3a,6a-dimethyl-1,2,3,4,5,6-hexahydropentalenyl-2-yl]oxy]-2-(2-methoxyphenyl)ethyl]-5-methyl-6-oxazol-2-yl-2,4-dioxo-thieno[2,3-d]pyrimid-3-yl-2-meth yl-propanoic acid

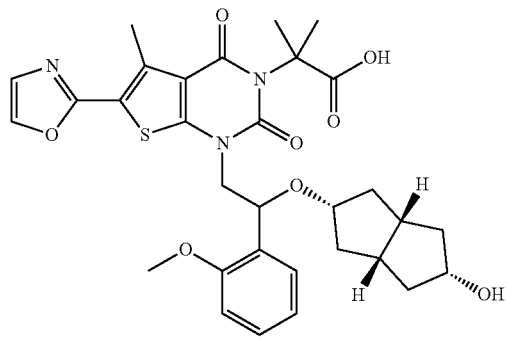 [SMILES: COc1ccccc1C(Cn1c(=O)n(C(C)(C)C(=O)O)c(=O)c2c(C)c(-c3ncco3)sc21)O[C@H]1C[C@H]2C[C@@H](O)C[C@H]2C1]

Step 1) (3aR,6aS)-3a,5',5',6a-tetramethylspiro[1,3,4,6-tetrahydropentalenyl-5,2'-1,3-dioxane]-2-one 3a,6a-Dimethyl-1,3,4,6-tetrahydropentalenyl-2,5-dione (3.00 g, 18.0 mmol), 2,2-dimethtylpropane-1,3-diol (1.90 g, 18.2 mmol) and p-toluene sulfonic acid (0.40 g, 2.3 mmol) were dissolved in toluene (20 mL) under N$_2$. The mixture was heated to 115° C. and stirred for 12 hours. The reaction mixture was concentrated in vacuo to remove the solvent, and the residue was purified by silica gel column chromatography (PE/EA (V/V)=6/1) to give the title compound as colorless oil (3.00 g, 65.9%).

Step 2) (3'aR,6'aS)-3'a,5,5,6'a-tetramethylspiro[1,3-dioxane-2,5'-2,3,4,6-tetrahydro-1H-pentalen]-2'-ol To a solution of (3aR,6aS)-3a,5',5',6a-tetramethylspiro[1,3,4,6-tetrahydropentalenyl-5,2'-1,3-dioxane]-2-one (3.00 g, 11.9 mmol) in anhydrous methanol (15 mL) was added sodium borohydride (0.60 g, 16.0 mmol) in portions on an ice bath under $N_2$. The mixture was stirred for 2 hours. The mixture was quenched with water (50 mL) by dropwise addition. The resulting mixture was extracted with ethyl acetate (120 mL×2). The combined organic phases were washed with saturated brine (50 mL), dried over anhydrous sodium sulfate, filtered by suction filtration. The filtrate was concentrated in vacuo. The residue was purified by silica gel chromatograph (PE/EtOAc (V/V)=2/1) to give the title compound as colorless oil (2.26 g, 74.7%).

Step 3) 2-[(3'aS,6'aR)-3'a,5,5,6'a-tetramethylspiro[1,3-dioxane-2,5'-2,3,4,6-tetrahydro-1H-pentalenyl]-2'-yl]oxy-2-(2-methoxyphenyl)acetic acid To a solution of (3'aR,6'aS)-3'a,5,5,6'a-tetramethylspiro[1,3-dioxane-2,5'-2,3,4,6-tetrahydro-1H-pentalen]-2'-ol (2.30 g, 9.04 mmol) in anhydrous tetrahydrofuran (20 mL) was added sodium hydride (1.20 g, 30.0 mmol, 60%) in portions on an ice bath under $N_2$. After stirring for 15 min on the ice bath, a solution of 2-bromo-2-(methoxyphenyl) acetic acid (1.80 g, 7.34 mmol) in anhydrous tetrahydrofuran (10 mL) was added to the mixture. After the addition, the mixture was moved to rt and stirred for another 4 hours. The mixture was quenched with water (30 mL) by dropwise addition on an ice bath, the resulting mixture was extracted with ethyl acetate (30 mL×2). The combined water layers were adjusted to pH about 3 with dilute hydrochloric acid (2 N), and then extracted with ethyl acetate (30 mL×2). The combined organic layers were washed with saturated brine (30 mL), dried over anhydrous sodium sulfate, filtered by suction filtration. The filtrate was concentrated in vacuo to give the title compound as light yellow oil (1.60 g, 52.1%).

MS (ESI, pos. ion) m/z: 419.3[M+H]$^+$;

Step 4) 2-[(3'aS,6'aR)-3'a,5,5,6'a-tetramethylspiro[1,3-dioxane-2,5'-2,3,4,6-tetrahydro-1H-pentalenyl]-2'-yl]oxy-2-(2-methoxyphenyl)ethanol To a solution of 2-[(3'aS,6'aR)-3'a,5,5,6'a-tetramethylspiro[1,3-dioxane-2,5'-2,3,4,6-tetrahydro-1H-pentalenyl]-2'-yl]oxy-2-(2-methoxyphenyl)acetic acid (1.90 g, 4.54 mmol) in anhydrous tetrahydrofuran (20 mL) was added lithium aluminum hydride (0.45 g, 12.0 mmol) in portions on an ice bath. After the mixture was stable, the mixture was moved to rt and stirred for 2 hours. The mixture was quenched with water (0.45 mL) by dropwise addition on an ice bath. And then to the mixture were added sodium hydroxide aqueous solution (0.45 mL, 15%) and water (1.35 mL) in turn. The resulting mixture was stirred at rt for another 15 min, and anhydrous sodium sulfate was added, the mixture was further stirred for 15 min. The mixture was filtered by suction filtration. The filtrate was concentrated in vacuo. The residue was purified by silica gel chromatograph (PE/EtOAc (V/V)=6/1) to give the title compound as colorless oil (0.55 g, 30.1%).

MS (ESI, pos. ion) m/z: 427.3[M+Na]$^+$;

Step 5) t-butyl 2-[1-[2-[(3'aS,6'aR)-3'a,5,5,6'a-tetramethylspiro[1,3-dioxane-2,5'-2,3,4,6-tetrahydro-1H-pentalenyl]-2'-yl]oxy-2-(2-methoxyphenyl)ethyl]-6-bromo-5-methyl-2,4-dioxo-thieno[2,3-d]pyrimid-3-yl]-2-methyl-propionate t-Butyl 2-(6-bromo-5-methyl-2,4-dioxo-1H-thieno[2,3-d]pyrimid-3-yl)-2-methyl-propionate (0.60 g, 1.5 mmol), 2-[(3'aS,6'aR)-3'a,5,5,6'a-tetramethylspiro[1,3-dioxane-2,5'-2,3,4,6-tetrahydro-1H-pentalenyl]-2'-yl]oxy-2-(2-methoxyphenyl)ethanol (0.54 g, 1.3 mmol), triphenylphosphine (0.75 g, 2.8 mmol) were dissolved in anhydrous tetrahydrofuran (15 mL) at rt under $N_2$. Diisopropylazodicarboxylate (0.56 g, 2.7 mmol) was added to the mixture under $N_2$, the resulting mixture was stirred at rt for 12 hours. The reaction mixture was concentrated in vacuo to remove the solvent, and the residue was purified by silica gel column chromatography (PE/EA (V/V)=6/1) to give the title compound as white solid (1.10 g, 99.0%).

Step 6) t-butyl 2-[1-[2-[(3'aS,6'aR)-3'a,5,5,6'a-tetramethylspiro[1,3-dioxane-2,5'-2,3,4,6-tetrahydro-1H-pentalenyl]-2'-yl]oxy-2-(2-methoxyphenyl)ethyl]-5-methyl-6-oxazol-2-yl-2,4-dioxo-thieno[2,3-d]pyrimid-3-yl]-2-methyl-propionate t-Butyl 2-[1-[2-[(3'aS,6'aR)-3'a,5,5,6'a-tetramethylspiro[1,3-dioxane-2,5'-2,3,4,6-tetrahydro-1H-pentalenyl]-2'-yl]oxy-2-(2-methoxyphenyl)ethyl]-6-bromo-5-methyl-2,4-dioxo-thieno[2,3-d]pyrimid-3-yl]-2-methyl-propionate (1.10 g, 1.39 mmol) and 2-tributylstannyloxazole (1.50 g, 4.19 mmol) were dissolved in toluene (20 mL) at rt under $N_2$, and then palladium tetrakis-(triphenylphosphine) (0.80 g, 0.69 mmol) was added. The mixture was stirred at 110° C. for 12 hours. The reaction mixture was concentrated in vacuo to remove the solvent, and the residue was purified by silica gel column chromatography (PE/EA (V/V)=8/1) to give the title compound as white solid (0.61 g, 56.0%).

Step 7) 2-[1-[2-[[(3aS,6aR)-3a,6a-dimethyl-5-oxa-2,3,4,6-tetrahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid t-Butyl 2-[1-[2-[(3'aS,6'aR)-3'a,5,5,6'a-tetramethylspiro[1,3-dioxane-2,5'-2,3,4,6-tetrahydro-1H-pentalenyl]-2'-yl]oxy-2-(2-methoxyphenyl)ethyl]-5-methyl-6-oxazol-2-yl-2,4-dioxo-thieno[2,3-d]pyrimid-3-yl]-2-methyl-propionate (0.61 g, 0.78 mmol) was dissolved in DCM (15 mL) at rt, and then 2,2,2-trifluoracetic acid (5 mL) was added. The mixture was stirred for 4 hours. The reaction mixture was concentrated in vacuo to remove the solvent, and the residue was purified by silica gel column chromatography (PE/EA (V/V)=1/1) to give the title compound as light yellow solid (0.36 g, 72.0%).

MS (ESI, pos. ion) m/z: 636.2[M+H]$^+$;

Step 8) 2-[1-[2-[[(3aR,6aS)-5-hydroxy-3a,6a-dimethyl-1,2,3,4,5,6-hexahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid To a solution of 2-[1-[2-[[(3aS,6aR)-3a,6a-dimethyl-5-oxa-2,3,4,6-tetrahydro-1H-pentalen-2-yl]oxy]-2-(2- methoxyphenyl)ethyl]-5-methyl-6-oxazol-2-yl-2,4-dioxo-thieno[2,3-d]pyrimid-3-yl]-2-methyl-propanoic acid (0.36 g, 0.57 mmol) in anhydrous methanol (10 mL) was added sodium borohydride (0.08 g, 2.0 mmol) in portions on an ice bath under $N_2$. The mixture was stirred at rt for 5 hours. The mixture was quenched with water (10 mL) by dropwise addition. The resulting mixture was extracted with ethyl acetate (20 mL×2). The combined organic phases were washed with saturated brine (20 mL), dried over anhydrous sodium sulfate, filtered by suction filtration. The filtrate was concentrated in vacuo. The residue was purified by silica gel chromatograph (PE/EtOAc (V/V)=1/1) to give the title compound as white solid (0.32 g, 89.0%).

MS (ESI, pos. ion) m/z: 638.3[M+H]$^+$;

$^1$H NMR (400 MHz, CDCl$_3$) δ 7.72 (s, 1H), 7.52 (d, J=6.7 Hz, 1H), 7.33-7.29 (m, 1H), 7.25 (s, 1H), 7.03 (t, J=7.4 Hz, 1H), 6.87 (d, J=8.2 Hz, 1H), 5.29-5.22 (m, 1H), 4.22-4.01 (s, 3H), 3.87 (s, 3H), 3.75-3.69 (m, 1H), 2.85 (s, 3H), 1.90 (s, 3H), 1.85 (s, 3H), 1.83-1.76 (m, 2H), 1.76-1.68 (m, 2H), 1.53-1.51 (m, 1H), 1.43-1.35 (m, 3H), 0.98 (s, 3H), 0.96 (s, 3H).

Example 8

2-[1-[2-[[(3aR,6aS)-5-amino-1,2,3,3a,4,5,6,6a-octahydropentalen-2-yl)oxy]-2-(2-methoxyphenyl)ethyl]-5-methyl-6-oxazol-2-yl2,4-dioxo-thieno[2,3-d]pyrimid-3-yl]-2-methyl-propanoic acid hydrochloride

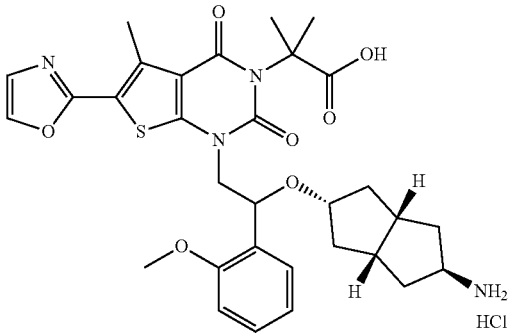 [SMILES: COc1ccccc1C(Cn1c(=O)n(C(C)(C)C(=O)O)c(=O)c2c(C)c(-c3ncco3)sc21)O[C@H]1C[C@H]2C[C@H](N)C[C@H]2C1 ; Cl]

Step 1) t-butyl 2-[1-[2-[[(3aR,6aS)-5-oxa-2,3,3a,4,6,6a-hexahydro-1H-pentalenyl-2-yl)oxy]ethyl]-5-methyl-6-oxazol-2-yl-2,4-dioxo-thieno[2,3-d]pyrimid-3-yl]-2-methyl-propionate t-Butyl 2-[1-[2-[(3'aR,6'aS)-5,5-dimethylspiro[1,3-dioxane-2,5'-2,3,3a,4,6,6a-hexahydro-1H-pentalenyl]-2'-yl]oxy]-2-(2-methoxyphenyl)ethyl]-5-methyl-6-oxazol-2-yl-2,4-dioxo-thieno[2,3-d]pyrimid-3-yl]-2-methyl-propionate (300 mg, 0.40 mmol) (prepared according to example 6) was dissolved in tetrahydrofuran (10 mL), and then hydrochloric acid aqueous solution (6.0 mL, 2 N) was added at rt. The mixture was stirred for 24 hours. To the mixture was added ethyl acetate (30 mL), and the mixture was stirred for 10 min. After the mixture was partitioned, the water phase was extracted with ethyl acetate (20 mL×2). The combined organic phases were washed with saturated aqueous NaCl and dried over anhydrous sodium sulfate, and filtered. The filtrate was concentrated in vacuo to get the title compound as light yellow oil (260 mg, 97.9%).

MS (ESI, pos. ion) m/z: 664.2[M+H]$^+$;

Step 2) t-butyl 2-[1-[2-[[(3aR,6aS)-5-hydroxy-1,2,3,3a,4,5,6,6a-octahydropentalen-2-yl)oxy]-2-(2-methoxyphenyl)ethyl]-5-methyl-6-oxazol-2-yl-2,4-dioxo-thieno[2,3-d]pyrimid-3-yl]-2-methyl-propionate t-Butyl 2-[1-[2-[[(3aR,6aS)-5-oxa-2,3,3a,4,6,6a-hexahydro-1H-pentalenyl-2-yl)oxy]ethyl]-5-methyl-6-oxazol-2-yl-2,4-dioxo-thieno[2,3-d]pyrimid-3-yl]-2-methyl-propionate (260 mg, 0.39 mmol) was dissolved in ethyl acetate (10.0 mL), the solution was cooled to 0° C. And then sodium borohydride (30 mg, 0.78 mmol) was added in portions. The mixture was stirred at 0° C. for 10 min, and then at rt for 30 min. The mixture was cooled to 0° C., and quenched with saturated aqueous ammonium chloride (0.5 mL). To the mixture was added water (10 mL) and ethyl acetate (20 mL), and the mixture was stirred for 10 min. After the mixture was partitioned, the water phase was extracted with ethyl acetate (20 mL×2). The combined organic phases were washed with saturated aqueous NaCl and dried over anhydrous sodium sulfate, and filtered. The filtrate was concentrated in vacuo to get the title compound as off-white solid (246 mg, 94.3%).

Step 3) t-butyl 2-[1-[2-[[(3aR,6aS)-5-methylsulfonyloxy-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate t-Butyl 2-[1-[2-[[(3aR,6aS)-5-hydroxy-1,2,3,3a,4,5,6,6a-octahydropentalen-2-yl)oxy]-2-(2-methoxyphenyl)ethyl]-5-methyl-6-oxazol-2-yl-2,4-dioxo-thieno[2,3-d]pyrimid-3-yl]-2-methyl-propionate (240 mg, 0.36 mmol) was dissolved in DCM (5.0 mL), and then triethylamine (0.1 mL, 0.70 mmol) was added. The solution was cooled to 0° C. And then methylsufonyl chloride (62 mg, 0.54 mmol) was added dropwise. The mixture was stirred at 0° C. for 1 hour. The mixture was quenched with water (5.0 mL), the mixture was stirred for 10 min. After the mixture was partitioned. The water phase was extracted with DCM (10.0 mL). The combined organic phases were washed with saturated brine (20 mL), dried over anhydrous sodium sulfate, and filtered. The filtrate was concentrated in vacuo. The residue was purified by silica gel chromatograph (PE/EtOAc (V/V)=7/3) to give the title compound as off-white solid (220 mg, 82.0%).

MS (ESI, pos. ion) m/z: 774.2[M+H]$^+$;

Step 4) t-butyl 2-[1-[2-[[(3aR,6aS)-5-azido-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate t-Butyl 2-[1-[2-[[(3aR,6aS)-5-methylsulfonyloxy-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate (220 mg, 0.30 mmol) was dissolved in N,N-dimethylformamide (3.0 mL), and then sodium azide (23 mg, 0.35 mmol) was added. The mixture was stirred at 60° C. for 23 hours. The mixture was quenched with water (10 mL), the mixture was stirred for 10 min. After the mixture was partitioned. The water phase was extracted with DCM (20 mL). The combined organic phases were washed with saturated brine (20 mL), dried over anhydrous sodium sulfate, and filtered. The filtrate was concentrated in vacuo. The residue was purified by silica gel chromatograph (PE/EtOAc (V/V)=7/3) to give the title compound as off-white solid (200 mg, 97.9%).

Step 5) t-butyl 2-[1-[2-[[(3aR,6aS)-5-amino-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate t-Butyl 2-[1-[2-[[(3aR,6aS)-5-azido-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate (200 mg, 0.29 mmol) was dissolved in methanol (5.0 mL), and then palladium on carbon (20 mg, 0.19 mmol, 10%) was added. The mixture was stirred at rt under $H_2$ for 1.5 hours. The mixture was filtered, the filter cake was washed with methanol (20 mL). The filtrate was concentrated in vacuo to get the title compound as off-white solid (165 mg, 85.7%).

MS (ESI, pos. ion) m/z: 665.3[M+H]$^+$;

Step 6) 2-[1-[2-[[(3aR,6aS)-5-amino-1,2,3,3a,4,5,6,6a-octahydropentalen-2-yl]oxy]-2-(2-methoxyphenyl)ethyl]-5-methyl-6-oxazol-2-yl2,4-dioxo-thieno[2,3-d]pyrimid-3-yl]-2-methyl-propanoic acid hydrochloride t-Butyl 2-[1-[2-[[(3aR,6aS)-5-amino-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate (165 mg, 0.25 mmol) was dissolved in a solution of hydrogen chloride in ethyl acetate (5.0 mL). The mixture was stirred at rt for 10 hours. The mixture was filtered. The filtrate was concentrated in vacuo. The residue was purified by pre-HPLC to get the title compound as off-white solid (7.0 mg, 4.4%).

MS (ESI, pos. ion) m/z: 609.2[M+H]$^+$;
$^1$H NMR (400 MHz, CD$_3$OD) δ 7.98 (s, 1H), 7.46 (d, J=7.3 Hz, 1H), 7.29 (d, J=11.9 Hz, 2H), 7.08-6.89 (m, 2H), 5.36-5.29 (m, 1H), 4.25-3.85 (m, 2H), 3.82 (s, 3H), 3.80-3.72 (m, 1H), 3.56-3.43 (m, 1H), 2.79 (s, 3H), 2.65-2.50 (m, 2H), 1.95 (m, 2H), 1.81 (s, 3H), 1.77 (s, 3H), 1.77-1.54 (m, 5H).

Example 9

2-[1-[2-(1,2,3,3a,4,5,6,6a-octahydrocyclopenteno[c]pyrrole-5-oxy)-2-(2-methoxyphenyl)ethyl]-5-methyl-6-oxazol-2-yl-2,4-dioxo-thieno[2,3-d]pyrimid-3-yl]-2-methyl-propanoic acid hydrochloride

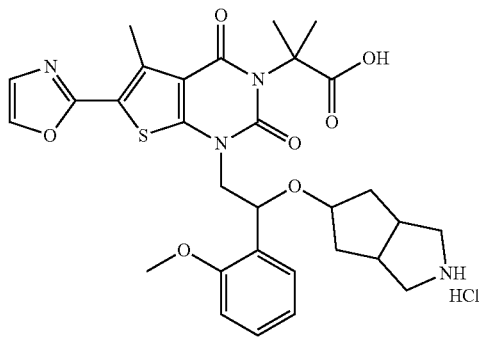 [SMILES: COc1ccccc1C(Cn1c(=O)n(C(C)(C)C(=O)O)c(=O)c2c(C)c(-c3ncco3)sc21)OC1CC2CNCC2C1 ; Cl]

Step 1) t-butyl 5-hydroxy-3,3a,4,5,6,6a-hexahydro-1H-cyclopenteno[c]pyrrole-2-carboxylate To a solution of t-butyl 5-oxo-1,3,3a,4,6,6a-hexahydro-cyclopenteno[c]pyrrole-2-carboxylate (2.50 g, 11.1 mmol) in anhydrous methanol (15 mL) was added sodium borohydride (0.56 g, 15.0 mmol) in portions on an ice bath under $N_2$. The mixture was stirred for 2 hours. The mixture was quenched with water (50 mL) by dropwise addition. The resulting mixture was extracted with ethyl acetate (120 mL×2). The combined organic phases were washed with saturated brine (50 mL), dried over anhydrous sodium sulfate, filtered by suction filtration. The filtrate was concentrated in vacuo. The residue was purified by silica gel chromatograph (PE/EtOAc (V/V)=2/1) to give the title compound as colorless oil (2.50 g, 99.1%).

Step 2) 2-[(2-t-butyloxycarboryl-3,3a,4,5,6,6a-hexahydro-1H-cyclopenteno[c]pyrrole-5-yl)oxy]-2-(2-methoxyphenyl)acetic acid To a solution of t-butyl 5-hydroxy-3,3a,4,5,6,6a-hexahydro-1H-cyclopenteno[c]pyrrole-2-carboxylate (2.50 g, 11.0 mmol) in anhydrous tetrahydrofuran (20 mL) was added sodium hydride (1.00 g, 25.0 mmol, 60%) in portions on an ice bath under $N_2$. After stirring for 15 min, a solution of 2-bromo-2-(methoxyphenyl)acetic acid (2.00 g, 8.16 mmol) in anhydrous tetrahydrofuran (10 mL) was added to the mixture. After the addition, the mixture was moved to rt and stirred for another 4 hours. The mixture was quenched with water (30 mL) by dropwise addition on an ice bath, the resulting mixture was extracted with ethyl acetate (30 mL×2). The combined water layers were adjusted to pH about 5 with dilute hydrochloric acid (2 N), and then extracted with ethyl acetate (30 mL×2). The combined organic layers were washed with saturated brine (30 mL), dried over anhydrous sodium sulfate, filtered by suction filtration. The filtrate was concentrated in vacuo to give the title compound as light yellow oil (2.80 g, 87.6%).

Step 3) t-butyl 5-[2-hydroxy-1-(2-methoxyphenyl)ethoxy]-3,3a,4,5,6,6a-hexahydro-1H-cyclopenteno[c]pyrrole-2-carboxylate To a solution of 2-[(2-t-butyloxycarboryl-3,3a,4,5,6,6a-hexahydro-1H-cyclopenteno[c]pyrrole-5-yl)oxy]-2-(2-methoxyphenyl)acetic acid (1.00 g, 2.55 mmol) in anhydrous tetrahydrofuran (20 mL) was added lithium aluminum hydride (0.17 g, 4.3 mmol) in portions on an ice bath. After the mixture was stable, the mixture was moved to rt and stirred for 2 hours. The mixture was quenched with water (0.17 mL) by dropwise addition on an ice bath. And then to the mixture were added sodium hydroxide solution (0.17 mL, 15%) and water (0.51 mL) in turn. The resulting mixture was stirred at rt for another 15 min, and anhydrous sodium sulfate was added, the mixture was further stirred for 15 min. The mixture was filtered by suction filtration. The filtrate was concentrated in vacuo. The residue was purified by silica gel chromatograph (PE/EtOAc (V/V)=6/1) to give the title compound as colorless oil (0.32 g, 33.1%).

MS (ESI, pos. ion) m/z: 400.3[M+Na]$^+$;

Step 4) t-butyl 5-[2-[3-(2-t-butoxy-1,1-dimethyl-2-oxo-ethyl)-5-methyl-6-oxazol-2-yl-2,4-dioxo-thieno[2,3-d]pyrimid-1-yl]-1-(2-methoxyphenyl)ethoxy]-3,3a,4,5,6,6a-hexahydro-1H-cyclopenteno[c]pyrrole-2-carboxylate t-Butyl 2-(6-bromo-5-methyl-2,4-dioxo-1H-thieno[2,3-d]pyrimid-3-yl)-2-methyl-propionate (0.95 g, 2.4 mmol), t-butyl 5-[2-hydroxy-1-(2-methoxyphenyl)ethoxy]-3,3a,4,5,6,6a-hexahydro-1H-cyclopenteno[c]pyrrole-2-carboxylate (0.80 g, 2.1 mmol), triphenylphosphine (1.10 g, 4.15 mmol) were dissolved in anhydrous tetrahydrofuran (25 mL) at rt under $N_2$. Diisopropylazodicarboxylate (0.90 g, 4.4 mmol) was added to the mixture under $N_2$, the resulting mixture was stirred at rt for 12 hours and concentrated in vacuo. The residue was purified by silica gel chromatograph (PE/EtOAc (V/V)=6/1) to give the title compound as white solid (0.78 g, 48.0%).

MS (ESI, pos. ion) m/z: 785.2[M+Na]$^+$;

Step 5) t-butyl 5-[2-[3-(2-t-butoxy-1,1-dimethyl-2-oxo-ethyl)-6-oxazol-2-yl-2,4-dioxo-thieno[2,3-d]pyrimid-1-yl]-1-(2-methoxyphenyl)ethoxy]-3,3a,4,5,6,6a-hexahydro-1H-cyclopenteno[c]pyrrole-2-carboxylate t-Butyl 5-[2-[3-(2-t-butoxy-1,1-dimethyl-2-oxo-ethyl)-5-methyl-6-oxazol-2-yl-2,4-dioxo-thieno[2,3-d]pyrimid-1-yl]-1-(2-methoxyphenyl)ethoxy]-3,3a,4,5,6,6a-hexahydro-1H-cyclopenteno[c]pyrrole-2-carboxylate (0.78 g, 1.0 mmol) and 2-tributylstannyloxazole (1.10 g, 3.07 mmol) were dissolved in toluene (20 mL) at rt under $N_2$, and then palladium tetrakis-(triphenylphosphine) (0.60 g, 0.52 mmol) was added. The mixture was stirred at 110° C. for 12 hours. The reaction mixture was concentrated in vacuo to remove the solvent, and the residue was purified by silica gel column chromatography (PE/EA (V/V)=6/1) to give the title compound as white solid (0.31 g, 40.0%).

MS (ESI, pos. ion) m/z: 773.3[M+Na]$^+$;

Step 6) 2-[1-[2-(1,2,3,3a,4,5,6,6a-octahydrocyclopenteno[c]pyrrole-5-oxy)-2-(2-methoxyphenyl)ethyl]-5-methyl-6-oxazol-2-yl-2,4-dioxo-thieno[2,3-d]pyrimid-3-yl]-2-methyl-propanoic acid hydrochloride t-Butyl 5-[2-[3-(2-t-butoxy-1,1-dimethyl-2-oxo-ethyl)-6-oxazol-2-yl-2,4-dioxo-thieno[2,3-d]pyrimid-1-yl]-1-(2-methoxyphenyl)ethoxy]-3,3a,4,5,6,6a-hexahydro-1H-cyclopenteno[c]pyrrole-2-carboxylate (0.27 g, 1.0 mmol) was dissolved in ethyl acetate (5 mL) at rt, and then a solution of HCl in EtOAc (5 mL) was added. The mixture was stirred at rt for 4 hours. The reaction mixture was concentrated in vacuo to remove the solvent, and the residue was purified by silica gel column chromatography (PE/EA (V/V)=1/1) to give the title compound as white solid (0.21 g, 98.0%).

MS (ESI, pos. ion) m/z: 595.8[M–HCl+H]$^+$;

$^1$H NMR (400 MHz, CDCl$_3$) δ 10.34 (s, 1H), 7.72 (s, 1H), 7.39-7.33 (m, 2H), 7.22 (s, 1H), 7.06-6.94 (m, 2H), 5.25 (m, 1H), 4.80 (m, 1H), 3.98 (s, 3H), 3.85 (m, 1H), 3.78 (m, 1H), 3.59 (m, 1H), 3.45 (s, 1H), 2.94 (m, 2H), 2.85 (s, 3H), 1.96 (s, 3H), 1.85 (s, 3H), 1.77 (m, 2H), 1.60 (m, 1H), 1.28-1.22 (m, 3H).

Example 10

2-[1-[2-(2-methoxyphenyl)-2-[(2-methylsulfonyl-3,3a,4,5,6,6a-hexahydro-1H-cyclopenteno[c]pyrrole-5-yl)oxy]ethyl]-5-methyl-6-oxazol-2-yl-2,4-dioxo-thieno[2,3-d]pyrimid-3-yl]-2-methyl-propanoic acid

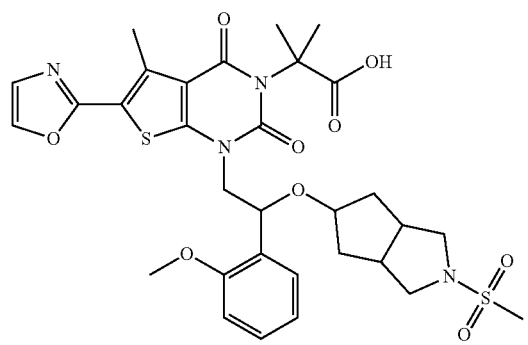 [SMILES: COc1ccccc1C(Cn1c(=O)n(C(C)(C)C(=O)O)c(=O)c2c(C)c(-c3ncco3)sc21)OC1CC2CN(S(C)(=O)=O)CC2C1]

Step 1) t-butyl 5-benzyloxy-3,3a,4,5,6,6a-hexahydro-1H-cyclopenteno[c]pyrrole-2-carboxylate t-Butyl 5-hydroxy-3,3a,4,5,6,6a-hexahydro-1H-cyclopenteno[c]pyrrole-2-carboxylate (2.60 g, 11.4 mmol) was dissolved in tetrahydrofuran (50 mL). The solution was cooled to 0° C., and sodium hydride (0.686 g, 17.15 mmol, 60%) was added in portions. After the addition, the mixture was moved to rt and stirred for 30 min, and then benzyl bromide (2.54 g, 14.9 mmol) was added slowly. The mixture was stirred at rt overnight. The mixture was poured into ice water. The resulting mixture was extracted with ethyl acetate (300 mL×2). The combined organic phases were washed with saturated brine, dried over anhydrous sodium sulfate, filtered by suction filtration. The filtrate was concentrated in vacuo. The residue was purified by silica gel chromatograph (PE/EtOAc (V/V)=6/1) to give the title compound as yellow oil (2.63 g, 72.4%).

MS (ESI, pos. ion) m/z: 340.5[M+Na]$^+$;

Step 2) 5-benzyloxy-1,2,3,3a,4,5,6,6a-octahydrocyclopenteno[c]pyrrole hydrochloride t-Butyl 5-benzyloxy-3,3a,4,5,6,6a-hexahydro-1H-cyclopenteno[c]pyrrole-2-carboxylate was dissolved in a solution of HCl in EtOAc (15 mL). The mixture was stirred for 1 hour. The mixture was filter. The filter cake was washed with EtOAc (3 mL×3) and dried in vacuo to get the title compound as yellow solid (1.20 g, 100%). This crude product was used in next step without further purification.

MS (ESI, pos. ion) m/z: 218.4[M+H]$^+$;

Step 3) 5-benzyloxy-2-methylsulfonyl-3,3a,4,5,6,6a-hexahydro-1H-cyclopenteno[c]pyrrole 5-Benzyloxy-1,2,3,3a,4,5,6,6a-octahydrocyclopenteno[c]pyrrole hydrochloride (1.52 g, 6.99 mmol) was dissolved in DCM (30 mL), and then triethylamine (2.95 mL, 0.70 mmol) was added. The solution was cooled to 0° C. And then methylsufonyl chloride (1.20 g, 10.49 mmol) was added dropwise. The mixture was stirred at rt for 2.5 hour. The mixture was quenched with water (10 mL), the mixture was stirred for 10 min. After the mixture was partitioned. The water phase was extracted with DCM (20 mL×2). The combined organic phases were washed with saturated brine, dried over anhydrous sodium sulfate, and filtered. The filtrate was concentrated in vacuo. The residue was purified by silica gel chromatograph (PE/EtOAc (V/V)=3/1) to give the title compound as an off-white solid (1.76 g, 85.2%).

MS (ESI, pos. ion) m/z: 296.3[M+H]$^+$;

Step 4) 2-methylsulfonyl-3,3a,4,5,6,6a-hexahydro-1H-cyclopenteno[c]pyrrole-5-ol 5-Benzyloxy-2-methylsulfonyl-3,3a,4,5,6,6a-hexahydro-1H-cyclopenteno[c]pyrrole (1.76 g, 5.96 mmol) was dissolved in methanol (50 mL), and then palladium hydroxide (176 mg, 1.25 mmol) and glacial acetic acid (2.0 mL) were added. The system was replaced with hydrogen gas 3 times, and the mixture was stirred at rt under the hydrogen pressure of 4.0 MPa for 24 hours. The mixture was filtered. The filtrate was concentrated in vacuo to get the title compound as a light yellow oil (1.16 g, 94.8%).

MS (ESI, pos. ion) m/z: 206.1[M+H]$^+$;

Step 5) 2-(2-methoxyphenyl)-2-[(2-methylsulfonyl-3,3a,4,5,6,6a-hexahydro-1H-cyclopenteno[c]pyrrole-5-yl)oxy]acetic acid 2-Methylsulfonyl-3,3a,4,5,6,6a-hexahydro-1H-cyclopenteno[c]pyrrole-5-ol (1.16 g, 5.65 mmol) was dissolved in tetrahydrofuran (50 mL). The mixture was cooled to 0° C. under N$_2$, and sodium hydride (678 mg, 16.95 mmol, 60%) was added. The mixture was stirred for 10 min and further stirred at rt for 30 min, and then 2-bromo-2-(2-fluorophenyl)acetic acid (1.52 g, 6.22 mmol) was added. The resulting mixture was stirred at rt for 18 hours. The mixture was poured into ice water (50 g) to quenched the reaction, and then ethyl acetate (50 mL) was added. The mixture was stirred for 10 min. After the mixture was partitioned, the water phase was adjusted to pH about 2 with dilute hydrochloric acid (1 N) and extracted with ethyl acetate (100 mL×2). The combined organic phases were washed with saturated aqueous NaCl and dried over anhydrous sodium sulfate, and filtered. The filtrate was concentrated in vacuo to get the title compound as a light yellow oil (1.96 g, 93.9%).

MS (ESI, pos. ion) m/z: 370.2[M+H]$^+$;

Step 6) 2-(2-methoxyphenyl)-2-[(2-methylsulfonyl-3,3a,4,5,6,6a-hexahydro-1H-cyclopenteno[c]pyrrole-5-yl)oxy]ethanol 2-(2-Methoxyphenyl)-2-[(2-methylsulfonyl-3,3a,4,5,6,6a-hexahydro-1H-cyclopenteno[c]pyrrole-5-yl)oxy]acetic acid (1.96 g, 5.31 mmol) was dissolved in tetrahydrofuran (50 mL). The mixture was cooled to −5° C. under N$_2$, and lithium aluminum hydride (0.519 g, 13.26 mmol) was added in portions. The mixture was stirred for 2 hours. To the mixture were added water (0.3 mL), sodium hydroxide aqueous solution (0.3 mL, 10%) and water (1.0 mL) dropwise slowly in turn. And then anhydrous sodium sulfate was added, the resulting mixture was stirred at rt for 30 min. The mixture was filtered. The filter cake was washed with EtOAc (10 mL×4). The filtrate was concentrated in vacuo. The residue was purified by silica gel chromatograph (PE/EtOAc (V/V)=4/1) to give the title compound as a light yellow oil (0.340 g, 18.0%).

MS (ESI, pos. ion) m/z: 378.2[M+Na]$^+$;

Step 7) t-butyl(diphenyl)silyl 2-[1-[2-(2-methoxyphenyl)-2-[(2-methylsulfonyl-3,3a,4,5,6,6a-hexahydro-1H-cyclopenteno[c]pyrrole-5-yl)oxy]-5-methyl-6-oxazol-2-yl-2,4-dioxo-thieno[2,3-d]pyrimid-3-yl]-2-methyl-propionate 2-(2-Methoxyphenyl)-2-[(2-methylsulfonyl-3,3a,4,5,6,6a-hexahydro-1H-cyclopenteno[c]pyrrole-5-yl)oxy]ethanol (130 mg, 0.36 mmol), diisopropyl azodicarboxylate (143 mg, 0.69 mmol) and t-butyl(diphenyl)silyl 2-methyl-2-(5-methyl-6-oxazol-2-yl-2,4-dioxo-1H-thieno[2,3-d]pyrimid-3-yl)-propionate (200 mg, 0.34 mmol) were dissolved in tetrahydrofuran (10.0 mL). To the mixture was added triphenylphosphine (184 mg, 0.69 mmol) in portions under N$_2$. The mixture was stirred at rt for 13 hours. The reaction mixture was concentrated in vacuo to remove the solvent, and the residue was purified by silica gel column chromatography (PE/EA (V/V)=15/1) to give the title compound as an off-white solid (300 mg, 94.4%).

Step 8) 2-[1-[2-(2-methoxyphenyl)-2-[(2-methylsulfonyl-3,3a,4,5,6,6a-hexahydro-1H-cyclopenteno[c]pyrrole-5-yl)oxy]ethyl]-5-methyl-6-oxazol-2-yl-2,4-dioxo-thieno[2,3-d]pyrimid-3-yl]-2-methyl-propanoic acid t-Butyl(diphenyl)silyl 2-[1-[2-(2-methoxyphenyl)-2-[(2-methylsulfonyl-3,3a,4,5,6,6a-hexahydro-1H-cyclopenteno[c]pyrrole-5-yl)oxy]-5-methyl-6-oxazol-2-yl-2,4-dioxo-thieno[2,3-d]pyrimid-3-yl]-2-methyl-propionate (300 mg, 0.33 mmol) was dissolved in tetrahydrofuran (2.0 mL). To the mixture was added a solution of tetrabutylammonium fluoride in tetrahydrofuran (1.0 mol/L, 0.45 mL, 0.45 mmol). The mixture was stirred at rt for 20 min. The mixture was quenched with water (10 mL). The resulting mixture was extracted with ethyl acetate (20 mL×2). The combined organic phases were washed with saturated brine, dried over anhydrous sodium sulfate, and filtered. The filtrate was concentrated in vacuo. The residue was purified by pre-HPLC to give the title compound as an off-white solid (51 mg, 23.0%).

MS (ESI, pos. ion) m/z: 673.1 [M+H]$^+$;

$^1$H NMR (400 MHz, CDCl$_3$) δ 7.71 (d, J=16.2 Hz, 1H), 7.47-7.28 (m, 2H), 7.04-6.94 (m, 1H), 6.90-6.85 (m, 1H), 4.58-4.55 (m, 1H), 3.92-3.86 (m, 3H), 3.85 (s, 3H), 3.38-3.29 (m, 2H), 3.25-3.18 (m, 2H), 2.95-2.91 (m, 3H), 2.90-2.61 (m, 3H), 2.59-2.55 (m, 2H), 2.24-1.98 (m, 2H), 1.91 (s, 3H), 1.81 (s, 3H), 1.69-1.52 (m, 2H).

Example 11

2-[1-[2-(6-azaspiro[3.3]heptane-2-oxy-2-(2-methoxyphenyl)ethyl]-5-methyl-6-oxazol-2-yl-2,4-dioxo-thieno[2,3-d]pyrimid-3-yl]-2-methyl-propanoic acid hydrochloride

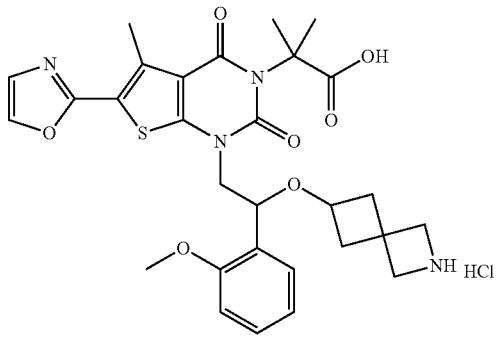 [SMILES: COc1ccccc1C(Cn1c(=O)n(C(C)(C)C(=O)O)c(=O)c2c(C)c(-c3ncco3)sc21)OC1CC2(CNC2)C1 ; Cl]

Step 1) t-butyl 2-hydroxy-6-azaspiro[3.3]heptane-6-carboxylate t-Butyl 2-oxo-6-azaspiro[3.3]heptane-6-carboxylate (2.00 g, 9.47 mmol) was dissolved in EtOAc (40 mL). The mixture was cooled to 0° C., and sodium borohydride (548 mg, 14.19 mmol) was added in portions, the mixture was stirred for 10 min at 0° C., and then further stirred at rt for 30 min. The mixture was cooled to 0° C., and quenched with saturated aqueous ammonium chloride (2.0 mL). The mixture was stirred for 30 min, water (20 mL) and ethyl acetate (50 mL) were added, and the mixture was stirred for 10 min. After the mixture was partitioned, the water phase was extracted with ethyl acetate (100 mL×2). The combined organic phases were washed with saturated aqueous NaCl and dried over anhydrous sodium sulfate, and filtered. The filtrate was concentrated in vacuo to get the title compound as an off-white solid (1.80 g, 89.2%).

MS (ESI, pos. ion) m/z: 236.1[M+H]$^+$;

Step 2) 2-[(6-t-butoxycarbonyl-6-azaspiro[3.3]heptane-2-yl)oxy]-2-(2-methoxyphenyl)acetic acid t-Butyl 2-hydroxy-6-azaspiro[3.3]heptane-6-carboxylate (1.80 g, 8.44 mmol) was dissolved in tetrahydrofuran (40 mL). The mixture was cooled to 0° C. under N$_2$, and sodium hydride (1.01 g, 25.3 mmol, 60%) was added. The mixture was stirred for 10 min and further stirred at rt for 30 min, and then 2-bromo-2-(2-methoxyphenyl)acetic acid (1.86 g, 7.59 mmol) was added. The resulting mixture was stirred at rt for 18 hours. The mixture was cooled to 0° C., and quenched with saturated aqueous ammonium chloride (0.5 mL). The mixture was stirred for 30 min, water (10 mL) and ethyl acetate (20 mL) were added, and the mixture was stirred for 10 min. After the mixture was partitioned, the water phase was adjusted to pH about 3 with dilute hydrochloric acid (1 N) and extracted with ethyl acetate (20 mL×2). The combined organic phases were washed with saturated aqueous NaCl and dried over anhydrous sodium sulfate, and filtered. The filtrate was concentrated in vacuo to get the title compound as a red oil (2.9 g, 90.9%).

MS (ESI, pos. ion) m/z: 400.1[M+Na]$^+$;

Step 3) t-butyl 2-[2-hydroxy-1-(2-methoxyphenyl)ethoxy]-6-azaspiro[3.3]heptane-6-carboxylate 2-[(6-t-Butoxycarbonyl-6-azaspiro[3.3]heptane-2-yl)oxy]-2-(2-methoxyphenyl)acetic acid (1.00 g, 2.65 mmol) was dissolved in tetrahydrofuran (30 mL). The mixture was cooled to 0° C. under N$_2$, and lithium aluminum hydride (207 mg, 5.29 mmol) was added in portions. The mixture was stirred for 2 hours. To the mixture were added water (0.3 mL), sodium hydroxide aqueous solution (0.3 mL, 10%) and water (1.0 mL) dropwise slowly in turn. And then the mixture was stirred at rt, anhydrous sodium sulfate was added, the resulting mixture was further stirred at rt for 30 min. The mixture was filtered. The filter cake was washed with EtOAc (10 mL×4). The filtrate was concentrated in vacuo. The residue was purified by silica gel chromatograph (PE/EtOAc (V/V)=7/3) to give the title compound as an off-white solid (416 mg, 43.1%).

MS (ESI, pos. ion) m/z: 386.5[M+Na]$^+$;

Step 4) t-butyl 2-[2-[3-[2-t-butyl(diphenyl)silyl]oxy-1,1-dimethyl-2-oxa-ethyl]-5-methyl-6-oxazol-2-yl-2,4-dioxo-thieno[2,3-d]pyrimid-1-yl]-1-(2-methoxyphenyl)ethoxy]-6-azaspiro[3.3]heptane-6-carboxylate t-Butyl 2-[2-hydroxy-1-(2-methoxyphenyl)ethoxy]-6-azaspiro[3.3]heptane-6-carboxylate (209 mg, 0.57 mmol), triphenylphosphine (278 mg, 1.05 mmol) and t-butyl(diphenyl)silyl 2-methyl-2-(5-methyl-6-oxazol-2-yl-2,4-dioxo-1H-thieno[2,3-d]pyrimid-3-yl)propionate (300 mg, 0.52 mmol) (prepared according to the method of compound 95.4 described in WO2013071169A1) were added to tetrahydrofuran (6 mL), diisopropyl azodicarboxylate (216 mg, 1.05 mmol) was added dropwise under N$_2$. The mixture was stirred at rt for 15 hours and concentrated in vacuo. The residue was purified by silica gel chromatograph (PE/EtOAc (V/V)=79/1) to give the title compound as an off-white solid (244 mg, 50.7%).

Step 5) 2-[1-[2-(6-azaspiro[3.3]heptane-2-oxy)-2-(2-methoxyphenyl)ethyl]-5-methyl-6-oxazol-2-yl-2,4-dioxo-thieno[2,3-d]pyrimid-3-yl]-2-methyl-propanoic acid hydrochloride t-Butyl 2-[2-[3-[2-t-butyl(diphenyl)silyl]oxy-1,1-dimethyl-2-oxa-ethyl]-5-methyl-6-oxazol-2-yl-2,4-dioxo-thieno[2,3-d]pyrimid-1-yl]-1-(2-methoxyphenyl)ethoxy]-6-azaspiro[3.3]heptane-6-carboxylate (244 mg, 1.0 mmol) was dissolved in a solution of HCl in EtOAc (5.0 mL). The mixture was stirred at rt for 1 hour. The mixture was filtered. The filtrate was concentrated in vacuo. The residue was purified by pre-HPLC to get the title compound as an off-white solid (54 mg, 32.9%).

MS (ESI, pos. ion) m/z: 581.1 [M+H]$^+$;

$^1$H NMR (400 MHz, CD$_3$OD) δ 7.98 (s, 1H), 7.46-7.41 (m, 1H), 7.32-7.25 (m, 2H), 7.01 (t, J=7.4 Hz, 1H), 6.94 (d, J=8.2 Hz, 1H), 5.21-5.15 (m, 1H), 4.11-4.06 (m, 1H), 4.05-4.02 (m, 1H), 3.95 (s, 2H), 3.92 (d, J=2.5 Hz, 2H), 3.86-3.80 (m, 4H), 2.79 (s, 3H), 2.53-2.41 (m, 2H), 2.18-2.11 (m, 1H), 2.07-2.00 (m, 1H), 1.80 (s, 3H), 1.77 (s, 3H).

Example 12

2-[1-[2-(2-methoxyphenyl)-2-[(6-methyl-6-azaspiro[3.3]heptane-2-yl)oxy]ethyl]-5-methyl-6-oxazol-2-yl-2,4-dioxo-thieno[2,3-d]pyrimid-3-yl]-2-methyl-propanoic acid

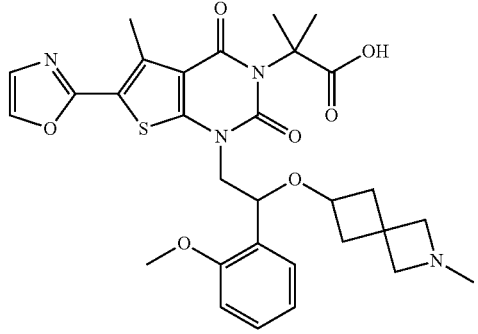 [SMILES: COc1ccccc1C(Cn1c(=O)n(C(C)(C)C(=O)O)c(=O)c2c(C)c(-c3ncco3)sc21)OC1CC2(C1)CN(C)C2]

Step 1) 2-(2-methoxyphenyl)-2-[(6-methyl-6-azaspiro[3.3]heptane-2-yl)oxy]ethanol 2-[(6-t-Butoxycarbonyl-6-azaspiro[3.3]heptane-2-yl)oxy]-2-(2-methoxyphenyl)acetic acid (800 mg, 2.12 mmol) (prepared according to step 2 of example 11) was dissolved in tetrahydrofuran (10.0 mL). The mixture was cooled to 0° C. under $N_2$, and lithium aluminum hydride (248 mg, 6.34 mmol) was added in portions. The mixture was stirred at 40° C. for 2 hours. To the mixture were added water (0.3 mL), sodium hydroxide aqueous solution (0.3 mL, 10%) and water (1.0 mL) dropwise slowly in turn. And then the mixture was stirred at rt, anhydrous sodium sulfate was added, the resulting mixture was further stirred at rt for 30 min. The mixture was filtered. The filter cake was washed with EtOAc (10 mL×4). The filtrate was concentrated in vacuo. The residue was purified by silica gel chromatograph (MeOH/DCM (V/V)=1/9) to give the title compound as a light yellow oil (330 mg, 56.1%).

MS (ESI, pos. ion) m/z: 278.1[M+H]$^+$;

Step 2) t-butyl(diphenyl)silyl 2-[1-[2-(2-methoxyphenyl)-2-[(6-methyl-6-azaspiro[3.3]heptane-2-yl)oxy]ethyl]-5-methyl-6-oxazol-2-yl-2,4-dioxo-thieno[2,3-d]pyrimid-3-yl]-2-methyl-propionate 2-(2-Methoxyphenyl)-2-[(6-methyl-6-azaspiro[3.3]heptane-2-yl)oxy]ethanol (265 mg, 0.95 mmol), diisopropyl azodicarboxylate (260 mg, 1.74 mmol) and t-butyl(diphenyl)silyl 2-methyl-2-(5-methyl-6-oxazol-2-yl-2,4-dioxo-1H-thieno[2,3-d]pyrimid-3-yl)-propionate (500 mg, 0.87 mmol) (prepared according to the preparation method of compound 95.4 described in WO2013071169A1) were dissolved in tetrahydrofuran (20.0 mL). To the mixture was added a solution of triphenylphosphine (462 mg, 1.74 mmol) in tetrahydrofuran (3.0 mL) dropwise under $N_2$. The mixture was stirred at rt for 4 hours. The mixture was concentrated in vacuo. The residue was purified by column chromatography on silica gel eluted with (methanol/dichloromethane (V/V)=1/9) to give the title compound as an off-white solid, 500 mg, 68.8%).

MS (ESI, pos. ion) m/z: 595.1[M-TBDPS+H]$^+$;

Step 3) 2-[1-[2-(2-methoxyphenyl)-2-[(6-methyl-6-azaspiro[3.3]heptane-2-yl)oxy]ethyl]-5-methyl-6-oxazol-2-yl-2,4-dioxo-thieno[2,3-d]pyrimid-3-yl]-2-methyl-propanoic acid t-Butyl(diphenyl)silyl 2-[1-[2-(2-methoxyphenyl)-2-[(6-methyl-6-azaspiro[3.3]heptane-2-yl)oxy]ethyl]-5-methyl-6-oxazol-2-yl-2,4-dioxo-thieno[2,3-d]pyrimid-3-yl]-2-methyl-propionate (500 mg, 0.60 mmol) was dissolved in tetrahydrofuran (10.0 mL). To the mixture was added a solution of tetrabutylammonium fluoride in tetrahydrofuran (1.0 mmol/L, 3.6 mL, 3.60 mmol). The mixture was stirred at rt for 3 hours. The mixture was concentrated in vacuo. The residue was purified by pre-HPLC to get the title compound as an off-white solid (120 mg, 33.6%).

MS (ESI, pos. ion) m/z: 595.1 [M+H]$^+$;
$^1$H NMR (400 MHz, DMSO-d$_6$) δ 8.22 (s, 1H), 7.44-7.34 (m, 2H), 7.32-7.25 (m, 1H), 7.30-6.96 (m, 2H), 5.08-4.96 (m, 1H), 4.12-4.03 (m, 1H), 4.02-3.92 (m, 1H), 3.77 (s, 3H), 3.75-3.70 (m, 1H), 3.69-3.66 (m, 2H), 3.65-3.60 (m, 2H), 2.74 (s, 3H), 2.51 (s, 3H), 2.35-2.29 (m, 2H), 1.95-1.91 (m, 1H), 1.83-1.78 (m, 1H), 1.67 (s, 3H), 1.64 (s, 3H).

Example 13

2-[1-[2-(3,3a,4,5,6,6a-hexahydro-1H-cyclopenteno[c]furan5-oxy)-2-(2-methoxyphenyl)ethyl]-5-methyl-6-oxazol-2-yl-2,4-dioxo-thieno[2,3-d]pyrimid-3-yl]-2-methyl-propanoic acid

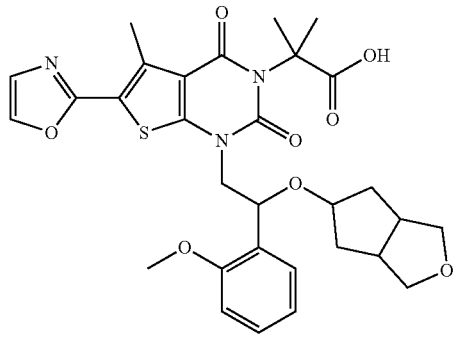 [SMILES: COc1ccccc1C(Cn1c(=O)n(C(C)(C)C(=O)O)c(=O)c2c(C)c(-c3ncco3)sc21)OC1CC2COCC2C1]

Step 1) dimethyl 4-oxocyclopentane-1,2-dicarboxylate

To a solution of 4-oxocyclopentane-1,2-dicarboxylic acid (20.00 g, 58.09 mmol) in methanol (150 mL) was added thionyl chloride (25.3 mL, 349 mmol) dropwise at rt. The mixture was stirred at 66° C. for 2 hours. The mixture was cooled to rt and quenched with water (200 mL). The resulting mixture was extracted with EtOAc (300 mL). The organic layer was washed with saturated sodium bicarbonate solution (100 mL) and sodium chloride solution (100 mL) in turn, and dried over anhydrous sodium sulfate, and concentrated in vacuo to get the title compound as a white solid (23.26 g, 100%).

Step 2) dimethyl 4-hydroxycyclopentane-1,2-dicarboxylate

To a solution of dimethyl 4-oxocyclopentane-1,2-dicarboxylate (10.00 g, 49.95 mmol) in methanol (50 mL) was added sodium borohydride (2.32 g, 60.1 mmol) at −5° C. After the addition, the mixture was stirred for 2 hours. The mixture were quenched with saturated ammonium chloride solution (10 mL). And then anhydrous sodium sulfate (10 g) was added, the resulting mixture was stirred for 10 min. The mixture was filtered by suction filtration. The filter cake was washed with EtOAc (10 mL×2). The filtrate was concentrated in vacuo. The residue was purified by silica gel chromatograph (PE/EtOAc (V/V)=1/1) to give the title compound as a colorless oil (6.14 g, 60.77%).

Step 3) dimethyl 4-benzyloxycyclopentane-1,2-dicarboxylate

To a solution of dimethyl 4-hydroxycyclopentane-1,2-dicarboxylate (6.13 g, 30.3 mmol) in anhydrous N,N-dimethylformamide (60 mL) was added sodium hydride (1.82 g, 45.5 mmol, 60%) in portions on an ice bath. The mixture was stirred at rt for 30 min, and then benzyl bromide (7.2 mL, 61 mmol) was added dropwise slowly. After the addition, the mixture was stirred at rt for 2 hours. The mixture was quenched with water (40 mL) by dropwise addition. The resulting mixture was extracted with ethyl acetate (50 mL×2). The combined organic phases were washed with saturated brine (50 mL), dried over anhydrous sodium sulfate, filtered by suction filtration. The filtrate was concentrated in vacuo. The residue was purified by silica gel chromatograph (PE/EtOAc (V/V)=6/1) to give the title compound as a light yellow oil (3.84 g, 43.3%).

MS (ESI, pos. ion) m/z: 293.2[M+H]$^+$;

Step 4) [4-benzyloxy-2-(hydroxymethyl)cyclopentyl]methanol

To a solution of dimethyl 4-benzyloxycyclopentane-1,2-dicarboxylate (3.84 g, 13.1 mmol) in anhydrous tetrahydrofuran (40 mL) was added lithium aluminum hydride (2.00 g, 51 mmol) in portions on an ice bath. The mixture was moved to rt and stirred overnight. The mixture was quenched with water (100 mL) by dropwise addition. The resulting mixture was adjusted to pH about 3 with hydrochloric acid (4 N) and extracted with ethyl acetate (100 mL×2). The combined organic phases were washed with saturated brine (100 mL), dried over anhydrous sodium sulfate, filtered by suction filtration. The filtrate was concentrated in vacuo. The residue was purified by silica gel chromatograph (PE/EtOAc (V/V)=1/2) to give the title compound as a light yellow oil (1.60 g, 52%).

$^1$H NMR (400 MHz, CDCl$_3$) δ 7.38-7.27 (m, 5H), 4.47 (s, 2H), 4.03-3.97 (m, 1H), 3.74-3.66 (m, 2H), 3.47 (t, J=9.7 Hz, 1H), 3.34 (t, J=9.9 Hz, 1H), 2.23-2.05 (m, 2H), 2.05-1.96 (m, 1H), 1.96-1.84 (m, 1H), 1.53-1.38 (m, 2H).

Step 5) 5-benzyloxy-3,3a,4,5,6,6a-hexahydro-1H-cyclopenteno[c]furan

To a solution of [4-benzyloxy-2-(hydroxymethyl)cyclopentyl]methanol (1.54 g, 6.52 mmol) in anhydrous tetrahydrofuran (40 mL) was added n-butyllithium (2.9 mL, 7.3 mmol, 2.5 mol/L) dropwise slowly at −20° C. under N$_2$. The mixture was stirred for 30 min, and a solution of p-toluenesulfochloride (1.38 g, 7.17 mmol) in anhydrous tetrahydrofuran (10 mL) was added. The mixture was moved to rt and stirred for 1 hour. The mixture was cooled to −20° C., and n-butyllithium (2.9 mL, 7.3 mmol, 2.5 mol/L) was added dropwise slowly. The resulting mixture was stirred for 10 min, and heated to 70° C. and stirred overnight. The mixture was quenched with water (50 mL) by dropwise addition. The resulting mixture was extracted with ethyl acetate (100 mL×2). The combined organic phases were washed with saturated brine (50 mL), dried over anhydrous sodium sulfate, filtered by suction filtration. The filtrate was concentrated in vacuo. The residue was purified by silica gel chromatograph (PE/EtOAc (V/V)=5/1) to give the title compound as a colorless oil (1.22 g, 85.8%).

MS (ESI, pos. ion) m/z: 219.1[M+H]$^+$;

$^1$H NMR (400 MHz, CDCl$_3$) δ 7.41-7.28 (m, 5H), 4.55 (dd, J=13.2, 6.6 Hz, 1H), 4.50 (s, 2H), 3.90 (dt, J=11.3, 6.9 Hz, 2H), 3.38 (dd, J=10.9, 7.1 Hz, 1H), 3.30 (dd, J=10.9, 7.1 Hz, 1H), 2.50-2.36 (m, 1H), 2.29 (dt, J=12.6, 6.5 Hz, 1H), 2.04-1.88 (m, 2H), 1.55 (td, J=12.7, 7.7 Hz, 1H), 1.44 (td, J=12.3, 5.5 Hz, 1H).

Step 6) 3,3a,4,5,6,6a-hexahydro-1H-cyclopenteno[c]furan-5-ol

5-Benzyloxy-3,3a,4,5,6,6a-hexahydro-1H-cyclopenteno[c]furan (1.22 g, 5.59 mmol) was dissolved in anhydrous methanol (10 mL), and glacial acetic acid (6 mL) and Pd/C (0.15 g, 10%) were added. The mixture was stirred under the hydrogen pressure of 5 MPa at rt for 3 hours. The reaction was stopped and filtered by suction filtration. The filtrate was concentrated in vacuo. The residue was dissolved in ethyl acetate (50 mL). The mixture was washed with saturated brine (30 mL×2), dried over anhydrous sodium sulfate, filtered by suction filtration. The filtrate was concentrated in vacuo. The residue was purified by silica gel chromatograph (EtOAc) to give the title compound as a colorless oil (0.60 g, 83.8%).

Step 7) 2-(3,3a,4,5,6,6a-hexahydro-1H-cyclopenteno[c]furan-5-oxy)-2-(2-methoxyphenyl) acetic acid 3,3a,4,5,6,6a-Hexahydro-1H-cyclopenteno[c]furan-5-ol (0.60 g, 4.68 mmol) was dissolved in tetrahydrofuran (25 mL). The mixture was cooled to 0° C. under N$_2$, and sodium hydride (0.75 g, 19 mmol, 60%) was added. The mixture was stirred for 10 min and further stirred at rt for 30 min, and then 2-bromo-2-(2-fluorophenyl)acetic acid (1.15 g, 4.69 mmol) was added. The resulting mixture was stirred at rt for 4.5 hours. The mixture was poured into ice water (50 g) to quenched the reaction, and then ethyl acetate (40 mL) was added. The mixture was stirred for 10 min. After the mixture was partitioned, the water phase was adjusted to pH about 2 with dilute hydrochloric acid (4N) and extracted with ethyl acetate (50 mL×2). The combined organic phases were washed with saturated aqueous NaCl and dried over anhydrous sodium sulfate, and filtered. The filtrate was concentrated in vacuo to get the title compound as a light yellow oil (1.29 g, 94.3%).

MS (ESI, neg. ion) m/z: 291.3[M−H]$^-$;

Step 8) 2-(3,3a,4,5,6,6a-hexahydro-1H-cyclopenteno[c]furan-5-oxy)-2-(2-methoxyphenyl) ethanol 2-(3,3a,4,5,6,6a-Hexahydro-1H-cyclopenteno[c]furan-5-oxy)-2-(2-methoxyphenyl)acetic acid (1.29 g, 4.41 mmol) was dissolved in tetrahydrofuran (30 mL). The mixture was cooled to −5° C. under N$_2$, and lithium aluminum hydride (0.34 g, 9.0 mmol) was added in portions. The mixture was stirred overnight. The mixture was quenched with water (30 mL) by dropwise addition. The resulting mixture was adjusted to pH about 2 with hydrochloric acid (4 N) and extracted with ethyl acetate (100 mL×2). The combined organic phases were washed with saturated brine (50 mL), dried over anhydrous sodium sulfate, filtered by suction filtration. The filtrate was concentrated in vacuo. The residue was purified by silica gel chromatograph (PE/EtOAc (V/V)=1/1) to give the title compound as a light yellow oil (0.566 g, 46.1%).

$^1$H NMR (400 MHz, CDCl$_3$) δ 7.38 (t, J=6.2 Hz, 1H), 7.31-7.26 (m, 1H), 7.00 (t, J=7.5 Hz, 1H), 6.88 (d, J=8.2 Hz, 1H), 4.94 (dd, J=8.2, 3.2 Hz, 1H), 4.43 (dd, J=32.3, 6.7 Hz, 1H), 3.95-3.85 (m, 2H), 3.84 (s, 3H), 3.71-3.64 (m, 1H), 3.54 (dt, J=11.4, 7.7 Hz, 1H), 3.42-3.33 (m, 1H), 3.28-3.22 (m, 1H), 2.50-2.26 (m, 1H), 2.25-2.10 (m, 1H), 1.94-1.89 (m, 1H), 1.87-1.79 (m, 1H), 1.51-1.41 (m, 2H).

Step 9) t-butyl(diphenyl)silyl 2-[1-[2-(3,3a,4,5,6,6a-hexahydro-1H-cyclopenteno[c]furan-5-oxy)-2-(2-methoxyphenyl)ethyl]-5-methyl-6-oxazol-2-yl-2,4-dioxo-thieno[2,3-d]pyrimid-3-yl]-2-methyl-propionate 2-(3,3a,4,5,6,6a-Hexahydro-1H-cyclopenteno[c]furan-5-oxy)-2-(2-methoxyphenyl)ethanol (0.212 g, 0.762 mmol), diisopropyl azodicarboxylate (0.2 mL, 1.0 mmol) and t-butyl(diphenyl)silyl 2-methyl-2-(5-methyl-6-oxazol-2-yl-2,4-dioxo-1H-thieno[2,3-d]pyrimid-3-yl)-propionate (0.350 g, 0.61 mmol) were dissolved in tetrahydrofuran (10.0 mL). To the mixture was added triphenylphosphine (0.245 mg, 0.915 mmol) in portions under N$_2$. The mixture was stirred at rt for 18 hours. The reaction mixture was concentrated in vacuo to remove the solvent, and the residue was purified by silica gel column chromatography (PE/EA (V/V)=2/1) to give the title compound as an off-white solid (0.390 g, 76.6%).

Step 10) 2-[1-[2-(3,3a,4,5,6,6a-hexahydro-1H-cyclopenteno[c]furan-5-oxy)-2-(2-methoxyphenyl)ethyl]-5-methyl-6-oxazol-2-yl-2,4-dioxo-thieno[2,3-d]pyrimid-3-yl]-2-methyl-propanoic acid t-Butyl(diphenyl)silyl 2-[1-[2-(3,3a,4,5,6,6a-hexahydro-1H-cyclopenteno[c]furan-5-oxy)-2-(2-methoxyphenyl)ethyl]-5-methyl-6-oxazol-2-yl-2,4-dioxo-thieno[2,3-d]pyrimid-3-yl]-2-methyl-propionate (0.190 g, 0.228 mmol) was dissolved in tetrahydrofuran (2.0 mL). To the mixture was added a solution of tetrabutylammonium fluoride in tetrahydrofuran (1.0 mol/L, 0.35 mL, 0.35 mmol). The mixture was stirred at rt for 2 hours. The reaction mixture was concentrated in vacuo to remove the solvent, and the residue was purified by silica gel column chromatography (EA (V/V)) to give the title compound as a white solid (0.071 g, 52%).

MS (ESI, pos. ion) m/z: 596.3 [M+H]$^+$;

$^1$H NMR (400 MHz, CDCl$_3$) δ 7.72 (s, 1H), 7.53 (t, J=7.4 Hz, 1H), 7.34-7.29 (m, 1H), 7.24 (s, 1H), 7.05 (t, J=7.4 Hz, 1H), 6.88 (d, J=8.2 Hz, 1H), 5.26 (dd, J=13.1, 6.0 Hz, 1H), 4.34-4.26 (m, 1H), 4.24-4.04 (m, 2H), 3.88 (s, 3H), 3.85-3.78 (m, 2H), 3.31-3.24 (m, 1H), 3.20 (dd, J=10.9, 7.1 Hz, 1H), 2.86 (s, 3H), 2.28-2.19 (m, 2H), 1.88 (s, 3H), 1.84 (s, 3H), 1.81-1.75 (m, 1H), 1.61 (dd, J=13.1, 6.2 Hz, 1H), 1.43-1.34 (m, 1H), 1.19-1.06 (m, 1H).

Example 14

2-[1-[2-[[(3aR,6aS)-5-hydroxy-5-methyl-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-meth yl-propanoic acid

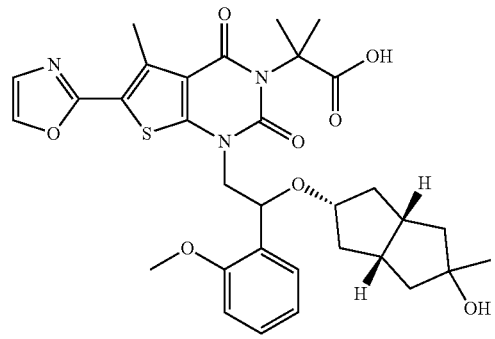 [SMILES: COc1ccccc1C(Cn1c(=O)n(C(C)(C)C(=O)O)c(=O)c2c(C)c(-c3ncco3)sc21)O[C@@H]1C[C@@H]2CC(C)(O)C[C@@H]2C1]

Step 1) (3aR,6aS)-5-[2-hydroxy-1-(2-methoxyphenyl)ethoxy]-2-methyl-3,3a,4,5,6,6a-hexahydro-1H-pentalen-2-ol (3aR,6aS)-5-[2-Hydroxy-1-(2-methoxyphenyl)ethoxy]-3,3a,4,5,6,6a-hexahydro-1H-pentalen-2-one (300 mg, 1.0 mmol) was dissolved in anhydrous tetrahydrofuran (50 mL) under N$_2$. The mixture was cooled to −10° C., and a solution of methyl magnesium bromide in ethyl ether (3 mL, 9 mmol, 3 mol/L) was added dropwise. After the addition, the mixture was stirred at for 10° C. hour. The reaction was quenched with saturated aqueous ammonium chloride (5 mL). The mixture was concentrated to remove most of solvent. To the residue was added water (30 mL) and EtOAc (40 mL), the mixture was partitioned. The organic layer was dried over anhydrous sodium sulfate, and filtered by suction filtration. The filtrate was concentrated in vacuo. The residue was purified by silica gel column chromatography PE/EtOAc (V/V=1/1) to give the title compound as a white solid (180 mg, 57%).

Step 2) t-butyl(diphenyl)silyl 2-[1-[2-[[(3aR,6aS)-5-hydroxy-5-methyl-2,3,3a,4,6,6a-hexahydro-1H-pentalen-2-yl]oxy]-2-(2-methoxyphenyl)ethyl]-5-methyl-6-oxazol-2-yl-2,4-di oxo-thieno[2,3-d]pyrimid-3-yl]-2-methyl-propionate To a solution of (3aR,6aS)-5-[2-hydroxy-1-(2-methoxyphenyl)ethoxy]-2-methyl-3,3a,4,5,6,6a-hexahydro-1H-pentalen-2-ol (180 mg, 0.59 mmol), t-butyl(diphenyl)silyl 2-methyl-2-(5-methyl-6-oxazol-2-yl-2,4-dioxo-1H-thieno[2,3-d]pyrimid-3-yl)-propionate (280 mg, 0.49 mmol) and triphenylphosphine (310 mg, 1.18 mmol) in anhydrous tetrahydrofuran (10 mL) was added diisopropyl azodicarboxylate (0.24 mL, 1.2 mmol) dropwise slowly at 0° C. under N$_2$. After the addition, the mixture was stirred for 14 hours. The reaction mixture was concentrated in vacuo to remove the solvent, and the residue was purified by silica gel column chromatography (PE/EA (V/V)=10/1) to give the title compound as a light yellow solid (148 mg, 29%).

Step 3) 2-[1-[2-[[(3aR,6aS)-5-hydroxy-5-methyl-2, 3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid To a solution of t-butyl(diphenyl)silyl 2-[1-[2-[[(3aR, 6aS)-5-hydroxy-5-methyl-2,3,3a,4,6,6a-hexahydro-1H-pentalen-2-yl)oxy)-2-(2-methoxyphenyl)ethyl]-5-methyl-6-oxazol-2-yl-2,4-dioxo-thieno[2,3-d]pyrimid-3-yl]-2-methyl-propionate (145 mg, 0.17 mmol) in tetrahydrofuran (10 mL) was added a solution of tetrabutylammonium fluoride in tetrahydrofuran (0.5 mL, 1 mol/L). The mixture was stirred for 3 hours. The mixture was concentrated. To the residue was added water (30 mL) and ethyl acetate (30 mL). The resulting mixture was partitioned. The organic layer was dried over anhydrous sodium sulfate, and filtered by suction filtration. The filtrate was concentrated in vacuo to give the title compound (30 mg, 27.5%).

MS (ESI, pos. ion) m/z: 646.2[M+Na]+;
$^1$H NMR (400 MHz, CDCl$_3$) δ 7.71 (s, 1H), 7.51 (dd, J=7.5, 1.3 Hz, 1H), 7.31-7.27 (m, 1H), 7.24 (s, 1H), 7.01 (t, J=7.4 Hz, 1H), 6.87 (d, J=8.2 Hz, 1H), 5.29 (dd, J=8.8, 4.0 Hz, 1H), 4.32-4.24 (m, 1H), 4.01-3.96 (m, 1H), 3.89 (s, 3H), 3.81-3.71 (m, 1H), 2.83 (s, 3H), 2.28-2.37 (m, 2H), 1.99-1.89 (m, 2H), 1.86 (s, 3H), 1.83 (s, 3H), 1.80-1.75 (m, 2H), 1.73-1.68 (m, 1H), 1.66-1.63 (m, 2H), 1.58-1.50 (m, 1H), 1.24 (s, 3H).

Example 15

2-[1-[2-[(5-cyano-1,2,3,3a,4,5,6,6a-octahydropentalen-2-yl)oxy]-2-(2-methoxyphenyl)ethyl]-5-methyl-6-oxazol-2-yl-2,4-dioxo-thieno[2,3-d]pyrimid-3-yl]-2-methyl-propanoic acid The mixture was stirred at rt for 4 hours The reaction mixture was concentrated in vacuo to remove the solvent, and the residue was purified by silica gel column chromatography (PE/EA (V/V)=3/1) to give the title compound as a colorless oil (0.15 g, 31.2%).

Step 2) 2-[1-[2-[[(3aR,6aS)-5-cyano-1,2,3,3a,4,5,6, 6a-octahydropentalen-2-yl)oxy]-2-(2-methoxyphenyl)ethyl]-5-methyl-6-oxazol-2-yl-2,4-dioxo-thieno[2,3-d]pyrimid-3-yl]-2-methyl-propanoic acid t-Butyl 2-[1-[2-[[(3aR,6aS)-5-cyano-1,2,3,3a,4,5,6,6a-octahydropentalen-2-yl)oxy]-2-(2-methoxyphenyl)ethyl]-5-methyl-6-oxazol-2-yl-2,4-dioxo-thieno[2,3-d]pyrimid-3-yl]-2-methyl-propionate (0.25 g, 0.37 mmol) was dissolved in EtOAc (5 mL) at rt, and a solution of hydrogen chloride in ethyl acetate (10 mL) was added. The mixture was stirred for 6 hours. The reaction mixture was concentrated in vacuo to remove the solvent, and the residue was purified by silica gel column chromatography (PE/EA (V/V)=1/1) to give the title compound as a white solid (0.21 g, 92.0%).

MS (ESI, pos. ion) m/z: 619.1[M+H]+;
$^1$H NMR (400 MHz, CDCl$_3$) δ 7.73 (s, 1H), 7.49 (d, J=6.6 Hz, 1H), 7.34-7.29 (m, 1H), 7.24 (s, 1H), 7.04 (t, J=7.7 Hz, 1H), 6.87 (d, J=8.0 Hz, 1H), 5.33-5.26 (m, 1H), 4.13-4.02 (m, 2H), 3.85 (s, 3H), 3.75-3.70 (m, 1H), 2.87 (s, 3H), 2.85-2.76 (m, 1H), 2.52-2.50 (m, 2H), 2.00-1.92 (m, 5H), 1.88 (s, 3H), 1.86 (s, 3H), 1.77-1.70 (m, 3H).

Example 16

2-[1-[2-[[(3aR,6aS)-5-methoxy-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methylpropanoic acid

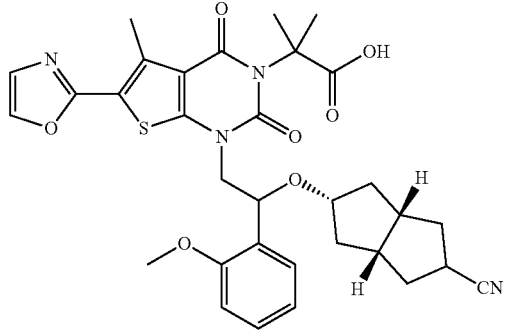 [SMILES: COc1ccccc1C(Cn1c(=O)n(C(C)(C)C(=O)O)c(=O)c2c(C)c(-c3ncco3)sc21)O[C@H]1C[C@H]2CC(C#N)C[C@H]2C1]

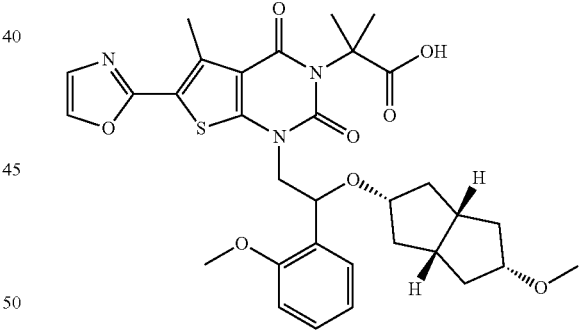

Step 1) t-butyl 2-[1-[2-[[(3aR,6aS)-5-cyano-1,2,3, 3a,4,5,6,6a-octahydropentalen-2-yl)oxy]-2-(2-methoxyphenyl)ethyl]-5-methyl-6-oxazol-2-yl-2,4-dioxo-thieno[2,3-d]pyrimid-3-yl]-2-methyl-propionate t-Butyl 2-[1-[2-[[(3aR,6aS)-5-oxa-2,3,3a,4,6,6a-hexahydro-1H-pentalenyl-2-yl)oxy]ethyl]-5-methyl-6-oxazol-2-yl-2,4-dioxo-thieno[2,3-d]pyrimid-3-yl]-2-methyl-propionate (prepared according to step 1 of example 8) (0.47 g, 0.71 mmol), p-toluenesulfonylmethyl isocyanide (0.32 g, 1.8 mmol) and ethanol (0.20 mL, 3.4 mmol) were dissolved in ethylene glycol dimethyl ether (10 mL). And then potassium t-butoxide (0.25 g, 2.2 mmol) was added in portions.

Step 1) [2-[[(3aR,6aS)-5-benzyloxy-1,2,3,3a,4,5,6, 6a-octahydropentalen-2-yl]oxy]-2-(2-methoxyphenyl)ethoxy]-t-butyldimethylsilane

[2-[[(3aR,6aS)-5-Benzyloxy-1,2,3,3a,4,5,6,6a-octahydropentalen-2-yl)oxy]-2-(2-methoxyphenyl)ethanol (1.00 g, 2.61 mmol) was dissolved in DCM (20 mL), and then imidazole (360 mg, 5.23 mmol) was added. The solution was cooled to 0° C. And then t-butyldimethylsilylchloride (591 mg, 3.92 mmol) was added dropwise. The mixture was stirred at 0° C. for 35 min. To the mixture was added water (10 mL), the mixture was stirred for 10 min. After the mixture was partitioned. The water phase was extracted with DCM (20 mL×2). The combined organic phases were washed with saturated brine, dried over anhydrous sodium sulfate, and filtered. The filtrate was concentrated in vacuo. The residue was purified by silica gel chromatograph (EtOAc/PE (V/V)=1/12) to give the title compound as a light yellow solid (1.23 g, 94.7%).

MS (ESI, pos. ion) m/z: 519.2[M+Na]$^+$;

Step 2) (3aR,6aS)-5-[2-[t-butyl(dimethyl)silyl]oxy-1-(2-methoxyphenyl)ethoxy]-1,2,3,3a,4,5,6,6a-octahydropentalen-2-ol

[2-[[(3aR,6aS)-5-benzyloxy-1,2,3,3a,4,5,6,6a-octahydropentalen-2-yl]oxy]-2-(2-methoxyphenyl)ethoxy]-t-butyldimethylsilane (1.23 g, 2.48 mmol) was dissolved in methanol (20.0 mL), and then palladium on carbon (123 mg, 0.12 mmol, 10%) was added. The mixture was stirred at rt under H$_2$ for 3 hours. The mixture was filtered, the filter cake was washed with methanol (20.0 mL). The filtrate was concentrated in vacuo to remove the solvent, and the residue was purified by silica gel column chromatography (EA/PE (V/V)=1/12) to give the title compound as a light yellow oil (0.88 g, 87.4%).

MS (ESI, pos. ion) m/z: 429.3[M+Na]$^+$;

Step 3) 2-[[(3aR,6aS)-5-methoxy-1,2,3,3a,4,5,6,6a-octahydropentalen-2-yl]oxy]-2-(2-methoxyphenyl)ethoxy]-t-butyldimethylsilane (3aR,6aS)-5-[2-[t-Butyl(dimethyl)silyl]oxy-1-(2-methoxyphenyl)ethoxy]-1,2,3,3a,4,5,6,6a-octahydropentalen-2-ol (200 mg, 0.49 mmol) was dissolved in tetrahydrofuran (5.0 mL). The mixture was cooled to 0° C. under N$_2$, and sodium hydride (24 mg, 0.60 mmol, 60%) was added in portions. The mixture was stirred for 2 hours. To the mixture was added iodomethane (77.2 mg, 0.54 mmol) dropwise slowly, and the mixture was stirred at rt for 24 hours. And then to the mixture was added water (10 mL), the mixture was stirred for 10 min. After the mixture was partitioned. The water phase was extracted with DCM (20 mL×2). The combined organic phases were washed with saturated brine, dried over anhydrous sodium sulfate, and filtered. The filtrate was concentrated in vacuo. The residue was purified by silica gel chromatograph (PE/EtOAc (V/V)=15/1) to give the title compound as a light yellow solid (178 mg, 86.0%).

MS (ESI, pos. ion) m/z: 443.4 [M+Na]$^+$

Step 4) 2-[[(3aR,6aS)-5-methoxy-1,2,3,3a,4,5,6,6a-octahydropentalen-2-yl]oxy]-2-(2-methoxyphenyl)ethanol 2-[[(3aR,6aS)-5-Methoxy-1,2,3,3a,4,5,6,6a-octahydropentalen-2-yl]oxy]-2-(2-methoxyphenyl)ethoxy]-t-butyldimethylsilane (178 mg, 0.42 mmol) was dissolved in tetrahydrofuran (2.0 mL), and then tetrabutylammonium fluoride (1.3 mL, 1.30 mmol) was added. The mixture was stirred at rt for 3 hours. The mixture was quenched with water (50 mL), and extracted with EtOAc (30 mL×2). The combined organic phases were washed with saturated brine, dried over anhydrous sodium sulfate, and filtered. The filtrate was concentrated in vacuo. The residue was purified by silica gel chromatograph (PE/EtOAc (V/V)=4/1) to give the title compound as an off-white solid (125 mg, 96.4%).

MS (ESI, pos. ion) m/z: 329.2 [M+Na]$^+$;

Step 5) t-butyl(diphenyl)silyl 2-[1-[2-[[(3aR,6aS)-5-methoxy-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate 2-[[(3aR,6aS)-5-Methoxy-1,2,3,3a,4,5,6,6a-octahydropentalen-2-yl]oxy]-2-(2-methoxyphenyl)ethanol (337 mg, 1.10 mmol), triphenylphosphine (555 mg, 2.09 mmol) and t-butyl(diphenyl)silyl 2-methyl-2-(5-methyl-6-oxazol-2-yl-2,4-dioxo-1H-thieno[2,3-d]pyrimid-3-yl)propionate (600 mg, 1.05 mmol) were added to tetrahydrofuran (20.0 mL). The mixture was stirred under N$_2$ for 5 min, diisopropyl azodicarboxylate (432 mg, 2.09 mmol) was added dropwise. The mixture was stirred at rt for 3.5 hours and concentrated in vacuo. The residue was purified by silica gel chromatograph (PE/EtOAc (V/V)=8/1) to give the title compound as a light yellow oil (450 mg, 49.9%).

Step 6) 2-[1-[2-[[(3aR,6aS)-5-methoxy-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methylpropanoic acid t-Butyl(diphenyl)silyl 2-[1-[2-[[(3aR,6aS)-5-methoxy-1,2,3,3a,4,5,6,6a-octahydropentalen-2-yl]oxy]-2-(2-methoxyphenyl)ethyl)-5-methyl-6-oxazol-2-yl-2,4-dioxo-thien o[2,3-d]pyrimid-3-yl]-2-methyl-propionate (450 mg, 0.52 mmol) was dissolved in tetrahydrofuran (5.0 mL). To the mixture was added a solution of tetrabutylammonium fluoride in tetrahydrofuran (1.0 mol/L, 3.2 mL, 3.20 mmol). The mixture was stirred at rt for 2 hours. The reaction mixture was concentrated in vacuo to remove the solvent, and the residue was purified by silica gel column chromatography (EA) to give the title compound as a white solid (30 mg, 9.2%).

MS (ESI, pos. ion) m/z: 624.1 [M+H]$^+$;
$^1$H NMR (400 MHz, CDCl$_3$) δ 7.66 (s, 1H), 7.59-7.52 (m, 1H), 7.29-7.25 (m, 1H), 7.21 (s, 1H), 7.00 (t, J=7.4 Hz, 1H), 6.86 (d, J=8.2 Hz, 1H), 5.17-5.15 (m, 1H), 4.63-4.59 (m, 1H), 4.50-4.47 (m, 1H), 3.85 (s, 3H), 3.83-3.76 (m, 2H), 3.31 (s, 3H), 2.84 (s, 3H), 2.38-2.26 (m, 2H), 2.11-2.07 (m, 1H), 2.01-1.95 (m, 2H), 1.90-1.86 (m, 5H), 1.76 (s, 3H), 1.73-1.68 (m, 2H).

Example 17

2-[1-[2-[[(3aR,6aS)-5-fluoro-1,2,3,3a,4,5,6,6a-octahydropentalen-2-yl]oxy]-2-(2-methoxyphenyl)ethyl)-5-methyl-6-oxazol-2-yl-2,4-dioxo-thieno[2,3-d]pyrimid-3-yl]-2-methyl-propanoic acid

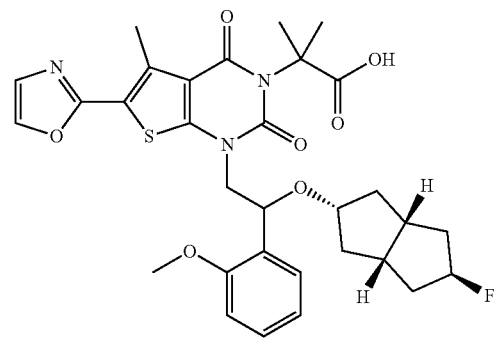 [SMILES: COc1ccccc1C(Cn1c(=O)n(C(C)(C)C(=O)O)c(=O)c2c(C)c(-c3ncco3)sc21)O[C@H]1C[C@H]2C[C@H](F)C[C@H]2C1]

Step 1) (3'aS,6'aR)-2'-fluoro-5,5-dimethyl-spiro[1,3-dioxane-2,5'-2,3,3a,4,6,6a-hexahydro-1H-pentalene]

To a solution of (3a'R,6a'S)-5,5-dimethylspiro[1,3-dioxane-2,5'-2,3,3a,4,6,6a-hexahydro-1H-pentalen]-5'-ol (2.0 g, 8.8 mmol) in DCM (10 mL) was added diethylaminosulfur trifluoride (2.3 mL, 18 mmol) dropwise slowly at 0° C. The mixture was moved to rt and stirred for 17 hours. The mixture was poured into ice water (100 mL) to quenched the reaction, and then extracted with DCM (50 mL), and then concentrated in vacuo to get the title compound as a black oil (2.0 g, 99%).

Step 2) (3aS,6aR)-5-fluoro-3,3a,4,5,6,6a-hexahydro-1H-pentalen-2-one

To a solution of (3'aS,6'aR)-2'-fluoro-5,5-dimethyl-spiro[1,3-dioxane-2,5'-2,3,3a,4,6,6a-hexahydro-1H-pentalene] (2.0 g, 8.8 mmol) in tetrahydrofuran (20 mL) was added concentrated hydrochloric acid (2 mL, 36%) at rt. The mixture was stirred for 2 hours. The mixture was concentrated. To the residue was added water (100 mL) and ethyl acetate (100 mL). The resulting mixture was partitioned. The organic layer was adjusted to pH about neutral and dried over anhydrous sodium sulfate, and filtered by suction filtration. The filtrate was concentrated in vacuo to give the title compound as a brown oil (0.77 g, 62%).

Step 3) (3aR,6aS)-5-fluoro-1,2,3,3a,4,5,6,6a-octahydropentalen-2-ol

To a solution of (3aS,6aR)-5-fluoro-3,3a,4,5,6,6a-hexahydro-1H-pentalen-2-one (0.77 g, 5.4 mmol) in methanol (5 mL) was added sodium borohydride (0.31 g, 8.2 mmol) at 0° C. The mixture was stirred for 30 min. The reaction was quenched with water (2 mL). The mixture was concentrated. To the residue was added water (40 mL) and EtOAc (40 mL), the mixture was partitioned. The organic layer was dried over anhydrous sodium sulfate, and filtered by suction filtration. The filtrate was concentrated in vacuo. The residue was purified by silica gel column chromatography PE/EtOAc (V/V=10/1) to give the title compound as a colorless oil (530 mg, 68%).

$^1$H NMR (400 MHz, CDCl$_3$) δ 5.28-5.15 (m, 1H), 4.37-4.32 (m, 1H), 2.76-2.62 (m, 2H), 2.30-2.16 (m, 2H), 2.12-2.03 (m, 2H), 1.79-1.73 (m, 1H), 1.69-1.62 (m, 1H).

Step 4) 2-[[(3aR,6aS)-5-fluoro-1,2,3,3a,4,5,6,6a-octahydropentalen-2-yl)oxy]-2-(2-methoxyphenyl)acetic acid To a solution of (3aR,6aS)-5-fluoro-1,2,3,3a,4,5,6,6a-octahydropentalen-2-ol (300 mg, 2.1 mmol) in anhydrous tetrahydrofuran (10 mL) was added sodium hydride (340 mg, 60%) at 0° C. The mixture was stirred for 1 hour and a solution of 2-bromo-2-(2-methoxyphenyl)acetic acid (510 mg, 2.1 mmol) in anhydrous tetrahydrofuran (5 mL) was added dropwise slowly. After the addition, the mixture was moved to rt and stirred for 16 hours. The mixture was cooled to 0° C. and quenched with water (5 mL). The mixture was concentrated, and to the residue was added water (100 mL) and ethyl acetate (100 mL), the resulting mixture was partitioned. The combined water layers were adjusted to pH about 2 with hydrochloric acid (4 N), and then extracted with ethyl acetate (100 mL). The organic layer was washed with saturated brine (100 mL×2), dried over anhydrous sodium sulfate, filtered by suction filtration. The filtrate was concentrated in vacuo to give the title compound as a light yellow oil (350 mg, 54.56%).

LC-MS (ES/API, pos. ion) m/z: 331.0 [M+Na]$^+$

Step 5) 2-[[(3aR,6aS)-5-fluoro-1,2,3,3a,4,5,6,6a-octahydropentalen-2-yl]oxy]-2-(2-methoxyphenyl)ethanol To a solution of 2-[[(3aR,6aS)-5-fluoro-1,2,3,3a,4,5,6,6a-octahydropentalen-2-yl)oxy]-2-(2-methoxyphenyl)acetic acid (350 mg, 1.14 mmol) in anhydrous tetrahydrofuran (10 mL) was added lithium aluminum hydride (26 mg, 0.68 mmol) at 0° C. After the addition, the mixture was moved to rt and stirred for 2 hours. The mixture was cooled to 0° C. and quenched with water (1 mL). The mixture was concentrated to remove most of solvent. To the residue was added hydrochloric acid (100 mL, 4 N), and the mixture was stirred for 5 min, and extracted with EtOAc (100 mL). The organic layer was dried over anhydrous sodium sulfate, and filtered by suction filtration. The filtrate was concentrated in vacuo. The residue was purified by silica gel column chromatography PE/EtOAc (V/V=6/1) to give the title compound as a colorless oil (210 mg, 62.83%).

MS (ES/API, pos. ion) m/z: 317.1 [M+Na]$^+$ $^1$H NMR (400 MHz, CDCl$_3$) δ 7.35 (dd, J=7.5, 1.4 Hz, 1H), 7.26 (dd, J=15.7, 1.7 Hz, 1H), 6.97 (t, J=7.4 Hz, 1H), 6.87 (d, J=8.2 Hz, 1H), 5.20 (d, J=53.0 Hz, 1H), 4.94 (dd, J=7.9, 3.3 Hz, 1H), 3.95-3.85 (m, 1H), 3.82 (s, 3H), 3.66-3.53 (m, 1H), 3.52-3.47 (m, 1H), 2.68-2.47 (m, 2H), 2.25-2.15 (m, 2H), 2.15-2.06 (m, 2H), 2.04-1.95 (m, 1H), 1.77-1.69 (m, 1H), 1.52-1.40 (m, 2H).

Step 6) t-butyl(diphenyl)silyl 2-[1-[2-[[(3aR,6aS)-5-fluoro-1,2,3,3a,4,5,6,6a-octahydropentalen-2-yl]oxy]-2-(2-methoxyphenyl)ethyl)-5-methyl-6-oxazol-2-yl-2,4-dioxo-thieno[2,3-d]pyrimid-3-yl]-2-methyl-propionate To a solution of 2-[[(3aR,6aS)-5-fluoro-1,2,3,3a,4,5,6,6a-octahydropentalen-2-yl]oxy]-2-(2-methoxyphenyl)ethanol (130 mg, 0.44 mmol), t-butyl(diphenyl)silyl 2-methyl-2-(5-methyl-6-oxazol-2-yl-2,4-dioxo-1H-thieno[2,3-d]pyrimid-3-yl)-propionate (250 mg, 0.43 mmol) and triphenylphosphine (230 mg, 0.88 mmol) in anhydrous tetrahydrofuran (10 mL) was added diisopropyl azodicarboxylate (0.18 mL, 0.91 mmol) dropwise slowly at 0° C. under N$_2$. After the addition, the mixture was stirred at rt for 12 hours. The reaction mixture was concentrated in vacuo to remove the solvent, and the residue was purified by silica gel column chromatography (PE/EA (V/V)=5/1) to give the title compound as a light yellow solid (235 mg, 62.6%).

Step 7) 2-[1-[2-[[(3aR,6aS)-5-fluoro-1,2,3,3a,4,5,6,6a-octahydropentalen-2-yl]oxy]-2-(2-methoxyphenyl)ethyl)-5-methyl-6-oxazol-2-yl-2,4-dioxo-thieno[2,3-d]pyrimid-3-yl]-2-methyl-propanoic acid To a solution of t-butyl(diphenyl)silyl 2-[1-[2-[[(3aR,6aS)-5-fluoro-1,2,3,3a,4,5,6,6a-octahydropentalen-2-yl]oxy]-2-(2-methoxyphenyl)ethyl)-5-methyl-6-oxazol-2-yl-2,4-dioxo-thieno[2,3-d]pyrimid-3-yl]-2-methyl-propionate (235 mg, 0.28 mmol) in tetrahydrofuran (10 mL) was added a solution of tetrabutylammonium fluoride in tetrahydrofuran (1.3 mL, 1 mol/L) at rt. The mixture was stirred for 1.5 hours. The mixture was concentrated. To the residue was added water (30 mL) and ethyl acetate (30 mL). The resulting mixture was partitioned. The organic layer was dried over anhydrous sodium sulfate, and filtered by suction filtration. The filtrate was concentrated in vacuo. The residue was purified by pre-HPLC to give the title compound as a white solid (109 mg, 33.0%).

MS (ES/API, pos. ion) m/z: 612.2 [M+H]⁺

¹H NMR (400 MHz, CDCl₃) δ 7.70 (s, 1H), 7.48 (dd, J=7.5, 1.3 Hz, 1H), 7.30-7.27 (m, 1H), 7.22 (s, 1H), 7.02 (t, J=7.4 Hz, 1H), 6.85 (d, J=8.2 Hz, 1H), 5.35-5.29 (m, 1H), 4.90 (d, J=53.1 Hz, 1H), 4.19-4.10 (m, 1H), 3.99-3.90 (m, 1H), 3.84 (s, 3H), 3.82-3.79 (m, 1H), 2.84 (s, 3H), 2.61-2.46 (m, 2H), 2.16-1.95 (m, 2H), 1.86 (s, 3H), 1.83 (s, 3H), 1.83-1.76 (m, 2H), 1.51-1.37 (m, 4H).

Example 18

2-[1-[2-[[(3aR,6aS)-5-hydroxy-5-(trifluoromethyl)-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid

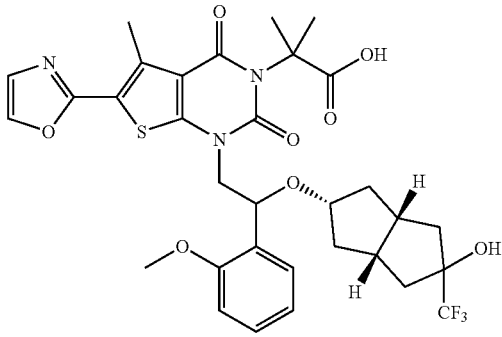 [SMILES: COc1ccccc1C(Cn1c(=O)n(C(C)(C)C(=O)O)c(=O)c2c(C)c(-c3ncco3)sc21)O[C@@H]1C[C@@H]2CC(O)(C(F)(F)F)C[C@@H]2C1]

Step 1) (3aR,6aS)-5-[2-hydroxy-1-(2-methoxyphenyl)ethoxy]-2-(trifluoromethyl)-3,3a,4,5,6,6a-hexahydro-1H-pentalen-2-ol To a solution of (3aR,6aS)-5-[2-Hydroxy-1-(2-methoxyphenyl)ethoxy]-3,3a,4,5,6,6a-hexahydro-1H-pentalen-2-one (100 mg, 0.34 mmol) in tetrahydrofuran (50 mL) was added trifluoromethyltriethylsilane (0.15 mL, 1.0 mmol) at rt under N₂. The mixture was cooled to 0° C., and a solution of tetrabutylammonium fluoride in THF (1.0 mL, 1 mol/L) was added. After the addition, the mixture was stirred at for 12 hour. The mixture was concentrated. To the residue was added water (30 mL) and EtOAc (30 mL), the mixture was partitioned. The organic layer was dried over anhydrous sodium sulfate, and filtered by suction filtration. The filtrate was concentrated in vacuo. The residue was purified by silica gel column chromatography PE/EtOAc (V/V=3/1) to give the title compound as a white solid (88 mg, 71%).

MS (ES/API, neg. ion) m/z: 405.1[M+HCOO]⁻

Step 2) t-butyl(diphenyl)silyl 2-[1-[2-[[(3aR,6aS)-5-hydroxy-5-(trifluoromethyl)-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate To a solution of (3aR,6aS)-5-[2-hydroxy-1-(2-methoxyphenyl)ethoxy]-2-(trifluoromethyl)-3,3a,4,5,6,6a-hexahydro-1H-pentalen-2-ol (85 mg, 0.24 mmol), t-butyl(diphenyl)silyl 2-methyl-2-(5-methyl-6-oxazol-2-yl-2,4-dioxo-1H-thieno[2,3-d]pyrimid-3-yl)-propionate (150 mg, 0.26 mmol) and triphenylphosphine (125 mg, 0.47 mmol) in anhydrous tetrahydrofuran (5 mL) was added diisopropyl azodicarboxylate (0.1 mL, 0.5 mmol) dropwise slowly at 0° C. under N₂. After the addition, the mixture was stirred at rt for 5 hours. The reaction mixture was concentrated in vacuo to remove the solvent, and the residue was purified by silica gel column chromatography (PE/EA (V/V)=4/1) to give the title compound as a light yellow solid (140 mg, 65%).

Step 3) 2-[1-[2-[[(3aR,6aS)-5-hydroxy-5-(trifluoromethyl)-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid To a solution of t-butyl(diphenyl)silyl 2-[1-[2-[[(3aR,6aS)-5-hydroxy-5-trifluoromethyl-2,3,3a,4,6,6a-hexahydro-1H-pentalen-2-yl)oxy]-2-(2-methoxyphenyl)ethyl]-5-methyl-6-oxazol-2-yl-2,4-dioxo-thieno[2,3-d]pyrimid-3-yl]-2-methyl-propionate (140 mg, 0.15 mmol) in tetrahydrofuran (10 mL) was added a solution of tetrabutylammonium fluoride in tetrahydrofuran (0.5 mL, 1 mol/L) at rt. The mixture was stirred for 2 hours. The mixture was concentrated. To the residue was added water (30 mL) and ethyl acetate (30 mL). The resulting mixture was partitioned. The organic layer was dried over anhydrous sodium sulfate, and filtered by suction filtration. The filtrate was concentrated in vacuo. The residue was purified by pre-HPLC to give the title compound as a white solid (21 mg, 20%).

MS (ES/API, neg. ion) m/z: 676.0[M−H]⁻;

¹H NMR (400 MHz, CDCl₃) δ 7.70 (s, 1H), 7.52 (d, J=6.8 Hz, 1H), 7.29-7.31 (m, 1H), 7.21 (s, 1H), 7.01 (t, J=7.4 Hz, 1H), 6.89 (d, J=8.2 Hz, 1H), 5.28-5.32 (m, 1H), 4.30-4.36 (m, 1H), 3.98-4.01 (m, 1H), 3.93 (s, 3H), 3.75-3.80 (m, 1H), 2.81 (s, 3H), 2.46-2.38 (m, 2H), 2.17-1.90 (m, 6H), 1.81 (s, 3H), 1.79 (s, 3H), 1.63-1.69 (m, 2H).

Example 19

2-[1-[2-[[(3aR,6aS)-5-ethyl-5-hydroxy-2,3,3a,4,6,6a-hexahydro-1H-pentalen-2-yl]oxy]-2-(2-methoxyphenyl)ethyl)-5-methyl-6-oxazol-2-yl-2,4-dioxo-thieno[2,3-d]pyrimid-3-yl]-2-methyl-propanoic acid

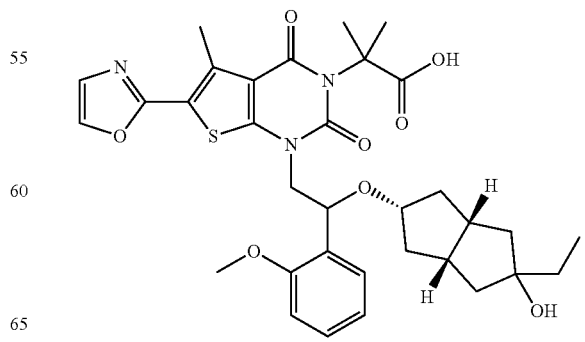

Step 1) (3aR,6aS)-5-[2-[t-butyl(dimethyl)silyl]oxy-1-(2-methoxyphenyl)ethoxy]-2-ethyl-3,3a,4,5,6,6a-hexahydro-1H-pentalen-2-ol To a solution of (3aR,6aS)-5-[2-hydroxy-1-(2-methoxyphenyl)ethoxy]-3,3a,4,5,6,6a-hexahydro-1H-pentalen-2-one (230 mg, 0.57 mmol) in anhydrous tetrahydrofuran (10 mL) was added a solution of ethyl magnesium bromide in ethyl ether (3.4 mL, 3.4 mmol, 1 mol/L) dropwise under $N_2$ on an ice bath. After the addition, the mixture was stirred at rt for 1 hour. The reaction was quenched with water (2 mL) on an ice bath. The mixture was concentrated to remove most of solvent. To the residue was added water (30 mL) and EtOAc (30 mL), the mixture was partitioned. The organic layer was dried over anhydrous sodium sulfate, and filtered by suction filtration. The filtrate was concentrated in vacuo to give the title compound as a colorless oil (240 mg, 97.12%).

MS (ES/API, pos. ion) m/z: 457.1 [M+Na]$^+$

Step 2) (3aR,6aS)-2-ethyl-5-[2-hydroxy-1-(2-methoxyphenyl)ethoxy]-3,3a,4,5,6,6a-hexahydro-1H-pentalen-2-ol To a solution of (3aR,6aS)-5-[2-[t-butyl(dimethyl)silyl]oxy-1-(2-methoxyphenyl) ethoxy]-2-ethyl-3,3a,4,5,6,6a-hexahydro-1H-pentalen-2-ol (240 mg, 0.55 mmol) in anhydrous tetrahydrofuran (20 mL) was added a solution of tetrabutylammonium fluoride (1 mol/L) in tetrahydrofuran (1.2 mL, 3 mol/L) at rt. After the addition, the mixture was stirred for 1 hour. The mixture was concentrated to remove most of solvent. To the residue was added water (50 mL) and EtOAc (50 mL), the mixture was partitioned. The organic layer was dried over anhydrous sodium sulfate, and filtered by suction filtration. The filtrate was concentrated in vacuo. The residue was purified by silica gel column chromatography PE/EtOAc (V/V=2/1) to give the title compound as a white solid (110 mg, 62%).

MS (ES/API, pos. ion) m/z: 343.3 [M+Na]$^+$

Step 3) t-butyl(diphenyl)silyl 2-[1-[2-[[(3aR,6aS)-5-ethyl-5-hydroxy-2,3,3a,4,6,6a-hexahydro-1H-pentalen-2-yl]oxy]-2-(2-methoxyphenyl)ethyl]-5-methyl-6-oxazol-2-yl-2,4-di oxo-thieno[2,3-d]pyrimid-3-yl]-2-methyl-propionate To a solution of (3aR,6aS)-2-ethyl-5-[2-hydroxy-1-(2-methoxyphenyl) ethoxy]-3,3a,4,5,6,6a-hexahydro-1H-pentalen-2-ol (110 mg, 0.34 mmol), t-butyl(diphenyl)silyl 2-methyl-2-(5-methyl-6-oxazol-2-yl-2,4-dioxo-1H-thieno[2,3-d]pyrimid-3-yl)-propionate (200 mg, 0.35 mmol) and triphenylphosphine (180 mg, 0.69 mmol) in anhydrous tetrahydrofuran (10 mL) was added diisopropyl azodicarboxylate (0.15 mL, 0.76 mmol) dropwise slowly under $N_2$. After the addition, the mixture was stirred for 3 hours. The reaction mixture was concentrated in vacuo to remove the solvent, and the residue was purified by silica gel column chromatography (PE/EA (V/V)=8/1) to give the title compound as a light yellow solid (240 mg, 80%).

Step 4) 2-[1-[2-[[(3aR,6aS)-5-ethyl-5-hydroxy-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid To a solution of t-butyl(diphenyl)silyl 2-[1-[2-[[(3aR,6aS)-5-ethyl-5-hydroxy-2,3,3a,4,6,6a-hexahydro-1H-pentalen-2-yl]oxy)-2-(2-methoxyphenyl)ethyl]-5-methyl-6-oxazol-2-yl-2,4-dioxo-thieno[2,3-d]pyrimid-3-yl]-2-methyl-propionate (240 mg, 0.27 mmol) in tetrahydrofuran (20 mL) was added a solution of tetrabutylammonium fluoride in tetrahydrofuran (2.0 mL, 1 mol/L) at rt. The mixture was stirred for 1 hours. The mixture was concentrated in vacuo. To the mixture was added water (50 mL) and ethyl acetate (50 mL). The resulting mixture was partitioned. The organic layer was washed with saturated brine (40 mL×2), dried over anhydrous sodium sulfate, and filtered by suction filtration. The filtrate was concentrated in vacuo. The residue was purified by pre-HPLC to give the title compound as a white solid (59 mg, 27%).

MS (ES/API, neg. ion) m/z: 636.2[M–H]$^-$;

$^1$H NMR (400 MHz, CDCl$^3$) δ 7.70 (s, 1H), 7.53 (d, J=6.5 Hz, 1H), 7.30 (d, J=7.1 Hz, 1H), 7.22 (s, 1H), 7.02 (t, J=7.5 Hz, 1H), 6.88 (d, J=8.2 Hz, 1H), 5.27-5.30 (m, 1H), 4.30-4.34 (m, 1H), 3.91 (s, 3H), 3.90-3.83 (m, 1H), 3.78-3.68 (m, 1H), 2.85 (s, 3H), 2.32-2.28 (m, 2H), 2.00-1.95 (m, 2H), 1.88 (s, 3H), 1.83 (s, 3H), 1.82-1.71 (m, 4H), 1.58-1.61 (m, 2H), 1.47-1.53 (m, 2H), 0.89 (t, 3H).

Example 20

2-[1-[2-[[(3aR,6aS)-5-hydroxy-1,2,3,3a,4,5,6,6a-octahydropentalen-2-yl]oxy]-2-(2-fluorophenyl)ethyl]-5-methyl-6-oxazol-2-yl-2,4-dioxo-thieno[2,3-d]pyrimid-3-yl]-2-methyl-propanoic acid

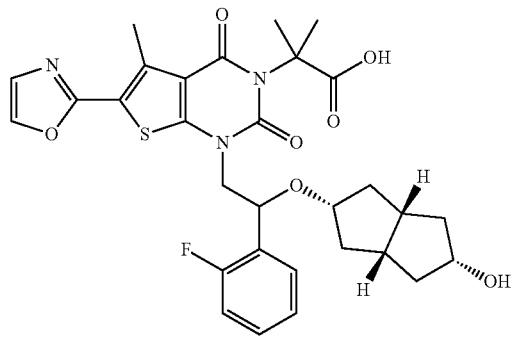 [SMILES: Cc1c(-c2ncco2)sc2c1c(=O)n(C(C)(C)C(=O)O)c(=O)n2CC(O[C@H]1C[C@H]2C[C@@H](O)C[C@H]2C1)c1ccccc1F]

The title compound was prepared from 2-bromo-2-(2-fluorophenyl)acetic acid (165 mg, 0.84 mmol) according to the method described in example 1. The obtained title compound is off-white solid (30 mg, 23.2%).

MS (ESI, pos. ion) m/z: 598.3 [M+H]$^+$;

$^1$H NMR (400 MHz, CDCl$_3$) δ 7.70 (s, 1H), 7.55 (t, J=6.8 Hz, 1H), 7.34-7.29 (m, 6.8 Hz, 1H), 7.24-7.18 (m, 2H), 7.07 (t, J=9.2 Hz, 1H), 5.28 (t, J=6.4 Hz, 1H), 4.16-4.11 (m, 3H), 3.83-3.74 (m, 1H), 2.84 (s, 3H), 2.28-2.23 (m, 2H), 2.07-1.91 (m, 4H), 1.87 (s, 3H), 1.83 (s, 3H), 1.68-1.61 (m, 2H), 1.60-1.53 (m, 2H).

Example 21

2-[1-[2-[[(3aR,6aS)-5,5-difluoro-2,3,3a,4,6,6a-hexahydro-1H-pentalen-2-yl]oxy]-2-(2-methoxyphenyl)ethyl)-5-methyl-6-oxazol-2-yl-2,4-dioxo-thieno[2,3-d]pyrimid-3-yl]-2-methyl-propanoic acid

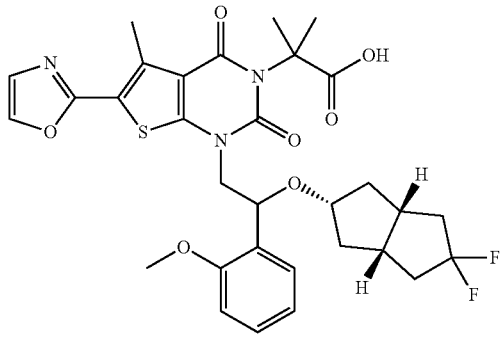 [SMILES: COc1ccccc1C(Cn1c(=O)n(C(C)(C)C(=O)O)c(=O)c2c(C)c(-c3ncco3)sc21)O[C@@H]1C[C@@H]2CC(F)(F)C[C@@H]2C1]

Step 1) (3aR,6aS)-5,5-difluoro-5',5'-dimethyl-spiro[1,3,3a,4,6,6a-hexahydropentalenyl-2,2'-1,3-dioxane]

To a solution of (3aR,6aS)-5',5'-dimethylspiro[1,3,3a,4,6,6a-hexahydropentalenyl-5,2'-1,3-dioxane]-2-one (2.0 g, 8.9 mmol) in DCM (10 mL) was added diethylaminosulfur trifluoride (4.0 mL, 31 mmol) dropwise slowly at 0° C. The mixture was moved to rt and stirred for 16 hours. The mixture was poured into ice water (100 mL) to quenched the reaction, and then extracted with DCM (50 mL), and then concentrated in vacuo to get the title compound as a black oil (2.1 g, 96%).

Step 2) (3aR,6aS)-5,5-difluoro-1,3,3a,4,6,6a-hexahydropentalen-2-one

To a solution of (3aR,6aS)-5,5-difluoro-5',5'-dimethyl-spiro[1,3,3a,4,6,6a-hexahydropentalenyl-2,2'-1,3-dioxane] (2.1 g, 8.5 mmol) in tetrahydrofuran (20 mL) was added concentrated hydrochloric acid (2 mL, 36%) at rt. The mixture was stirred at rt for 1 hours. The mixture was concentrated. To the residue was added water (100 mL) and ethyl acetate (100 mL). The resulting mixture was partitioned. The organic layer was adjusted to pH about neutral and dried over anhydrous sodium sulfate, and filtered by suction filtration. The filtrate was concentrated in vacuo to give the title compound as a brown oil (0.96 g, 70%).

Step 3) (3aR,6aS)-5,5-difluoro-2,3,3a,4,6,6a-hexahydro-1H-pentalen-2-ol

To a solution of (3aR,6aS)-5,5-difluoro-1,3,3a,4,6,6a-hexahydropentalen-2-one (0.96 g, 6.0 mmol) in methanol (10 mL) was added sodium borohydride (0.35 g, 9.3 mmol) at 0° C. The mixture was stirred for 15 min. The reaction was quenched with water (2 mL). The mixture was concentrated to remove most of solvent. To the residue was added water (40 mL) and EtOAc (40 mL), the mixture was partitioned. The organic layer was dried over anhydrous sodium sulfate, and filtered by suction filtration. The filtrate was concentrated in vacuo. The residue was purified by silica gel column chromatography PE/EtOAc (V/V=6/1) to give the title compound as a colorless oil (360 mg, 37%).

$^1$H NMR (400 MHz, CDCl$_3$) δ 4.34-4.26 (m, 1H), 2.68-2.55 (m, 2H), 2.22-2.34 (m, 2H), 2.15-1.99 (m, 4H), 1.59-1.51 (m, 2H).

Step 4) 2-[[(3aR,6aS)-5,5-difluoro-2,3,3a,4,6,6a-hexahydro-1H-pentalen-2-yl]oxy]-2-(2-methoxyphenyl)acetic acid To a solution of (3aR,6aS)-5,5-difluoro-2,3,3a,4,6,6a-hexahydro-1H-pentalen-2-ol (350 mg, 2.16 mmol) in anhydrous tetrahydrofuran (10 mL) was added sodium hydride (340 mg, 8.5 mmol, 60%) at 0° C. The mixture was stirred for 1 hour and a solution of 2-bromo-2-(2-methoxyphenyl)acetic acid (530 mg, 2.16 mmol) in anhydrous tetrahydrofuran (5 mL) was added dropwise slowly. After the addition, the mixture was moved to rt and stirred for 17 hours. The mixture was cooled to 0° C. and quenched with water (5 mL). The mixture was concentrated to remove most of solvent, and to the residue was added water (30 mL) and ethyl acetate (30 mL), the resulting mixture was partitioned. The combined water layers were adjusted to pH about 2 with hydrochloric acid (4 N), and then extracted with ethyl acetate (40 mL). The organic layer was washed with saturated brine (30 mL×2), dried over anhydrous sodium sulfate, filtered by suction filtration. The filtrate was concentrated in vacuo to give the title compound as a light yellow oil (610 mg, 86.6%).

Step 5) 2-[[(3aR,6aS)-5,5-difluoro-2,3,3a,4,6,6a-hexahydro-1H-pentalen-2-yl]oxy]-2-(2-methoxyphenyl)ethanol To a solution of 2-[[(3aR,6aS)-5,5-difluoro-2,3,3a,4,6,6a-hexahydro-1H-pentalen-2-yl]oxy]-2-(2-methoxyphenyl)acetic acid (610 mg, 1.87 mmol) in anhydrous tetrahydrofuran (20 mL) was added lithium aluminum hydride (280 mg, 7.38 mmol) at 0° C. After the addition, the mixture was moved to rt and stirred for 2 hours. The mixture was quenched with water (5 mL). The mixture was concentrated in vacuo to remove most of solvent. To the residue was added hydrochloric acid (50 mL, 4 N), and the mixture was stirred for 5 min, and extracted with EtOAc (50 mL). The organic layer was dried over anhydrous sodium sulfate, and filtered by suction filtration. The filtrate was concentrated in vacuo. The residue was purified by silica gel column chromatography PE/EtOAc (V/V=6/1) to give the title compound as a colorless oil (320 mg, 55%).

$^1$H NMR (400 MHz, CDCl$_3$) δ 7.36 (d, J=7.5 Hz, 1H), 7.24-2.29 (m, 1H), 6.98 (t, J=7.3 Hz, 1H), 6.87 (d, J=8.2 Hz, 1H), 4.94-4.97 (m, 1H), 3.83-3.88 (m, 1H), 3.82 (s, 3H), 3.70-3.62 (m, 1H), 3.51-3.57 (m, 1H), 2.59-2.44 (m, 2H), 2.32-2.19 (m, 2H), 2.16-2.09 (m, 2H), 2.04-1.93 (m, 2H), 1.69-1.60 (m, 2H).

Step 6) t-butyl(diphenyl)silyl 2-[1-[2-[[3aR,6aS)-5,5-difluoro-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate To a solution of 2-[[(3aR,6aS)-5,5-difluoro-2,3,3a,4,6,6a-hexahydro-1H-pentalen-2-yl]oxy]-2-(2-methoxyphenyl)ethanol (320 mg, 1.0 mmol), t-butyl(diphenyl)silyl 2-methyl-2-(5-methyl-6-oxazol-2-yl-2,4-dioxo-1H-thieno[2,3-d]pyrimid-3-yl)-propionate (580 mg, 1.0 mmol) and triphenylphosphine (540 mg, 2.06 mmol) in anhydrous tetrahydrofuran (10 mL) was added diisopropyl azodicarboxylate (0.40 mL, 2.0 mmol) dropwise slowly at 0° C. under N$_2$. After the addition, the mixture was stirred at rt for 15 hours. The reaction mixture was concentrated in vacuo to remove the solvent, and the residue was purified by silica gel column chromatography (PE/EA (V/V)=5/1) to give the title compound as a light yellow syrup (736 mg, 83%).

Step 7) 2-[1-[2-[[(3aR,6aS)-5,5-difluoro-2,3,3a,4,6,6a-hexahydro-1H-pentalen-2-yl]oxy]-2-(2-methoxyphenyl)ethyl)-5-methyl-6-oxazol-2-yl-2,4-dioxo-thieno[2,3-d]pyrimid-3-yl]-2-methyl-propanoic acid To a solution of t-butyl(diphenyl)silyl 2-[1-[2-[[(3aR,6aS)-5,5-difluoro-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate (736 mg, 0.85 mmol) in tetrahydrofuran (10 mL) was added a solution of tetrabutylammonium fluoride in tetrahydrofuran (2.5 mL, 1 mol/L) at rt. The mixture was stirred at rt for 1 hours. The mixture was concentrated. To the residue was added water (100 mL) and EtOAc (100 mL), the mixture was partitioned. The organic layer was dried over anhydrous sodium sulfate, and filtered by suction filtration. The filtrate was concentrated in vacuo. The residue was purified by silica gel column chromatography EtOAc to give the title compound as a white solid (118 mg, 22%).

MS (ES/API, pos. ion) m/z: 630.1 [M+H]$^+$ $^1$H NMR (400 MHz, CDCl$_3$) δ 7.69 (s, 1H), 7.50 (d, J=6.4 Hz, 1H), 7.30-7.23 (m, 1H), 7.21 (s, 1H), 7.02 (t, J=7.4 Hz, 1H), 6.84 (d, J=8.2 Hz, 1H), 5.33-5.28 (m, 1H), 4.16-4.11 (m, 1H), 4.04-4.00 (m, 1H), 3.82 (s, 3H), 3.83-3.78 (m, 1H), 2.83 (s, 3H), 2.49-2.41 (m, 2H), 2.23-2.03 (m, 6H), 1.87 (s, 3H), 1.83 (s, 3H), 1.55-1.46 (m, 2H).

Example 22

2-[1-[2-[[(2S,3aS,6aR)-4,5-dihydroxy-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid

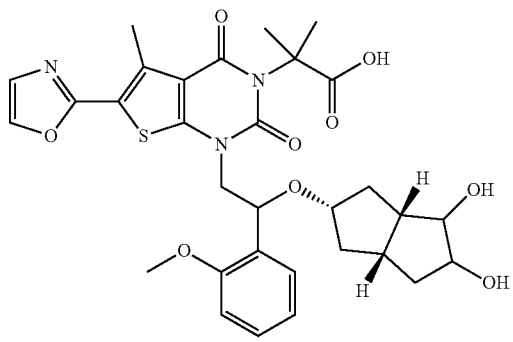 [SMILES: COc1ccccc1C(Cn1c(=O)n(C(C)(C)C(=O)O)c(=O)c2c(C)c(-c3ncco3)sc21)O[C@H]1C[C@H]2CC(O)C(O)[C@H]2C1]

Step 1) [2-[[(3aR,6aS)-5-benzyloxy-1,2,3,3a,4,5,6,6a-octahydropentalen-2-yl]oxy]-2-(2-methoxyphenyl)ethoxy]-t-butyl-dimethylsilane To a solution of 2-[[(3aR,6aS)-5-benzyloxy-1,2,3,3a,4,5,6,6a-octahydropentalen-2-yl]oxy]-2-(2-methoxyphenyl) ethanol (2.60 g, 6.80 mmol) in DCM (30 mL) were added imidazole (1.17 g, 17.0 mmol) and t-butyldimethylsilylchloride (2.09 g, 13.6 mmol) in turn on an ice bath. After the system was stable, the mixture was moved to rt and stirred for 2 hours. The reaction mixture was stopped and filtered by suction filtration, the filter cake was washed with DCM (10 mL). The filtrate was concentrated in vacuo to remove the solvent, and the residue was purified by silica gel column chromatography (PE/EA (V/V)=10/1) to give the title compound as a colorless oil (3.20 g, 94.8%).

Step 2) (3aR,6aS)-5-[2-[t-butyl(dimethyl)silyl]oxy-1-(2-methoxyphenyl)ethoxy]-1,2,3,3a,4,5,6,6a-octahydropentalen-2-ol

[2-[[(3aR,6aS)-5-Benzyloxy-1,2,3,3a,4,5,6,6a-octahydropentalen-2-yl]oxy]-2-(2-methoxyphenyl)ethoxy]-t-butyldimethylsilane (3.20 g, 6.44 mmol) was dissolved in methanol (20 mL) and tetrahydrofuran (10 mL), and then palladium on carbon (0.32 g, 10%) was added. The mixture was stirred at rt under H$_2$ for 2 hours. The mixture was filtered by suction filtration. The filtrate was concentrated in vacuo to get the title compound as a colorless oil (2.62 g, 100%).

Step 3) [(3aR,6aS)-5-[2-[t-butyl(dimethyl)silyl]oxy-1-(2-methoxyphenyl)ethoxy]-1,2,3,3a,4,5,6,6a-octahydropentalen-2-yl] mesylate To a solution of (3aR,6aS)-5-[2-[t-butyl(dimethyl)silyl]oxy-1-(2-methoxyphenyl)ethoxy]-1,2,3,3a,4,5,6,6a-octahydropentalen-2-ol (2.62 g, 6.44 mmol) and triethylamine (3 mL, 21.4 mmol) in acetone (30 mL) was added methylsulfonyl chloride (1 mL, 12.9 mmol) dropwise slowly on an ice bath. The mixture was stirred at rt overnight. The mixture was filtered by suction filtration and the filtrate was concentrated in vacuo to remove the solvent, and the residue was purified by silica gel column chromatography (PE/EA (V/V)=4/1) to give the title compound as a colorless oil (1.884 g, 60.3%).

MS (ESI, pos. ion) m/z: 507.3[M+Na]$^+$;

Step 4) [2-[[(2S,3aR,6aS)-1,2,3,3a,4,6a-hexahydropentalen-2-yl]oxy]-2-(2-methoxyphenyl) ethoxy]-t-butyl-dimethylsilane To a solution of [(3aR,6aS)-5-[2-[t-butyl(dimethyl)silyl]oxy-1-(2-methoxyphenyl)ethoxy]-1,2,3,3a,4,5,6,6a-octahydropentalen-2-yl] mesylate (1.88 g, 3.88 mmol) in toluene (20 mL) was added 1,8-diazabicyclo[5.4.0]-7-undecene (1.2 mL, 12.9 mmol) dropwise slowly at rt. The mixture was stirred at 120° C. overnight. The mixture was cooled to rt and adjusted to pH about 5 with dilute hydrochloric acid (2 N) and extracted with ethyl acetate (100 mL). The organic phase was washed with water (100 mL), saturated brine (100 mL), dried over anhydrous sodium sulfate, filtered by suction filtration. The filtrate was concentrated in vacuo. The residue was purified by silica gel chromatograph (PE/EtOAc (V/V)=10/1) to give the title compound as a colorless oil (0.693 g, 46.0%).

MS (ESI, pos. ion) m/z: 411.1[M+Na]$^+$;

Step 5) 2-[[(2S,3aR,6aS)-1,2,3,3a,4,6a-hexahydropentalen-2-yl]oxy]-2-(2-methoxyphenyl) ethanol

[2-[[(2S,3aR,6aS)-1,2,3,3a,4,6a-hexahydropentalen-2-yl]oxy]-2-(2-methoxyphenyl)ethoxy]-t-butyl-dimethylsilane (0.693 g, 1.78 mmol) was dissolved in tetrahydrofuran (10 mL), and then a solution of tetrabutylammonium fluoride (1 mmol/L) in tetrahydrofuran (2.7 mL, 2.7 mmol) was added. The mixture was stirred at rt for 3 hours. The reaction mixture was concentrated in vacuo to remove the solvent, and the residue was purified by silica gel column chromatography (PE/EA (V/V)=10/1) to give the title compound as a colorless oil (0.334 g, 68.3%).

MS (ESI, pos. ion) m/z: 297.1[M+Na]$^+$;

$^1$H NMR (400 MHz, CDCl$_3$) δ 7.40 (dd, J=7.5, 1.4 Hz, 1H), 7.30-7.24 (m, 1H), 6.99 (t, J=7.4 Hz, 1H), 6.87 (d, J=8.2 Hz, 1H), 5.79-5.74 (m, 1H), 5.68-5.64 (m, 1H), 4.92 (dd, J=9.0, 3.1 Hz, 1H), 3.90-3.85 (m, 1H), 3.84 (s, 3H), 3.66-3.59 (m, 1H), 3.43-3.34 (m, 1H), 3.22-3.15 (m, 1H), 2.78-2.64 (m, 2H), 2.64-2.55 (m, 1H), 2.41-2.33 (m, 1H), 2.00-1.90 (m, 1H), 1.89-1.82 (m, 1H), 1.79-1.71 (m, 1H), 1.69-1.65 (m, 1H).

Step 6) t-butyl(diphenyl)silyl 2-[1-[2-[[(2S,3aR,6aS)-1,2,3,3a,4,6a-hexahydropentalen-2-yl]oxy]-2-(2-methoxyphenyl)ethyl]-5-methyl-6-oxazol-2-yl-2,4-dioxo-thieno[2,3-d]pyrimid-3-yl]-2-methylpropionate To a solution of 2-[[(2S,3aR,6aS)-1,2,3,3a,4,6a-hexahydropentalen-2-yl]oxy]-2-(2-methoxyphenyl)ethanol (0.147 g, 0.536 mmol), t-butyl(diphenyl)silyl 2-methyl-2-(5-methyl-6-oxazol-2-yl-2,4-dioxo-1H-thieno[2,3-d]pyrimid-3-yl)-propionate (0.338 g, 0.589 mmol) and triphenylphosphine (0.287 g, 1.07 mmol) in anhydrous tetrahydrofuran (6 mL) was added diisopropyl azodicarboxylate (0.22 mL, 1.10 mmol) dropwise slowly under N$_2$. After the addition, the mixture was stirred at rt overnight. The reaction mixture was concentrated in vacuo to remove the solvent, and the residue was purified by silica gel column chromatography (PE/EA (V/V)=9/1) to give the title compound as a white solid (0.346 g, 77.8%).

Step 7) t-butyl(diphenyl)silyl 2-(1-(2-(2-methoxyphenyl)-2-(((1bS,3S,4aS)-octahydropentalen[1,2-b]epoxyvin-3-yl)oxy)ethyl)-5-methyl-6-(oxazol-2-yl)-2,4-dioxo-1,2-dihydrothieno[2,3-d]pyrimid-3(4H)-yl)-2-methylpropionate To a solution of t-butyl(diphenyl)silyl 2-[1-[2-[[(2S,3aR,6aS)-1,2,3,3a,4,6a-hexahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate (0.346 g, 0.417 mmol) in DCM (6 mL) was added 3-chloroperoxybenzoic acid (0.089 g, 0.44 mmol) at rt. The mixture was stirred for 6 hours. The reaction was quenched with saturated sodium thiosulfate solution (20 mL). The organic layer was washed with saturated aqueous sodium bicarbonate solution (20 mL) and saturated aqueous sodium chloride (20 mL) in turn, dried over anhydrous sodium sulfate, filtered by suction filtration. The filtrate was concentrated in vacuo. The residue was purified by silica gel chromatograph (PE/EtOAc (V/V)=5/1) to give the title compound as a white solid (0.276 g, 78.3%).

Step 8) 2-[1-[2-[[(2S,3aS,6aR)-4,5-dihydroxy-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methylpropanoic acid To a solution of t-butyl(diphenyl)silyl 2-(1-(2-(2-methoxyphenyl)-2-(((1bS,3S,4aS)-octahydropentalen[1,2-b]epoxyvin-3-yl)oxy)ethyl)-5-methyl-6-(oxazol-2-yl)-2,4-dioxo-1,2-dihydrothieno[2,3-d]pyrimid-3(4H)-yl)-2-methylpropionate (0.276 g, 0.326 mmol) in tetrahydrofuran (4 mL) was added dilute sulfuric acid (1.2 mL, 3 mol/L) at rt. The mixture was stirred at 40° C. overnight. The mixture was concentrated, and to the residue was added water. A solid precipitated out. The mixture was filtered by suction filtration, the filter cake was washed with water (10 mL) and purified by pre-HPLC to get title compound as a white solid (0.035 g, 17%).

MS (ESI, pos. ion) m/z: 626.3[M+H]$^+$;

$^1$H NMR (400 MHz, DMSO-d$_6$) δ 12.38 (s, 1H), 8.21 (s, 1H), 7.41 (d, J=7.5 Hz, 1H), 7.38 (s, 1H), 7.34-7.27 (m, 1H), 7.07-6.96 (m, 2H), 5.20-5.13 (m, 1H), 4.54-4.44 (m, 2H), 3.83 (s, 3H), 3.80-3.75 (m, 1H), 3.69-3.63 (m, 1H), 3.62-3.58 (m, 1H), 2.76 (s, 3H), 2.25-2.15 (m, 1H), 2.04-1.95 (m, 2H), 1.93-1.86 (m, 1H), 1.85-1.76 (m, 1H), 1.74-1.70 (m, 1H), 1.68 (s, 3H), 1.64 (s, 3H), 1.49-1.37 (m, 2H), 1.37-1.26 (m, 2H).

Example 23

2-[1-[2-[[(3aR,6aS)-5-cyclopropyl-5-hydroxy-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methylpropanoic acid

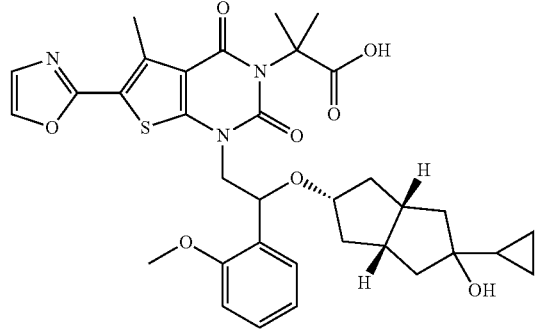 [SMILES: COc1ccccc1C(Cn1c(=O)n(C(C)(C)C(=O)O)c(=O)c2c(C)c(-c3ncco3)sc21)O[C@@H]1C[C@@H]2CC(O)(C3CC3)C[C@@H]2C1]

Step 1) (3aR,6aS)-5-[2-[t-butyl(dimethyl)silyl]oxy-1-(2-methoxyphenyl)ethoxy]-2-cyclopropyl-3,3a,4,5,6,6a-hexahydro-1H-pentalen-2-ol To a solution of (3aR,6aS)-5-[2-[t-butyl(dimethyl)silyl]oxy-1-(2-methoxyphenyl)ethoxy]-3,3a,4,5,6,6a-hexahydro-1H-pentalen-2-one (400 mg, 0.99 mmol) in anhydrous tetrahydrofuran (20 mL) was added a solution of cyclopropyl magnesium bromide in tetrahydrofuran (3.0 mL, 3.0 mmol, 1 mol/L) dropwise under N$_2$ on an ice bath. After the addition, the mixture was stirred at rt for 21 hour. The mixture was quenched with water (2 mL) on an ice bath. The resulting mixture was extracted with ethyl acetate (30 mL×2). The combined organic phases were dried over anhydrous sodium sulfate, filtered by suction filtration. The filtrate was concentrated in vacuo. The residue was purified by silica gel chromatograph (PE/EtOAc (V/V)=4/1) to give the title compound as a light yellow oil (198 mg, 44.8%).

MS (ES/API, pos. ion) m/z: 469.4 [M+Na]+

Step 2) (3aR,6aS)-2-cyclopropyl-5-[2-hydroxy-1-(2-methoxyphenyl)ethoxy]-3,3a,4,5,6,6a-hexahydro-1H-pentalen-2-ol To a solution of (3aR,6aS)-5-[2-[t-butyl(dimethyl)silyl]oxy-1-(2-methoxyphenyl) ethoxy]-2-cyclopropyl-3,3a,4,5, 6,6a-hexahydro-1H-pentalen-2-ol (198 mg, 0.44 mmol) in anhydrous tetrahydrofuran (10 mL) was added a solution of tetrabutylammonium fluoride (1 mol/L) in tetrahydrofuran (0.9 mL, 0.9 mmol) at rt. After the addition, the mixture was stirred for 1 hour. The mixture was concentrated to remove most of solvent. To the residue was added water (50 mL) to quench the reaction, and the mixture was extracted with EtOAc (30 mL×2), the mixture was partitioned. The organic layer was dried over anhydrous sodium sulfate, and filtered by suction filtration. The filtrate was concentrated in vacuo. The residue was purified by silica gel column chromatography PE/EtOAc (V/V=3/1) to give the title compound as a white solid (125 mg, 84.8%).

MS (ES/API, pos. ion) m/z: 355.3 [M+Na]+

Step 3) t-butyl(diphenyl)silyl 2-[1-[2-[[(3aR,6aS)-5-cyclopropyl-5-hydroxy-2,3,3a,4,6,6a-hexahydro-1H-pentalen-2-yl]oxy]-2-(2-methoxyphenyl)ethyl]-5-methyl-6-oxazol-2-yl-2,4-di oxo-thieno[2,3-d]pyrimid-3-yl]-2-methyl-propionate To a solution of (3aR,6aS)-2-cyclopropyl-5-[2-hydroxy-1-(2-methoxyphenyl) ethoxy]-3,3a,4,5,6,6a-hexahydro-1H-pentalen-2-ol (121 mg, 0.36 mmol), t-butyl(diphenyl)silyl 2-methyl-2-(5-methyl-6-oxazol-2-yl-2,4-dioxo-1H-thieno[2,3-d]pyrimid-3-yl)-propionate (200 mg, 0.35 mmol) and triphenylphosphine (184 mg, 0.69 mmol) in anhydrous tetrahydrofuran (10 mL) was added diisopropyl azodicarboxylate (143 mg, 0.69 mmol) dropwise slowly under N$_2$. After the addition, the mixture was stirred for 21 hours. The reaction mixture was concentrated in vacuo to remove the solvent, and the residue was purified by silica gel column chromatography (PE/EA (V/V)=4/1) to give the title compound as an off-white solid (245 mg, 97.1%).

Step 4) 2-[1-[2-[[(3aR,6aS)-5-cyclopropyl-5-hydroxy-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid To a solution of t-butyl(diphenyl)silyl 2-[1-[2-[[(3aR,6aS)-5-cyclopropyl-5-hydroxy-2,3,3a,4,6,6a-hexahydro-1H-pentalen-2-yl]oxy)-2-(2-methoxyphenyl)ethyl]-5-methyl-6-oxazol-2-yl-2,4-dioxo-thieno[2,3-d]pyrimid-3-yl]-2-methyl-propionate (245 mg, 0.27 mmol) in tetrahydrofuran (2.0 mL) was added a solution of tetrabutylammonium fluoride in tetrahydrofuran (0.8 mL, 0.8 mmol, 1 mol/L) at rt. The mixture was stirred for 2 hours. The mixture was quenched with water (10 mL) and extracted with ethyl acetate (20 mL×2). The resulting mixture was partitioned. The organic layer was washed with saturated brine, dried over anhydrous sodium sulfate, and filtered by suction filtration. The filtrate was concentrated in vacuo. The residue was purified by pre-HPLC to give the title compound as a white solid (52 mg, 29.0%).

MS (ES/API, neg. ion) m/z: 648.3[M–H]–

$^1$H NMR (400 MHz, CDCl$_3$) δ 7.69 (s, 1H), 7.54-7.52 (m, 1H), 7.31-7.26 (m, 1H), 7.21 (s, 1H), 7.01 (t, J=7.4 Hz, 1H), 6.87 (d, J=8.2 Hz, 1H), 5.29-5.26 (m, 1H), 4.32-4.26 (m, 1H), 3.99-3.93 (m, 1H), 3.89 (s, 3H), 3.76-3.68 (m, 1H), 2.84 (s, 3H), 2.31-2.27 (m, 2H), 2.02-1.91 (m, 2H), 1.86 (s, 3H), 1.83 (s, 3H), 1.77-1.66 (m, 3H), 1.57-1.51 (m, 3H), 1.00-0.93 (m, 1H), 0.37-0.31 (m, 2H), 0.28-0.25 (m, 2H).

Example 24

2-[1-[2-[[(3aR,6aS)-5-hydroxy-1,2,3,3a,4,5,6,6a-octahydropentalen-2-yl]oxy]-2-[2-(difluoromethoxy)phenyl]ethyl]-5-methyl-6-oxazol-2-yl-2,4-dioxo-thieno[2,3-d]pyrimid-3-yl]-2-meth yl-propanoic acid

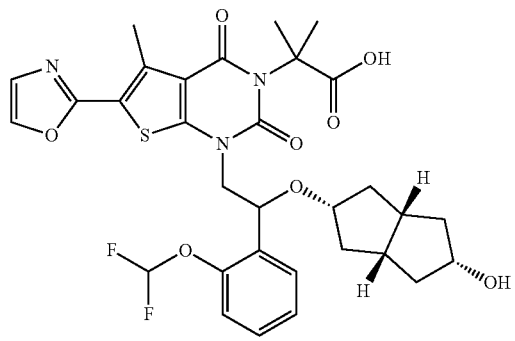 [SMILES: Cc1c(-c2ncco2)sc2c1c(=O)n(C(C)(C)C(=O)O)c(=O)n2CC(O[C@H]1C[C@H]2C[C@@H](O)C[C@H]2C1)c1ccccc1OC(F)F]

The title compound was prepared from 2-[2-(difluoromethoxy)phenyl]acetic acid (3.00 g, 14.8 mmol) according to the method described in example 1. The obtained title compound is gray solid (0.80 g, 8.4%).

MS (ESI, neg. ion) m/z: 644.3[M–H]–;

$^1$H NMR (400 MHz, CDCl$_3$) δ 7.72 (d, J=5.9 Hz, 1H), 7.62 (d, J=6.1 Hz, 1H), 7.35 (t, J=9.5 Hz, 1H), 7.31 (t, J=8.1 Hz, 1H), 7.24 (s, 1H), 7.19 (d, J=7.7 Hz, 1H), 6.71 (d, J=2.2 Hz, 1H), 5.32-5.28 (m, 1H), 4.25-4.16 (m, 2H), 4.07 (d, J=12.9 Hz, 1H), 3.81-3.77 (m, 1H), 2.86 (s, 3H), 2.30-2.20 (m, 2H), 1.94-1.90 (m, 2H), 1.85 (s, 3H), 1.81 (s, 3H), 1.71-1.64 (m, 2H), 1.64-1.56 (m, 2H), 1.52-1.50 (m, 1H), 1.49-1.47 (m, 1H).

Example 25

2-[1-[2-[[(3aS,6aR)-5-(cyanomethyl)-1,2,3,3a,4,5,6,6a-octahydropentalen-2-yl]oxy]-2-(2-methoxyphenyl)ethyl)-5-methyl-6-oxazol-2-yl-2,4-dioxo-thieno[2,3-d]pyrimid-3-yl]-2-methyl-propanoic acid

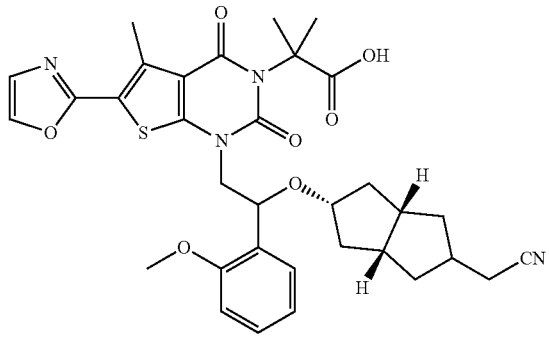 [SMILES: COc1ccccc1C(Cn1c(=O)n(C(C)(C)C(=O)O)c(=O)c2c(C)c(-c3ncco3)sc21)O[C@H]1C[C@H]2CC(CC#N)C[C@H]2C1]

Step 1) 2-[(3aR,6aS)-5-[2-[t-butyl(dimethyl)silyl]oxy-1-(2-methoxyphenyl)ethoxy]-3,3a,4,5,6,6a-hexahydro-1H-pentalen-2-ylidene]acetonitrile A solution of dimethyl cyanomethylphosphate (197 mg, 1.11 mmol) in tetrahydrofuran (20.0 mL) was cooled to −20° C. under $N_2$. To the solution was added a solution of n-butyl lithium in n-hexane (0.9 mL, 2.0 mmol, 2.5 mol/L) dropwise. After the addition, the mixture was stirred at rt for 30 min. To the solution was added a solution of (3aS,6aR)-5-[2-[t-butyl(dimethyl)silyl]oxy-1-(2-methoxyphenyl)ethoxy]-3,3a,4,5,6,6a-hexahydro-1H-pentalen-2-one (300 mg, 0.74 mmol) in tetrahydrofuran (1.0 mL) dropwise at 0° C. After the addition, the mixture was stirred at rt for 21 hours. The mixture was quenched with water (10.0 mL) at 0° C. The resulting mixture was extracted with ethyl acetate (30 mL×2). The combined organic phases were dried over anhydrous sodium sulfate, filtered by suction filtration. The filtrate was concentrated in vacuo to give the title compound as a light yellow oil (310 mg, 97.8%).

MS (ES/API, pos. ion) m/z: 314.3 [M-TBS+H]$^+$

Step 2) 2-[(3aS,6aR)-5-[2-[t-butyl(dimethyl)silyl]oxy-1-(2-methoxyphenyl)ethoxy]-1,2,3,3a,4,5,6,6a-octahydropentalen-2-yl]acetonitrile 2-[(3aR,6aS)-5-[2-[t-Butyl(dimethyl)silyl]oxy-1-(2-methoxyphenyl)ethoxy]-3,3a,4,5,6,6a-hexahydro-1H-pentalen-2-ylidene]acetonitrile (310 mg, 0.72 mmol) was dissolved in methanol (10.0 mL), and then palladium on carbon (31 mg, 0.29 mmol, 10%) was added. The system gas was replaced with $H_2$ 3 times, the mixture was stirred at rt under $H_2$ for 30 min. The mixture was filtered. The filter cake was washed with methanol (10). The filtrate was concentrated in vacuo to get the title compound as a light yellow oil (310 mg, 99.5%).

MS (ES/API, pos. ion) m/z: 452.4 [M+Na]$^+$

Step 3) 2-[(3aS,6aR)-5-[2-hydroxy-1-(2-methoxyphenyl)ethoxy]-1,2,3,3a,4,5,6,6a-octahydropentalen-2-yl]acetonitrile To a solution of 2-[(3aS,6aR)-5-[2-[t-butyl(dimethyl)silyl]oxy-1-(2-methoxyphenyl)ethoxy]-1,2,3,3a,4,5,6,6a-octahydropentalen-2-yl]acetonitrile (310 mg, 0.72 mmol) in anhydrous tetrahydrofuran (10 mL) was added a solution of tetrabutylammonium fluoride in tetrahydrofuran (2.1 mL, 2.0 mmol, 1.0 mol/L) at rt. After the addition, the mixture was stirred for 30 min. The mixture was quenched with water (10 mL). The resulting mixture was extracted with ethyl acetate (20 mL×2). The combined organic phases were dried over anhydrous sodium sulfate, filtered by suction filtration. The filtrate was concentrated in vacuo. The residue was purified by silica gel chromatograph (PE/EtOAc (V/V)=4/1) to give the title compound as a white solid (120 mg, 80.7%).

MS (ES/API, pos. ion) m/z: 316.3 [M+H]$^+$

Step 4) t-butyl(diphenyl)silyl 2-[1-[2-[[(3aS,6aR)-5-(cyanomethyl)-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate To a solution of 2-[(3aS,6aR)-5-[2-hydroxy-1-(2-methoxyphenyl)ethoxy]-1,2,3,3a,4,5,6,6a-octahydropentalen-2-yl]acetonitrile (115 mg, 0.36 mmol), t-butyl(diphenyl)silyl 2-methyl-2-(5-methyl-6-oxazol-2-yl-2,4-dioxo-1H-thieno[2,3-d]pyrimid-3-yl)-propionate (200 mg, 0.35 mmol) and triphenylphosphine (184 mg, 0.69 mmol) in anhydrous tetrahydrofuran (10 mL) was added diisopropyl azodicarboxylate (144 mg, 0.69 mmol) dropwise slowly under $N_2$. After the addition, the mixture was stirred for 2.5 hours. The reaction mixture was concentrated in vacuo to remove the solvent, and the residue was purified by silica gel column chromatography (PE/EA (V/V)=6/1) to give the title compound as an off-white solid (200 mg, 65.8%).

Step 5) 2-[1-[2-[[(3aS,6aR)-5-(cyanomethyl)-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid t-Butyl(diphenyl)silyl 2-[1-[2-[[(3aS,6aR)-5-(cyanomethyl)-1,2,3,3a,4,5,6,6a-octahydropentalen-2-yl]oxy]-2-(2-methoxyphenyl)ethyl]-5-methyl-6-oxazol-2-yl-2,4-dioxo-thien o[2,3-d]pyrimid-3-yl]-2-methyl-propionate (200 mg, 0.23 mmol) was dissolved in tetrahydrofuran (20 mL). To the mixture was added a solution of tetrabutylammonium fluoride in tetrahydrofuran (1.0 mol/L, 0.7 mL, 0.7 mmol) at rt. The mixture was stirred at rt for 1.5 hours. The mixture was quenched with water (10 mL). The resulting mixture was extracted with ethyl acetate (20 mL×2). The combined organic phases were washed with saturated brine, dried over anhydrous sodium sulfate, filtered by suction filtration. The filtrate was concentrated in vacuo. The residue was purified by silica gel chromatograph (PE/EtOAc (V/V)=1/1) to give the title compound as a white solid (12 mg, 8.3%).

MS (ES/API, neg. ion) m/z: 633.1[M+H]$^+$ $^1$H NMR (400 MHz, CDCl$_3$) δ 7.69 (s, 1H), 7.50 (d, J=7.3 Hz, 1H), 7.28-7.22 (m, 2H), 7.01 (t, J=7.4 Hz, 1H), 6.82 (d, J=8.2 Hz, 1H), 5.30-5.27 (m, 1H), 4.09-4.04 (m, 2H), 3.86-3.82 (m, 1H), 3.80 (s, 3H), 2.84 (s, 3H), 2.37-2.29 (m, 2H), 2.25-2.20 (m, 1H), 2.09-1.98 (m, 3H), 1.93-1.86 (m, 2H), 1.84 (s, 3H), 1.81 (s, 3H), 1.41-1.33 (m, 2H), 1.17-1.04 (m, 3H).

Example 26

2-[1-[2-[[(3aR,6aS)-5-cyano-5-hydroxy-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid

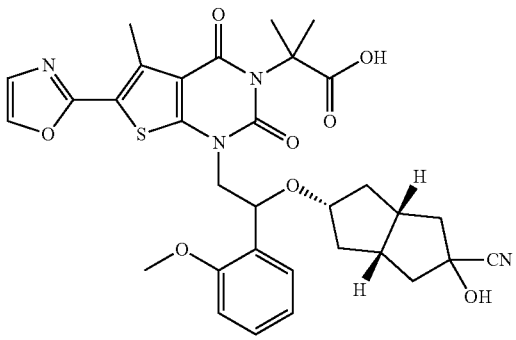 [SMILES: COc1ccccc1C(Cn1c(=O)n(C(C)(C)C(=O)O)c(=O)c2c(C)c(-c3ncco3)sc21)O[C@@H]1C[C@@H]2CC(O)(C#N)C[C@@H]2C1]

Step 1) (3aR,6aS)-5-[2-hydroxy-1-(2-methoxyphenyl)ethoxy]-3,3a,4,5,6,6a-hexahydro-1H-pentalen-2-one To a solution of (3aS,6aR)-5-[2-[t-butyl(dimethyl)silyl]oxy-1-(2-methoxyphenyl)ethoxy]-3,3a,4,5,6,6a-hexahydro-1H-pentalen-2-one (1.00 g, 2.50 mmol) in anhydrous tetrahydrofuran (10 mL) was added a solution of tetrabutylammonium fluoride (1 mol/L) in tetrahydrofuran (3.7 mL, 3.70 mmol) at rt. After the addition, the mixture was stirred for 40 min. The mixture was concentrated to remove most of solvent. To the residue was added water (100 mL) and EtOAc (100 mL), the mixture was partitioned. The organic layer was dried over anhydrous sodium sulfate, and filtered by suction filtration. The filtrate was concentrated in vacuo. The residue was purified by silica gel column chromatography DCM/EtOAc (V/V=10/1) to give the title compound as a white solid (0.52 g, 70%).

MS (ES/API, pos. ion) m/z: 313.1 [M+Na]$^+$

Step 2) (3aR,6aS)-2-hydroxy-5-[2-hydroxy-1-(2-methoxyphenyl)ethoxy]-3,3a,4,5,6,6a-hexahydro-1H-pentalen-2-carbonitrile To a solution of (3aR,6aS)-5-[2-hydroxy-1-(2-methoxyphenyl)ethoxy]-3,3a,4,5,6,6a-hexahydro-1H-pentalen-2-one (900 mg, 3.10 mmol) in anhydrous tetrahydrofuran (10 mL) were added trimethylsilyl cyanide (0.85 mL, 6.2 mmol) and a solution of tetrabutylammonium fluoride in tetrahydrofuran (6.0 mL, 6.0 mmol, 1 mol/L) in turn under $N_2$ at rt. After the addition, the mixture was stirred at rt for 15 hours. The reaction was quenched with dilute hydrochloric acid (1 mL, 2 N). The mixture was concentrated to remove most of solvent. To the residue was added water (20 mL) and EtOAc (20 mL), the mixture was partitioned. The organic layer was dried over anhydrous sodium sulfate, and filtered by suction filtration. The filtrate was concentrated in vacuo. The residue was purified by silica gel column chromatography PE/EtOAc (V/V=3/1) to give the title compound as a white solid (190 mg, 19.32%).

MS (ES/API, pos. ion) m/z: 318.3 [M+H]$^+$ $^1$H NMR (400 MHz, CD$_3$OD) δ 7.31-7.35 (m, 1H), 7.28-7.21 (m, 1H), 6.91-6.98 (m, 2H), 3.96-3.89 (m, 1H), 3.84 (m, 3H), 3.56-3.43 (m, 2H), 2.87-2.71 (m, 2H), 2.63-2.46 (m, 2H), 2.41-2.32 (m, 1H), 2.23-2.27 (m, 1H), 2.10-1.95 (m, 2H), 1.80-1.84 (m, 1H), 1.67-1.58 (m, 1H).

Step 3) t-butyl(diphenyl)silyl 2-[1-[2-[[(3aR,6aS)-5-cyano-5-hydroxy-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate To a solution of (3aR,6aS)-2-hydroxy-5-[2-hydroxy-1-(2-methoxyphenyl) ethoxy]-3,3a,4,5,6,6a-hexahydro-1H-pentalen-2-carbonitrile (91 mg, 0.29 mmol), t-butyl(diphenyl)silyl 2-methyl-2-(5-methyl-6-oxazol-2-yl-2,4-dioxo-1H-thieno[2,3-d]pyrimid-3-yl)-propionate (150 mg, 0.26 mmol) and triphenylphosphine (105 mg, 0.39 mmol) in anhydrous tetrahydrofuran (10 mL) was added diisopropyl azodicarboxylate (0.08 mL, 0.40 mmol) dropwise slowly under $N_2$. After the addition, the mixture was stirred at rt overnight. The reaction mixture was concentrated in vacuo to remove the solvent, and the residue was purified by silica gel column chromatography (PE/EA (V/V)=2/1) to give the title compound as a white solid (228 mg, 99.9%).

Step 4) 2-[1-[2-[[(3aR,6aS)-5-cyano-5-hydroxy-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid To a solution of t-butyl(diphenyl)silyl 2-[1-[2-[[(3aR,6aS)-5-cyano-5-hydroxy-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate (228 mg, 0.26 mmol) in tetrahydrofuran (6 mL) was added a solution of tetrabutylammonium fluoride in tetrahydrofuran (0.4 mL, 0.4 mmol, 1 mol/L) at rt. The mixture was stirred for 30 min. The mixture was concentrated in vacuo. The residue was purified by column chromatography on silica gel eluted with (DCM/MeOH (V/V)=8/1) to give the title compound as a white solid, 40 mg, 24%).

MS (ES/API, neg. ion) m/z: 635.0[M+H]$^+$;

$^1$H NMR (400 MHz, CDCl$_3$) δ 7.71 (s, 1H), 7.49 (d, J=7.4 Hz, 1H), 7.32-7.25 (m, 1H), 7.23 (s, 1H), 7.04 (t, J=7.4 Hz, 1H), 6.84 (d, J=8.1 Hz, 1H), 5.31 (dd, J=8.8, 4.6 Hz, 1H), 4.12-4.06 (m, 2H), 4.00-3.88 (m, 1H), 3.82 (s, 3H), 2.86 (s, 3H), 2.68-2.59 (m, 2H), 2.50-2.42 (m, 1H), 2.41-2.33 (m, 1H), 2.20-2.11 (m, 1H), 2.09-1.97 (m, 3H), 1.88 (s, 3H), 1.84 (s, 3H), 1.64-1.59 (m, 1H), 1.58-1.52 (m, 1H).

Example 27

2-[1-[2-[[(3aS,6aR)-5-(cyanomethyl)-5-hydroxy-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid

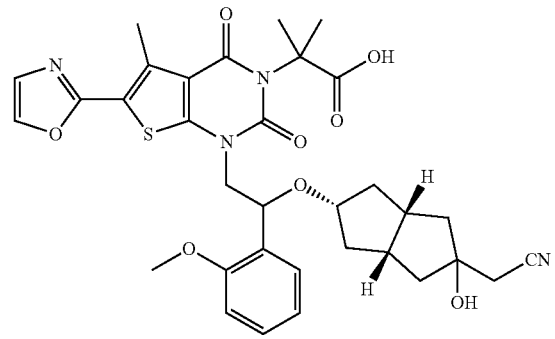 [SMILES: COc1ccccc1C(Cn1c(=O)n(C(C)(C)C(=O)O)c(=O)c2c(C)c(-c3ncco3)sc21)O[C@@H]1C[C@@H]2CC(O)(CC#N)C[C@@H]2C1]

Step 1) 2-[(3aS,6aR)-5-[2-[t-butyl(dimethyl)silyl]oxy-1-(2-methoxyphenyl)ethoxy]-2-hydroxy-3,3a,4,5,6,6a-hexahydro-1H-pentalen-2-yl]acetonitrile Acetonitrile (5.0 mL) was cooled to −78° C. under $N_2$. To the solution was added a solution of n-butyl lithium in n-hexane (0.3 mL, 0.8 mmol, 2.5 mol/L) dropwise. After the addition, the mixture was stirred for 10 min and further stirred at rt for 30 min. To the solution was added a solution of (3aS,6aR)-5-[2-[t-butyl(dimethyl)silyl]oxy-1-(2-methoxyphenyl) ethoxy]-3,3a,4,5,6,6a-hexahydro-1H-pentalen-2-one (100 mg, 0.25 mmol) in acetonitrile (1.0 mL) dropwise at −78° C. After the addition, the mixture was stirred at rt for 19 hours. The mixture was quenched with water (10.0 mL) at −10° C. The resulting mixture was extracted with ethyl acetate (20 mL×2). The combined organic phases were dried over anhydrous sodium sulfate, filtered by suction filtration. The filtrate was concentrated in vacuo. The residue was purified by silica gel chromatograph (PE/EtOAc (V/V)=4/1) to give the title compound as a light yellow oil (35 mg, 31.8%).

MS (ES/API, pos. ion) m/z: 468.4 [M+Na]⁺

Step 2) 2-[(3aS,6aR)-2-hydroxy-5-[2-hydroxy-1-(2-methoxyphenyl)ethoxy]-3,3a,4,5,6,6a-hexahydro-1H-pentalen-2-yl]acetonitrile To a solution of 2-[(3aS,6aR)-5-[2-[t-butyl(dimethyl)silyl]oxy-1-(2-methoxyphenyl)ethoxy]-2-hydroxy-3,3a,4,5,6,6a-hexahydro-1H-pentalen-2-yl]acetonitrile (200 mg, 0.45 mmol) in anhydrous tetrahydrofuran (10 mL) was added a solution of tetrabutylammonium fluoride (1 mol/L) in tetrahydrofuran (1.4 mL, 1.4 mol/L) at rt. After the addition, the mixture was stirred for 17 hour. The mixture was quenched with water (10 mL). The resulting mixture was extracted with ethyl acetate (20 mL×2). The combined organic phases were dried over anhydrous sodium sulfate, filtered by suction filtration. The filtrate was concentrated in vacuo. The residue was purified by silica gel chromatograph (PE/EtOAc (V/V)=1/1) to give the title compound as a white solid (120 mg, 80.7%).

MS (ES/API, pos. ion) m/z: 332.3 [M+Na]⁺

Step 3) t-butyl(diphenyl)silyl 2-[1-[2-[[(3aS,6aR)-5-(cyanomethyl)-5-hydroxy-2,3,3a,4,6,6a-hexahydro-1H-pentalen-2-yl]oxy]-2-(2-methoxyphenyl)ethyl]-5-methyl-6-oxazol-2-yl-2,4-di oxo-thieno[2,3-d] pyrimid-3-yl]-2-methyl-propionate To a solution of 2-[(3aS,6aR)-2-hydroxy-5-[2-hydroxy-1-(2-methoxyphenyl) ethoxy]-3,3a,4,5,6,6a-hexahydro-1H-pentalen-2-yl]acetonitrile (120 mg, 0.36 mmol), t-butyl(diphenyl)silyl 2-methyl-2-(5-methyl-6-oxazol-2-yl-2,4-dioxo-1H-thieno[2,3-d]pyrimid-3-yl)-propionate (200 mg, 0.35 mmol) and triphenylphosphine (184 mg, 0.69 mmol) in anhydrous tetrahydrofuran (10 mL) was added diisopropyl azodicarboxylate (143 mg, 0.69 mmol) dropwise slowly under N₂. After the addition, the mixture was stirred for 18 hours. The reaction mixture was concentrated in vacuo to remove the solvent, and the residue was purified by silica gel column chromatography (PE/EA (V/V)=4/1) to give the title compound as an off-white solid (240 mg, 77.6%).

Step 4) 2-[1-[2-[[(3aS,6aR)-5-(cyanomethyl)-5-hydroxy-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid To a solution of t-butyl(diphenyl)silyl 2-[1-[2-[[(3aS,6aR)-5-(cyanomethyl)-5-hydroxy-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate (240 mg, 0.27 mmol) in tetrahydrofuran (20 mL) was added a solution of tetrabutylammonium fluoride in tetrahydrofuran (0.8 mL, 0.8 mmol, 1 mol/L) at rt. The mixture was stirred for 4.5 hours. The mixture was quenched with water (10 mL), and extracted with EtOAc (20 mL×2). The combined organic phases were washed with saturated brine, dried over anhydrous sodium sulfate, and filtered by suction filtration. The filtrate was concentrated in vacuo. The residue was purified by silica gel chromatograph (EtOAc) to give the title compound as a white solid (59 mg, 27%).

MS (ES/API, neg. ion) m/z: 649.3[M+H]+
¹H NMR (400 MHz, CDCl₃) δ 7.71 (s, 1H), 7.46 (d, J=6.5 Hz, 1H), 7.31-7.26 (m, 2H), 7.00 (t, J=7.4 Hz, 1H), 6.87 (d, J=8.2 Hz, 1H), 5.31-5.28 (m, 1H), 4.37-4.23 (m, 1H), 4.07-4.01 (m, 1H), 3.89 (s, 3H), 3.83-3.76 (m, 1H), 2.82 (s, 3H), 2.54 (s, 2H), 2.46-2.34 (m, 2H), 2.02-1.97 (m, 1H), 1.94-1.89 (m, 2H), 1.87-1.83 (m, 2H), 1.81 (s, 3H), 1.80 (s, 3H), 1.78-1.57 (m, 3H).

Example 28

2-[1-[2-[[(3aR,6aS)-5-butyl-5-hydroxy-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid

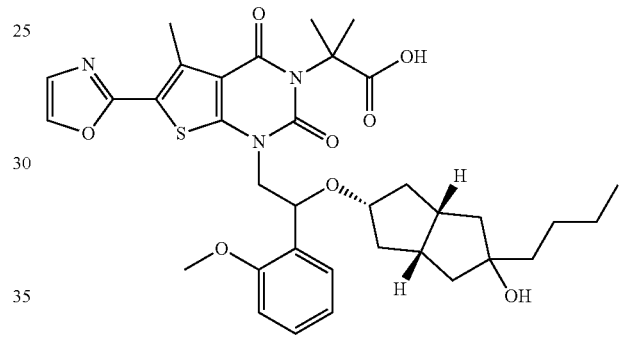

Step 1) (3aR,6aS)-5-[2-[t-butyl(dimethyl)silyl]oxy-1-(2-methoxyphenyl)ethoxy]-2-ethyl-3,3a,4,5,6,6a-hexahydro-1H-pentalen-2-ol To a solution of (3aS,6aR)-5-[2-[t-butyl(dimethyl)silyl] oxy-1-(2-methoxyphenyl) ethoxy]-3,3a,4,5,6,6a-hexahydro-1H-pentalen-2-one (650 mg, 1.607 mmol) in anhydrous tetrahydrofuran (5 mL) was added a solution of cyclopropyl magnesium bromide in tetrahydrofuran (1.2 mL, 3.0 mmol, 2.5 mol/L) dropwise under N₂ on an ice bath. After the addition, the mixture was stirred for 4 hours. The reaction was quenched with saturated aqueous ammonium chloride (3 mL). The mixture was concentrated to remove most of solvent. To the residue was added water (50 mL) and EtOAc (50 mL), the mixture was partitioned. The organic layer was dried over anhydrous sodium sulfate, and filtered by suction filtration. The filtrate was concentrated in vacuo to give the title compound as a colorless oil (410 mg, 55.16%).

Step 2) (3aR,6aS)-2-butyl-5-[2-hydroxy-1-(2-methoxyphenyl)ethoxy]-3,3a,4,5,6,6a-hexahydro-1H-pentalen-2-ol To a solution of (3aR,6aS)-5-[2-[t-butyl(dimethyl)silyl] oxy-1-(2-methoxyphenyl)ethoxy]-2-ethyl-3,3a,4,5,6,6a- hexahydro-1H-pentalen-2-ol (410 mg, 0.886 mmol) in anhydrous tetrahydrofuran (10 mL) was added a solution of tetrabutylammonium fluoride (1 mol/L) in tetrahydrofuran (1.0 mL, 1.0 mmol) at rt. After the addition, the mixture was stirred for 1 hour. The mixture was concentrated to remove most of solvent. To the residue was added water (50 mL) and EtOAc (50 mL), the mixture was partitioned. The organic layer was dried over anhydrous sodium sulfate, and filtered by suction filtration. The filtrate was concentrated in vacuo. The residue was purified by silica gel column chromatography DCM/EtOAc (V/V=10/1) to give the title compound as a colorless oil (230 mg, 74.48%).

MS (ES/API, pos. ion) m/z: 371.3 [M+Na]$^+$

Step 3) t-butyl(diphenyl)silyl 2-[1-[2-[[(3aR,6aS)-5-butyl-5-hydroxy-2,3,3a,4,6,6a-hexahydro-1H-pentalen-2-yl]oxy]-2-(2-methoxyphenyl)ethyl]-5-methyl-6-oxazol-2-yl-2,4-di oxo-thieno[2,3-d]pyrimid-3-yl]-2-methyl-propionate To a solution of (3aR,6aS)-2-butyl-5-[2-hydroxy-1-(2-methoxyphenyl)ethoxy]-3,3a,4,5,6,6a-hexahydro-1H-pentalen-2-ol (107 mg, 0.307 mmol), t-butyl(diphenyl)silyl 2-methyl-2-(5-methyl-6-oxazol-2-yl-2,4-dioxo-1H-thieno[2,3-d]pyrimid-3-yl)-propionate (160 mg, 0.279 mmol) and triphenylphosphine (150 mg, 0.56 mmol) in anhydrous tetrahydrofuran (6 mL) was added diisopropyl azodicarboxylate (0.12 mL, 0.56 mmol) dropwise slowly under N$_2$. After the addition, the mixture was stirred for 19 hours. The reaction mixture was concentrated in vacuo to remove the solvent, and the residue was purified by silica gel column chromatography (PE/EA (V/V)=3/1) to give the title compound as a light yellow oil (252 mg, 100%).

Step 4) 2-[1-[2-[[(3aR,6aS)-5-butyl-5-hydroxy-2,3,3a,4,6,6a-hexahydro-1H-pentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid To a solution of t-butyl(diphenyl)silyl 2-[1-[2-[[(3aR,6aS)-5-butyl-5-hydroxy-2,3,3a,4,6,6a-hexahydro-1H-pentalen-2-yl]oxy)-2-(2-methoxyphenyl)ethyl]-5-methyl-6-oxazol-2-yl-2,4-dioxo-thieno[2,3-d]pyrimid-3-yl]-2-methyl-propionate (252 mg, 0.279 mmol) in tetrahydrofuran (5 mL) was added a solution of tetrabutylammonium fluoride in tetrahydrofuran (0.42 mL, 0.42 mmol, 1 mol/L) at rt. The mixture was stirred for 2 hours. The reaction mixture was concentrated in vacuo to remove the solvent, and the residue was purified by silica gel column chromatography (EA) to give the title compound as a white solid (35 mg, 19%).

MS (ESI, pos. ion) m/z: 688.1[M+H]$^+$;

$^1$H NMR (400 MHz, CDCl$_3$) δ 7.72 (s, 1H), 7.56 (d, J=6.6 Hz, 1H), 7.33-7.29 (m, 1H), 7.23 (s, 1H), 7.04 (t, J=7.4 Hz, 1H), 6.90 (d, J=8.2 Hz, 1H), 5.30 (dd, J=9.1, 3.5 Hz, 1H), 4.36-4.29 (m, 1H), 3.94 (s, 3H), 3.86-3.80 (m, 1H), 3.78-3.70 (m, 1H), 2.87 (s, 3H), 2.34-2.30 (m, 2H), 2.05-1.95 (m, 4H), 1.91 (s, 3H), 1.85 (s, 3H), 1.82-1.73 (m, 3H), 1.68-1.55 (m, 4H), 1.53-1.41 (m, 3H), 0.91 (t, J=6.5 Hz, 3H).

Example 29

2-[1-[2-[[(3aR,6aS)-5-methylsulfonyl-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid

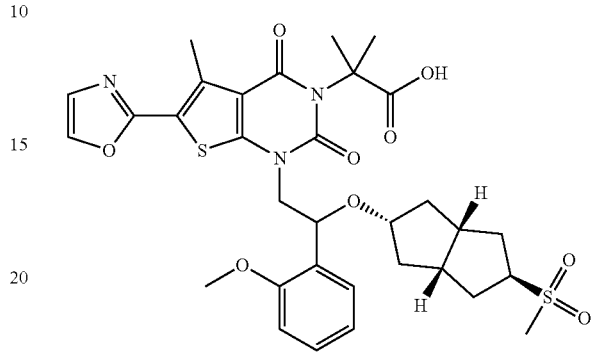

Step 1) [(3aR,6aS)-5-benzyloxy-1,2,3,3a,4,5,6,6a-octahydropentalen-2-yl] mesylate To a solution of (3aR,6aS)-5-benzyloxy-1,2,3,3a,4,5,6,6a-octahydropentalen-2-ol (4.00 g, 17.2 mmol) and triethylamine (4.9 mL, 35 mmol) in acetone (60 mL) was added methylsulfonyl chloride (1.73 mL, 22.4 mmol) dropwise slowly on an ice bath. The mixture was stirred at rt for 3 hours. The reaction was filtered by suction filtration. The filtrate was concentrated in vacuo. The residue was dissolved in ethyl acetate (80 mL). The mixture was washed with water (50 mL) and saturated brine (50 mL) in turn, dried over anhydrous sodium sulfate, filtered by suction filtration. The filtrate was concentrated in vacuo to give the title compound as a yellow brown oil (5.34 g, 100%). This crude product was used in next step without further purification.

Step 2) (3aR,6aS)-2-benzyloxy-5-methylthio-1,2,3,3a,4,5,6,6a-octahydropentalen

To a solution of [(3aR,6aS)-5-benzyloxy-1,2,3,3a,4,5,6,6a-octahydropentalen-2-yl]mesylate (5.34 g, 17.2 mmol) in anhydrous N,N-dimethylformamide (50 mL) was added anhydrous sodium methylmercaptide (1.52 g, 20.6 mmol). The mixture was stirred at 80° C. overnight, and then cooled to rt, and quenched with water (200 mmol) and extracted with ethyl acetate (100 mL). The organic phase was washed with water (100 mL), saturated brine (100 mL), dried over anhydrous sodium sulfate, filtered by suction filtration. The filtrate was concentrated in vacuo. The residue was purified by silica gel chromatograph (PE/EtOAc (V/V)=4/1) to give the title compound as a colorless oil (2.00 g, 44.3%).

$^1$H NMR (400 MHz, CDCl$_3$) δ 7.37-7.28 (m, 5H), 4.51 (s, 2H), 3.90-3.81 (m, 1H), 3.27-3.20 (m, 1H), 2.59-2.52 (m, 2H), 2.21-2.13 (m, 2H), 2.11 (s, 3H), 1.90-1.85 (m, 2H), 1.75-1.68 (m, 3H), 1.42-1.33 (m, 2H).

Step 3) (3aR,6aS)-2-benzyloxy-5-methylsulfonyl-1,2,3,3a,4,5,6,6a-octahydropentalen To a solution of (3aR,6aS)-2-benzyloxy-5-methylthio-1,2,3,3a,4,5,6,6a-octahydropentalen (1.70 g, 6.48 mmol) in DCM (20 mL) was added 3-chloroperoxybenzoic acid (4.50 g, 25.8 mmol) in portions on an ice bath under $N_2$. The mixture was stirred at rt for 8 hours. The mixture was quenched with sodium bisulfite solution (20 mL) by dropwise addition, and then saturated sodium bicarbonate solution (20 mL) was further added. The resulting mixture was extracted with ethyl acetate (120 mL×2). The combined organic phases were washed with saturated brine (50 mL), and then concentrated in vacuo. The residue was purified by silica gel chromatograph (PE/EtOAc (V/V)=4/1) to give the title compound as a colorless oil (1.80 g, 94.4%).

Step 4) (3aR,6aS)-5-methylsulfonyl-1,2,3,3a,4,5,6,6a-octahydropentalen-2-ol

To a solution of (3aR,6aS)-2-benzyloxy-5-methylsulfonyl-1,2,3,3a,4,5,6,6a-octahydropentalen (0.80 g, 2.7 mmol) in anhydrous methanol (15 mL) was added palladium on carbon (0.10 g, 10%) at rt. The mixture was stirred under $H_2$ for 8 hours. The reaction mixture filtered by suction filtration and the filtrate was concentrated in vacuo to remove the solvent, and the residue was purified by silica gel column chromatography (PE/EA (V/V)=1/1) to give the title compound as a white solid (0.40 g, 72.0%).

Step 5) 2-[[(3aR,6aS)-5-methylsulfonyl-1,2,3,3a,4,5,6,6a-octahydropentalen-2-yl]oxy]-2-(2-methoxyphenyl)acetic acid To a solution of (3aR,6aS)-5-methylsulfonyl-1,2,3,3a,4,5,6,6a-octahydropentalen-2-ol (0.40 g, 2.0 mmol) in anhydrous tetrahydrofuran (10 mL) was added sodium hydride (0.30 g, 7.5 mmol, 60%) in portions on an ice bath under $N_2$. After stirring for 15 min, a solution of 2-bromo-2-(methoxyphenyl)acetic acid (0.50 g, 2.0 mmol) in anhydrous tetrahydrofuran (10 mL) was added to the mixture. After the addition, the mixture was moved to rt and stirred for another 8 hours. The mixture was quenched with water (30 mL) by dropwise addition on an ice bath, the resulting mixture was washed with ethyl acetate (30 mL×2). The combined water layers were adjusted to pH about 3 with dilute hydrochloric acid (2N), and then extracted with ethyl acetate (30 mL×2). The combined organic layers were washed with saturated brine (30 mL), dried over anhydrous sodium sulfate, filtered by suction filtration. The filtrate was concentrated in vacuo to give the title compound as a light yellow oil (0.70 g, 97.0%). This crude product was used in next step without further purification.

MS (ESI, neg. ion) m/z: 345.1 [M−H]$^-$;

Step 6) 2-[[(3aR,6aS)-5-methylsulfonyl-1,2,3,3a,4,5,6,6a-octahydropentalen-2-yl]oxy]-2-(2-methoxyphenyl)ethanol To a solution of 2-[[(3aR,6aS)-5-methylsulfonyl-1,2,3,3a,4,5,6,6a-octahydropentalen-2-yl]oxy]-2-(2-methoxyphenyl) acetic acid (2.20 g, 5.63 mmol) in anhydrous tetrahydrofuran (10 mL) was added lithium aluminum hydride (0.15 g, 4.0 mmol) in portions on an ice bath. After the mixture was stable, the mixture was moved to rt and stirred for 4 hours. The mixture was quenched with water (0.15 mL) by dropwise addition on an ice bath. And then to the mixture were added sodium hydroxide solution (0.15 mL, 15%) and water (0.45 mL) in turn. The resulting mixture was stirred at rt for another 15 min, and anhydrous sodium sulfate was added, the mixture was further stirred for 15 min. The mixture was filtered by suction filtration. The filtrate was concentrated in vacuo. The residue was purified by silica gel chromatograph (PE/EtOAc (V/V)=2/1) to give the title compound as a colorless oil (0.30 g, 45.0%).

MS (ESI, pos. ion) m/z: 355.0[M+H]$^+$;

Step 7) t-butyl(diphenyl)silyl 2-[1-[2-[[(3aR,6aS)-5-methylsulfonyl-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate t-Butyl(diphenyl)silyl 2-methyl-2-(5-methyl-6-oxazolyl-2,4-dioxo-1H-thieno[2,3-d]pyrimid-3-yl)propionate (0.25 g, 0.44 mmol), 2-[[(3aR,6aS)-5-methylsulfonyl-1,2,3,3a,4,5,6,6a-octahydropentalen-2-yl]oxy]-2-(2-methoxyphenyl)ethanol (0.16 g, 0.45 mmol), triphenylphosphine (0.25 g, 0.95 mmol) were dissolved in anhydrous tetrahydrofuran (10 mL) at rt. Diisopropylazodicarboxylate (0.21 g, 0.20 mmol) was added to the mixture under $N_2$, the resulting mixture was stirred at rt for 12 hours and concentrated in vacuo. The residue was purified by silica gel chromatograph (PE/EtOAc (V/V)=2/1) to give the title compound as a yellow oil (0.15 g, 37.0%).

Step 8) 2-[1-[2-[[(3aR,6aS)-5-methylsulfonyl-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid To a solution of t-butyl(diphenyl)silyl 2-[1-[2-[[(3aR,6aS)-5-methylsulfonyl-1,2,3,3a,4,5,6,6a-octahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate (0.11 g, 0.12 mmol) in tetrahydrofuran (4 mL) was added a solution of tetrabutylammonium fluoride in tetrahydrofuran (4 mL, 1 mol/L) at rt. The mixture was stirred for 1 hours. The reaction mixture was concentrated in vacuo to remove the solvent, and the residue was purified by silica gel column chromatography (PE/EA (V/V)=1/1) to give the title compound as a light red solid (0.060 g, 74.0%).

MS (ESI, pos. ion) m/z: 672.2[M+H]$^+$;

$^1$H NMR (400 MHz, CDCl$_3$) δ 7.72 (s, 1H), 7.56-7.49 (m, 1H), 7.35 (t, J=7.0 Hz 1H), 7.24 (d, J=6.2 Hz 1H), 7.05 (t, J=7.5 Hz, 1H), 6.89 (d, J=8.0 Hz, 1H), 5.32-5.24 (m, 1H), 4.20-4.12 (m, 1H), 4.08-4.06 (m, 1H), 3.89 (s, 3H), 3.77-3.71 (m, 1H), 3.59-3.52 (m, 1H), 2.87 (s, 3H), 2.86 (s, 3H), 2.54-2.48 (m, 2H), 2.14-2.01 (m, 4H), 1.88 (s, 3H), 1.88 (s, 3H), 1.85-1.65 (m, 4H).

Example 30

2-[1-[2-(2-methoxyphenyl)-2[(1S,2S,4S)-1,7,7-trimethylnorborn-2-yl]oxy-ethyl]-5-methyl-6-oxazol-2-yl-2,4-dioxo-thieno[2,3-d]pyrimid-3-yl]-2-methyl-propanoic acid

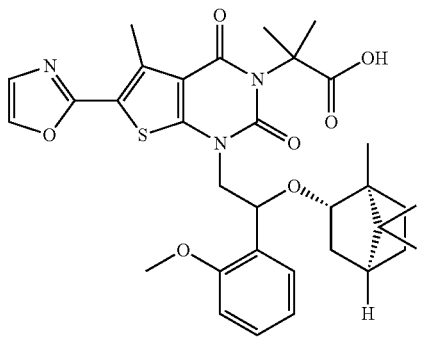 [SMILES: COc1ccccc1C(Cn1c(=O)n(C(C)(C)C(=O)O)c(=O)c2c(C)c(-c3ncco3)sc21)O[C@H]1C[C@@H]2CC[C@@]1(C)C2(C)C]

Step 1) 2-(2-methoxyphenyl)-2-[(1S,2R,4S)-1,7,7-trimethylnorborn-2-yl]oxy-acetic acid To a solution of 2-norneol (3.90 g, 12.2 mmol) in anhydrous tetrahydrofuran (40 mL) was added sodium hydride (1.96 g, 49.0 mmol) in portions on an ice bath under $N_2$. After stirring for 1 hour at rt, a solution of 2-bromo-2-(methoxyphenyl)acetic acid (3.00 g, 12.2 mmol) in anhydrous tetrahydrofuran (50 mL) was added dropwise to the mixture. After the addition, the mixture was moved to rt and stirred for another 8 hours. The mixture was quenched with water (40 mL) by dropwise addition on an ice bath, the resulting mixture was concentrated to remove most of solvent, and the water phase was washed with ethyl acetate (40 mL×2). The combined water layers were adjusted to pH about 3 with dilute hydrochloric acid (4N), and then extracted with ethyl acetate (50 mL×2). The combined organic layers were washed with saturated brine (30 mL), dried over anhydrous sodium sulfate, filtered by suction filtration. The filtrate was concentrated in vacuo to give the title compound as a light yellow oil (3.90 g, 100%). This crude product was used in next step without further purification.

MS (ESI, neg. ion) m/z: 317.3[M−H]⁻;

Step 2) 2-(2-methoxyphenyl)-2-[(1S,2R,4S)-1,7,7-trimethylnorborn-2-yl]oxy-ethanol 2-(2-Methoxyphenyl)-2-[(1S,2R,4S)-1,7,7-trimethylnorborn-2-yl]oxy-acetic acid (3.90 g, 12.2 mmol) was dissolved in tetrahydrofuran (40 mL). The mixture was cooled to 0° C. under $N_2$, and lithium aluminum hydride (0.93 g, 25.0 mmol) was added in portions. The mixture was stirred at rt overnight. The mixture was quenched with water (30 mL) by dropwise addition. The resulting mixture was adjusted to pH about 2 with hydrochloric acid (4 N) and extracted with ethyl acetate (100 mL×2). The combined organic phases were washed with saturated brine (50 mL), dried over anhydrous sodium sulfate, and filtered. The filtrate was concentrated in vacuo. The residue was purified by silica gel chromatograph (PE/EtOAc (V/V)=6/1) to give the title compound as a colorless oil (0.100 g, 2.68%).

MS (ESI, pos. ion) m/z: 327.1[M+Na]⁺;

¹H NMR (400 MHz, CDCl₃) δ 7.47-7.39 (m, 1H), 7.30-7.24 (m, 1H), 7.02-6.96 (m, 1H), 6.90-6.85 (m, 1H), 4.97-4.89 (m, 1H), 3.84 (d, J=1.1 Hz, 3H), 3.77-3.69 (m, 1H), 3.68-3.61 (m, 1H), 3.60-3.48 (m, 1H), 2.33-2.29 (m, 1H), 2.20-2.10 (m, 1H), 1.81-1.67 (m, 2H), 1.37-1.23 (m, 3H), 1.00 (s, 1H), 0.94-0.90 (m, 1H), 0.89-0.87 (m, 2H), 0.86 (d, J=2.6 Hz, 3H), 0.77 (d, J=19.0 Hz, 3H).

Step 3) t-butyl(diphenyl)silyl 2-[1-[2-(2-methoxyphenyl)-2[(1S,2S,4S)-1,7,7-trimethylnorborn-2-yl]oxy-ethyl]-5-methyl-6-oxazol-2-yl-2,4-dioxo-thieno[2,3-d]pyrimid-3-yl]-2-methyl-propionate 2-(2-methoxyphenyl)-2-[(1S,2R,4S)-1,7,7-trimethylnorborn-2-yl]oxy-ethanol (0.14 g, 0.46 mmol), triphenylphosphine (0.25 mg, 0.92 mmol) and t-butyl(diphenyl)silyl 2-methyl-2-(5-methyl-6-oxazol-2-yl-2,4-dioxo-1H-thieno[2,3-d]pyrimid-3-yl)propionate (0.29 g, 0.51 mmol) were added to tetrahydrofuran (5 mL). Diisopropyl azodicarboxylate (0.19 mL, 0.95 mmol) was added to the mixture dropwise under $N_2$. The mixture was stirred at rt overnight and concentrated in vacuo. The residue was purified by silica gel chromatograph (PE/EtOAc (V/V)=8/1) to give the title compound as a colorless oil (0.38 g, 96.3%).

Step 4) 2-[1-[2-(2-methoxyphenyl)-2[(1S,2S,4S)-1,7,7-trimethylnorborn-2-yl]oxy-ethyl]-5-methyl-6-oxazol-2-yl-2,4-dioxo-thieno[2,3-d]pyrimid-3-yl]-2-methyl-propanoic acid t-Butyl(diphenyl)silyl 2-[1-[2-(2-methoxyphenyl)-2[(1S,2S,4S)-1,7,7-trimethylnorborn-2-yl]oxy-ethyl]-5-methyl-6-oxazol-2-yl-2,4-dioxo-thieno[2,3-d]pyrimid-3-yl]-2-methyl-propionate (0.38 g, 0.44 mmol) was dissolved in tetrahydrofuran (6 mL). To the mixture was added a solution of tetrabutylammonium fluoride in tetrahydrofuran (1.0 mol/L, 0.70 mL, 0.67 mmol). The mixture was stirred at rt for 2 hours. The reaction mixture was concentrated in vacuo to remove the solvent, and the residue was purified by silica gel column chromatography (EA) to give the title compound as a white solid (0.90 mg, 31.5%).

MS (ESI, pos. ion) m/z: 622.4 [M+H]⁺;

¹H NMR (400 MHz, CDCl₃) δ 7.72 (s, 1H), 7.59-7.54 (m, 1H), 7.34-7.29 (m, 1H), 7.24 (s, 1H), 7.04 (t, J=7.5 Hz, 1H), 6.90 (d, J=8.2 Hz, 1H), 5.31-5.26 (m, 1H), 4.23-3.90 (m, 2H), 3.91 (s, 3H), 3.50 (d, J=8.3 Hz, 1H), 2.87 (s, 3H), 2.04-1.95 (m, 1H), 1.92 (s, 3H), 1.87 (s, 3H), 1.83-1.74 (m, 1H), 1.66-1.57 (m, 1H), 1.13-1.03 (m, 1H), 0.92-0.84 (m, 2H), 0.81 (s, 3H), 0.75 (s, 3H), 0.65 (s, 3H), 0.64-0.58 (m, 1H).

Example 31

2-[1-[2-(1-adamantylmethoxy)-2-(2-methoxyphenyl)ethyl]-5-methyl-6-oxazol-2-yl-2,4-dioxo-thieno[2,3-d]pyrimid-3-yl]-2-methyl-propanoic acid

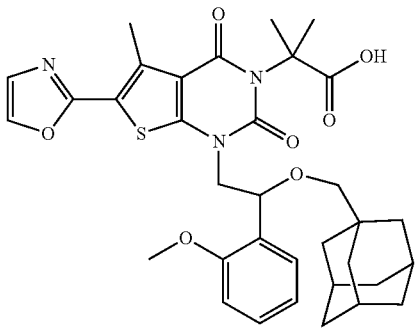 [SMILES: COc1ccccc1C(Cn1c(=O)n(C(C)(C)C(=O)O)c(=O)c2c(C)c(-c3ncco3)sc21)OCC12CC3CC(CC(C3)C1)C2]

Step 1)
2-(1-adamantylmethoxy)-2-(2-methoxyphenyl)acetic acid

1-Adamantane methanol (1.00 g, 6.01 mmol) was dissolved in tetrahydrofuran (20 mL). The mixture was cooled to 0° C. under $N_2$, and sodium hydride (722 mg, 18.05 mmol) was added. The mixture was stirred for 10 min and further stirred at rt for 30 min, and then 2-bromo-2-(2-methoxyphenyl)acetic acid (1.40 g, 5.70 mmol) was added. The resulting mixture was stirred at rt for 2 hours. The mixture was cooled to 0° C., and quenched with water (50 mL). The mixture was stirred for 10 min. After the mixture was partitioned, the water phase was adjusted to pH about 3 with dilute hydrochloric acid (1 N) and extracted with ethyl acetate (100 mL×3). The combined organic phases were washed with saturated aqueous NaCl and dried over anhydrous sodium sulfate, and filtered. The filtrate was concentrated in vacuo to get the title compound as a red oil (1.30 g, 65.3%).

MS (ESI, neg. ion) m/z: 329.1[M−H]$^-$;

Step 2)
2-(1-adamantylmethoxy)-2-(2-methoxyphenyl)ethanol 2-(1-Adamantylmethoxy)-2-(2-methoxyphenyl)acetic acid (500 mg, 1.51 mmol) was dissolved in tetrahydrofuran (20 mL). The mixture was cooled to 0° C. under $N_2$, and lithium aluminum hydride (118 mg, 3.02 mmol) was added in portions. The mixture was stirred at rt for 9 hours. To the mixture were added water (0.1 mL), sodium hydroxide aqueous solution (0.1 mL, 10%) and water (0.3 mL) dropwise slowly in turn. And then the mixture was stirred at rt, anhydrous sodium sulfate was added, the resulting mixture was further stirred at rt for 30 min. The mixture was filtered. The filter cake was washed with EtOAc (10 mL×4). The filtrate was concentrated in vacuo. The residue was purified by silica gel chromatograph (PE/EtOAc (V/V)=7/3) to give the title compound as a light yellow oil (60 mg, 12.5%).

MS (ESI, pos. ion) m/z: 339.1[M+Na]$^+$;

Step 3) t-butyl(diphenyl)silyl 2-[1-[2-(1-adamantylmethoxy)-2-(2-methoxyphenyl)ethyl]-5-methyl-6-oxazol-2-yl-2,4-dioxo-thieno[2,3-d]pyrimid-3-yl]-2-methyl-propionate 2-(1-Adamantylmethoxy)-2-(2-methoxyphenyl)ethanol (169 mg, 0.53 mmol), diisopropyl azodicarboxylate (202 mg, 0.98 mmol) and t-butyl(diphenyl)silyl 2-methyl-2-(5-methyl-6-oxazol-2-yl-2,4-dioxo-1H-thieno[2,3-d]pyrimid-3-yl)propionate (280 mg, 0.49 mmol) were added to tetrahydrofuran (10.0 mL). A solution of triphenylphosphine (295 mg, 0.98 mmol) in tetrahydrofuran (1.0 mL) was added to the mixture dropwise under $N_2$. The mixture was stirred at rt for 22 hours and concentrated in vacuo. The residue was purified by silica gel chromatograph (PE/EtOAc (V/V)=15/1) to give the title compound as an off-white oil (292 mg, 68.6%).

Step 4) 2-[1-[2-(1-adamantylmethoxy)-2-(2-methoxyphenyl)ethyl]-5-methyl-6-oxazol-2-yl-2,4-dioxo-thieno[2,3-d]pyrimid-3-yl]-2-methyl-propanoic acid t-Butyl(diphenyl)silyl 2-[1-[2-(1-adamantylmethoxy)-2-(2-methoxyphenyl)ethyl]-5-methyl-6-oxazol-2-yl-2,4-dioxo-thieno[2,3-d]pyrimid-3-yl]-2-methyl-propionate (280 mg, 0.32 mmol) was dissolved in tetrahydrofuran (10.0 mL). To the mixture was added a solution of tetrabutylammonium fluoride in tetrahydrofuran (1.0 mmol/L, 2.0 mL, 2.00 mmol). The mixture was stirred at rt for 5 hours. The reaction mixture was concentrated in vacuo to remove the solvent, and the residue was purified by silica gel column chromatography (EA) to give the title compound as a white solid (78 mg, 38.3%).

MS (ESI, pos. ion) m/z: 634.2 [M+H]$^+$;
$^1$H NMR (400 MHz, CDCl$_3$) δ 7.68 (d, J=8.1 Hz, 1H), 7.46-7.44 (m, 1H), 7.31-7.27 (m, 1H), 7.22 (s, 1H), 7.03-6.99 (m, 1H), 6.90-6.85 (m, 1H), 5.19-5.15 (m, 1H), 4.20-1.16 (m, 1H), 4.07-3.95 (m, 1H), 3.85 (s, 3H), 3.06-3.00 (m, 1H), 2.83 (s, 3H), 2.66 (d, J=9.0 Hz, 1H), 1.90-1.87 (m, 3H), 1.86-1.80 (m, 6H), 1.63-1.56 (m, 4H), 1.52-1.47 (m, 2H), 1.43-1.38 (m, 3H), 1.36-1.30 (m, 3H).

Example 32

2-[1-[2-[[(1S,3S,5R)-6,8-dioxabicyclo[3.2.1]oct-3-yl]oxy]-2-(2-methoxyphenyl)-5-methyl-6-oxazol-2-yl-2,4-dioxo-thieno[2,3-d]pyrimid-3-yl]-2-methyl-propanoic acid

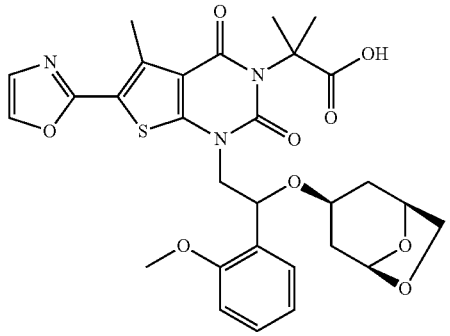 [SMILES: COc1ccccc1C(Cn1c(=O)n(C(C)(C)C(=O)O)c(=O)c2c(C)c(-c3ncco3)sc21)O[C@H]1C[C@H]2CO[C@@H](C1)O2]

Step 1) [(1R,2S,3S,4R,5R)-3-hydroxy-4-(p-tolylsulfonyl)-6,8-dioxabicyclo[3.2.1]oct-2-yl]-4-methyl-benzenesulfonic acid To a solution of (1R,2S,3S,4R,5R)-6,8-dioxabicyclo[3.2.1]octane-2,3,4-triol (3.00 g, 18.5 mmol) in pyridine (18 mL) was added p-toluensulfonyl chloride (7.84 g, 40.7 mmol) at −10° C. under N₂. The mixture was stirred at −10° C. overnight. The mixture was quenched with water (300 mL) and stirred for 20 min, and concentrated to remove water. The residue was dissolved in EtOAc (150 mL). The mixture was washed with saturated ammonium chloride solution (100 mL) and saturated brine (100 mL), and dried over anhydrous sodium sulfate, and filtered. The filtrate was concentrated in vacuo. The residue was purified by silica gel chromatograph (PE/EtOAc (V/V)=2/1) to give the title compound as an off-white solid (7.31 g, 84.0%).

MS (ESI, pos. ion) m/z: 471.2[M+H]$^+$;

1H NMR (400 MHz, DMSO) δ 7.79 (dd, J=8.2, 4.8 Hz, 4H), 7.49 (dd, J=8.2, 3.0 Hz, 5H), 6.05 (d, J=4.2 Hz, 1H), 5.27 (s, 1H), 4.54 (d, J=5.3 Hz, 1H), 4.32 (s, 1H), 4.04 (s, 1H), 4.02 (d, J=4.9 Hz, 1H), 3.59-3.52 (m, 2H), 2.46 (d, J=4.7 Hz, 1H), 2.43 (s, 6H).

Step 2) (1S,3S,5R)-6,8-dioxabicyclo[3.2.1]octane-3-ol

To a solution of [(1R,2S,3S,4R,5R)-3-hydroxy-4-(p-tolyl-sulfonyl)-6,8-dioxabicyclo[3.2.1]oct-2-yl]-4-methylbenzenesulfonic acid (6.74 g, 14.32 mmol) in anhydrous tetrahydrofuran (50 mL) was added lithium aluminum hydride (5.60 g, 143 mmol) in portions. After the system was stable, the mixture was stirred at 70° C. overnight. The mixture was quenched with water (2 mL) at −10° C., and EtOAc (50 mL) and anhydrous sodium sulfate (10 g) were added, the mixture was stirred for 10 min and filtered by suction filtration. The filtrate was concentrated in vacuo. The residue was purified by silica gel column chromatography EtOAc to give the title compound as a white solid (0.364 g, 19.5%).

GC-MS: 130.00;

$^1$H NMR (400 MHz, DMSO-d$_6$) δ 5.42 (s, 1H), 4.44 (s, 1H), 4.22 (d, J=6.2 Hz, 1H), 3.89 (t, J=5.1 Hz, 1H), 3.54-3.48 (m, 1H), 3.40 (s, 1H), 2.04-1.98 (m, 1H), 1.81-1.75 (m, 1H), 1.73-1.64 (m, 2H).

Step 3) 2-[[(1S,3S,5R)-6,8-dioxabicyclo[3.2.1]oct-3-yl]oxy]-2-(2-methoxyphenyl)acetic acid (1S,3S,5R)-6,8-Dioxabicyclo[3.2.1]octane-3-ol (0.364 g, 2.80 mmol) was dissolved in anhydrous tetrahydrofuran (10 mL). The mixture was cooled to 0° C. under N₂, and sodium hydride (0.29 g, 7.3 mmol, 60%) was added. The mixture was stirred for 10 min and further stirred at rt for 1 hour, and then a solution of 2-bromo-2-(2-fluorophenyl)acetic acid (0.600 g, 2.45 mmol) in anhydrous tetrahydrofuran (4 mL) was added. The resulting mixture was stirred at rt overnight. The mixture was poured into ice water (50 g) to quenched the reaction, and then ethyl acetate (10 mL) was added. The mixture was stirred for 10 min. After the mixture was partitioned, the water phase was adjusted to pH about 2 with dilute hydrochloric acid (1 N) and extracted with ethyl acetate (30 mL×2). The combined organic phases were washed with saturated aqueous NaCl (30 mL) and dried over anhydrous sodium sulfate, and filtered. The filtrate was concentrated in vacuo to get the title compound as a light yellow brown oil (0.721 g, 100%).

Step 4) 2-[[(1S,3S,5R)-6,8-dioxabicyclo[3.2.1]oct-3-yl]oxy]-2-(2-methoxyphenyl)ethanol 2-[[(1S,3S,5R)-6,8-Dioxabicyclo[3.2.1]oct-3-yl]oxy]-2-(2-methoxyphenyl)acetic acid (0.721 g, 2.45 mmol) was dissolved in anhydrous tetrahydrofuran (15 mL). The mixture was cooled to 0° C. under N₂, and lithium aluminum hydride (0.19 g, 5.0 mmol) was added in portions. The mixture was stirred for 4.5 hours. The mixture were quenched with water (2 mL) at 0° C. And then EtOAc (50 mL) and anhydrous sodium sulfate (5 g) was added, the resulting mixture was stirred for 10 min. The mixture was filtered by suction filtration. The filtrate was concentrated in vacuo. The residue was purified by silica gel chromatograph (PE/EtOAc (V/V)=1/1) to give the title compound (0.435 g, 63.3%).

MS (ESI, pos. ion) m/z: 303.2[M+Na]$^+$;

$^1$H NMR (400 MHz, CDCl$_3$) δ 7.42 (dd, J=7.5, 1.1 Hz, 1H), 7.30-7.24 (m, 1H), 6.98 (t, J=7.4 Hz, 1H), 6.86 (d, J=8.2 Hz, 1H), 5.66 (s, 1H), 4.93 (dd, J=9.4, 2.5 Hz, 1H), 4.59 (s, 1H), 4.53 (d, J=6.5 Hz, 1H), 3.90-3.85 (m, 1H), 3.83 (s, 3H), 3.79 (t, J=5.3 Hz, 1H), 3.73 (d, J=10.2 Hz, 1H), 3.67 (s, 1H), 3.43 (dd, J=10.9, 9.6 Hz, 1H), 2.38 (d, J=15.0 Hz, 1H), 2.27-2.21 (m, 1H), 2.01 (d, J=14.6 Hz, 1H), 1.76-1.69 (m, 1H).

Step 5) t-butyl(diphenyl)silyl 2-[1-[2-[[(1S,3S,5R)-6,8-dioxabicyclo[3.2.1]oct-3-yl]oxy]-2-(2-methoxyphenyl)-5-methyl-6-oxazol-2-yl-2,4-dioxo-thieno[2,3-d]pyrimid-3-yl]-2-methyl-propionate 2-[[(1S,3S,5R)-6,8-Dioxabicyclo[3.2.1]oct-3-yl]oxy]-2-(2-methoxyphenyl)ethanol (81 mg, 0.29 mmol), diisopropyl azodicarboxylate (0.08 mL, 0.40 mmol) and t-butyl(diphenyl)silyl 2-methyl-2-(5-methyl-6-oxazol-2-yl-2,4-dioxo-1H-thieno[2,3-d]pyrimid-3-yl)-propionate (150 mg, 0.261 mmol) were dissolved in tetrahydrofuran (10 mL). To the mixture was added triphenylphosphine (105 mg, 0.392 mmol) in portions under N₂. The mixture was stirred at rt for 10 hours. The reaction mixture was concentrated in vacuo to remove the solvent, and the residue was purified by silica gel column chromatography (PE/EA (V/V)=3/1) to give the title compound as an off-white solid (219 mg, 100%).

Step 6) 2-[1-[2-[[(1S,3S,5R)-6,8-dioxabicyclo[3.2.1]oct-3-yl]oxy]-2-(2-methoxyphenyl)-5-methyl-6-oxazol-2-yl-2,4-dioxo-thieno[2,3-d]pyrimid-3-yl]-2-methyl-propanoic acid t-Butyl(diphenyl)silyl 2-[1-[2-[[(1S,3S,5R)-6,8-dioxabicyclo[3.2.1]oct-3-yl]oxy]-2-(2-methoxyphenyl)-5-methyl-6-oxazol-2-yl-2,4-dioxo-thieno[2,3-d]pyrimid-3-yl]-2-methyl-propionate (219 mg, 0.262 mmol) was dissolved in tetrahydrofuran (4 mL). To the mixture was added a solution of tetrabutylammonium fluoride in tetrahydrofuran (1.0 mol/L, 0.52 mL, 0.52 mmol). The mixture was stirred at rt for 2 hours. The mixture was concentrated in vacuo. The residue was purified by column chromatography on silica gel eluted with (DCM/MeOH (V/V)=8/1) to give the title compound as a white solid, 81 mg, 52%).

MS (ESI, pos. ion) m/z: 598.3 [M+H]$^+$;

$^1$H NMR (400 MHz, CDCl$_3$) δ 7.73 (s, 1H), 7.50 (dd, J=7.5, 1.1 Hz, 1H), 7.35-7.30 (m, 1H), 7.24 (s, 1H), 7.04 (t, J=7.4 Hz, 1H), 6.91 (d, J=8.2 Hz, 1H), 5.48 (dd, J=9.7, 4.3 Hz, 1H), 5.40 (s, 1H), 4.38-4.30 (m, 1H), 4.29-4.23 (m, 1H), 3.91 (s, 3H), 3.75-3.65 (m, 1H), 3.51-3.45 (m), 3.44-3.38 (m, 1H), 2.89 (s, 3H), 2.12-2.05 (m, 1H), 2.05-1.94 (m, 1H), 1.92 (s, 3H), 1.91 (s, 3H), 1.88-1.76 (m, 2H), 1.62-1.57 (m, 1H).

Example 33

2-[1-[2-[[(2S,3aR,6aS)-1,2,3,3a,4,6a-hexahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propanoic acid

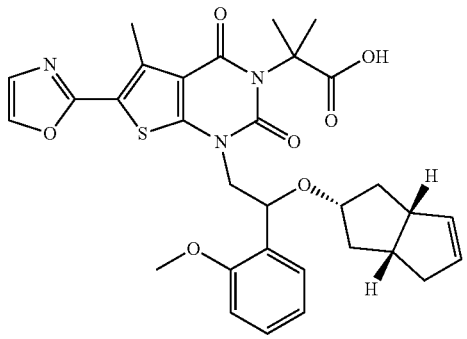 [SMILES: COc1ccccc1C(Cn1c(=O)n(C(C)(C)C(=O)O)c(=O)c2c(C)c(-c3ncco3)sc21)O[C@H]1C[C@H]2CC=C[C@H]2C1]

t-Butyl(diphenyl)silyl 2-[1-[2-[[(2S,3aR,6aS)-1,2,3,3a,4,6a-hexahydropentalen-2-yl]oxy]-2-(2-methoxyphenyl)ethyl]-5-methyl-6-oxazol-2-yl-2,4-dioxo-thieno[2,3-d]pyrimid-3-yl]-2-methyl-propionate (230 mg, 0.27 mmol) was dissolved in tetrahydrofuran (10.0 mL). To the mixture was added a solution of tetrabutylammonium fluoride in tetrahydrofuran (1.0 mol/L, 2.3 mL, 2.3 mmol). The mixture was stirred at rt for 2 hours. To the mixture was added water (10 mL) and ethyl acetate (20 mL×2). The resulting mixture was partitioned. The organic layer was washed with saturated brine, dried over anhydrous sodium sulfate, and filtered by suction filtration. The filtrate was concentrated in vacuo. The residue was purified by pre-HPLC to give the title compound as a white solid (49 mg, 29.0%).

MS (ES/API, pos. ion) m/z: 592.2[M+H]$^+$;

$^1$H NMR (400 MHz, CDCl$_3$) δ 7.69 (s, 1H), 7.52 (d, J=7.5 Hz, 1H), 7.28-7.24 (m, 2H), 7.22 (s, 1H), 7.03-6.99 (m, 1H), 6.83 (d, J=8.2 Hz, 1H), 5.58-5.33 (m, 2H), 5.32-5.25 (m, 1H), 4.13-3.96 (m, 2H), 3.83 (s, 3H), 3.73-3.66 (m, 1H), 2.95-2.86 (m, 1H), 2.84 (s, 3H), 2.50-2.36 (m, 2H), 2.06-1.90 (m, 3H), 1.86 (s, 3H), 1.83 (s, 3H), 1.35-1.26 (m, 2H).

Bioassay

1. Acetyl-CoA Carboxylase Inhibition Activity Assay In Vitro:

1) Test Method

The inhibitory action of the compounds against ACC1 or ACC2 was determined by using ADP-Clo™ kinase assay kit from Promega. The ADP-Glo™ Kinase Assay is a luminescent ADP detection assay to measure enzymatic activity by quantifying the amount of ADP produced during an enzyme reaction. The assay is performed in two steps; first, after the enzyme reaction, an equal volume of ADP-Glo™ Reagent is added to terminate the reaction and deplete the remaining ATP. Second, the Kinase Detection Reagent is added to simultaneously convert ADP to ATP and allow the newly synthesized ATP to be measured using a luciferase/luciferin reaction. Luminescence can be correlated to ADP concentrations by using an ATP-to-ADP conversion curve.

The detailed procedure is as follows.

a. 4.5 μL/well of ACC1/ACC2 working solution (2.22 nM) was added to a 384-well reaction plate (PerkinElmer, 6007290).

b. The compound (10 mM) was diluted with 100% DMSO 500 times to a concentration of 20 μM, the dilute compound solution was diluted 1:3 in succession in a 384-well dilution plate (3657, corning) to gradient concentrations of 20, 6.67, 2.22, 0.74, 0.25, 0.082, 0.027, 0.009, 0.003, 0.001, 0 μM;

c. 0.5 μL/well of the compound solution (prepared in step b) was added to the 384-well reaction plate (prepared in step a), the plate was centrifuged at 1000 rpm and incubated at 25° C. for 15 minutes;

d. 0.5 μL/well of substrate mixture (ATP (10 mM), Acetyl-CoA (2 mM), NaHCO$_3$ (1000 mM)) was transfered into the 384-well reaction plate, the plate was centrifuged at 1000 rpm and incubated at 25° C. for 30 minutes. The compound final gradient concentrations in the reaction system were 1000, 333.3, 111.1, 37.04, 12.35, 4.12, 1.37, 0.46, 0.15, 0.05, 0 nM. The final concentration of DMSO was 5%; the final concentration of ACC1/ACC2 is 1 nM.

e. 10 μL/well of ADP-Glo solution was transfered into the 384-well reaction plate, the plate was centrifuged at 1000 rpm and incubated at 25° C. for 40 minutes.

f. 20 L/well of kinase detection reagent was transfered into the 384-well reaction plate, the plate was centrifuged at 1000 rpm and incubated at 25° C. for 40 minutes.

g. Relative Light Units (RLU) was read on an Envision multifunction plate reader. The signal intensity represents the level of ACC1/ACC2 kinase activity.

The ACC1/ACC2 working solution, substrate mixture, ADP-Glo solution and kinase detection reagent used in the assay are all prepared by using 1× kinase reaction buffer [hydroxyethylpiperazineethanesulfonic acid (HEPES, 50 mM), MgCl$_2$ (2 mM), lauryl polyglycol ether (BRIJ-35, 0.01%), potassium citrate (2 mM), bovine serum albumin (BSA, 50 μg/mL), dithiothreitol (DTT, 2 mM)].

Data for each concentration, as well as the positive and negative controls were averaged, and the standard deviation was calculated. Percent inhibition was calculated by the formula: 100×(average negative control−compound)/(average negative control−average positive control). The IC$_{50}$ for each compound was calculated by fitting the data with a nonlinear regression equation: Y=Bottom+(Top−Bottom)/(1+10^((Log IC$_{50}$−X)×HillSlope)), where X is the log of compound concentration and Y is percent inhibition. 0.1 μM ND-630 was as positive control in the assay.

2. Results

Results of in vitro ACC1 and ACC2 inhibition assays are shown in table 2

TABLE 2

Inhibition activity of the compound against ACC1 and ACC2 in vitro

| Compound | ACC1 IC$_{50}$ (nM) | ACC2 IC$_{50}$ (nM) |
|---|---|---|
| Example 1 | 0.93 | ND |
| Example 10 | 0.81 | 1.76 |
| Example 13 | 1.76 | 4.24 |
| Example 14 | 1.43 | ND |
| Example 15 | 1.64 | 6.53 |
| Example 17 | 2.24 | ND |
| Example 18 | 0.89 | ND |
| Example 19 | 0.88 | 5.45 |
| Example 21 | 1.43 | 4.07 |
| Example 22 | 1.55 | 8.44 |
| Example 23 | 0.67 | 1.13 |
| Example 26 | 1.43 | 5.40 |

TABLE 2-continued

Inhibition activity of the compound against ACC1 and ACC2 in vitro

| Compound | ACC1 IC$_{50}$ (nM) | ACC2 IC$_{50}$ (nM) |
| --- | --- | --- |
| Example 27 | 1.56 | 4.80 |
| Example 29 | 0.47 | 2.19 |
| Example 32 | 1.21 | 2.74 |

"ND" stands for "not assayed";

The results of the assay indicates that the compounds of the invention have better inhibition activity effects on ACC1 and/or ACC2

2. Pharmacokinetic Test:

1) Test Method

Experimental animals: 6 healthy male adult SD rats (purchased from Hunan SJA Laboratory Animal Co.; Ltd) were randomized into 2 groups, 3 in each group, the groups were administered by intravenous injection or gavage respectively.

Preparation of drugs: an amount of the compound was scaled, and the target concentrate of the compound was prepared by addition of 5% DMSO, 10% Kolliphor HS15 and 85% saline (0.9%).

Administration and samples collection: the animals were fasted 12 hours before administration and provided again 3 hours post-administration, SD rats were administered by intravenous injection from hindlimb peduncular veins (1 mg/kg) and by gavage (PO, 5 mg/kg). 200-400 μL of blood was collected at different time points 0, 0.083, 0.25, 0.5, 1, 2, 4, 6, 8, 24 h from rats tail vein. The blood collected at each time point was placed in K$_2$EDTA anticoagulant tube, and stored at a couveuse with ice bags. All the samples in 15 min were centrifuged at 4600 r/min at 4° C. for 5 min, plasma samples were obtained, the concentrates of compound in the plasma samples were determined by LC/MS/MS, the pharmacokinetic parameters were calculated based on the drug concentration-time curve.

Pharmacokinetic properties of the compounds of the present invention were tested by the example above.

2) Test Results

The plasma concentration and exposure levels of the rats were high after oral administration of the compounds of the present invention, clear rate was low, and goog bioavailability. So the compounds of the present invention had good pharmacokinetic characteristics.

Finally, it should be noted that there are other ways to practice the invention. Accordingly, embodiments of the present invention is to be described as examples, but the present invention is not limited to the contents described, further modifications may be made within the scope of the present invention or the equivalents added in the claims. All publications or patents cited herein are incorporated by reference herein.

What is claimed is:

1. A compound having Formula (I) or a stereoisomer, a geometric isomer, a tautomer, a hydrate, a solvate, or a pharmaceutically acceptable salt thereof,

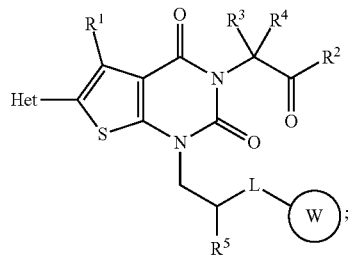

wherein:

Het is —C(=O)NR$^a$R$^b$, —C(=NR)NR$^a$R$^b$, —NH—C(=NR)NR$^a$R$^b$, 3-10 membered heterocyclyl or 5-10 membered heteroaryl; wherein each of 3-10 membered heterocyclyl and 5-10 membered heteroaryl is independently and optionally substituted with H, oxo (=O), F, Cl, Br, I, hydroxy, amino, nitro, cyano, C$_{1-6}$ alkyl, C$_{1-6}$ alkoxy, C$_{1-6}$ haloalkyl, carboxy and —C(=O)NH$_2$;

R$^1$ is H, F, Cl, Br, I, hydroxy, amino, nitro, cyano, C$_{1-6}$ alkyl, C$_{1-6}$ alkoxy or C$_{1-6}$ haloalkyl;

R$^2$ is —OR or —NR$^a$R$^b$;

each of R$^3$ and R$^4$ is independently H, C$_{1-6}$ alkyl, C$_{1-6}$ hydroxyalkyl or C$_{1-6}$ haloalkyl;

L is —O—, —O-methylene-, —O-ethylene-, —S— or —NH—;

R$^5$ is C$_{6-10}$ aryl or 5-10 membered heteroaryl, wherein each of C$_{6-10}$ aryl and 5-10 membered heteroaryl is independently and optionally substituted with 1, 2 or 3 R$^6$; wherein R$^6$ is H, F, Cl, Br, I, hydroxy, amino, nitro, cyano, C$_{1-6}$ alkyl, C$_{1-6}$ alkoxy, C$_{1-6}$ haloalkyl, C$_{1-6}$ haloalkoxy, C$_{1-6}$ cyanoalkyl or C$_{1-6}$ hydroxyalkyl; and W is fused cyclyl, bridged cyclyl or spiro cyclyl, wherein fused cyclyl, bridged cyclyl or spiro cyclyl is saturated or partially unsaturated 6-12 membered cyclyl containing 0, 1, 2, 3 or 4 heteroatoms independently selected from N, O or S; and wherein W is optionally substituted with 1, 2, 3, 4 or 5 substituents independently selected from oxo (=O), F, Cl, Br, I, hydroxy, amino, nitro, cyano, —C(=O)OR, —C(=O)NR$^a$R$^b$, —C(=NR)NR$^a$R$^b$, —NH—C(=NR)NR$^a$R$^b$, —SO$_2$R, —SO$_2$NR$^a$R$^b$, C$_{1-6}$ alkyl, C$_{3-6}$ cycloalkyl, C$_{1-6}$ alkoxy, C$_{1-6}$ haloalkoxy, C$_{1-6}$ alkylamino, C$_{1-6}$ haloalkyl, C$_{1-6}$ cyanoalkyl and C$_{1-6}$ hydroxyalkyl;

wherein each R, R$^a$ and R$^b$ is independently H, C$_{1-6}$ alkyl, C$_{1-6}$ haloalkyl or C$_{3-8}$ cycloalkyl; or R$^a$ and R$^b$, together with the N atom to which they are attached, form 3-10 membered heterocyclyl; and wherein 3-10 membered heterocyclyl is optionally substituted with oxo (=O), F, Cl, Br, I, hydroxy, amino, nitro, cyano, C$_{1-6}$ alkyl, C$_{1-6}$ alkoxy and C$_{1-6}$ haloalkyl.

2. The compound of claim 1, wherein Het is 5-6 membered heterocyclyl or 5-6 membered heteroaryl; and wherein each of 5-6 membered heterocyclyl and 5-6 membered heteroaryl is independently and optionally substituted with H, oxo (=O), F, Cl, Br, I, hydroxy, amino, nitro, cyano, C$_{1-3}$ alkyl, C$_{1-3}$ alkoxy, C$_{1-3}$ haloalkyl, carboxy and —C(=O)NH$_2$.

3. The compound of claim 1, wherein Het is pyrrolidyl, tetrahydrofuryl, imidazolidinyl, pyrazolidyl, tetrahydropyranyl, piperidyl, piperazinyl, morpholinyl, thiomorpholinyl, pyrrolyl, furyl, thienyl, pyrazolyl, imidazolyl, oxazolyl, thiazolyl, triazolyl, tetrazolyl, pyridyl, pyrimidinyl, pyridazinyl or pyrazinyl, wherein each of pyrrolidyl, tetrahydrofuryl, imidazolidinyl, pyrazolidyl, tetrahydropyranyl, piperidyl, piperazinyl, morpholinyl, thiomorpholinyl, pyrrolyl, furyl, thienyl, pyrazolyl, imidazolyl, oxazolyl, thiazolyl, triazolyl, tetrazolyl, pyridyl, pyrimidinyl, pyridazinyl and pyrazinyl is independently and optionally substituted with H, oxo (=O), F, Cl, Br, I, hydroxy, amino, nitro, cyano, methyl, ethyl, isopropyl, methoxy, ethoxy, isopropoxy, trifluoromethyl, difluoromethyl, carboxy and —C(=O)NH$_2$.

4. The compound of claim 1, wherein R$^1$ is H, F, Cl, Br, I, hydroxy, amino, nitro, cyano, C$_{1-3}$ alkyl, C$_{1-3}$ alkoxy or C$_{1-3}$ haloalkyl; and R$^2$ is —OR or —NR$^a$R$^b$;

wherein each R, R$^a$ and R$^b$ is independently H, C$_{1-3}$ alkyl, C$_{1-3}$ haloalkyl or C$_{3-6}$ cycloalkyl; or R$^a$ and R$^b$, together with the N atom to which they are attached, form 4-6 membered heterocyclyl; and wherein 4-6 membered heterocyclyl is optionally substituted with oxo (=O), F, Cl, Br, I, hydroxy, amino, nitro, cyano, C$_{1-3}$ alkyl, C$_{1-3}$ alkoxy and C$_{1-3}$ haloalkyl; and each of R$^3$ and R$^4$ is independently H, C$_{1-3}$ alkyl, C$_{1-3}$ hydroxyalkyl or C$_{1-3}$ haloalkyl.

5. The compound of claim 1, wherein R$^1$ is H, F, Cl, Br, I, hydroxy, amino, nitro, cyano, methyl, ethyl, methoxy, ethoxy, isopropoxy, trifluoromethyl, difluoromethyl or trifluoroethyl; and R$^2$ is —OR or —NR$^a$R$^b$;

wherein each R, R$^a$ and R$^b$ is independently H, methyl, ethyl, n-propyl, isopropyl, trifluoromethyl, difluoromethyl, trifluoroethyl, cyclopropyl, cyclobutyl, cyclopentyl or cyclohexyl;

or R$^a$ and R$^b$, together with the N atom to which they are attached, form heterocyclyl selected from heterocyclyl groups represented by formulae (I-a) to (I-k):

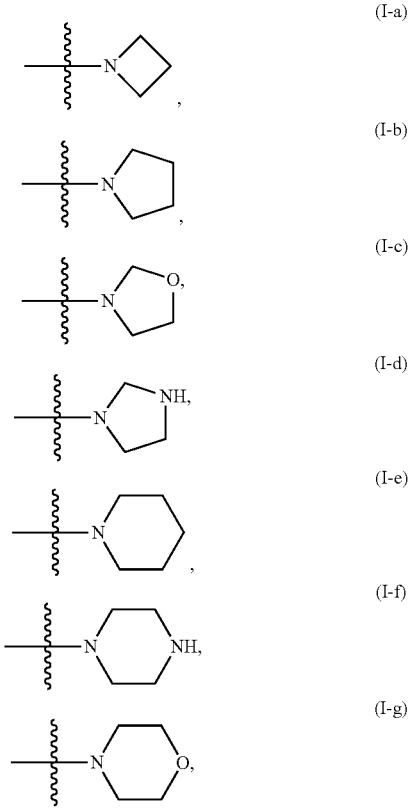

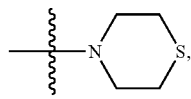
(I-h)

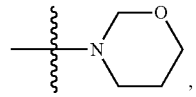
(I-i)

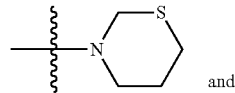
(I-j)

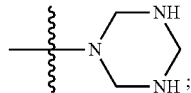
and
(I-k)

wherein the heterocyclyl groups represented by formulae (I-a) to (I-k) are optionally substituted with oxo (=O), F, Cl, Br, I, hydroxy, amino, nitro, cyano, methyl, ethyl, isopropyl, methoxy, ethoxy, trifluoromethyl, difluoromethyl or trifluoroethyl; and each of R$^3$ and R$^4$ is independently H, methyl, ethyl, n-propyl, hydroxymethyl, hydroxyethyl, trifluoromethyl or 2-fluoroethyl.

6. The compound of claim 1, wherein R$^5$ is phenyl, naphthyl, 1,2,3,4-tetrahydronaphthyl or 5-6 membered heteroaryl, wherein each of phenyl, naphthyl, 1,2,3,4-tetrahydronaphthyl and 5-6 membered heteroaryl is independently and optionally substituted with 1, 2 or 3 R$^6$; and wherein R$^6$ is H, F, Cl, Br, I, hydroxy, amino, nitro, cyano, C$_{1-3}$ alkyl, C$_{1-3}$ alkoxy, C$_{1-3}$ haloalkyl, C$_{1-3}$ haloalkoxy, C$_{1-3}$ cyanoalkyl or C$_{1-3}$ hydroxyalkyl.

7. The compound of claim 1, wherein R$^5$ is phenyl, naphthyl, 1,2,3,4-tetrahydronaphthyl, imidazolyl, pyrazolyl, furyl, thienyl, oxazolyl, oxadiazolyl, thiazolyl, thiadiazolyl, triazolyl, tetrazolyl, pyridyl, pyrimidinyl, pyranyl or pyridazinyl, wherein each of phenyl, naphthyl, 1,2,3,4-tetrahydronaphthyl, imidazolyl, pyrazolyl, furyl, thienyl, oxazolyl, oxadiazolyl, thiazolyl, thiadiazolyl, triazolyl, tetrazolyl, pyridyl, pyrimidinyl, pyranyl and pyridazinyl is independently and optionally substituted with 1, 2 or 3 R$^6$; and wherein R$^6$ is H, F, Cl, Br, I, hydroxy, amino, nitro, cyano, methyl, ethyl, n-propyl, isopropyl, methoxy, ethoxy, isopropoxy, trifluoromethyl, difluoromethyl, trifluoromethoxy, difluoromethoxy, hydroxymethyl, hydroxyethyl, cyanomethyl or cyanoethyl.

8. The compound of claim 1, wherein W has one of the following structures:

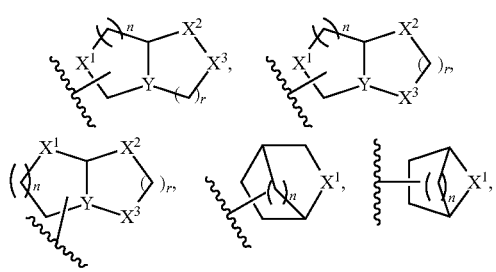

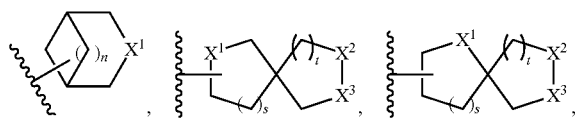

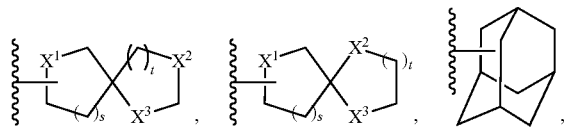

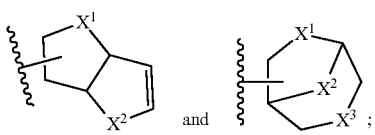

and each of $X^1$, $X^2$ and $X^3$ is independently a bond, —CH₂—, —O—, —S— or —NH—;

Y is CH or N;

each r, s, t and n is independently 0, 1, 2, or 3; and each W is optionally substituted with 1, 2, 3, 4 or 5 substituents independently selected from oxo (=O), F, Cl, Br, I, hydroxy, amino, nitro, cyano, —C(=O)OH, —C(=O)NH₂, —C(=NH)NH₂, —NH—C(=NH)NH₂, —SO₂CH₃, —SO₂C₂H₅, $C_{1-3}$ alkyl, $C_{3-6}$ cycloalkyl, $C_{1-3}$ alkoxy, $C_{1-3}$ haloalkoxy, $C_{1-3}$ alkylamino, $C_{1-3}$ haloalkyl, $C_{1-3}$ cyanoalkyl and $C_{1-3}$ hydroxyalkyl.

9. The compound of claim 1, wherein W has one of the following structures:

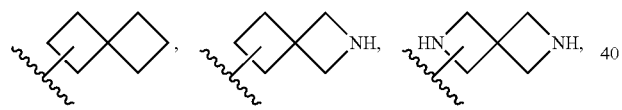

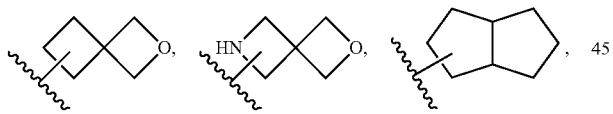

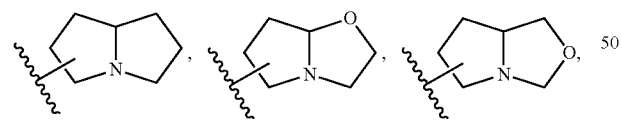

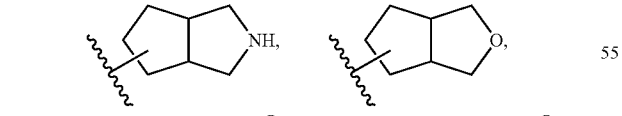

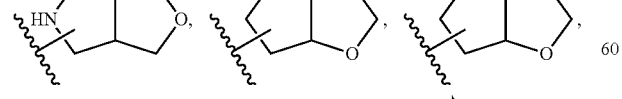

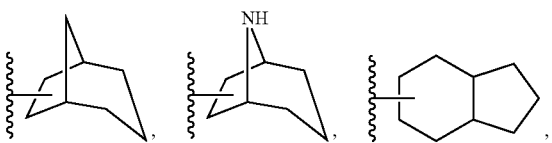

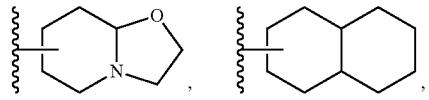

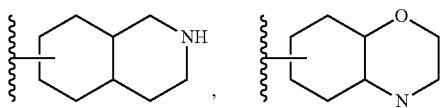

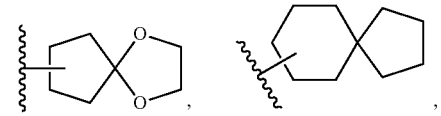

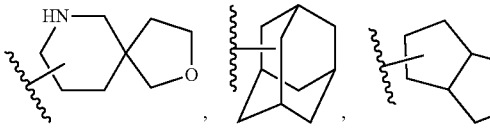

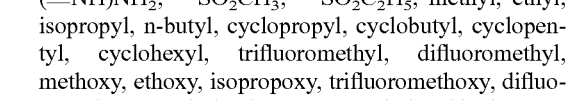

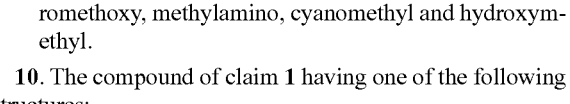

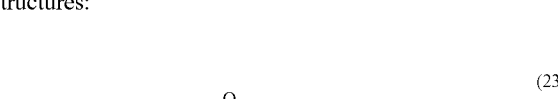

;

wherein each W is optionally substituted with 1, 2, 3, 4 or 5 substituents independently selected from oxo (=O), F, Cl, Br, I, hydroxy, amino, nitro, cyano, —C(=O)OH, —C(=O)NH₂, —C(=NH)NH₂, —NH—C(=NH)NH₂, —SO₂CH₃, —SO₂C₂H₅, methyl, ethyl, isopropyl, n-butyl, cyclopropyl, cyclobutyl, cyclopentyl, cyclohexyl, trifluoromethyl, difluoromethyl, methoxy, ethoxy, isopropoxy, trifluoromethoxy, difluoromethoxy, methylamino, cyanomethyl and hydroxymethyl.

10. The compound of claim 1 having one of the following structures:

(23)

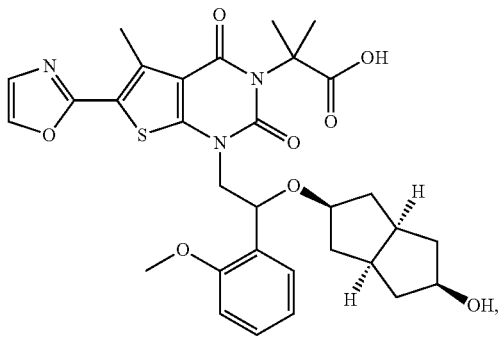

(24)
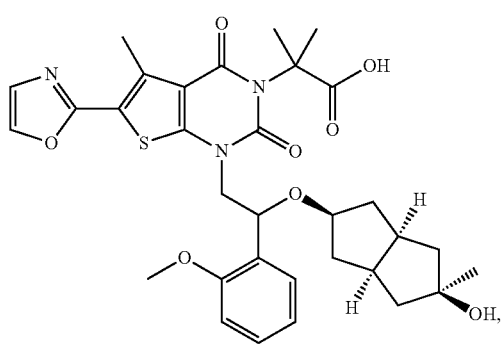
(25)
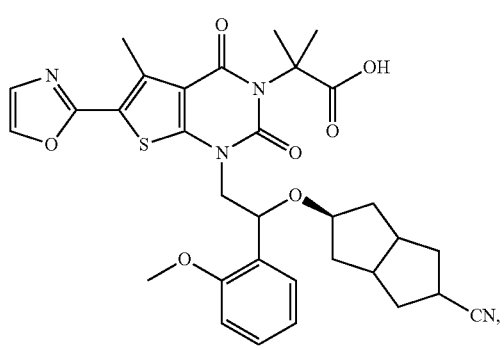
(26)
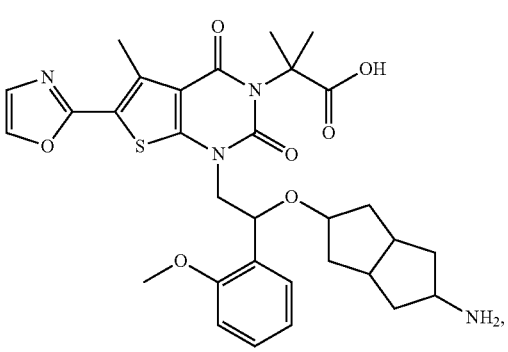
(27)
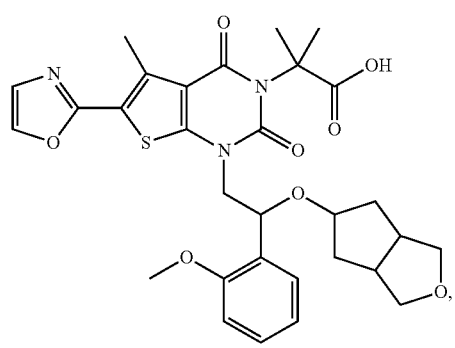
(28)
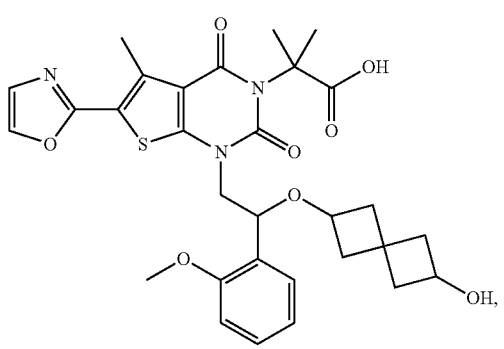
(29)
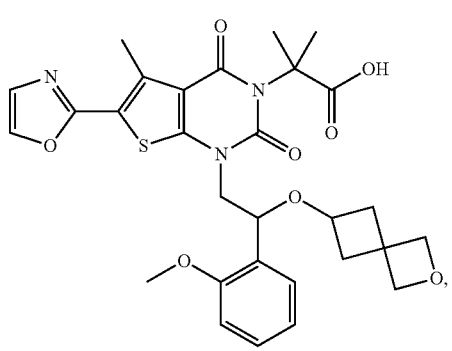
(30)
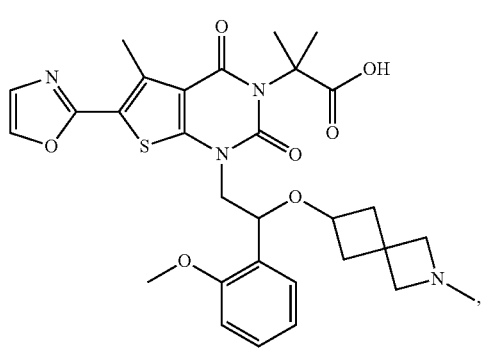
(31)
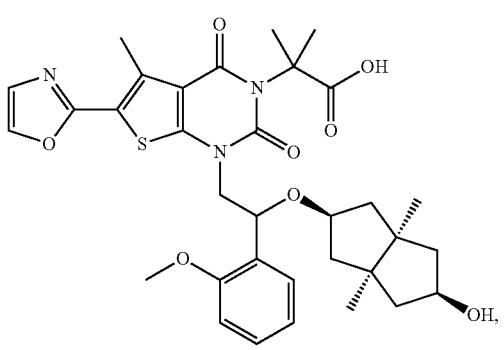

(32) 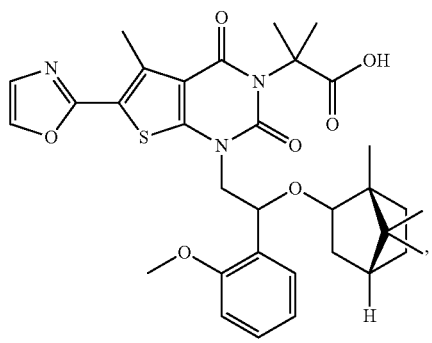
(33) 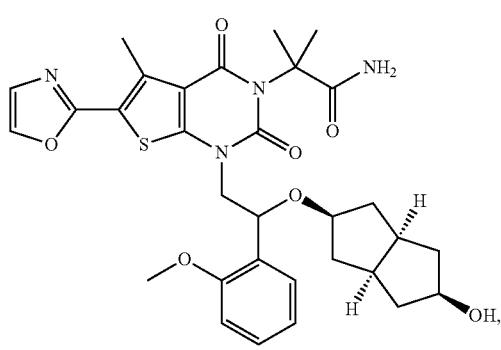
(34) 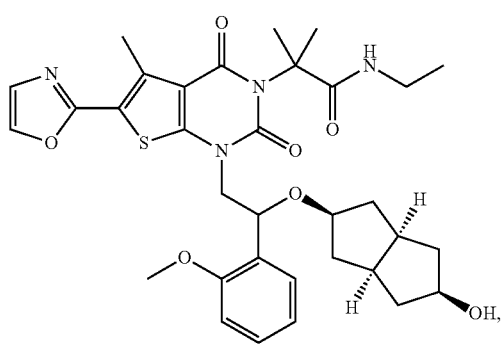
(35) 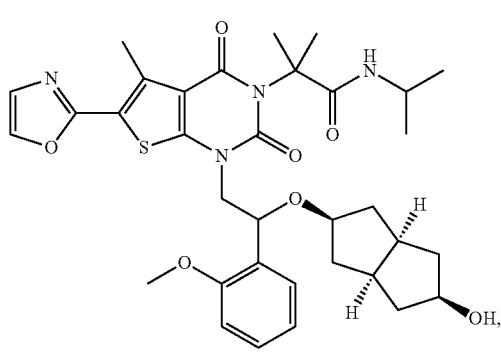
(36) 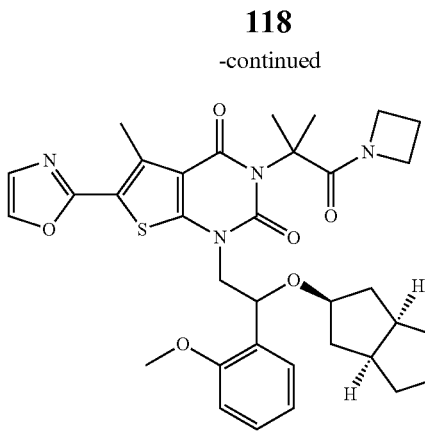
(37) 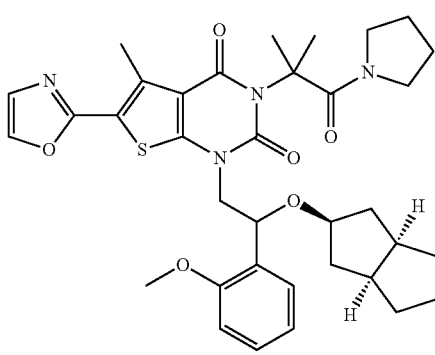
(38) 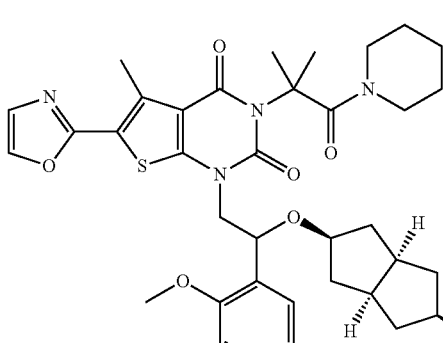
(39) 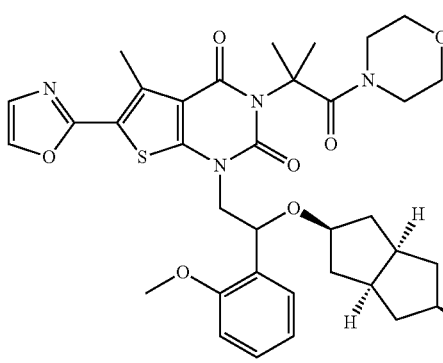

(40)
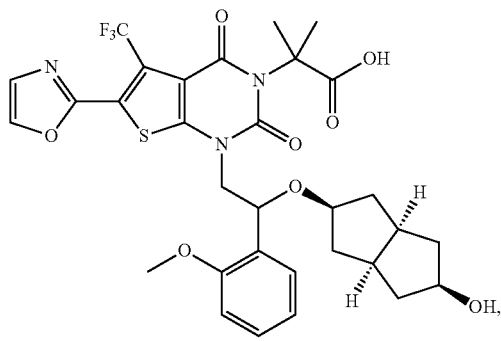
(41)
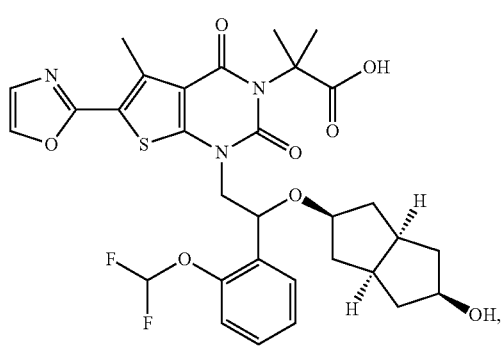
(42)
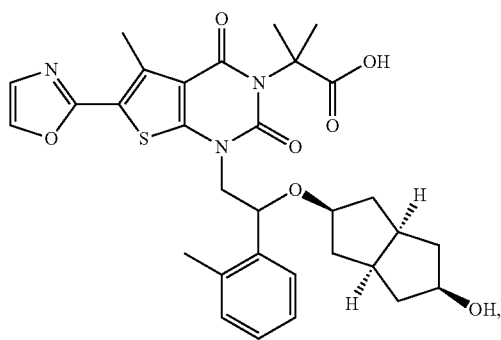
(43)
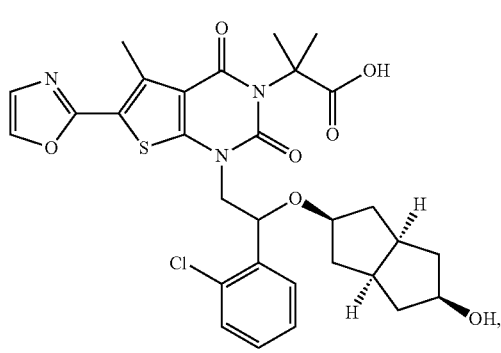
(44)
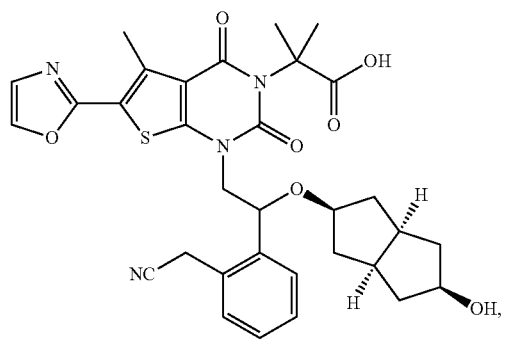
(46)
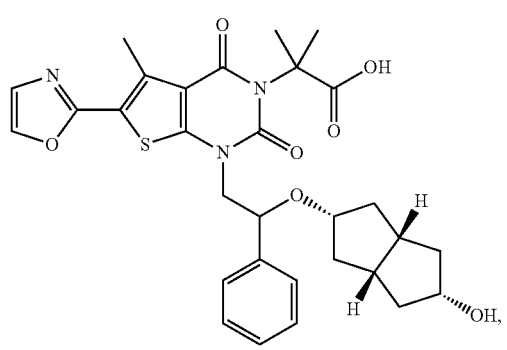
(48)
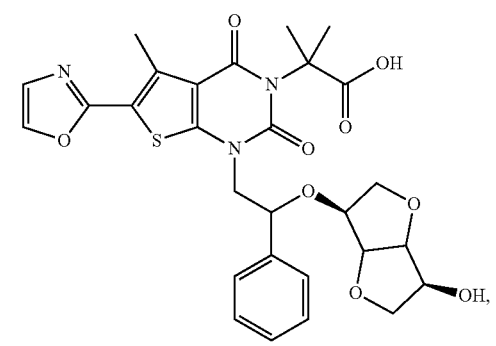
(50)
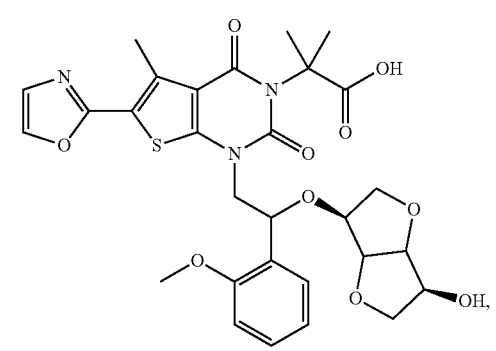

(52)
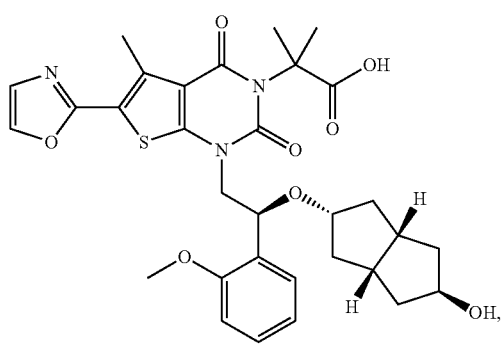
(53)
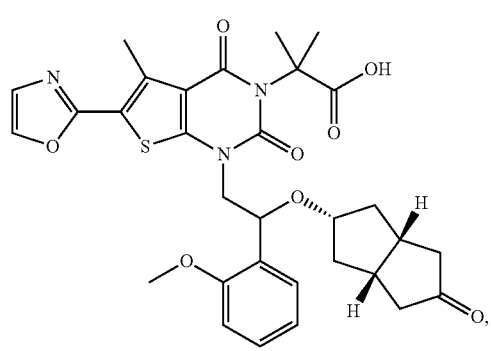
(54)
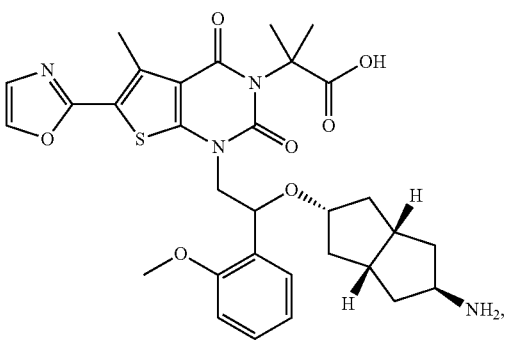
(55)
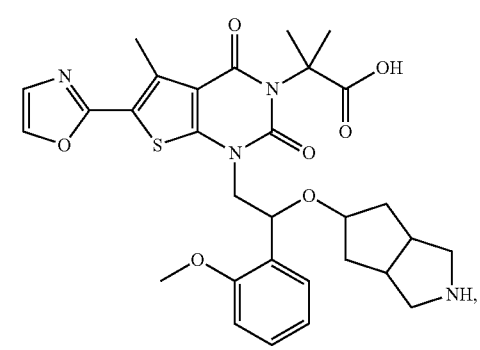
(56)
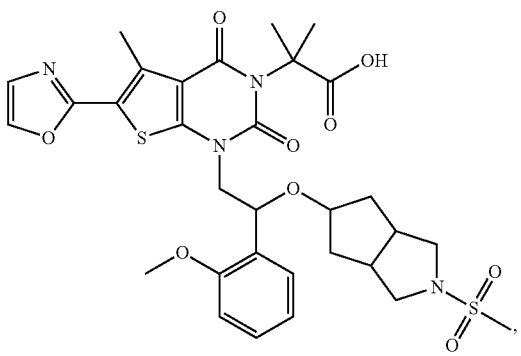
(57)
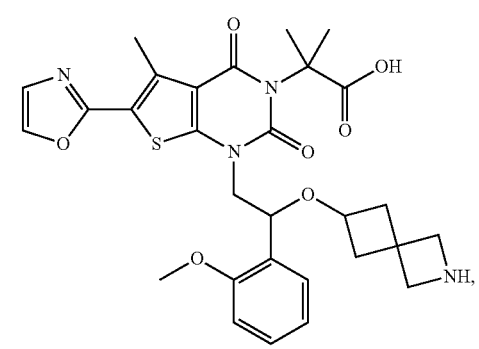
(58)
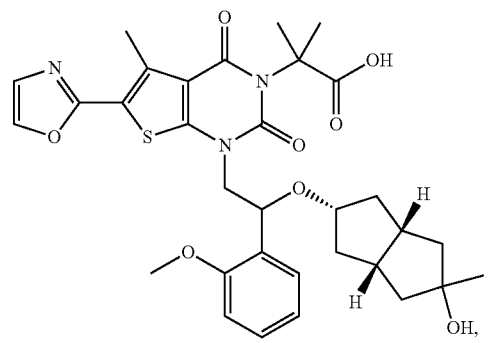
(59)
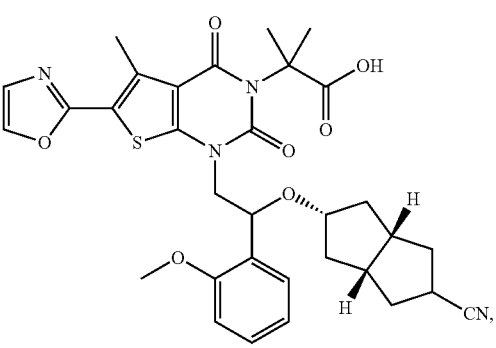

123
-continued
(60)
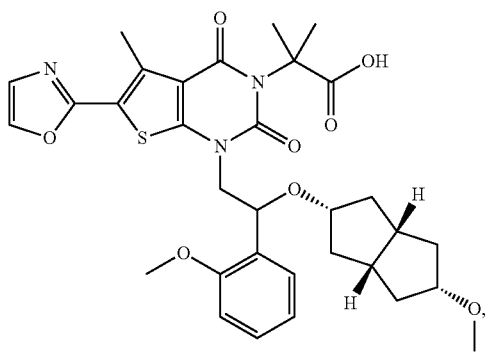
(61)
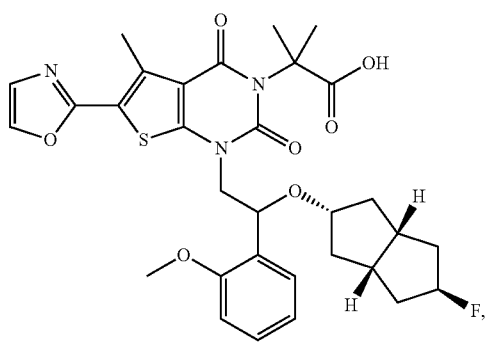
(62)
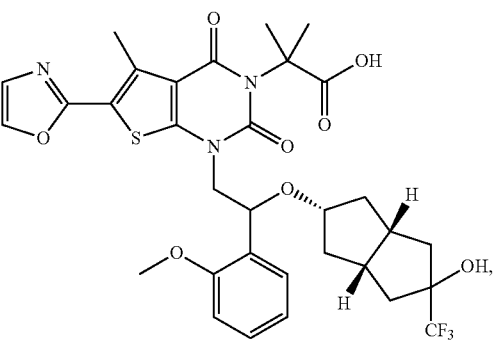
(63)
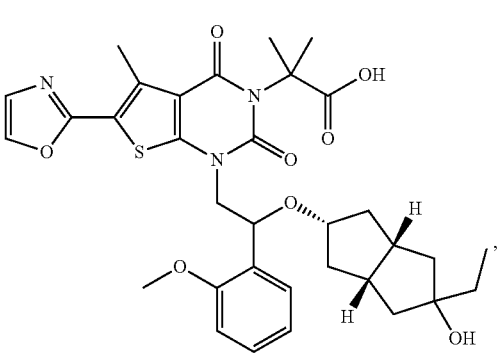
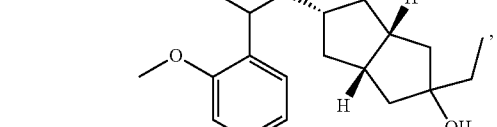
124
-continued
(64)
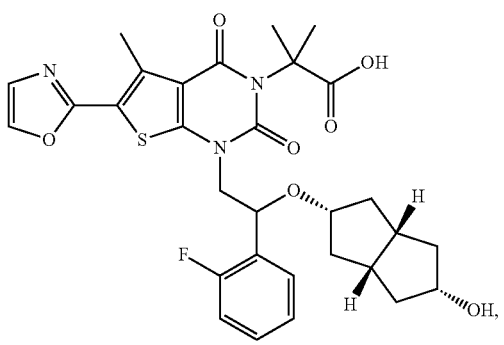
(65)
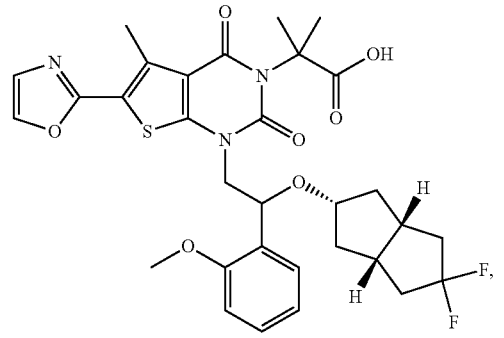
(66)
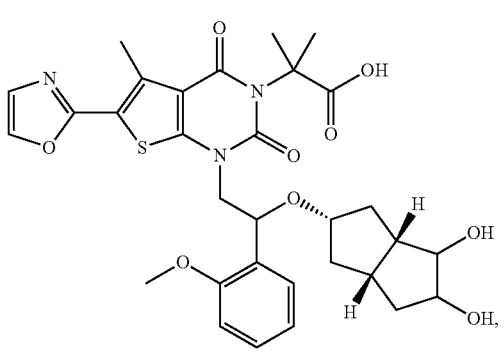
(67)
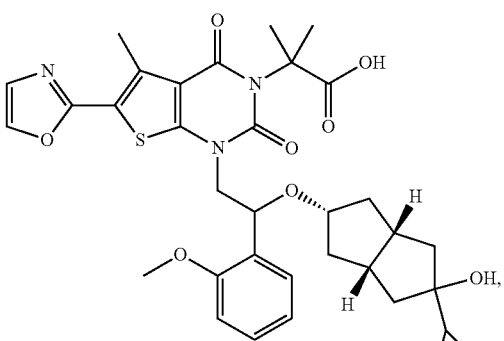

125
-continued
(68)
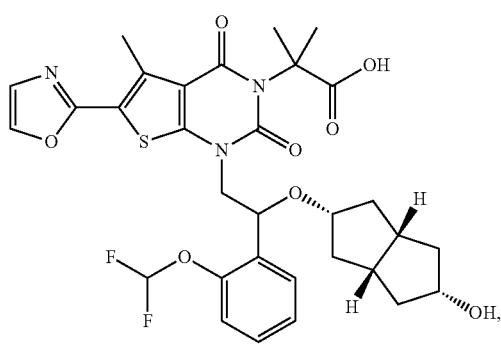
(69)
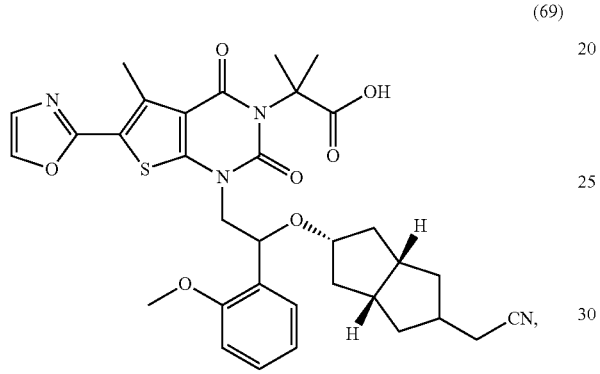
(70)
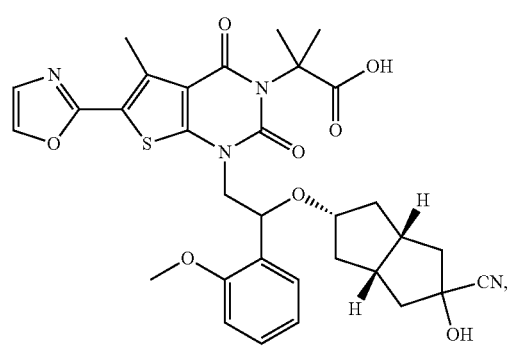
(71)
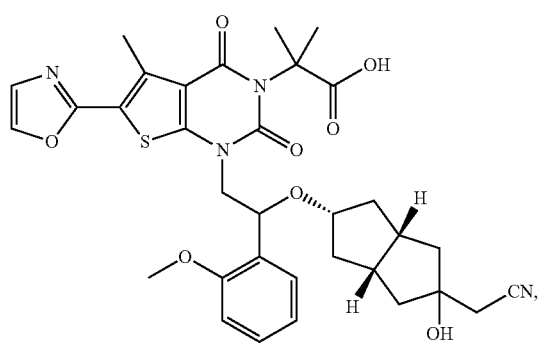
126
-continued
(72)
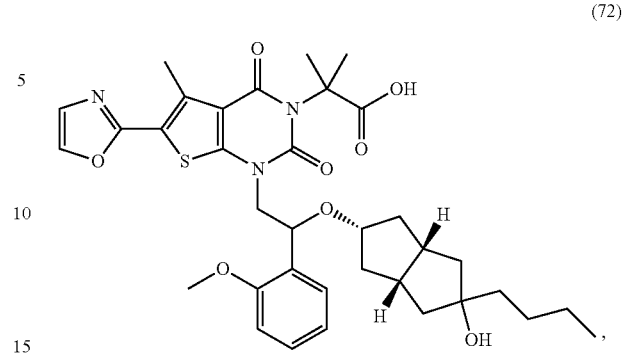
(73)
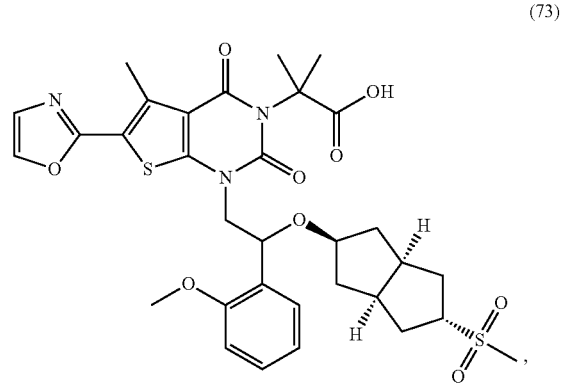
(74)
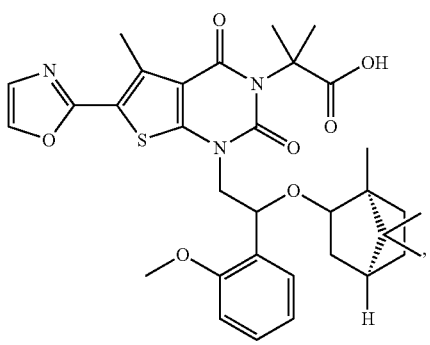
(75)
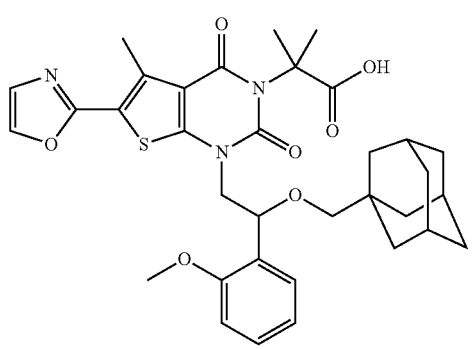

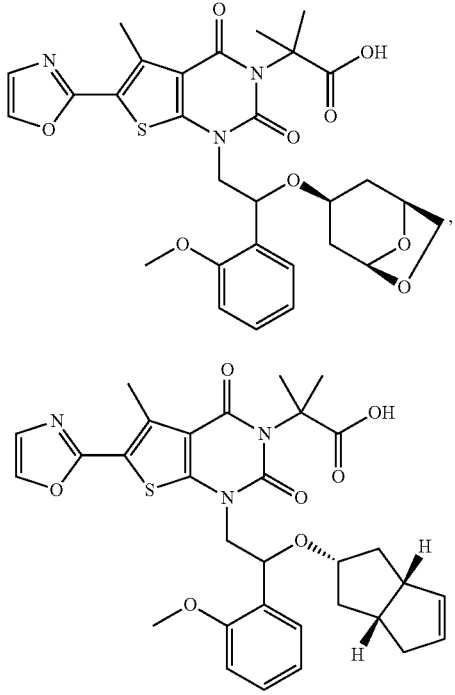

or a stereoisomer, a geometric isomer, a tautomer, an N oxide, a hydrate, a solvate, or a pharmaceutically acceptable salt thereof.

11. A pharmaceutical composition comprising the compound of claim 1.

12. The pharmaceutical composition of claim 11 further comprising a pharmaceutically acceptable carrier, excipient, diluent, adjuvant, vehicle or a combination thereof.

13. A method of treating or lessening a disorder or disease regulated by acetyl-CoA carboxylase in a patient comprising administering to the patient a therapeutically effective amount of the compound of claim 1, wherein the disorder or disease is obesity, metabolic syndrome, diabetes, non-alcoholic steatohepatitis, breast cancer, colorectal cancer or prostate cancer.

14. A method of treating or lessening a disorder or disease regulated by acetyl-CoA carboxylase in a patient comprising administering to the patient a therapeutically effective amount of the pharmaceutical composition of claim 11, wherein the disorder or disease is obesity, metabolic syndrome, diabetes, non-alcoholic steatohepatitis, breast cancer, colorectal cancer or prostate cancer.

* * * * *